US011254786B2

(12) United States Patent
Harth et al.

(10) Patent No.: US 11,254,786 B2
(45) Date of Patent: Feb. 22, 2022

(54) MULTIFUNCTIONAL DEGRADABLE NANOPARTICLES WITH CONTROL OVER SIZE AND FUNCTIONALITIES

(71) Applicant: Vanderbilt University, Nashville, TN (US)

(72) Inventors: Eva M. Harth, Houston, TX (US); David J. Calkins, Nashville, TN (US); Alice E. Van Der Ende, Antioch, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 16/547,392

(22) Filed: Aug. 21, 2019

(65) Prior Publication Data

US 2019/0375891 A1 Dec. 12, 2019

Related U.S. Application Data

(60) Division of application No. 15/682,278, filed on Aug. 21, 2017, now Pat. No. 10,442,890, which is a
(Continued)

(51) Int. Cl.
*C08G 63/91* (2006.01)
*C08G 63/08* (2006.01)
(Continued)

(52) U.S. Cl.
CPC .......... *C08G 63/912* (2013.01); *A61K 9/0048* (2013.01); *A61K 9/5153* (2013.01);
(Continued)

(58) Field of Classification Search
CPC .. C08G 63/06; C08G 63/912; C08G 2300/16; C08J 3/12; C08J 3/14; A61K 47/48907;
(Continued)

(56) References Cited

U.S. PATENT DOCUMENTS

| 4,767,872 A | 8/1988 | Doutheau et al. |
| 5,543,158 A | 8/1996 | Gref et al. |

(Continued)

FOREIGN PATENT DOCUMENTS

| CA | 3007559 A1 | 5/2009 |
| CA | 2704956 C | 2/2019 |

(Continued)

OTHER PUBLICATIONS

Akers, HJ, Ocular bioavailability of topically applied ophthalmic drugs, Am Pharm, 1983, NS23(1): pp. 33-36.
(Continued)

*Primary Examiner* — Shane Fang
(74) *Attorney, Agent, or Firm* — Cooley LLP; J. Dean Farmer; Ramsey Hilton

(57) ABSTRACT

In one aspect, the invention relates to polymers, crosslinked polymers, functionalized polymers, nanoparticles, and functionalized nanoparticles and methods of making and using same. In one aspect, the invention relates to degradable polymers and degradable nanoparticles. In one aspect, the invention relates to methods of preparing degradable nanoparticles and, more specifically, methods of controlling particle size during the preparation of degradable nanoparticles. In one aspect, the degradable nanoparticles are useful for complexing, delivering, and releasing payloads, including pharmaceutically active payloads. This abstract is intended as a scanning tool for purposes of searching in the particular art and is not intended to be limiting of the present invention.

12 Claims, 82 Drawing Sheets
Specification includes a Sequence Listing.

Related U.S. Application Data continuation of application No. 15/049,781, filed on Feb. 22, 2016, now Pat. No. 9,856,348, which is a continuation of application No. 13/520,775, filed as application No. PCT/US2011/020148 on Jan. 4, 2011, now abandoned, which is a continuation of application No. 12/651,710, filed on Jan. 4, 2010, now abandoned, which is a continuation-in-part of application No. PCT/US2008/082529, filed on Nov. 5, 2008.

(60) Provisional application No. 61/101,039, filed on Sep. 29, 2008, provisional application No. 61/100,752, filed on Sep. 28, 2008, provisional application No. 61/038,041, filed on Mar. 19, 2008, provisional application No. 60/985,608, filed on Nov. 5, 2007.

(51) Int. Cl.

| | |
|---|---|
| C08G 63/78 | (2006.01) |
| A61K 9/00 | (2006.01) |
| A61K 49/00 | (2006.01) |
| A61K 47/58 | (2017.01) |
| A61K 47/59 | (2017.01) |
| A61K 9/51 | (2006.01) |

(52) U.S. Cl.
CPC .............. *A61K 47/58* (2017.08); *A61K 47/59* (2017.08); *A61K 47/593* (2017.08); *A61K 47/595* (2017.08); *A61K 49/0041* (2013.01); *A61K 49/0056* (2013.01); *A61K 49/0093* (2013.01); *C08G 63/08* (2013.01); *C08G 63/78* (2013.01)

(58) Field of Classification Search
CPC ........ A61K 49/43; A61K 49/54; A61K 49/67; A61K 49/93
See application file for complete search history.

(56) References Cited

U.S. PATENT DOCUMENTS

| | | | |
|---|---|---|---|
| 6,048,736 | A | 4/2000 | Kosak |
| 6,196,993 | B1 | 3/2001 | Cohan et al. |
| 6,589,548 | B1 | 7/2003 | Oh et al. |
| 6,730,772 | B2 | 5/2004 | Shastri |
| 6,828,357 | B1 | 12/2004 | Martin et al. |
| 6,911,216 | B1 | 6/2005 | Roth et al. |
| 7,015,286 | B2 | 3/2006 | Heilmann et al. |
| 7,097,856 | B2 | 8/2006 | Frechet et al. |
| 7,935,782 | B2 | 5/2011 | Harth et al. |
| 8,138,301 | B2 | 3/2012 | Newkome et al. |
| 8,492,510 | B2 | 7/2013 | Harth et al. |
| 8,846,071 | B2 | 9/2014 | Kleiner |
| 8,969,622 | B2 | 3/2015 | Harth et al. |
| 9,856,348 | B2 | 1/2018 | Harth et al. |
| 10,442,890 | B2 | 10/2019 | Harth et al. |
| 2002/0076441 | A1 | 6/2002 | Shih et al. |
| 2002/0123609 | A1 | 9/2002 | Frechet et al. |
| 2003/0050426 | A1 | 3/2003 | Shastri |
| 2003/0129130 | A1 | 7/2003 | Guire et al. |
| 2005/0281883 | A1 | 12/2005 | Daniloff et al. |
| 2006/0216265 | A1 | 9/2006 | Goodman et al. |
| 2007/0200566 | A1 | 8/2007 | Clark et al. |
| 2008/0221043 | A1 | 9/2008 | Harth et al. |
| 2008/0233053 | A1 | 9/2008 | Gross et al. |
| 2009/0054619 | A1 | 2/2009 | Baker et al. |
| 2009/0163476 | A1 | 6/2009 | Milburn et al. |
| 2009/0306335 | A1 | 12/2009 | Harth et al. |
| 2010/0041859 | A1 | 2/2010 | Newkome et al. |
| 2011/0274620 | A1 | 11/2011 | Harth et al. |
| 2013/0142733 | A1 | 6/2013 | Harth et al. |
| 2016/0237208 | A1 | 8/2016 | Harth et al. |
| 2018/0142061 | A1 | 5/2018 | Harth et al. |

FOREIGN PATENT DOCUMENTS

| | | |
|---|---|---|
| EP | 2209496 A2 | 7/2010 |
| WO | WO-2004/072153 A1 | 8/2004 |
| WO | WO-2006/002365 A2 | 1/2006 |
| WO | WO-2008/024435 A2 | 2/2008 |
| WO | WO-2009/061854 A2 | 5/2009 |
| WO | WO-2011/082432 A1 | 7/2011 |

OTHER PUBLICATIONS

Bourges et al., Intraocular implants for extended drug delivery: Therapeutic application, Advanced Drug Deliver Review, 2006, 58(11): pp. 1182-1202.

Brinkley, Michael. Perspectives in Bioconjugate Chemistry. Meares, ed. American Chemical Society: Washington DC 1993: pp. 59-70.

Burke et al., RenaGel, a novel calcium- and aluminum-free phosphate binder, inhibits phosphate absorption in normal volunteers, Nephrol. Dial. Transplant., 1997, 12(8): pp. 1640-1644.

Cardona et al., Dendrimers functionalized with a single fluorescent dansyl group attached "off center": Synthesis and photophysical studies, Journal of the American Chemical Society, Jul. 2000, 122: pp. 6139-6144.

Chino et al., Synthesis of a Poly (vinyl ether) containing a benzocyclobutane moiety and its reaction with dienophiles, J. Poly. Sci. (A): Polymer Chemistry, 1999, 37: pp. 59-67.

Chung et al. Dendritic Oligoguanidines as Intracellular Translocators, Biopolymers (Pept. Sci.), 2004, 76: pp. 83-96.

Coupade et al. Novel human-derived cell-penetrating peptides for specific subcellular delivery of therapeutic biomolecules, Biochem. J., 2005, 390: pp. 407-418.

Croce et al., Approaches in the development of 3-D nanoscopic, multimodal vectors, E. Poly.Prep, ACS Fall 2005.

Feichtinger et al., Triurethane-protected guanidines and triflyldiurethane-protected guanidines: New reagents for guanidinylation reactions, J. Org. Chem., 1998, 63: pp. 8432-8439.

Fukati, S., Membrane-permeable arginine-rich peptides and the translocation mechanisms, Adv. Drug Del. Rev., 2005, 57: pp. 547-558.

Futaki et al., Translocation of branched-chain arginine peptides through cell membranes: flexibility in the spatial disposition of positive charges in membrane-permeable peptides, Biochemistry, 2002, 41: pp. 7925-7930.

Ghoroghchian et al., Near-infrared-emissive polymersomes: Self-assembled soft matter for in vivo optical imaging, PNAS, 2005, 102(8): pp. 2922-2927.

Gillies et al., Dendrimers and dendritic polymers in drug delivery, J. Drug Discov.Today, 2005, 10: pp. 35-43.

Gross et al., Retinal ganglion cell dysfunction induced by Hypoxia and Glutamate: Potential neuroprotective effects of β-blockers, Survey of Ophthalmology, 1999, 43(S1): pp. S162-S170.

Gupta et al., Intracellular delivery of large molecules and small particles by cell-penetrating proteins and peptides, Advanced Drug Delivery Review, 2005, 57(4): pp. 637-651.

Hallahan et al., Integrin-mediated targeting of drug delivery to irradiated tumor blood vessels, J. Cancer Cell., 2003, 3: pp. 63-74.

Hamilton et al., Effective Delivery of IgG-antibodies into infected cells via dendritic molecular transporter conjugate IgGMT, Molecular Biosystems, 2008, 4 (12): pp. 1209-1211.

Hans et al., Biodegradable nanoparticles for drug delivery and targeting, Curr. Opin. Solid State Mater. Sci., 2002, 6: pp. 319-327.

Hart, et al., New method for attachment of biomolecules to porous silicon, Chemical Communications 2003: pp. 322-323.

Harth et al., A facile approach to architecturally defined nanoparticles via intramolecular chain collapse, J. Am. Chem. Soc., 2002, 124: pp. 8653-8660.

Hatanaka et al., Synthesis of new heparinoids with high anticoagulant activity, J. Med. Chem., 1987, 30: pp. 810-814.

Hawker et al., New polymer synthesis by nitroxide mediated living radical polymerization, Chem. Rev., 2001, 101(12): pp. 3661-3688.

Hermanson, Greg. Bioconjugate Techniques 1996, pp. 220-221.

(56) References Cited

OTHER PUBLICATIONS

Huang et al. Dendritic molecular transporters provide control of delivery to intracellular compartments. Bioconjugate Chem., 2007, 18(2): pp. 403-409.
Huang et al., Nanocages derived from shell cross-linked micelle templates, J. Am. Chem. Soc., 1999, 121: pp. 3805-3806.
Kallinteri et al., Novel functionalized biodegradable polymers for nanoparticle drug delivery systems, Biomacromolecules2005, 6: pp. 1885-1894.
Kearsey, J. Strategies for intracellular drug delivery, The Drug Delivery Companies Report Autumn/ Winter. 2004 Pharmaventures Ltd.
Konstas et al., Twenty-four hour control of intraocular pressure with dorzolamide and timolol maleate in exfoliation and primary open-angle glaucoma, Eye, 2000, 14: pp. 73-77.
Kricheldorf et al., Polylactones 36. Macrocyclic Polymerization of Lactides with Cyclic Bu2Sn Initiators Derived from 1,2-Ethanediol, 2-Mercaptoethanol, and 1,2-Dimercaptoethane, Macromolecules, 1996, 25: pp. 1375-1381.
Kumar, et al., Preparation and characterization of cationic PLGA nanospheres as DNA carriers, Biomaterials, 2004, 25: pp. 1771-1777.
Latere et al., 2-Oxepane-1,5-dione : a precursor of a novel class of versatile semicrystalline biodegradable (co)polyesters, Macromolecules, 2002, 35: pp. 7857-7859.
Lee et al., Designed dendrimers for biological applications, Nat. Biotechnol., 2005, 23: pp. 1517-1526.
Lee et al., Formation of rotaxane dendrimers by supramolecular click chemistry, Bull. Korean Chem. Soc., 2007, 28(10): pp. 1837-1940.
Lu et al., Effects of molecular weight on the structure of poly(phenylene sulfide) crystallized at low temperature, Macromolecules, 1997, 30(20): pp. 6243-6250.
Lubetkin et al., A novel route for the preparation of narrow particle size distribution emulsions and microcapsules, Pesti. Sci., 1999, 55: pp. 1123-1125.
Liu et al., Designing dendrimers for drug delivery, J. Pharm. Sci. Technol. Today, 1999, 2: pp. 393-401.
McGehee et al., Semiconducting (conjugated) polymers as materials for solid-state lasers, Adv. Materials, 2000, 12(22): pp. 1655-1668.
Mecerreyes, et al., Ring-opening polymerization of 6-hydroxynon-8-enoic acid lactone: novel biodegradable copolymers containing allyl pendent groups, J. Polym. Sci. Part A: Polym. Chem. 2000, 38: pp. 870-875.
Mitchell et al., Polyarginine enters cells more efficiently than other polycationic homopolymers, Journal of Peptide Research, 2000, 56: pp. 318-325.
Möller et al., Sn(OTf)2 and Sc(OTf)3: Efficient and versatile catalysts for the controlled polymerization of lactones , J. Polym. Sci. Part A:Polym Chem., 2000, 38: pp. 2067-2074.
Newkome et al., Cascade polymers: Synthesis and characterization of one-directional arborols based on adamantine, J. Org. Chem., 1991, 56: pp. 7162-7167.
Newkome et al., Synthesis of benzyl-terminated dendrons for use in high-resolution capillary gas chromatography tetrahedron, Tetrahedron Letters 2001, 42: pp. 7537-7541.
Newkone et al., Design, synthesis and characterization of conifer-shaped dendritic architectures, Chemistry: a European Journal, 2006, 12(14): pp. 3726-3734.
Parrish et al., Functional polyesters prepared by polymerization of a-allyl (valerolactone) and its copolymerization with e-caprolactone and d-valerolactone, J. Polym. Sci.: Part A: Polym Chem, 2002, 40: pp. 1983-1990.
Parrish et al., PEG- and peptide-grafted aliphatic polyesters by click chemistry, J. Am. Chem. Soc., 2005, 127: pp. 7404-7410.
Riva et al., Functionalization of poly(e-caprolactone) by pendant hydroxyl, carboxylic acid and epoxide groups by atom transfer radical addition, Polymer, 2005, 46: pp. 8511-8518.

Sasatsu et al., In vitro and in vivo characterization of nanoparticles made of MeO-PEG amine/PLA block copolymer and PLA, Inter. J. Pharm., 2006, 317: pp. 167-174.
Smulders et al., Seeded emulsion polymerization of block copolymer core-shell nanoparticles with controlled particle size and molecular weight distribution using xanthate-based RAFT polymerization, Macromolecules, 2004, 34: pp. 4474-4483.
Somarajan et al., Controlled electrophoretic deposition of uniquely nanostructured star polymer films, J. Phys. Chem., 2008, 112: pp. 23-28.
Sun et al., Unsymmetric dendrimers containing a single ureidopyrimidine unit: Generation-dependent dimerization via Hydrogen Bonding, Organic letters 2005, 7: pp. 3845-3848 published online Aug. 11, 2005.
Taniguchi, et al., A chemoselective approach to grafting biodegradable polyesters, Macromolecules, 2005, 38(2): pp. 216-219.
Van Horn et al., Toward Cross-linked degradable polyester materials: investigations into the compatibility and use of reductive amination chemistry for cross-linking, Macromolecules, 2007, 40(5): pp. 1480-1488.
Vivès et al., A Truncated HIV-1 Tat Protein Basic Domain Rapidly Translocates through the Plasma Membrane and Accumulates in the Cell Nucleus, J. Biol. Chem., 1997, 272(25): pp. 16010-16017.
Wender et al., Dendrimeric molecular transporters: Synthesis and evaluation of tunable polyguanidino dendrimers that facilitate cellular uptake, Org. Lett., 2005, 7(22): pp. 4815-4818.
Wender et al., The design, synthesis, and evaluation of molecules that enable or enhance cellular uptake: Peptoid molecular transporters, Proc. Natl. Acad. Sci., 2000, 97: pp. 13003-13008.
Wu et al., Preparation and encapsulation of highly fluorescent conjugated polymer nanoparticles, Langmuir, 2006, 22: pp. 2956-2960.
Wu, et al., Site-specific conjugation of Boron-containing Dendrimers to anti-EGF receptor monoclonal antibody cetuximab (IMC-C225) and its evaluation as a potential delivery agent for neutron capture therapy, Bioconjugate Chemistry, 2004, 15: pp. 185-194.
Yadav et al., Synthesis of biologically active compounds of agricultural interest, Pure and Appl. Chem, 1990, 62:7: pp. 1333-1338.
Zhao et al., Intracellular cargo delivery using tat peptide and derivatives, Med. Res. Rev., 2004, 24: pp. 1-12.
Zweers et al., Biodegradable nanoparticles for local drug delivery, J. Controlled Release, 2003, 87: pp. 252-254.
Brannon-Peppas, Lisa, Int J. Pharm, 116, p. 1-9, 1995.
Lee et al, Polymer 40, p. 3787-3793, 1988.
Song et al Journal of Controlled Release, 413 (2-3), pp. 197-212, 1997.
International Preliminary Report on Patentability dated Feb. 24, 2009 by the International Searching Authority for Application PCT/US2007/018645 filed Aug. 23, 2007 and published as WO 2008/024435 on Feb. 28, 2008 (Applicant—Vanderbilt University // Inventor—Harth, et al.) (pp. 1-7).
International Search Report dated Sep. 18, 2008 by the International Searching Authority for Application PCT/US2007/018645 filed Aug. 23, 2007 and published as WO 2008/024435 on Feb. 28, 2008 (Applicant—Vanderbilt University // Inventor—Harth, et al.) (pp. 1-4).
Written Opinion dated Sep. 18, 2008 by the International Searching Authority for Application PCT/US2007/018645 filed Aug. 23, 2007 and published as WO 2008/024435 on Feb. 28, 2008 (Applicant—Vanderbilt University // Inventor—Harth, et al.) (pp. 1-6).
Amendment and Response filed Jul. 30, 2012 to the United States Patent and Trademark Office for U.S. Appl. No. 11/844,353, filed Aug. 23, 2007 and published as US-2008-0221043-A1 on Sep. 11, 2008 (Applicant—Vanderbilt University // Inventor—Harth, et al.) (pp. 1-14).
Amendment and Response to Office Action filed Nov. 1, 2011 to the United States Patent and Trademark Office for U.S. Appl. No. 11/844,353, filed Aug. 23, 2007 and published as US-2008-0221043-A1 on Sep. 11, 2008 (Applicant—Vanderbilt University // Inventor—Harth, et al.) (pp. 1-9).

(56) References Cited

OTHER PUBLICATIONS

Amendments and Response to an Office Action filed Mar. 9, 2011 to the United States Patent and Trademark Office for U.S. Appl. No. 11/844,353, filed Aug. 23, 2007 and published as US-2008-0221043-A1 on Sep. 11, 2008(Applicant—Vanderbilt University // Inventor—Harth, et al.) (pp. 1-16).
Applicant Initial Interview Summary dated Jul. 16, 2012 by the United States Patent and Trademark Office for U.S. Appl. No. 11/844,353, filed Aug. 23, 2007 and published as US-2008-0221043-A1 on Sep. 11, 2008 (Applicant—Vanderbilt University // Inventor—Harth, et al.) (pp. 1-4).
Examiner Interview Summary dated Jan. 30, 2012 by the United States Patent and Trademark Office for U.S. Appl. No. 11/844,353, filed Aug. 23, 2007 and published as US-2008-0221043-A1 on Sep. 11, 2008(Applicant—Vanderbilt University // Inventor—Harth, et al.) (pp. 1-2).
Final Office Action dated Jan. 30, 2012 by the United States Patent and Trademark Office for U.S. Appl. No. 11/844,353, filed Aug. 23, 2007 and published as US-2008-0221043-A1 on Sep. 11, 2008 (Applicant—Vanderbilt University // Inventor—Harth, et al.) (pp. 1-13).
Non-final Office Action dated Jun. 1, 2011 by the United States Patent and Trademark Office for U.S. Appl. No. 11/844,353, filed Aug. 23, 2007 and published as US-2008-0221043-A1 on Sep. 11, 2008 (Applicant—Vanderbilt University // Inventor—Harth, et al.) (pp. 1-15).
Non-final Office Action dated Sep. 9, 2010 by the United States Patent and Trademark Office for U.S. Appl. No. 11/844,353, filed Aug. 23, 2007 and published as US-2008-0221043-A1 on Sep. 11, 2008 (Applicant—Vanderbilt University // Inventor—Harth, et al.) (pp. 1-20).
Requirement for Restriction/Election dated Dec. 24, 2009 by the United States Patent and Trademark Office for U.S. Appl. No. 11/844,353, filed Aug. 23, 2007 and published as US-2008-0221043-A1 on Sep. 11, 2008(Applicant—Vanderbilt University // Inventor—Harth, et al.) (pp. 1-9).
Response to Restriction Requirement filed Jun. 24, 2010 to by the United States Patent and Trademark Office for U.S. Appl. No. 11/844,353, filed Aug. 23, 2007 and published as US-2008-0221043-A1 on Sep. 11, 2008(Applicant—Vanderbilt University // Inventor—Harth, et al.) (pp. 1-4).
European Search Opinion dated Jul. 4, 2012 by the European Patent Office for Application No. 08846997.8 filed Nov. 5, 2008 and published as 2209496 on Jul. 28, 2010 (Applicant—Vanderbilt University // Inventor—Harth, et al.) (pp. 1-3).
Supplemental European Search Report dated Jul. 4, 2012 by the European Patent Office for Application No. 08846997.8 filed Nov. 5, 2008 and published as 2209496 on Jul. 28, 2010 (Applicant—Vanderbilt University // Inventor—Harth, et al.) (pp. 1-3).
Examination Report dated Aug. 17, 2015 by the European Patent Office for Application No. 08846997.8 filed Nov. 5, 2008 and published as 2209496 on Jul. 28, 2010 (Applicant—Vanderbilt University// Inventor—Harth, et al.) (pp. 1-6).
International Preliminary Report on Patentability dated May 11, 2010 by the International Searching Authority for Application PCT/US2008/082529 filed Nov. 5, 2008 and published as WO 2009/061854 on May 14, 2009 (Applicant—Vanderbilt University// Inventor—Harth, et al.) (pp. 1-4).
International Search Report dated May 12, 2009 by the International Searching Authority for Application PCT/US2008/082529 filed Nov. 5, 2008 and published as WO 2009/061854 on May 14, 2009 (Applicant—Vanderbilt University // Inventor—Harth, et al.) (pp. 1-2).
Written Opinion dated May 12, 2009 by the International Searching Authority for Application PCT/US2008/082529 filed Nov. 5, 2008 and published as WO 2009/061854 on May 14, 2009(Applicant—Vanderbilt University // Inventor—Harth, et al.) (pp. 1-3).

Requirement for Restriction/Election filed Jan. 8, 2010 by the United States Patent and Trademark Office for U.S. Appl. No. 12/265,701, filed Nov. 5, 2008 and published as US-2009-0306335-A1 on Dec. 10, 2009 (Applicant—Vanderbilt University // Inventor—Harth, et al.) (pp. 1-8).
Response to Requirement for Restriction/Election filed Jul. 8, 2010 by the United States Patent and Trademark Office for U.S. Appl. No. 12/265,701, filed Nov. 5, 2008 and published as US-2009-0306335-A1 on Dec. 10, 2009 (Applicant—Vanderbilt University // Inventor—Harth, et al.) (pp. 1-16).
Amendments After Notice of Allowance filed Dec. 9, 2010 to the United States Patent and Trademark Office for U.S. Appl. No. 12/265,701, filed Nov. 5, 2008 and published as US-2009-0306335-A1 on Dec. 10, 2009 (Applicant—Vanderbilt University // Inventor—Harth, et al.) (pp. 1-2).
Examiner Interview Summary dated Sep. 23, 2010 by the United States Patent and Trademark Office for U.S. Appl. No. 12/265,701, filed Nov. 5, 2008 and published as US-2009-0306335-A1 on Dec. 10, 2009 (Applicant—Vanderbilt University // Inventor—Harth, et al.) (pp. 1-2).
Notice of Allowance and Fees Due dated Dec. 16, 2010 by the United States Patent and Trademark Office for U.S. Appl. No. 12/265,701, filed Nov. 5, 2008 and published as US-2009-0306335-A1 on Dec. 10, 2009 (Applicant—Vanderbilt University // Inventor—Harth, et al.) (pp. 1-2).
Notice of Allowance and Fees Due dated Sep. 23, 2010 by the United States Patent and Trademark Office for U.S. Appl. No. 12/265,701, filed Nov. 5, 2008 and published as US-2009-0306335-A1 on Dec. 10, 2009 (Applicant—Vanderbilt University // Inventor—Harth, et al.) (pp. 1-9).
Notice to File Corrected Application Papers dated Jan. 5, 2011 by the United States Patent and Trademark Office for U.S. Appl. No. 12/265,701, filed Nov. 5, 2008 and published as US-2009-0306335-A1 on Dec. 10, 2009 (Applicant—Vanderbilt University // Inventor—Harth, et al.) (pp. 1-3).
Notice to File Corrected Application Papers dated Nov. 3, 2010 by the United States Patent and Trademark Office for U.S. Appl. No. 12/265,701, filed Nov. 5, 2008 and published as US-2009-0306335-A1 on Dec. 10, 2009 (Applicant—Vanderbilt University // Inventor—Harth, et al.) (pp. 1-4).
Response to Notice to File Corrected Application filed Dec. 29, 2010 to the United States Patent and Trademark Office for U.S. Appl. No. 12/265,701, filed Nov. 5, 2008 and published as US-2009-0306335-A1 on Dec. 10, 2009 (Applicant—Vanderbilt University // Inventor—Harth, et al.) (pp. 1-15).
Response to Notice to File Corrected Application filed Mar. 7, 2011 to the United States Patent and Trademark Office for U.S. Appl. No. 12/265,701, filed Nov. 5, 2008 and published as US-2009-0306335-A1 on Dec. 10, 2009 (Applicant—Vanderbilt University // Inventor—Harth, et al.) (pp. 1-25).
Issue Notification filed Apr. 13, 2011 by the United States Patent and Trademark Office for U.S. Appl. No. 12/265,701, filed Nov. 5, 2008 and published as US-2009-0306335-A1 on Dec. 10, 2009 (Applicant—Vanderbilt University // Inventor—Harth, et al.) (pp. 1-1).
Notice to File Corrected Application Papers dated Dec. 10, 2010 by the United States Patent and Trademark Office for U.S. Appl. No. 12/953,173, filed Nov. 23, 2010 and published as US-2011-0257343-A1 on Oct. 20, 2011 (Applicant—Vanderbilt University // Inventor—Harth, et al.) (pp. 1-9).
Response to File Corrected Application Papers dated Jun. 10, 2011 by the United States Patent and Trademark Office for U.S. Appl. No. 12/953,173, filed Nov. 23, 2010 and published as US-2011-0257343-A1 on Oct. 20, 2011 (Applicant—Vanderbilt University // Inventor—Harth, et al.) (pp. 1-261).
Non-final Office Action dated May 30, 2012 by the United States Patent and Trademark Office for U.S. Appl. No. 12/953,173, filed Nov. 23, 2010and published as US-2011-0257343-A1 on Oct. 20, 2011 (Applicant—Vanderbilt University // Inventor—Harth, et al.) (pp. 1-9).

(56) References Cited

OTHER PUBLICATIONS

Response to Restriction Requirement filed May 14, 2012 to the United States Patent and Trademark Office for U.S. Appl. No. 12/953,173, filed Nov. 23, 2010 and published as US-2011-0257343-A1 on Oct. 20, 2011 (Applicant—Vanderbilt University // Inventor—Harth, et al.) (pp. 1-5).
Restriction/Election Requirement dated Dec. 14, 2011 by the United States Patent and Trademark Office for U.S. Appl. No. 12/953,173, filed Nov. 23, 2010 and published as US-2011-0257343-A1 on Oct. 20, 2011 (Applicant—Vanderbilt University // Inventor—Harth, et al.) (pp. 1-11).
Response to Office Action dated Oct. 1, 2012 to the United States Patent and Trademark Office for U.S. Appl. No. 12/953,173, filed Nov. 23, 2010and published as US-2011-0257343-A1 on Oct. 20, 2011 (Applicant—Vanderbilt University // Inventor—Harth, et al.) (pp. 1-14).
Final Rejection dated Nov. 13, 2012 by the United States Patent and Trademark Office for U.S. Appl. No. 12/953,173, filed Nov. 23, 2010 and published as US-2011-0257343-A1 on Oct. 20, 2011 (Applicant—Vanderbilt University // Inventor—Harth, et al.) (pp. 1-7).
Response After Final Rejection dated Dec. 6, 2012 by the United States Patent and Trademark Office for U.S. Appl. No. 12/953,173, filed Nov. 23, 2010 and published as US-2011-0257343-A1 on Oct. 20, 2011 (Applicant—Vanderbilt University // Inventor—Harth, et al.) (pp. 1-14).
Notice of Allowanace dated Jan. 4, 2013 by the United States Patent and Trademark Office for U.S. Appl. No. 12/953,173, filed Nov. 23, 2010 and published as US-2011-0257343-A1 on Oct. 20, 2011 (Applicant—Vanderbilt University // Inventor—Harth, et al.) (pp. 1-4).
Examiner Interview Summary dated Jan. 4, 2013 by the United States Patent and Trademark Office for U.S. Appl. No. 12/953,173, filed Nov. 23, 2010 and published as US-2011-0257343-A1 on Oct. 20, 2011 (Applicant—Vanderbilt University // Inventor—Harth, et al.) (pp. 1-5).
Notice to File Corrected Application Papers dated May 7, 2013 by the United States Patent and Trademark Office for U.S. Appl. No. 12/953,173, filed Nov. 23, 2010 and published as US-2011-0257343-A1 on Oct. 20, 2011 (Applicant—Vanderbilt University // Inventor—Harth, et al.) (pp. 1-3).
Response to File Corrected Application Papers dated Jun. 13, 2013 by the United States Patent and Trademark Office for U.S. Appl. No. 12/953,173, filed Nov. 23, 2010 and published as US-2011-0257343-A1 on Oct. 20, 2011 (Applicant—Vanderbilt University // Inventor—Harth, et al.) (pp. 1-3).
Issue Notification dated Jul. 3, 2013 by the United States Patent and Trademark Office for U.S. Appl. No. 12/953,173, filed Nov. 23, 2010 and published as US-2011-0257343-A1 on Oct. 20, 2011 (Applicant—Vanderbilt University // Inventor—Harth, et al.) (pp. 1-3).
International Preliminary Report on Patentability dated Jul. 4, 2012 by the International Searching Authority for Application PCT/US2011/020148 filed Jan. 4, 2011 (Applicant—Vanderbilt University // Inventor—Harth, et al.) (pp. 1-5).
International Search Report dated Apr. 6, 2011 by the International Searching Authority for Application PCT/US2011/020148 filed Jan. 4, 2011 (Applicant—Vanderbilt University // Inventor—Harth, et al.) (pp. 1-1).
Written Opinion dated Apr. 6, 2011 by the International Searching Authority for Application PCT/US2011/020148 filed Jan. 4, 2011 (Applicant—Vanderbilt University // Inventor—Harth, et al.) (pp. 1-4).
Applicant Response to Pre-Exam Formalities filed Aug. 27, 2010 to the United States Patent and Trademark Office for U.S. Appl. No. 12/651,710, filed Jan. 4, 2010 (Applicant—Vanderbilt University // Inventor—Harth, et al.) (pp. 1-526).

Final Rejection dated Jan. 14, 2013 by the United States Patent and Trademark Office for U.S. Appl. No. 12/651,710, filed Jan. 4, 2010 (Applicant—Vanderbilt University // Inventor—Harth, et al.) (pp. 1-7).
Non-Final Office Action dated Apr. 23, 2012 by the United States Patent and Trademark Office for U.S. Appl. No. 12/651,710, filed Jan. 4, 2010 (Applicant—Vanderbilt University // Inventor—Harth, et al.) (pp. 1-11).
Notice of Abandonment dated Sep. 16, 2010 by the United States Patent and Trademark Office for U.S. Appl. No. 12/651,710, filed Jan. 4, 2010 (Applicant—Vanderbilt University // Inventor—Harth, et al.) (pp. 1-2).
Notice to File Corrective Application Papers dated Jan. 21, 2011 by the United States Patent and Trademark Office for U.S. Appl. No. 12/651,710, filed Jan. 4, 2010 (Applicant—Vanderbilt University // Inventor—Harth, et al.) (pp. 1-2).
Petition to Revive Application Granted dated Jan. 3, 2011 by the United States Patent and Trademark Office for U.S. Appl. No. 12/651,710, filed Jan. 4, 2010 (Applicant—Vanderbilt University // Inventor—Harth, et al.) (pp. 1-5).
Request for Reconsideration of the Holding of Abandonment filed Oct. 25, 2010 to the United States Patent and Trademark Office for U.S. Appl. No. 12/651,710, filed Jan. 4, 2010 (Applicant—Vanderbilt University // Inventor—Harth, et al.) (pp. 1-541).
Requirement for Restriction/Election dated Nov. 16, 2011 by the United States Patent and Trademark Office for U.S. Appl. No. 12/651,710, filed Jan. 4, 2010 (Applicant—Vanderbilt University // Inventor—Harth, et al.) (pp. 1-10).
Response to Notice to File Corrective Application Papers filed Jul. 21, 2011 to the United States Patent and Trademark Office for U.S. Appl. No. 12/651,710, filed Jan. 4, 2010 (Applicant—Vanderbilt University // Inventor—Harth, et al.) (pp. 1-4).
Response to Office Action filed Oct. 23, 2012 to the United States Patent and Trademark Office for U.S. Appl. No. 12/651,710, filed Jan. 4, 2010 (Applicant—Vanderbilt University // Inventor—Harth, et al.) (pp. 1-11).
Response to Restriction/Election filed Feb. 16, 2012 to the United States Patent and Trademark Office for U.S. Appl. No. 12/651,710, filed Jan. 4, 2010 (Applicant—Vanderbilt University // Inventor—Harth, et al.) (pp. 1-13).
Amendment and Response to Non-Final Office Action filed Feb. 26, 2015 U.S. Appl. No. 12/651,710, filed Jan. 4, 2010 and published as US 2011/0274620 on Nov. 10, 2011 (Inventor—Harth et al ; Applicant—Vanderbilt University) (pp. 1-15).
Final Rejection dated Apr. 21, 2015 for U.S. Appl. No. 12/651,710, filed Jan. 4, 2010 and published as US 2011/0274620 on Nov. 10, 2011 (Inventor—Harth, et al.; Applicant—Vanderbilt University) (pp. 1-10).
Office Action dated Jan. 28, 2015, by the Canadian Intellectual Property Office for application No. 2,704,956, filed Nov. 5, 2008 (Inventor—Harth, et alll Applicant—Vanderbilt University) (5pages).
Response to Office Action dated Jul. 28, 2015, by the Canadian Intellectual Property Office for application No. 2,704,956, filed Nov. 5, 2008 (Inventor—Harth, et alll Applicant—Vanderbilt University) (50 pages).
Office Action dated Oct. 13, 2015, by the Canadian Intellectual Property Office for application No. 2,704,956, filed Nov. 5, 2008 (Inventor—Harth, et alll Applicant—Vanderbilt University) (4pages).
Response to Office Action dated Apr. 12, 2016, by the Canadian Intellectual Property Office for application No. 2,704,956, filed Nov. 5, 2008 (Inventor—Harth, et alll Applicant—Vanderbilt University) (73 pages).
Office Action dated May 17, 2016, by the Canadian Intellectual Property Office for application No. 2,704,956, filed Nov. 5, 2008 (Inventor—Harth, et alll Applicant—Vanderbilt University) (4pages).
Notice of Allowance dated Oct. 24, 2014 by the United States Patent and Trademark Office for U.S. Appl. No. 111844,353, filed Aug. 23, 2007 and published as US 2008-0221043 A1 on Sep. 11, 2008 (Applicant—Vanderbilt University// Inventor—Harth, et al.) (16 pages).

(56) References Cited

OTHER PUBLICATIONS

Amendment/Request for Reconsideration dated Aug. 14, 2014 to the United States Patent and Trademark Office for U.S. Appl. No. 11/844,353, filed Aug. 23, 2007 and published as US 2008-0221043 A1 on Sep. 11, 2008 (ApplicantVanderbilt University// Inventor—Harth, et al.) (11 pages).
Non-Final Rejection dated May 14, 2014 by the United States Patent and Trademark Office for U.S. Appl. No. 11/844,353, filed Aug. 23, 2007 and published as US 2008-0221043 A1 on Sep. 11, 2008 (Applicant—Vanderbilt University// Inventor—Harth, et al.) (20 pages).
Non-Final Rejection dated Sep. 26, 2014 by the United States Patent and Trademark Ofiice for U.S. Appl. No. 12/651,710, filed Jan. 4, 2010 and published as US 2011-0274620 A1 on Nov. 10, 2011 (Applicant—Vanderbilt University// Inventor—Harth, et al.) (15Pages).
Requirement for Restriction/Election dated Oct. 1, 2014 by the United States Patent and Trademark Office for U.S. Appl. No. 13/520,775, filed Jan. 4, 2011 and published as US-2013-0142733-A1 on Jun. 6, 2013 (Applicant—Vanderbilt University // Inventor—Harth, et al.) (pp. 1-10).
Response to Election Under Restriction Requirement filed Dec. 1, 2014 to the United States Patent and Trademark Office for U.S. Appl. No. 13/520,775, filed Jan. 4, 2011 and published as US-2013-0142733-A1 on Jun. 6, 2013 (Inventor—Harth, et al.; Applicant—Vanderbilt University) (pp. 1-13).
Non-Final Rejection dated Dec. 23, 2014 by the US Patent and Trademark Officefor U.S. Appl. No. 13/520,775, filed Jan. 4, 2011 and published as US-2013-0142733-A1 on Jun. 6, 2013 (Inventor—Harth, et al.; Applicant—Vanderbilt University) (pp. 1-13).
Response to Non-Final Office Action dated Jun. 23, 2015 for U.S. Appl. No. 13/520,775, filed Jan. 4, 2011 and published as US-2013-0142733-A1 on Jun. 6, 2013 (Inventor—Harth, et al.; Applicant—Vanderbilt University) (pp. 1-1).
Response After Final Office Action dated Oct. 5, 2015 for U.S. Appl. No. 12/651,710, filed Jan. 4, 2010 and published as US 2011-0274620 on Nov. 10, 2011 (Applicant—Vanderbilt University // Inventor—Harth, et al.) (pp. 1-13).
Advisory Action dated Oct. 26, 2015 for U.S. Appl. No. 12/651,710, filed Jan. 4, 2010 and published as US 2011-0274620 on Nov. 10, 2011 (Applicant—Vanderbilt University // Inventor—Harth, et al.) (pp. 1-4).
Final Rejection dated Aug. 26, 2015 for U.S. Appl. No. 13/520,775, filed Jan. 4, 2011 and published as US-2013-0142733-A1 on Jun. 6, 2013 (Inventor—Harth, et al.; Applicant—Vanderbilt University) (pp. 1-16).
Amendment and Response to Final Office Action dated Oct. 5, 2015 to the US Patent and Trademark Office for U.S. Appl. No. 12/651,710, filed Jan. 4, 2010 and published as US 2011/0274620 on Nov. 10, 2011 (Inventor—Harth, et al.; Applicant—Vanderbilt University) (pp. 1-1).
Non-Final Rejection dated Feb. 10, 2016 By the US Patent and Trademark Office for U.S. Appl. No. 12/651,710, filed Jan. 4, 2010 and published as US 2011/0274620 on Nov. 10, 2011 (Inventor—Harth, et al.; Applicant—Vanderbilt University) (pp. 1-1).
Non Final Rejection dated May 14, 2014 by the United States Patent and Trademark Office for U.S. Appl. No. 11/844,353, filed Aug. 23, 2007 and published as US-2008-0221043-A1 on Sep. 11, 2008 (Applicant—Vanderbilt University // Inventor—Harth, et al.) (pp. 1-20).
Amendment and Response to Final Office Action dated Aug. 17, 2014 to the US Patent and Trademark Office for U.S. Appl. No. 11/844,353, filed Aug. 23, 2007 and published as US-2008-0221043-A1 on Sep. 11, 2008 (Applicant—Vanderbilt University // Inventor—Harth, et al.) (pp. 1-1).
Notice of Allowance and Fees Due dated Oct. 24, 2014 by the United States Patent and Trademark Office for U.S. Appl. No. 11/844,353, filed Aug. 23, 2007 and published as US-2008-0221043-A1 on Sep. 11, 2008 (Applicant—Vanderbilt University // Inventor—Harth, et al.) (pp. 1-8).

Issue Notification dated Feb. 11, 2015 by the United States Patent and Trademark Office for U.S. Appl. No. 11/844,353, filed Aug. 23, 2007 and published as US-2008-0221043-A1 on Sep. 11, 2008 (Applicant—Vanderbilt University // Inventor—Harth, et al.) (pp. 1-1).
Response to Restriction Requirement filed Feb. 22, 2016 to by the United States Patent and Trademark Office for U.S. Appl. No. 14/637,105, filed Mar. 3, 2015, which was published as US 2015-0315174 A1 on Nov. 5, 2015 (Applicant—Vanderbilt University // Inventor—Harth, et al.) (pp. 1-13).
Office Action dated May 17, 2016 by the Canadian Patent Office for Canadian Application No. 2,704,956 which was filed on Nov. 5, 2008 (Inventor—Eva M. Harth et al; Applicant—Vanderbuilt University) (4 pages).
Final Rejection dated Oct. 17, 2016 By the US Patent and Trademark Office for U.S. Appl. No. 12/651,710, filed Jan. 4, 2010 and published as US 2011/0274620 on Nov. 10, 2011 (Inventor—Harth, et al.; Applicant—Vanderbilt University) (12 pages).
Non-Final Office Action dated Aug. 26, 2016 for U.S. Appl. No. 14/637,105, filed Mar. 3, 2015 and published as US 2015-0315174-A1 on Nov. 5, 2013 (Appliccant—Vanderbilt University // Inventor—Harth, et al.) (24 pages).
Notice of Abandonment dated Mar. 17, 2017 by the U.S. Patent and Trademark Office for U.S. Appl. No. 14/637,105, filed Mar. 3, 2015 and published as US 2015/0315174 on Nov. 5, 2015 (Inventor—Harth et al.; Applicant—Vanderbilt Univ.) (2 pages).
Office Action dated Jan. 10, 2017 by the Canadian Intellectual Property Office for Canadian Patent Application No. 2,704,956, which was filed on Nov. 5, 2008 (Inventor—Harth et al.; Applicant—Vanderbilt Univ.) (4 pages).
Communication Pursuant to Article 94(3) EPC dated Feb. 9, 2017 by the European Patent Office for European Patent Application No. 08846997.8, which was filed on Nov. 5, 2008 and published as 2209496 on Jul. 28, 2010 (Inventor—Harth et al.; Applicant—Vanderbilt Univ.) (6 pages).
Response to Final Office Action and Request for Continued Examination filed on Feb. 17, 2017 with the U.S. Patent and Trademark Office for U.S. Appl. No. 12/651,710, filed Jan. 4, 2010 and published as US 2011/0274620 on Nov. 10, 2011 (Inventor—Harth et al.; Applicant—Vanderbilt Univ.) (12 pages).
Non-Final Office Action dated May 26, 2017 by the U.S. Patent and Trademark Office for U.S. Appl. No. 12/651,710, filed Jan. 1, 2010 and published as US 2011/0274620 on Nov. 10, 2011 (Inventor—Harth et al.; Applicant—Vanderbilt Univ.) (15 pages).
Response to Office Action dated Jul. 10, 2017 by the Canadian Patent Office for CA Application No. 2,704,956, which was filed on Nov. 5, 2008 and published as CA 2704956 A1 on May 14, 2009 (Applicant—Vanderbilt University) (31 pages).
Response to Office Action dated Aug. 18, 2017 by the European Patent Office for EP Application No. 08846997.8, which was filed on Nov. 5, 2008 and published as EP2209496 on Jul. 28, 2010 (Applicant—Vanderbilt University) (53 pages).
Office Action dated Sep. 20, 2017 by the Canadian Patent Office for Patent Application No. 2704956, which was filed on Nov. 5, 2008 (Inventor—Harth et al.; Applicant—Vanderbilt University) (3 pages).
Notice of Abandonment dated May 9, 2016 by the U.S. Patent and Trademark Office for U.S. Appl. No. 13/520,775, filed Jan. 28, 2013 and published as US 2013/0142733 on Jun. 6, 2013 on (Inventor—Harth et al.; Applicant—Vanderbilt University) (2 pages).
Preliminary Amendment filed on Apr. 19, 2016 with the U.S. Patent and Trademark Office for U.S. Appl. No. 15/049,781, filed Feb. 22, 2016 and published as US 2016/0237208 on Aug. 18, 2016 (Inventor—Harth et al.; Applicant—Vanderbilt University) (20 pages).
Non-Final Office Action dated Apr. 20, 2017 with the U.S. Patent and Trademark Office for U.S. Appl. No. 15/049,781, filed Feb. 22, 2016 and published as US 2016/0237208 on Aug. 18, 2016 (Inventor—Harth et al.; Applicant—Vanderbilt University) (6 pages).
Response to Non-Final Office Action and Terminal Disclaimer filed on Jul. 18, 2017 with the U.S. Patent and Trademark Office for U.S. Appl. No. 15/049,781, filed Feb. 22, 2016 and published as US 2016/0237208 on Aug. 18, 2016 (Inventor—Harth et al.; Applicant—Vanderbilt University) (5 pages).

(56) References Cited

OTHER PUBLICATIONS

Terminal Disclaimer Review Decision dated Jul. 18, 2017 by the U.S. Patent and Trademark Office for U.S. Appl. No. 15/049,781, filed Feb. 22, 2016 and published as US 2016/0237208 on Aug. 18, 2016 (Inventor—Harth et al.; Applicant—Vanderbilt University) (1 page).

Notice of Allowance dated Aug. 16, 2017 by the U.S. Patent and Trademark Office for U.S. Appl. No. 15/049,781, filed Feb. 22, 2016 and published as US 2016/0237208 on Aug. 18, 2016 (Inventor—Harth et al.; Applicant—Vanderbilt University) (7 pages).

Notice of Allowance dated Sep. 6, 2017 by the U.S. Patent and Trademark Office for U.S. Appl. No. 15/049,781, filed Feb. 22, 2016 and published as US 2016/0237208 on Aug. 18, 2016 (Inventor—Harth et al.; Applicant—Vanderbilt University) (4 pages).

Response After Notice of Allowance filed on Oct. 26, 2017 with the U.S. Patent and Trademark Office for U.S. Appl. No. 15/049,781, filed Feb. 22, 2016 and published as US 2016/0237208 on Aug. 18, 2016 (Inventor—Harth et al.; Applicant—Vanderbilt University) (31 pages).

Response to Amendment dated Oct. 31, 2017 by the U.S. Patent and Trademark Office for U.S. Appl. No. 15/049,781, filed Feb. 22, 2016 and published as US 2016/0237208 on Aug. 18, 2016 (Inventor—Harth et al.; Applicant—Vanderbilt University) (2 pages).

Issue Notification dated Dec. 13, 2017 by the U.S. Patent and Trademark Office for U.S. Appl. No. 15/049,781, filed Feb. 22, 2016 now U.S. Pat. No. 9,856,348 on Jan. 2, 2018 (Inventor—Harth et al.) (1 page).

Preliminary Amendment dated Mar. 21, 2018 to the USPTO for U.S. Appl. No. 15/682,278, filed Aug. 21, 2017 now U.S. Pat. No. 10,442,890 on Oct. 15, 2019 (Inventor—Eva M. Harth) (8 Pages).

Requirement for Restriction/ Election dated Oct. 12, 2018 by the USPTO for U.S. Appl. No. 15/682,278, filed Aug. 21, 2017 now U.S. Pat. No. 10,442,890 on Oct. 15, 2019 (Inventor—Eva M. Harth) (6 Pages).

Response to Requirement for Restriction/ Election dated Apr. 10, 2019 to the USPTO for U.S. Appl. No. 15/682,278, filed Aug. 21, 2017 now U.S. Pat. No. 10,442,890 on Oct. 15, 2019 (Inventor—Eva M. Harth) (10 Pages).

Notice of Allowance dated May 21, 2019 by the USPTO for U.S. Appl. No. 15/682,278, filed Aug. 21, 2017 now U.S. Pat. No. 10,442,890 on Oct. 15, 2019 (Inventor—Eva M. Harth) (8 Pages).

Amendment After Notice of Allowance(Rule 312) dated Aug. 21, 2019 to the USPTO for U.S. Appl. No. 15/682,278, filed Aug. 21, 2017 now U.S. Pat. No. 10,442,890 on Oct. 15, 2019 (Inventor—Eva M. Harth) (2 Pages).

Issue Notification dated Sep. 25, 2019 by the USPTO for U.S. Appl. No. 15/682,278, filed Aug. 21, 2017 now U.S. Pat. No. 10,442,890 on Oct. 15, 2019 (Inventor—Eva M. Harth) (1 Page).

Parrish: "Aliphatic Polyesters With Pendent Unsaturation and Poly(Ethylene Glycol) Groups: Synthesis, Characterization, and Encapsulation Studies a Dissertation Presented",(2006), Retrieved from the Internet: URL:https://scholarworks.umass.edu/dissertations/AAI3215902/ [retrieved on Aug. 14, 2019].

European Search Report and Written Opinion dated Aug. 22, 2019 by the European Patent Office for EP Application No. 19172669.4, filed on Nov. 8, 2005 (Applicant—Vanderbilt University) (18 Pages).

10 μM concentration for 30 min.

|  | % NH$_2$ | % Maleimide Linker | Molecular Transporter TD-2 | Cy3 Dye |
|---|---|---|---|---|
| NP 1 | 26.9 | 0 | — | — |
| NP 2 | 30.1 | 0 | — | — |
| NP 3 | 9.7 | 0 | — | — |
| NP 4 | 3.3 | 12 | 10 | 3 |
| NP 5 | 18.7 | 19.5 | 8 | 9 |
| NP 6 | 9.5 | 9.7 | 8 | 6 |

FIG. 32 (Continued)

50 nm
7% cross-linking density
1.3% travatan, 0.38 mg/mL 400 nm
14% cross-linking density
22.4% bimatoprost, 3.58 mg/mL 700 nm
14% cross-linking density
29.35 % bimatoprost, 4.7 mg/mL Scheme 1. Synthesis of SVEC (vinylsulfonyl-ethyl carbonate) linker and attachement to the particle Scheme 2. Attachment of peptide with integrated thiol group from cysteins to linker modified particle Scheme 3. Attachment of Alexa Fluor dye to free amine groups of the particle (NHS ester to amine) and quenching of the residual amines before reductive amination of amines of peptides (bioactive compounds) to the keto groups of the particle.

Scheme 6. Nanoparticle formation from allyl functionalized AB$_b$D linear precursor with diamines.

Scheme 7. Nanoparticle formation from allyl functionalized ABDD linear precursor with diamines Scheme 8a. Nanoparticle formation from allyl functionalized ABbD linear precursor with diamines Scheme 8b. Strategy for attaching dendritic transporter to nanoparticle.

Scheme 8c. Sequential modification of collapsible nanoparticle.

Scheme 9a. Attachment of the targeting peptide to the SVEC system. The peptide shown is Seq. I.D. 1.

Scheme 9h. Attachment of the targeting peptide to a nanoparticle system. (Seq. ID. 2)

Scheme 10. Functionalization of organic quantum dots via intramolecular chain collapse. The peptide shown is Seq. I.D. 1.

Scheme 11. Deprotection of triflate with base and attachment of SVEC followed by the deprotection of acylhydrazone linker. The peptide shown is Seq. I.D. 1.

Scheme 12a. DOTA instead of Dye.

Scheme 12b. Synthesis of delivery of Imaging Reagents to the Eye for Testing.

Scheme 15. Attachment of targeting unit; also c-RGD. The peptide shown is Seq. I.D. 1.

Scheme 16. c-RGD

Scheme 17. Synthesis of C-RGD

Scheme 23. Attachment of c-RGD

Scheme 24. Combination of dendritic and peptidic scaffold.

Scheme 25. Synthesis of NP-P-MT-dye, ABbD-NP-594-cRGD-MT (12), utilizing thiol-ene chemistry.

Scheme 26. Synthesis of NP-P-MT-dye conjugate, ABtD-NP-594-MT utilizing reductive amination and thiol-ene chemistry.

MULTIFUNCTIONAL DEGRADABLE NANOPARTICLES WITH CONTROL OVER SIZE AND FUNCTIONALITIES

CROSS-REFERENCE TO RELATED APPLICATIONS

This application is a Divisional of U.S. patent application Ser. No. 15/682,278, filed Aug. 21, 2017; which is a Continuation of U.S. patent application Ser. No. 15/049,781, filed Feb. 22, 2016; which is a Continuation of U.S. patent application Ser. No. 13/520,775, filed Jan. 28, 2013; which is a National Phase Application of International Application No. PCT/US2011/020148, filed Jan. 4, 2011; which claims priority to U.S. application Ser. No. 12/651,710, filed Jan. 4, 2010; which is a Continuation-in-Part of International Application No. PCT/US2008/082529 filed Nov. 5, 2008; which claims priority to U.S. Provisional Application No. 61/101,039 filed Sep. 29, 2008, U.S. Provisional Application No. 61/100,752 filed Sep. 28, 2008, U.S. Provisional Application No. 61/038,041 filed Mar. 19, 2008, and 60/985,608, filed Nov. 5, 2007, which applications are hereby incorporated herein by reference in their entireties.

ACKNOWLEDGMENT

This invention was made with government support under a CAREER Award CHE-0645737 awarded by the National Science Foundation. The government has certain rights in the invention.

REFERENCE TO SEQUENCE LISTING

The Sequence Listing submitted Aug. 21, 2019, as a text file named "22000_0193U5_ST25.txt," created on Aug. 19, 2019, and having a size of 1,290 bytes is hereby incorporated by reference pursuant to 37 C.F.R. § 1.52(e)(5).

BACKGROUND

Biodegradable nanoparticles have received increasing attention as versatile drug delivery scaffolds to enhance the efficacy of therapeutics. Effectiveness of delivery, however, can be influenced by the particle size and morphology, as these parameters can greatly affect the biological function and fate of the material. [Zweers, M. L. T.; Grijpma, D. W.; Engbers, G. H. M.; Feijen, J., J. Controlled Release 2003, 87, 252-254.] Narrowly dispersed particles are highly preferred for use in delivery or sensing applications with respect to monitoring and predicting their behavior as their exhibit a more constant response to external stimuli. [Lubetkin, S.; Mulqueen, P.; Paterson, E. Pesti. Sci. 1999, 55, 1123-1125.]

One disadvantage of conventional methods is the irreproducibility in the size and shape of the particles, since these can be profoundly influenced by the stabilizer and the solvent used. [Kumar, M. N. V. R.; Bakowsky, U.; Lehr, C. M., Biomaterials 2004, 25, 1771-1777.] Another major drawback of conventional biodegradable nanoparticles, based on poly(ε-caprolactone) and other aliphatic polyesters, is the lack of pendant functional groups, which can make physiochemical, mechanical, and biological properties difficult to modify. [(a) Riva, R.; Lenoir, S.; Jerome, R.; Lecomte, P. Polymer 2005, 46, 8511-8518. (b) Sasatsu, M.; Onishi, H.; Machida, Y. Inter. J. Pharm. 2006, 317, 167-174.] The availability of functional groups is a desirable means of tailoring the properties of a particle, including hydrophilicity, biodegradation rate, and bioadhesion.

Therefore, there remains a need for methods and compositions that overcome these deficiencies and that effectively provide functionalized, degradable nanoparticles with reproducibility in particle size and shape.

SUMMARY

In accordance with the purpose(s) of the invention, as embodied and broadly described herein, the invention, in one aspect, relates to polymers, crosslinked polymers, functionalized polymers, nanoparticles, and functionalized nanoparticles and methods of making and using same.

Disclosed are methods of administering a pharmaceutical or biologically active agent to a cell comprising contacting the cell with a degradable polyester nanoparticle-agent complex (nanoparticle complex) thereby administering the pharmaceutical or biologically active agent to the cell.

Also disclosed are methods of modulating a receptor on a cell comprising contacting the receptor with a degradable polyester nanoparticle pharmaceutical or biologically active agent complex, wherein one or more pharmaceutical agents is encapsulated by a degradable polyester nanoparticle.

Also disclosed are methods of inhibiting VEGF activity in an eye in a subject comprising administering to the subject a degradable polyester nanoparticle pharmaceutical or biologically active agent complex (nanoparticle complex).

Also disclosed are methods of inhibiting carboninc anhydrase activity in an eye in a subject comprising administering to the subject an effective amount of a degradable polyester nanoparticle pharmaceutical or biologically active agent complex (nanoparticle complex).

Also disclosed are methods of treating a ophthalmic disorder comprising administering to a subject an effective amount of a degradable polyester nanoparticle pharmaceutical or biologically active agent complex (nanoparticle complex).

Also disclosed are crosslinked degradable nanoparticlea having a polyester backbone and one or more crosslinks having a structure selected from:

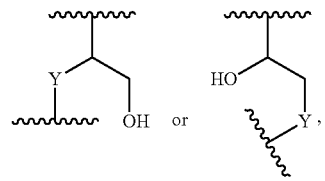

wherein Y is O, S, or N—R, wherein R is C1-C4 alkyl;

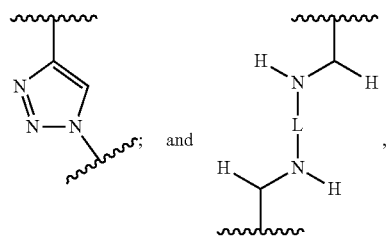

wherein L is a divalent alkyl chain or alkyloxyalkyl chain.

Also disclosed are compositions comprising a degradable polyester nanoparticle and, encapsulated therein, a biologically active agent, a pharmaceutically active agent, or an imaging agent.

Also disclosed are kits comprising a first degradable polyester nanoparticle and a first biologically active agent, first pharmaceutically active agent, or first imaging agent encapsulated within the first nanoparticle, and one or more of: a second biologically active agent, second pharmaceutically active agent, or second imaging agent encapsulated within the first nanoparticle, wherein the first biologically active agent, first pharmaceutically active agent, or first imaging agent is different from the second biologically active agent, second pharmaceutically active agent, or second imaging agent; or a second degradable polyester nanoparticle and a second biologically active agent, second pharmaceutically active agent, or second imaging agent encapsulated within the second nanoparticle, wherein the first biologically active agent, first pharmaceutically active agent, or first imaging agent is different from the second biologically active agent, second pharmaceutically active agent, or second imaging agent; a pharmaceutically acceptable carrier; or instructions for treating a disorder known to be treatable by the first biologically active agent or first pharmaceutically active agent.

Also disclosed are the products of the disclosed methods.

Also disclosed are methods of intracellular delivery comprising administering an effective amount of a disclosed nanoparticle to a subject.

Also disclosed are methods for the manufacture of a medicament for delivery of a biologically active agent, a pharmaceutically active agent, and/or an imaging moiety comprising combining at least one disclosed polymer or at least one disclosed nanoparticle with a pharmaceutically acceptable carrier.

Also disclosed are uses of a disclosed polymer or a disclosed nanoparticle to deliver a biologically active agent, a pharmaceutically active agent, and/or an imaging moiety.

Also disclosed are pharmaceutical compositions comprising a therapeutically effective amount of one or more disclosed polymer and/or one or more disclosed nanoparticle and a pharmaceutically acceptable carrier for administration in a subject, for example, a mammal.

Also disclosed are pharmaceutical compositions for diagnosing, treating, and/or preventing ophthalmic disorders, the compositions comprising a therapeutically effective amount of one or more disclosed polymer and/or one or more disclosed nanoparticle and a pharmaceutically acceptable carrier for administration in a subject, for example, a mammal. In one aspect, the compositions can be administered transcorneally.

Also disclosed are microparticles, and/or larger networks, for use as materials for tissue engineering and biogels in biomedical devices.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

FIG. 55A is a schematic representation of a 50 nm degradable nanoparticle (nanosponge), 7% cross-linking density, loaded with 1.3% travatan, 0.38 mg/mL. FIG. 55B is a schematic representation of a 400 nm degradable nanoparticle (nanosponge), 14% cross-linking density, loaded with 22.4% bimatoprost, 3.58 mg/mL. FIG. 55C is a schematic representation of a 700 nm degradable nanoparticle (nanosponge), 14% cross-linking density, loaded with 29.35% bimatoprost, 4.7 mg/mL. In a separate example, a more crystalline 700 nm degradable nanoparticle (nanosponge), 14% cross-linking density, was loaded with a 25.41% bimatoprost, 4.07 mg/mL.

Figure 1:
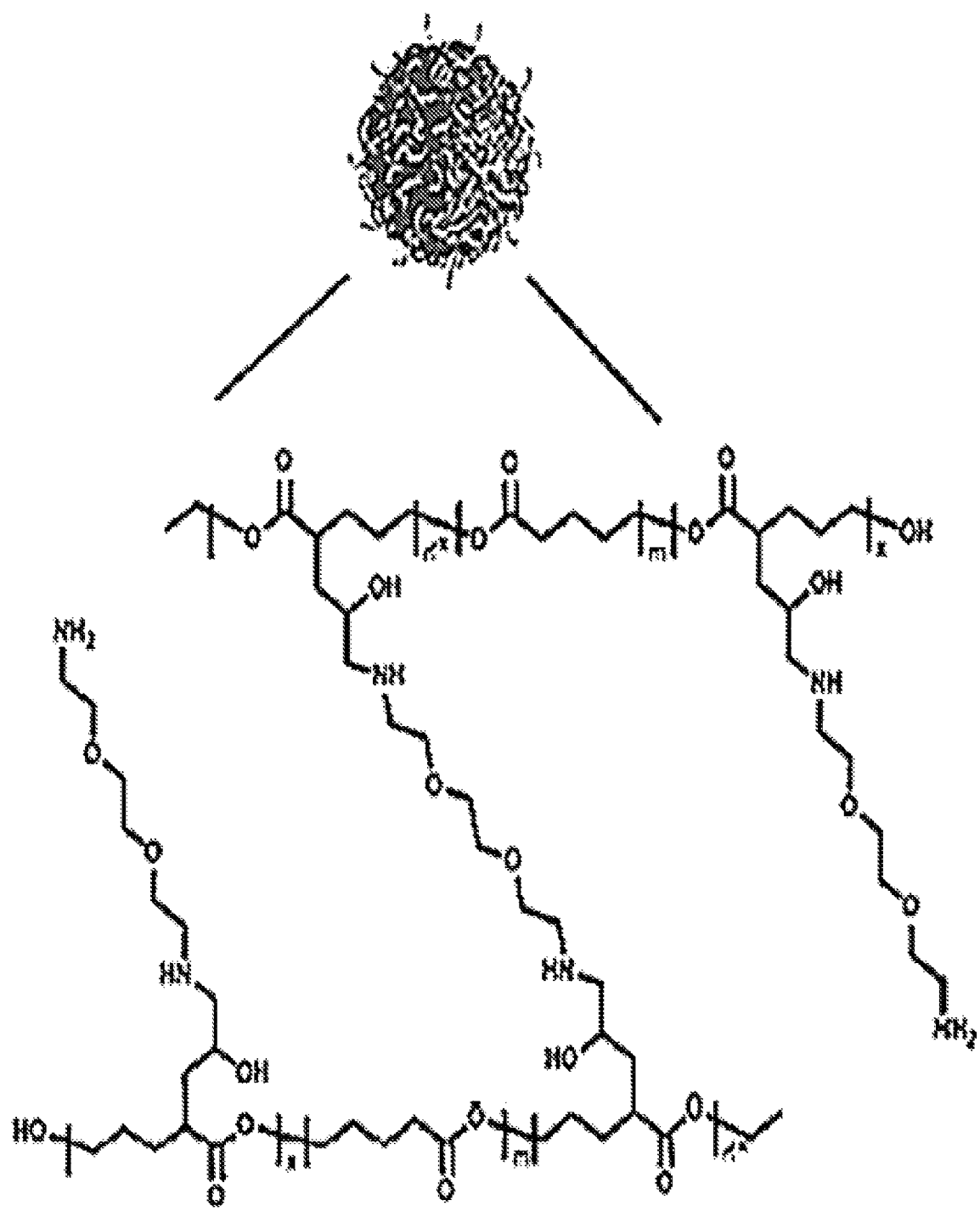
FIG. 1 shows hydrolytic biodegradation studies of (▲) 725.1±94.3 nm poly(vl-evl) nanoparticles to (♦) 30.71±2.21 nm AB nanoparticles. All particles are non-emulsified.
Figure 1:
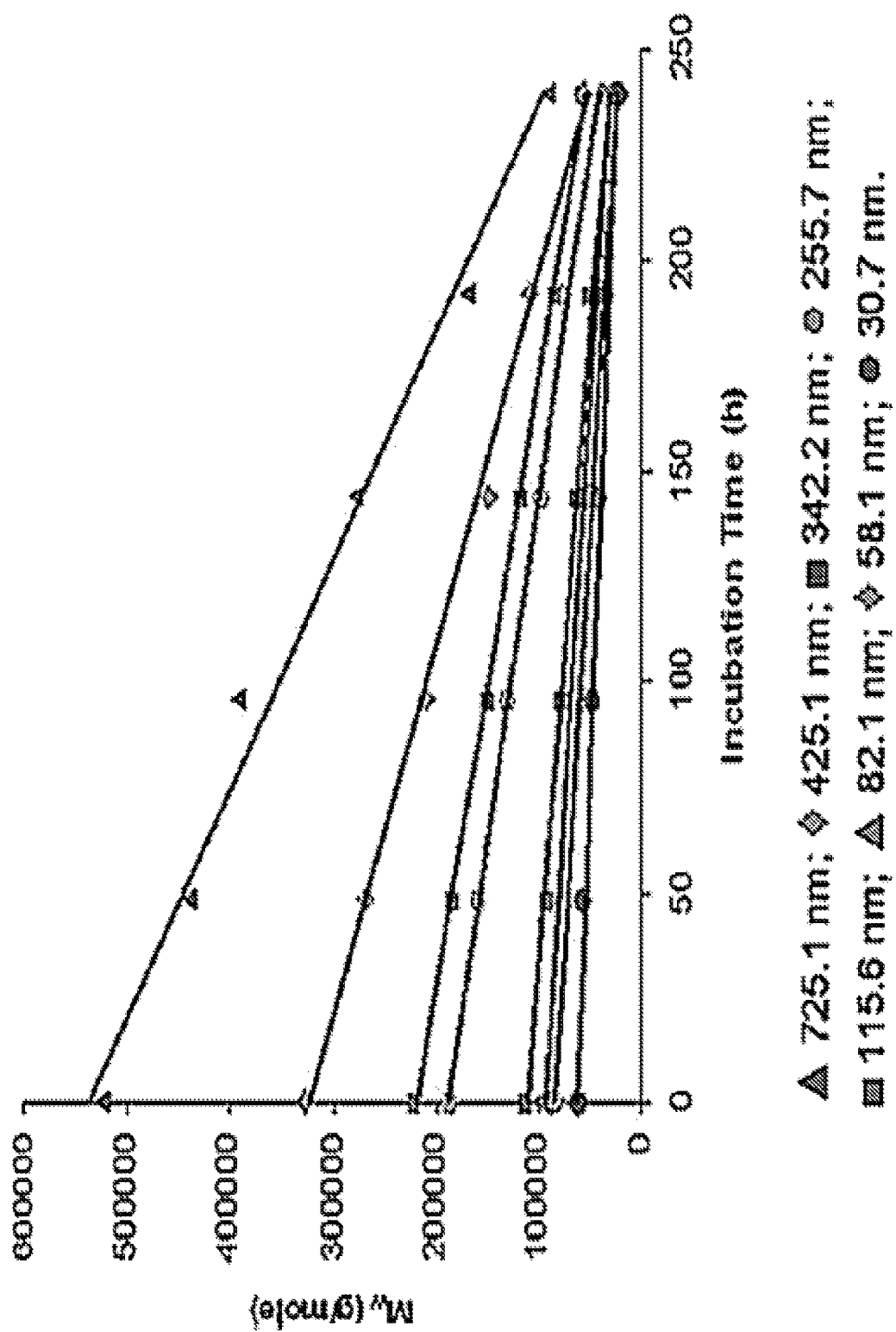

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with an ocular disorder" means having been subjected to a physical examination by a person of skill, for example, a physician, and found to have a disorder of the eye or eyes prior to treatment. As a further example, "diagnosed with glaucoma" means having been subjected to a physical examination by a person of skill, for example, a physician, and found to have glaucoma (e.g., "open angle" or "closed angle") prior to treatment.

As used herein, the phrase "identified to be in need of treatment for a disorder," or the like, refers to selection of a subject based upon need for treatment of the disorder. For example, a subject can be identified as having a need for treatment of a disorder (e.g., an occular disorder, glaucoma, "open angle" glaucoma, or "closed angle" glaucoma) based upon an earlier diagnosis by a person of skill and thereafter subjected to treatment for the disorder. As a further example, a subject can be identified as having a need for treatment of a disorder after administration by recognition of the subject's response to the treatment (i.e., alleviation of symptoms or prevention of disorder). It is contemplated that the identification can, in one aspect, be performed by a person different from the person making the diagnosis. It is also contemplated, in a further aspect, that the administration can be performed by one who subsequently performed the administration.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration (such as, for example, eye drops, creams, salves, and irrigation), intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition. It is further contemplated that administration methods include parenteral methods such as intravitreal, subcutaneous, intradermal, intravenous, epicutaneous, intraocular, conjunctival, subconjunctival, intracorneal, retrobulbar, and intramuscular injections.

As used herein, the term "subject" refers to a target of administration. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As used herein, the terms "effective amount" and "amount effective" refer to an amount that is sufficient to achieve a desired result or to have an effect on undesired symptoms, but is generally insufficient to cause adverse side affects. The specific effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In a further aspect, a preparation can be administered in a "diagnostically effective amount"; that is, an amount effective for diagnosis of a disease or condition. In a further aspect, a preparation can be administered in a "therapeutically effective amount"; that is, an amount effective for treatment of a disease or condition. In a further aspect, a preparation can be administered in a "prophylactically effective amount"; that is, an amount effective for prevention of a disease or condition.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "biologically active agent" or "bioactive agent" means an agent that is capable of providing a local or systemic biological, physiological, or therapeutic effect in the biological system to which it is applied. For example, the bioactive agent can act to control infection or inflammation, enhance cell growth and tissue regeneration, control tumor growth, act as an analgesic, promote anti-cell attachment, and enhance bone growth, among other functions. Other suitable bioactive agents can include antiviral agents, vaccines, hormones, antibodies (including active antibody fragments sFv, Fv, and Fab fragments), aptamers, peptide mimetics, functional nucleic acids, therapeutic proteins, peptides, or nucleic acids. Other bioactive agents include prodrugs, which are agents that are not biologically active when administered but, upon administration to a subject are converted to bioactive agents through metabolism or some other mechanism. Additionally, any of the compositions of the invention can contain combinations of two or more bioactive agents. It is understood that a biologically active agent can be used in connection with administration to various subjects, for example, to humans (i.e., medical administration) or to animals (i.e., veterinary administration).

As used herein, the term "pharmaceutically active agent" includes a "drug" or a "vaccine" and means a molecule, group of molecules, complex or substance administered to an organism for diagnostic, therapeutic, preventative medical, or veterinary purposes. This term include externally and internally administered topical, localized and systemic human and animal pharmaceuticals, treatments, remedies, nutraceuticals, cosmeceuticals, biologicals, devices, diagnostics and contraceptives, including preparations useful in clinical and veterinary screening, prevention, prophylaxis, healing, wellness, detection, imaging, diagnosis, therapy, surgery, monitoring, cosmetics, prosthetics, forensics and the like. This term may also be used in reference to agriceutical, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a bioactive effect, for example deoxyribonucleic acid (DNA) or ribonucleic acid (RNA). Pharmaceutically active agents include the herein disclosed categories and specific examples. It is not intended that the category be limited by the specific examples. Those of ordinary skill in the art will recognize also numerous other compounds that fall within the categories and that are useful according to the invention. Examples include a radiosensitizer, the combination of a radiosensitizer and a chemotherapeutic, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-I-antagonist, carbonic anhydrase inhibitors, prostaglandin analogs, a combination of an alpha agonist and a beta blocker, a combination of a carbonic anhydrase inhibitor and a beta blocker, an anticholinergic/antispasmodic agent, a vasopressin analogue, an antiarrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifungal agent, or a vaccine. In a further aspect, the pharmaceutically active agent can be coumarin, albumin, bromolidine, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritis antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetominophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, timol hemihydrate, levobunolol hydrochloride, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists (i.e., alpha adrenergic receptor agonist) such as clonidine, brimonidine tartrate, and apraclonidine hyrochloride; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; prostaglandin analogs such as latanoprost, travoprost, and bimatoprost; cholinergics (i.e., acetylcholine receptor agonists) such as pilocarpine hydrochloride and carbachol; glutamate receptor agonists such as the N-methyl D-aspartate receptor agonist memantine; anti-Vascular endothelial growth factor (VEGF) aptamers such as pegaptanib; anti-VEGF antibodies (including but not limited to anti-VEGF-A antibodies) such as ranibizumab and becacizumab; carbonic anhydrase inhibitors such as methazolamide, brinzolamide, dorzolamide hydrochloride, and acetazolamide; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and disopyramide phosphate; antiparkinsonian agents, such as dopamine, L-Dopa/Carbidopa, selegiline, dihydroergocryptine, pergolide, lisuride, apomorphine, and bromocryptine; antiangina agents and antihypertensive agents such as isosorbide mononitrate, isosorbide dinitrate, propranolol, atenolol and verapamil: anticoagulant and antiplatelet agents such as coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hdyrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides. It is understood that a pharmaceutically active agent can be used in connection with administration to various subjects, for example, to humans (i.e., medical administration) or to animals (i.e., veterinary administration).

As used herein, the term "ophthalmic disorders" and/or "ophthalmic conditions" refers to ophthalmic diseases, conditions, and/or disorders including, without limitation, those associated with the anterior chamber of the eye (i.e., hyphema, synechia); the choroid (i.e., choroidal detachment, choroidal melanoma, multifocal choroidopathy syndromes); the conjunctiva (i.e., conjunctivitis, cicatricial pemphigoid, filtering Bleb complications, conjunctival melanoma, Pharyngoconjunctival Fever, pterygium, conjunctival squamous cell carcinoma); connective tissue disorders (i.e., ankylosing spondylitis, pseudoxanthoma elasticum, corneal abrasion or edema, limbal dermoid, crystalline dystrophy keratits, keratoconjunctivitis, keratoconus, keratopathy (including but not limited to Thygeson's superficial punctuate keratopathy), megalocomea, corneal ulcer); dermatologic disorders (i.e., ecrodermatitis enteropathica, atopic dermatitis, ocular rosacea, psoriasis, Stevens-Johnson syndrome); endocrine disorders (i.e., pituitary apoplexy); extraocular disorders (i.e., Abducens Nerve Palsy, Brown syndrome, Duane syndrome, esotropia, exotropia, oculomotor nerve palsy); genetic disorders (i.e., albinism, Down syndrome, Peters Anomaly); the globe (i.e., anophthalmos, endophthalmitis); hematologic and cardiovascular disorders (i.e., Giant Cell Arteritis, hypertension, leukemias, Ocular Ischemic syndrome, sickle cell disease); infectious diseases (i.e., actinomycosis, botulism, HIV, diphtheria, *Escherichia coli*, Tuberculosis, ocular manifestations of syphilis); intraocular pressure (i.e., glaucoma, ocular hypotony, Posner-Schlossman syndrome), the iris and ciliary body (i.e., aniridia, iris prolaps, juvenile xanthogranuloma, ciliary body melanoma, iris melanoma, uveitis); the lacrimal system (i.e., alacrima, Dry Eye syndrome, lacrimal gland tumors); the lens (i.e., cataract, ectopia lentis, intraocular lens decentration or dislocation); the lid (i.e., blepharitis, dermatochalasis, distichiasis, ectropion, eyelid coloboma, Floppy Eye syndrome, trichiasis, xanthelasma); metabolic disorders (i.e., gout, hyperlipoproteinemia, Oculocerebrorenal syndrome); neurologic disorders (i.e., Bell Palsy, diplopia, multiple sclerosis); general ophthalmologic (i.e., red eye, cataracts, macular degeneration, red eye, macular degeneration); the optic nerve (i.e., miningioma, optic neuritis, optic neuropathy, papilledema); the orbit (i.e., orbital cellulits, orbital dermoid, orbital tumors); phakomatoses (i.e., ataxia-telangiectasia, neurofibromatosis-1); presbyopia; the pupil (i.e., anisocoria, Homer syndrome); refractive disorders (i.e., astigmatism, hyperopia, myopia); the retina (i.e., Coats disease, Eales disease, macular edema, retinitis, retinopathy); and the sclera (i.e., episcleritis, scleritis).

As used herein, the terms "imaging moiety" and "imaging agent" refer to any chemical groups or substance useful for imaging applications, as known to those of skill in the art. Examples of imaging agents include radioconjugate, cytotoxin, cytokine, Gadolinium-DTPA or a quantum dot, iron oxide, manganese oxide, and fluorescent agents such as Alexa Fluor dyes and Neuro DiO. In one aspect, an imaging agent can be provided in nanoparticular form or in microparticular form. In a further aspect, an imaging agent comprises Gadolinium-DTPA and iron oxide nanoparticles (magnetite), as specific MRI contrast agents. In a yet further aspect, an imaging agent comprises at least one near infrared dye, for example near infrared dyes based on a porphyrin and/or a phthalocyanine. See Ghoroghchian et al., Near-infrared-emissive polymersomes: Self-assembled soft matter for in vivo optical imaging, *PNAS*, 2005, vol. 102, no. 8, 2922-2927.

As used herein, the term "polymer" refers to a relatively high molecular weight organic compound, natural or synthetic, whose structure can be represented by a repeated small unit, the monomer (e.g., polyethylene, rubber, cellulose). Synthetic polymers are typically formed by addition or condensation polymerization of monomers.

As used herein, the term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers.

As used herein, the term "oligomer" refers to a relatively low molecular weight polymer in which the number of repeating units is between two and ten, for example, from two to eight, from two to six, or form two to four. In one aspect, a collection of oligomers can have an average number of repeating units of from about two to about ten, for example, from about two to about eight, from about two to about six, or form about two to about four.

As used herein, the term "reactive residue" refers to a moiety (e.g., a monomer residue) capable of undergoing chemical reaction at a reaction temperature and/or in response to a stimulus to form a reactive intermediate. In one aspect, a reactive residue is a moiety capable undergoing an intramolecular cross-linking reaction to provide intramolecular chain collapse.

As used herein, the term "polymerizable group" refers to a group (i.e., a chemical functionality) capable of undergoing a polymerization reaction at a polymerization temperature and/or in response to a polymerization initiator to form a polymer or an oligomer. In one aspect, the polymerization reaction is a radical polymerization (e.g., a vinyl polymerization). It is understood that catalysts can be employed in connection with the polymerization reaction. It is contemplated that, in various aspects, polymerizable groups can be used in step-growth or chain growth reactions. Exemplary polymerizable groups include residues of vinyl, styryl, acryloyl, methacryloyl, aryl, and heteroaryl compounds.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dode cyl, tetradecyl, hexadecyl, eicosyl, tetracosyl, and the like. The alkyl group can also be substituted or unsubstituted. The alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "carboxylic acid" as used herein is represented by the formula —C(O)OH.

The term "ester" as used herein is represented by the formula —OC(O)$A^1$ or —C(O)O$A^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula -$(A^1O(O)C$-$A^2$-$C(O)O)_a$— or -$(A^1O(O)C$-$A^2$-$OC(O))_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula $-(A^1O-A^2O)_a-$, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula $A^1C(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by the formula —SH.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

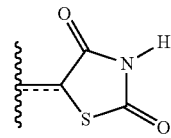

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Dendrimeric Compounds

Dendrimers can be ideal building blocks for biomedical applications, because of their precise architecture, high loading capacity, tunable solubility, immunogenicity, and bioconjugation capability. [Gillies, E. R.; Fréchet, J. M. J. Drug Discov. Today 2005, 10, 35.; Lee, C. C.; MacKay, J. A.; Fréchet, J. M. J.; Szoka, F. C. Nat. Biotechnol. 2005, 23, 1517.] The combination of the unique properties of dendrimers with membrane-permeable guanidino groups can lead to a more efficient-synthesis of membrane-permeable carrier molecules possessing high efficiency, for example, for bulk production.

The compounds of the invention are desirably based upon a compact, high branching multiplicity dendrimer, for example, the classic Newkome-type dendrimer. [Newkome, G. R.; Behera. R. K.; Moorefield, C. N.; Baker, G. R. J. Org. Chem. 1991, 56, 7162.] Newkome type dendrimers are typically 1→3 C-branched polyamide macromolecules, built from "Behera's Amine" monomer or its derivatives, and can be attached to a variety of starting cores, surfaces, and polymers.

It is also understood that the compounds of the invention can be tailored to enhance accumulation in specific sublocations of cells, such as the nucleus, the cytosol, or the mitochondria. Tailoring can be the selection of chemical moieties or groups having an affinity for a targeted subcellular region of a cell, for example an organelle, and the functionalization of the compounds with the selected chemical moieties or groups. Such tailoring of the compound structure can be accomplished using organic synthetic methodology know to those of skill in the art.

In one aspect, the invention relates to compounds comprising the structure:

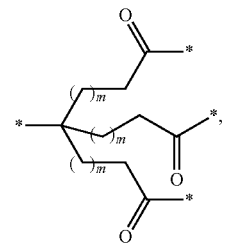

and at least one guanidinium residue, wherein m is zero or a positive integer. In certain aspects, m can be 0, 1, 2, 3, 4, 5, or 6 and each residue can be substituted or unsubstituted. In a further aspect, m is 1.

In one aspect, the invention relates to compounds comprising the structure:

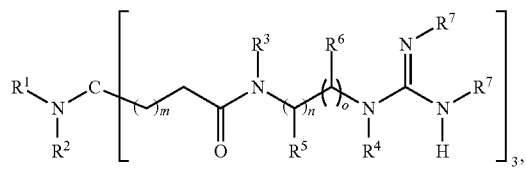

wherein n and o are, independently, zero or a positive integer; wherein $R^1$ and $R^2$ are, independently, hydrogen, oxygen, alkyl, acyl, thioacyl, or carbonyl; wherein $R^3$ is hydrogen, alkyloxycarbonyl, or alkyl; $R^4$ is hydrogen, or alkyloxycarbonyl; wherein $R^5$ and $R^6$ are, independently, hydrogen, or alkyl; and wherein $R^7$ is hydrogen or alkyloxycarbonyl.

In a further aspect, the compounds can comprise the structure:

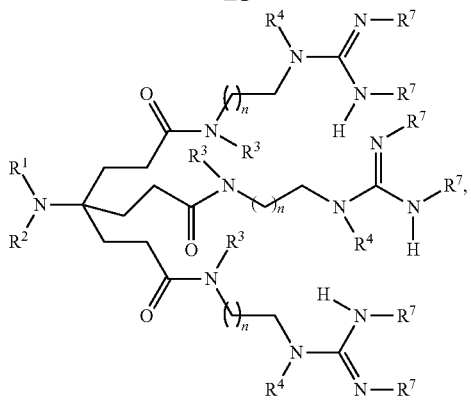

wherein n is an integer from 1 to 9; wherein $R^1$ and $R^2$ are, independently, hydrogen, oxygen, nitrogen, alkyl, acyl, thioacyl, carbonyl, or amine; wherein $R^3$ is hydrogen or alkyl; and wherein $R^4$ is hydrogen, or alkyloxycarbonyl, alkyl, or acyl. In certain aspects, n can be 0, 1, 2, 3, 4, 5, 6, 7, 8, or 9. In a further aspect, n is 1 or 5. In a further aspect, $R^4$ can be hydrogen or alkyloxycarbonyl. In a further aspect, $R^7$ is Boc, for example, t-Boc.

In one aspect, the compound comprises the structure:

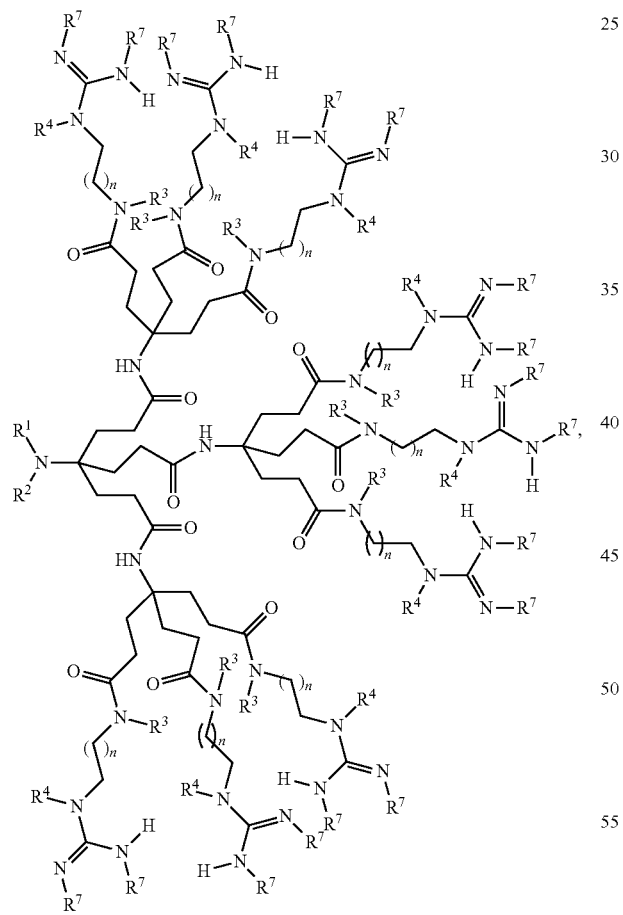

wherein n is an integer from 1 to 9; wherein $R^1$ and $R^2$ are, independently, hydrogen, amino, hydroxyl, alkyl, alkoxyl, acyl, carbonyl, or thioacyl; wherein $R^3$ is hydrogen or alkyl; and wherein $R^4$ is hydrogen, or alkyloxycarbonyl.

C. Methods of Making Dendrimeric Compounds

The disclosed methods typically employ a divergent method to prepare a G-1 dendrimer scaffold with nine end functionalities. Although the Newkome type dendrimer is well known, one of the drawbacks for a broader application of conventional methods is the elaborate synthesis of the monomer. In contrast, the "Behera's amine" gives the most compact, low molecular weight polyamide dendrimer possible; achieving the necessary nine end functionalities in just one generation of dendritic growth. As set forth below and in the Experimental section, following synthesis of the monomer through improved hydrogenation and work-up procedures, the G-1 dendritic nona-acid scaffold can be prepared in high yields (see FIGS. 6A and 6B).

Figure 20:
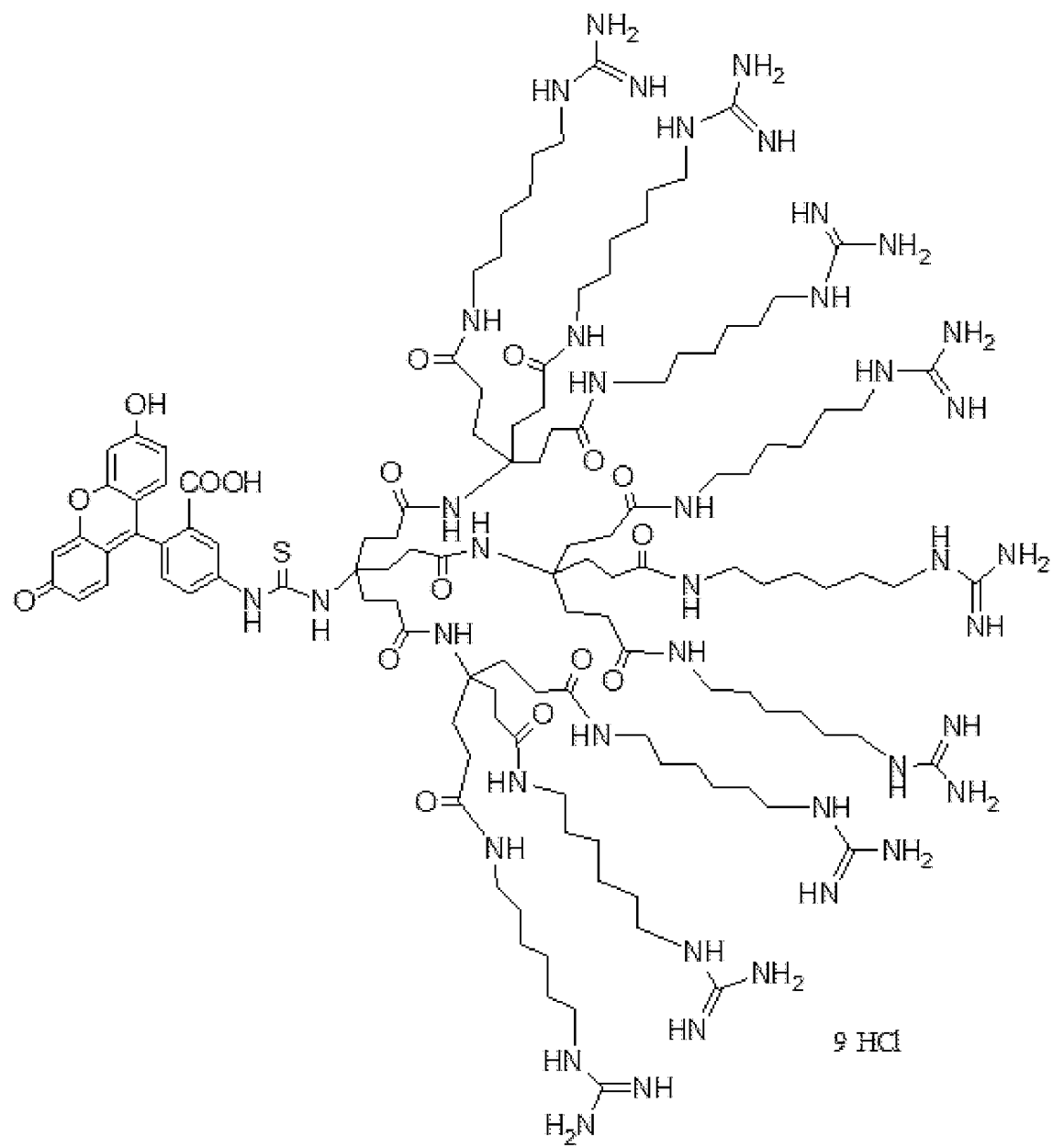
FIG. 20 shows a schematic representation of the structures for FD-1 and FD-2.

In order to introduce the guanidinium groups to the dendrimer exterior as shown in FIG. 20, the nine carboxylic acid groups were first converted into nine protected amine groups, by reaction with, for example, N-Boc ethylendiamine and N-Boc-1,6-diaminehexane through amide coupling reactions. After removal of the protecting groups, the nine free amines can be reacted with a guandinylating reagent [Feichtinger, K.; Sings, H. L.; Baker, T. J.; Matthews, K.; Goodman, M. J. Org. Chem. 1998, 63, 8432.] to give a guanidinylated dendritic scaffold in high yield.

For uptake evaluation and imaging function, a fluorophore can be conjugated to the focal point of the molecular transporter. The attachment of a fluorescein isothiocyanate (FITC) moiety to the guanidinylated scaffold can be achieved with a reduction of the nitro group at the focal point to an amino group via hydrogenation at room temperature in quantitative yields, followed by direct reaction with FITC to form the Boc-protected FITC-labeled guanidino-dendrimer. After deprotection of the Boc-protected guanidine groups, FITC-labeled dendritic molecules can be obtained and further purified by dialysis or HPLC.

In one aspect, the invention relates to methods of preparing compounds having the structure:

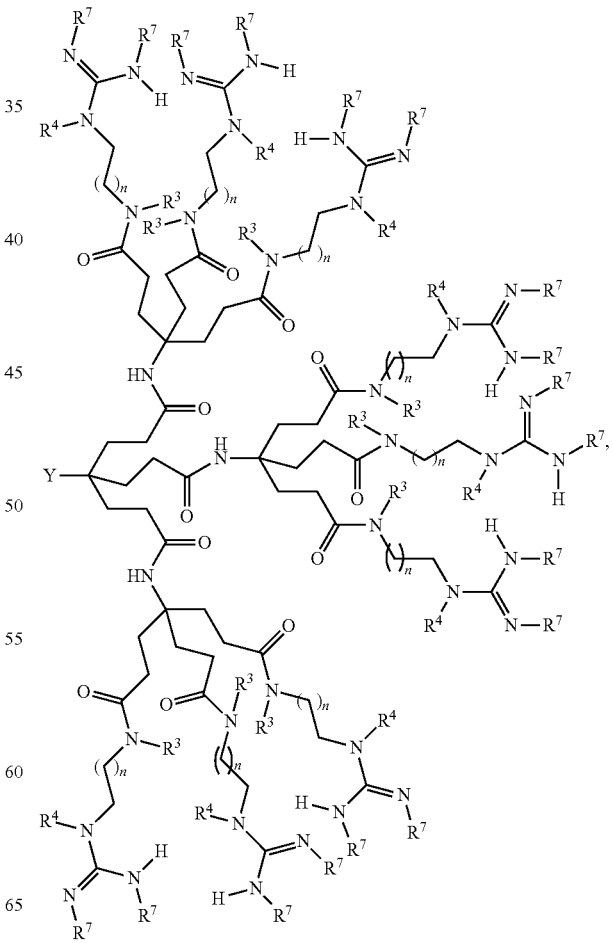

wherein n is an integer from 1 to 9, wherein $R^3$ is hydrogen or alkyl, wherein $R^4$ and $R^7$ are, independently, hydrogen, alkyloxycarbonyl, alkyl, or acyl; wherein $R^7$ is hydrogen, alkyl, or acyl; wherein Y comprises a nitro group, an amine group, an amide group, azide group, or an alkyloxycarbonyl protected amine group or a derivative thereof, the method comprising the steps of providing a first compound comprising the structure:

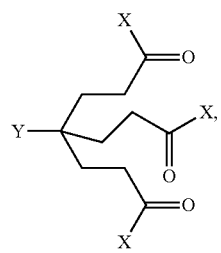

wherein X comprises OH, halogen, or OC(O)-alkyl; coupling the first compound with at least about three molar equivalents of a second compound comprising the structure:

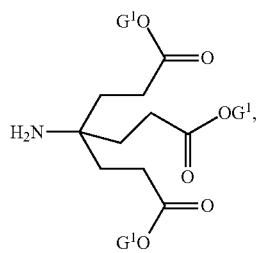

wherein $G^1$ is an ester-protecting group; removing the ester-protecting group; reacting the product of step (c) with at least about three molar equivalents of a third compound comprising the structure:

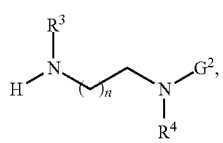

wherein $G^2$ is an amine-protecting group; removing the amine-protecting group; and functionalizing the product of step (e) with at least three molar equivalents of a guanidine-providing agent.

In a further aspect, the guanidine-providing agent comprises at least one of N,N'-diBoc-N''-triflylguanidine, N,N'-diCbz-N''-triflylguanidine, N,N'-dialloc-N''-triflylguanidine, N,N'-ditroc-N''-triflylguanidine, 1,3-diboc-2-(2-hydroxyethyl)guanidine, N,N'-diBoc-1H-pyrazole-1-carboxamidine, N,N'-diCbz-1H-pyrazole-1-carboxamidine, 1H-pyrazole-1-carboxamidine hydrochloride, 1,3-diboc-2-(2-hydroxyethyl)guanidine, 2-(2-aminoethyl)-1,3-diboc-guandine, or 1,3-diboc-2-(carboxymethyl)guanidine In a further aspect, the method further comprises the step of transforming Y into an amine to provide a compound comprising the structure:

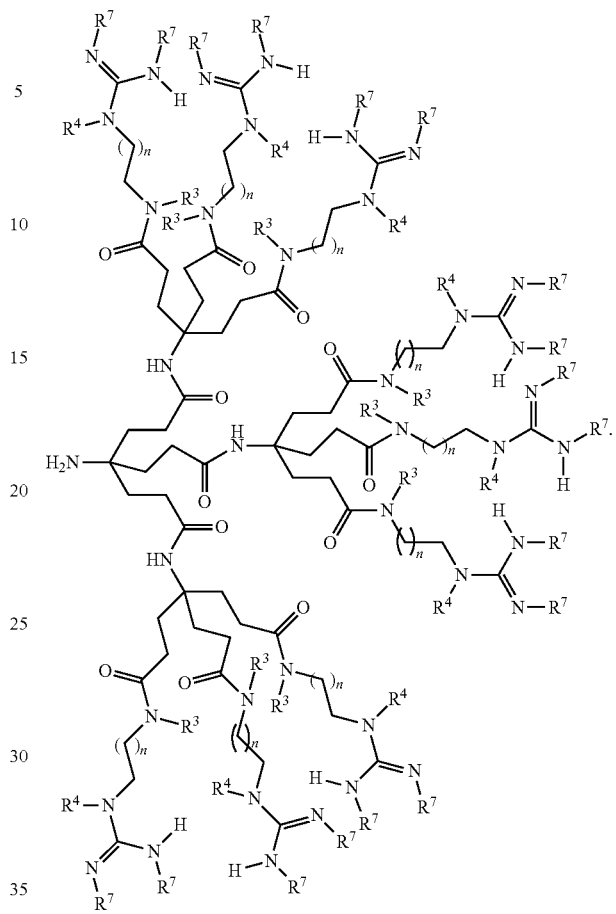

In a further aspect, the method further comprises the step of removing $R^7$. The removing step can be, for example, treatment with one or more reagents known to those of skill in the art for removing protecting groups.

In one aspect, the providing step comprises synthesis of the starting materials. Each starting material can be obtained commercially and/or prepared by those of skill in the art from commercially available compounds. For example, the nitroester shown below can be prepared using methodology from Newkone, G. R.; Behera, R. K.; Moorefield, C. N.; Baker, G. R.; *J. Org. Chem.* 1991, 56, 7162:

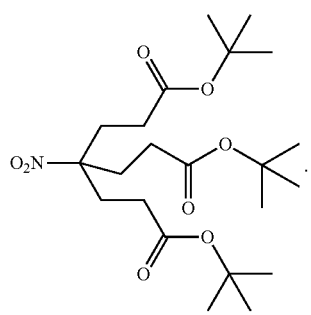 [SMILES: CC(C)(C)OC(=O)CCC(CCC(=O)OC(C)(C)C)(CCC(=O)OC(C)(C)C)[N+](=O)[O-]]

In a further aspect, the ester-protecting group comprises methyl, ethyl, or t-butyl.

In a further aspect, the amine-protecting group comprises a butyloxycarbonyl group, a trifluoroacyl group, a 9-fluorenylmethyloxycarbonyl group, an alloc group, or a carbobenzyloxy group.

In a further aspect, the method further comprises the step of acylating the amine with a compound comprising the structure:

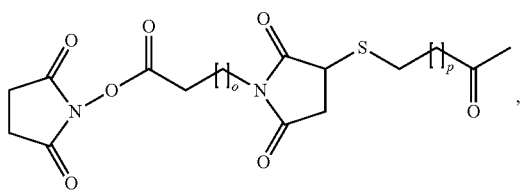

wherein o and p are, independently, zero or a positive integer. In a yet further aspect, the method further comprises the step of reacting the product of the acylating step with a payload compound comprising at least one amine group and at least one of a luminescent group, a biologically active group, or a pharmaceutically active group.

In a further aspect, the method further comprises the step of acylating the amine with a fourth compound comprising the structure:

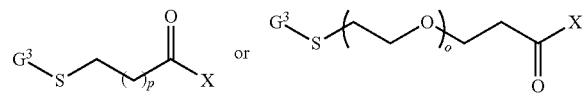

wherein o and p are, independently, zero or a positive integer, and wherein $G^3$ is an thiol-protecting group.

In a further aspect, the thiol protecting group comprises the structure:

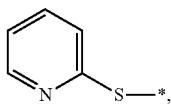

and
wherein the fourth compound comprises the structure:

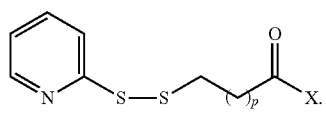

In a further aspect, the thiol-protecting group comprises the structure:

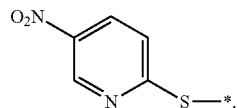

In a further aspect, the method further comprises the step of removing the thiol-protecting group, thereby providing a deprotected thiol. In a yet further aspect, the method further comprises the step of attaching the deprotected thiol to a thiol-functionalized payload. In a still further aspect, the thiol-functionalized payload comprises at least one of a luminescent group, a biologically-active group, or a pharmaceutically-active group.

D. Compositions

In one aspect, the invention relates to compositions comprising one or more compounds of the invention or one or more products of the methods of the invention.

1. Intracellular Delivery Compositions

In one aspect, the invention relates to intracellular delivery compositions comprising the general structure P-L-B-F, wherein P is payload moiety; wherein L is a linking moiety comprising the structure:

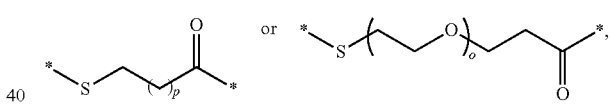

wherein o and p are, independently, zero or a positive integer; wherein B is a branching moiety comprising the structure:

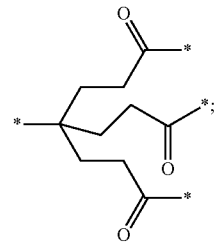

and
wherein F is a functional moiety comprising at least one guanidinium residue. In a further aspect, p is an integer from 0 to 6, for example, 0, 1, 2, 3, 4, 5, or 6. In a further aspect, the composition comprises at least six guanidinium residues, at least seven guanidinium residues, at least eight guanidinium residues, or at least nine guanidinium residues.

In one aspect, L-B-F comprises the structure:
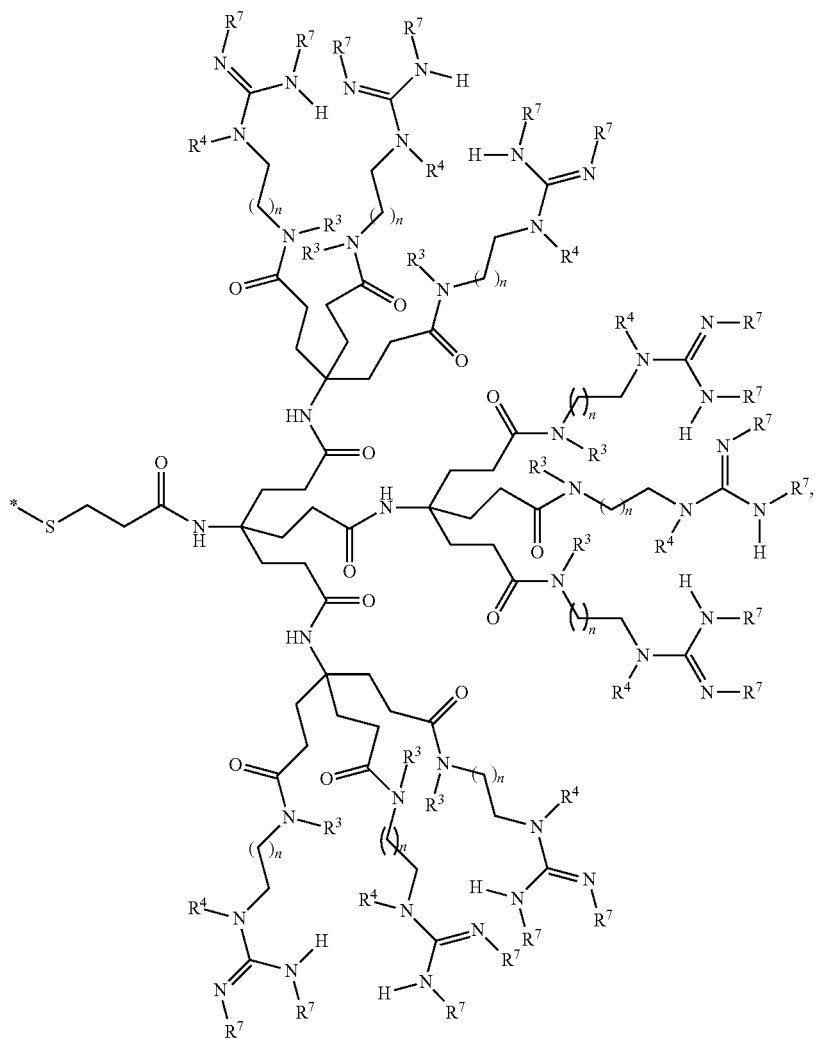
wherein n is an integer from 1 to 9; wherein $R^3$ is hydrogen or alkyl; wherein $R^4$ is hydrogen, alkyl or acyl; and wherein $R^7$ is hydrogen, alkyl or acyl.

In a further aspect, P-L-B-F comprises the structure:

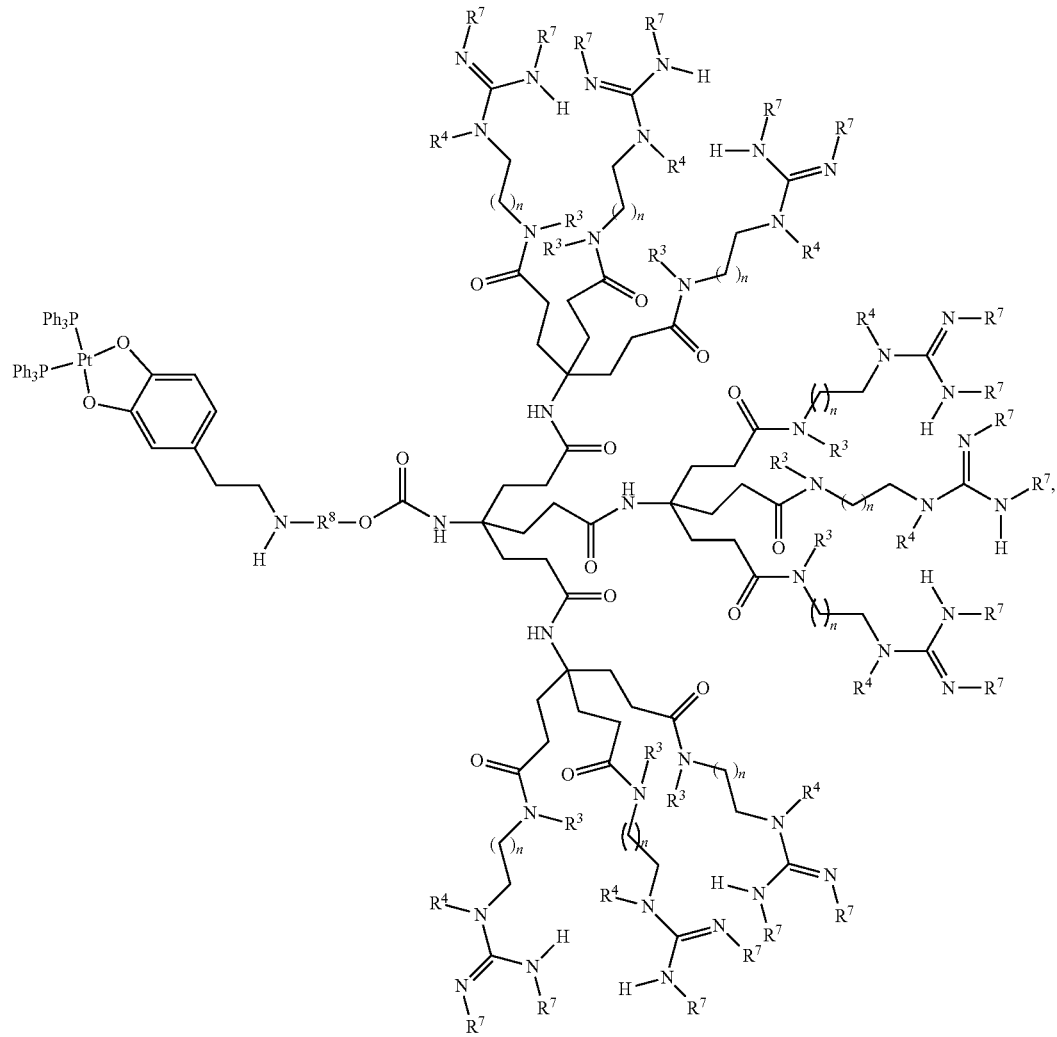

wherein n is an integer from 1 to 9; wherein $R^3$ is hydrogen or alkyl; wherein $R^4$ is hydrogen, alkyl or acyl; wherein $R^7$ is hydrogen, alkyl or acyl; and wherein $R^8$ comprises the structure:

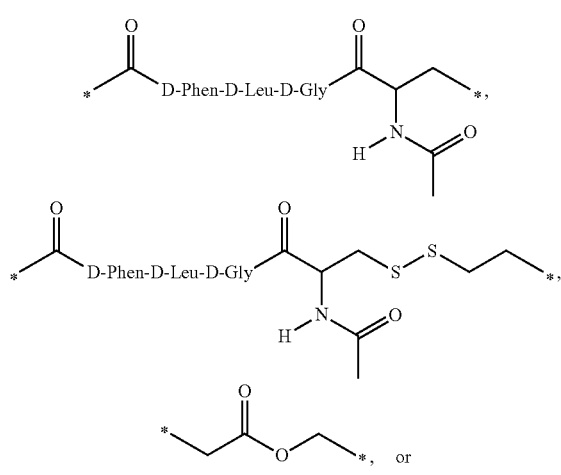

-continued

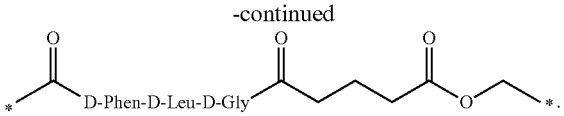

a. Payloads

Typically, the compounds of the invention can be functionalized to carry a payload. In various aspects, a payload compound can be attached or associated with a compound of the invention by covalent bonding, by ionic bonding, by coordination bonding, or by hydrogen bonding. In further aspects, a payload compound can be associated with a compound of the invention by hydrophilic interactions or hydrophobic interactions. In certain aspects, a payload compound is part of a compound of the invention, while in certain further aspects, payload compound is a separate compound from of a compound of the invention.

In one aspect, the payload moiety bears a thiol moiety. In a further aspect, the payload moiety is a luminescent group. For example, the luminescent group can comprise the structure:

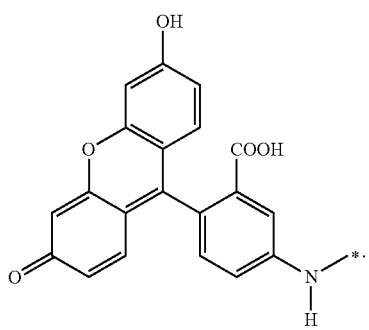 [SMILES: CNc1ccc(-c2c3ccc(=O)cc-3oc3cc(O)ccc23)c(C(=O)O)c1]

In certain aspects, the luminescent group is selected from a dansyl group, a coumarin group, an FITC group, a DOTA group, a catechol group, or a DPTA group. DOTA, catechol, and/or DPTA groups can be used for complexing, for example, lanthanides. Catechol can be used for complexing, for example, quantum dots, lanthanides, metals (such as iron or copper (e.g., radioactive Cu)), ironoxides, metal oxides, and/or platinum (e.g., cis-platinum).

In a further aspect, the payload moiety is a biologically-active group. For example, the biologically-active group can be selected from one or more of an oligonucleotide, a plasmid DNA, a protein, an immunoglobulin, an antisense oligoDNA, a peptide nucleic acid (PNA), or a peptide. For example, in various aspects, the biologically-active group can comprise one or more of β-galactosidase, horseradish peroxidase, RNase, anti-apoptotic proteins Bcl-X(L)/PEA-15, catalase, green fluorescence protein, heat shock protein 70, human glutamate dehydrogenase, ovalbumin, neuroproctectant Bcl-xL, E2 protein, phosphorothioate antisense oligonucleotides, anti-tetanus F(ab')$_2$, G protein, p16$^{INK4a}$, caspase-3, p14$^{INK4a}$, p27$^{kip1}$, Bak BH3 domain peptide, cGPK-Iα inhibitory peptide, IKKβ C-terminal peptide, PKA inhibitory peptide, MEK 1 N-terminal peptide, luciferin, RhoA, APO-BEC-1, Cre recombinase, H-Ras, Filmin-1, p16, HPC-1/syntaxin, Cdk2, E2f-1/p73/p53, influenza virus, antibodies, single chain antibodies, si-RNA, RNA derivatives, peptide 46, peptide 15, peptides that influence the immunoresponse, mitochondrial DNA, bacteria, birdflu virus, and/or bacteria.

In a further aspect, the payload moiety is a pharmaceutically-active group. For example, the pharmaceutically-active group is selected from a small molecular weight drug, a silica nanoparticle, a metal nanoparticle, a protein, a peptide, a linear polymer backbone, a hydrogel, a collapsed nanoparticle, a dendrimers, or a hyperbranched polymeric structure. For example, in various aspects, the pharmaceutically-active group can comprise one or more of superparamagnetic iron oxide particles, doxorubicin, methotrexate, liposome, multiple sclerosis agents, cis-platinum, paclitaxel, hormones, antioxidants, antimicrobials, antibacterial agents, antidepressants, sedatives, antihypertensive drugs, antibodies, a carbohydrate-based drug, cardioprotective εPKC agonist peptide, Fab fragments of the anti-melanoma antibody NRML-05, pan-carcinoma antibody NRLU-10, anti-CEA immunotoxin, liposome drugs, bromonidine, fusogenic, dendritic cell vaccines, VHL tumor suppressor peptide, HER-2, Pro-apoptotic Smac peptide, viralcapsids, and/or bacteria.

Figure 58:
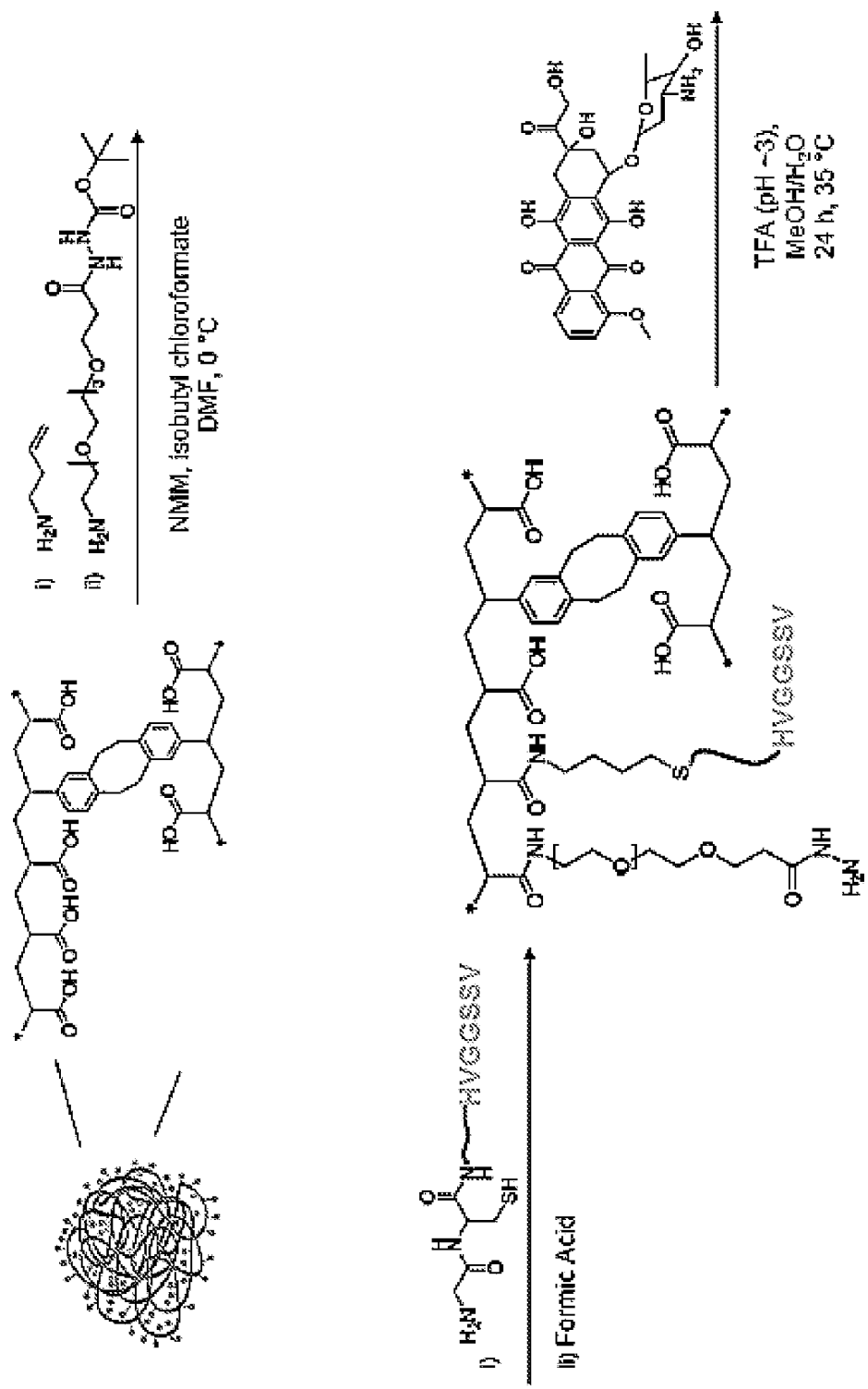
FIG. 58 shows the synthesis of a doxorubicin bioconjugate.

A doxorubicin bioconjujate, for example, can be synthesized as shown in FIG. 58.

In a still further aspect, the payload is an antibody, an intrabody, DNA, RNA, siRNA, among other biologically significant conjugates. For example, an antibody can be attached to the core of a disclosed dendrimer, through disclosed methods. Such compositions can be used to treat viral related disorders, such as, for example, HIV or influenza, among others. A specific example of an antibody suitable for use with the disclosed dendimers is an IgG antibody.

A disclosed dendrimer can also be attached to a protein is associated with a number of disorders, including cancer. For example, a disclosed protein-dendrimer can conjugate can be used to treat a cancer. An example is a p53 (tumor suppressor protein) dendrimer conjugate which can be capable of restoration of a mutant p53 transcriptional activity, to trigger apoptosis and stop tumor progression through the cytoplasm. A further example is a dendrimer-Huntingtin (protein responsible of Huntington's disease) conjugate which can aid in the inhibition of aberrant protein aggregation in a cellular model of Huntington's disease, by targeting huntingtin to the nucleus, through the action of the dendritic molecular transporter.

Further examples of conjugates that can be used in combination with the disclosed dendritic transporters include M and N intrabodies for RSV, RV6-26 Fab Rotavirus, Tat (HIV-1-transcription activator) for the inhibition of viral replication by sequestering Tat in the cytoplasm.

b. Intracellular Delivery

In one aspect, the invention relates to methods of intracellular delivery comprising administering an effective amount of one or more compounds of the invention or one or more compositions of the invention to a subject. In one aspect, The subject is a mammal, for example, a human. In a further aspect, the subject is a cell. The delivery can be, for example, oral, transmucosal, rectal, or subcutaneous administration or, for example, intravenous, intrathecal, intramuscular, intranasal, intraperitonel, or intraocular injection.

2. Pharmaceutical Compositions

A pharmaceutical composition comprising a therapeutically effective amount of one or more compounds of the invention or one or more compositions of the invention and a pharmaceutically acceptable carrier for administration in a mammal, for example, a human. The compositions can be, for example, granules, powders, tablets, or capsules.

a. Dosage

The specific therapeutically effective dose level for any particular patient will depend upon a variety of factors including the compound or composition being administered; the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days.

b. Carriers

A "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents, and dispersing agents. Prevention of the action of microorganisms may be ensured by the inclusion of various antibacterial and antifungal agents such as paraben, chlorobutanol, phenol, sorbic acid, and the like. It can also be desirable to include isotonic agents such as sugars, sodium chloride, and the like. Prolonged absorption of the injectable pharmaceutical form may be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations may be sterilized, for example, by filtration through a bacterial-retaining filter or by incorporating sterilizing agents in the form of sterile solid compositions which can be dissolved or dispersed in sterile water or other sterile injectable media just prior to use.

Suitable inert carriers can include sugars such as lactose. Desirably, at least 95% by weight of the particles of the active ingredient have an effective particle size in the range of 0.01 to 10 micrometers.

E. Synthesis and Characterization of "Bow-Tie" Dendritic Molecular Transporters by Orthogonal and Click Approach Disclosed is the synthesis and characterization of "Bow-Tie" dendritic architectures with orthogonally reactive groups, defined composition and functionality, which can be used as multi-drug carries for specific intracellular delivery. Huisgen cycloadditions or so called "click" reactions have been shown to be extremely versatile tools for advanced macromolecular design. However, little attempt has been made to utilize this approach to prepare multifunctional dendritic structures. In the disclosed approach, two orthogonal protected dendritic structures are combined by utilizing the "click" reaction. This strategy allows the controlled deprotection of the trifluoro protecting group to selectively attach the dithiopyridylpropionic acid the periphery of the macromolecule. In a further step, the BOC groups of the second dendritic scaffolds are deprotected to be guanydilated to the ethyl- or hexyl linker of the system. The bow-tie structure is the first of its kind that consists of a molecular transporter part and drug delivery entity on the other. The chemistry applied for the construction is high-yielding and, thus, gives the bow-tie delivery structure in the most straightforward approach. In this fashion, nine drug molecules, for example peptides, genes and oligonucleotides can be transported across cellular membranes.

Synthetic Pathway of Acid-Labile Azide-Linker-Dendron:

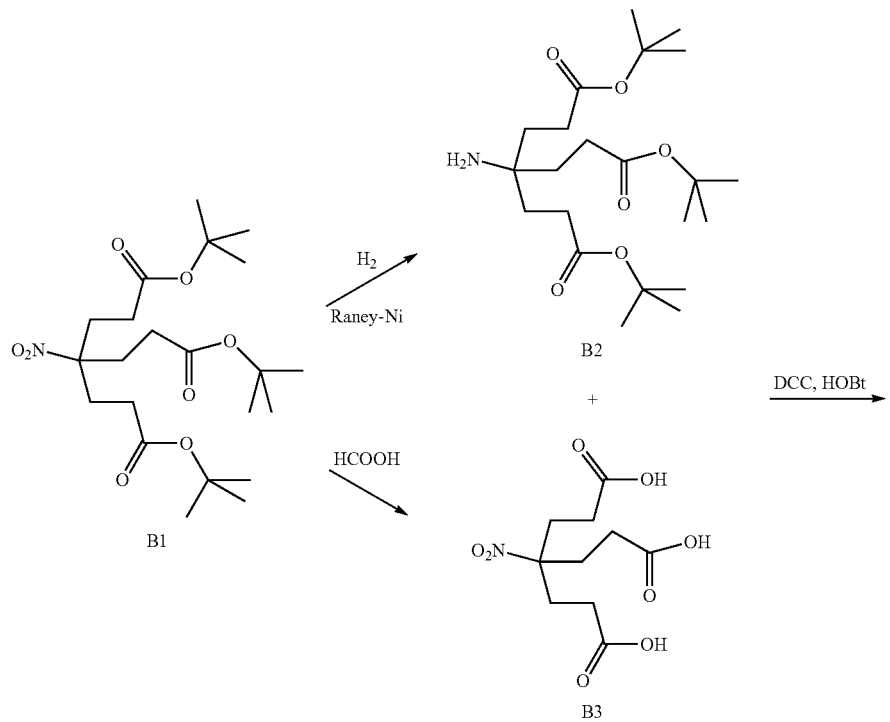

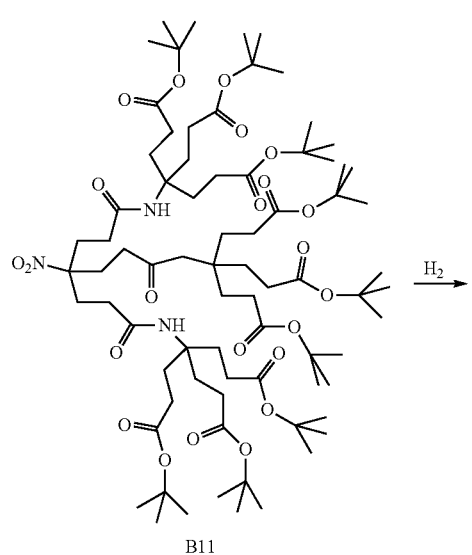
B11
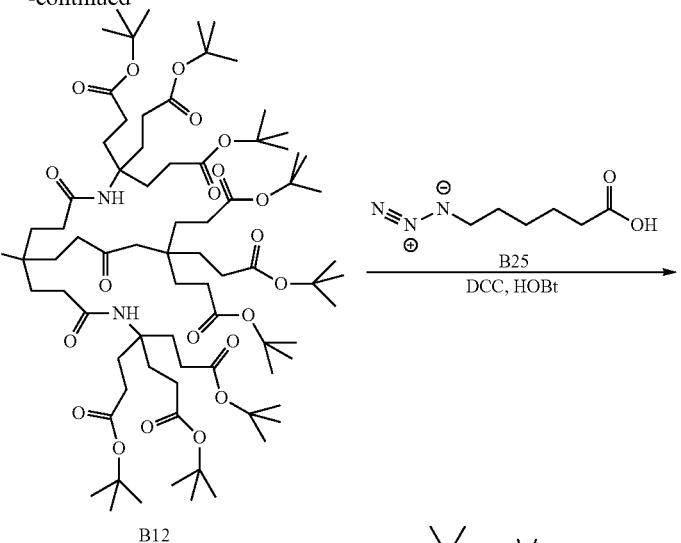
B12
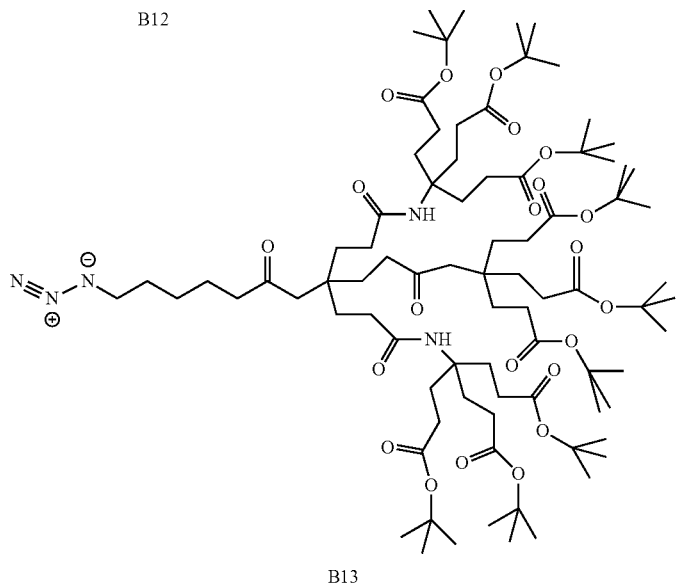
B13
Synthetic Pathway for Base-Labile Alkyne-Linker-Dendron:
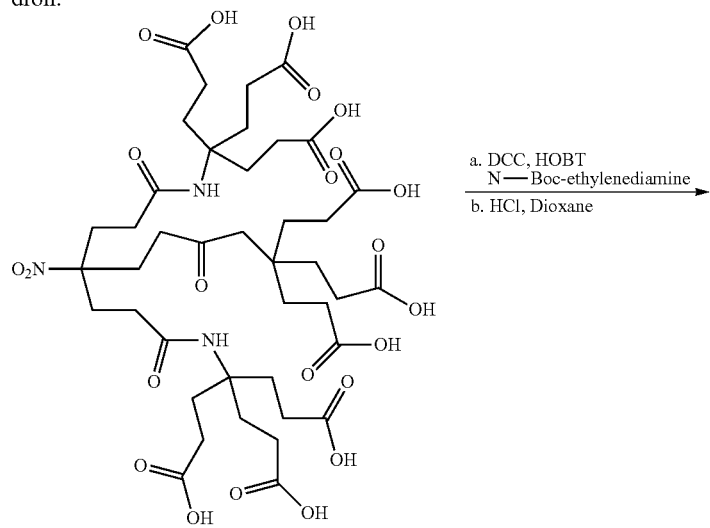
B4

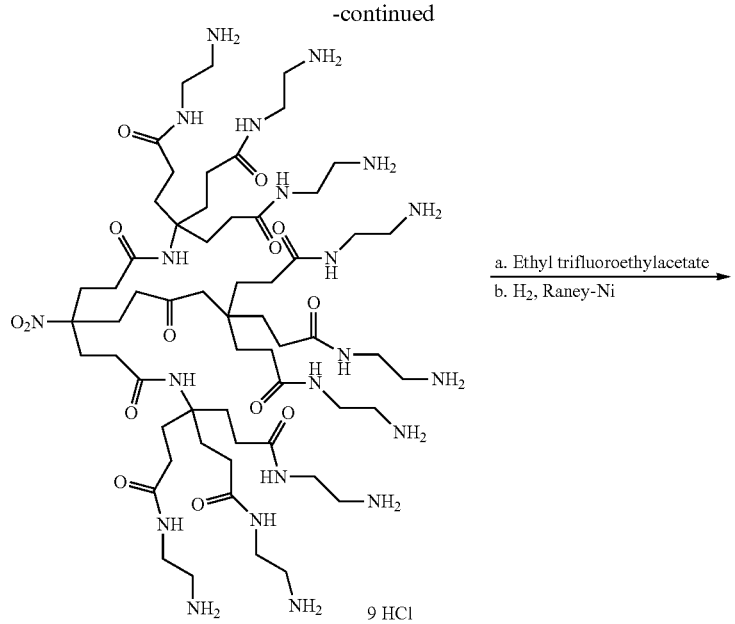
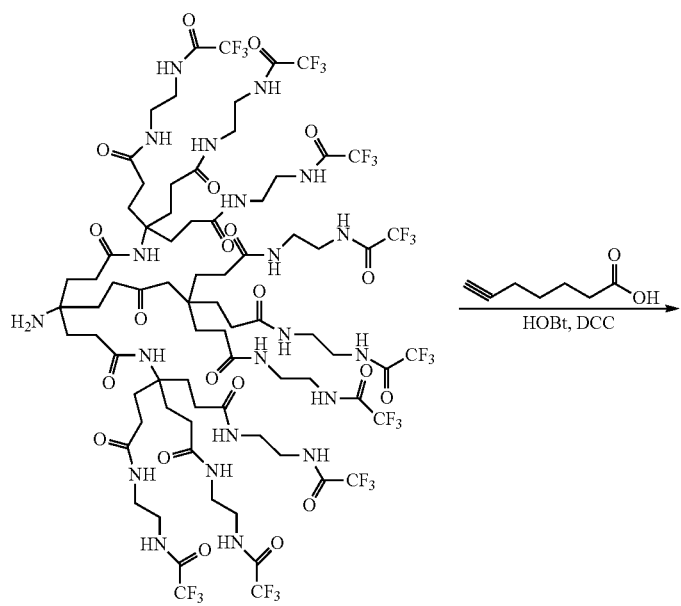

-continued
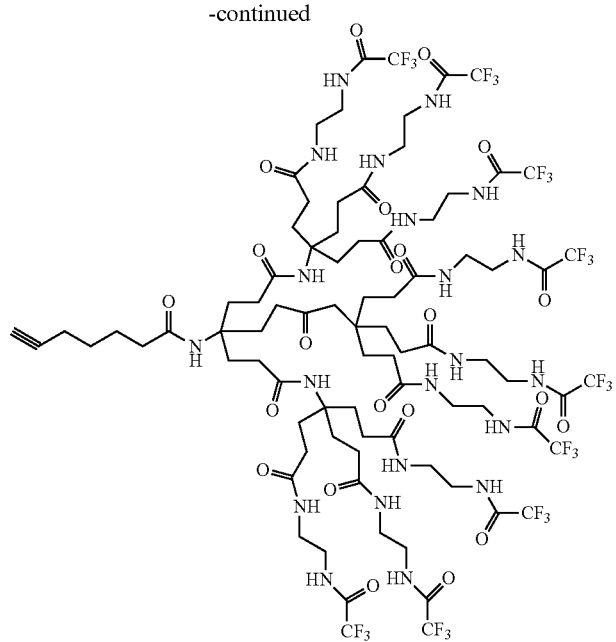
B15
Bifunctional Bow-Tie Synthesis by Click Reaction:
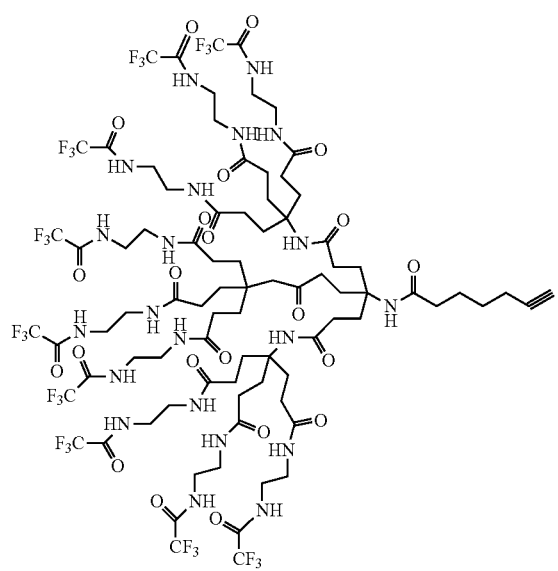
B15
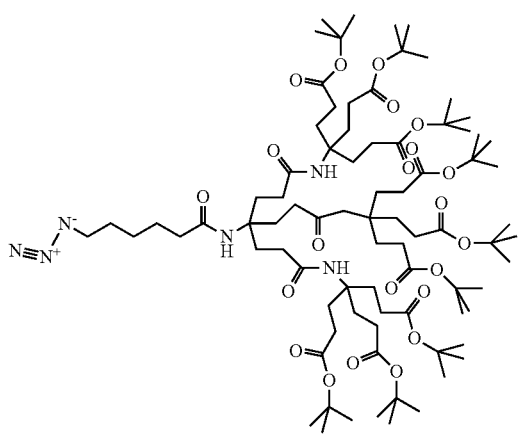
B13
Cu(Ph₃P)₃Br
i-Pr₂NEt, THF
Microwave -continued
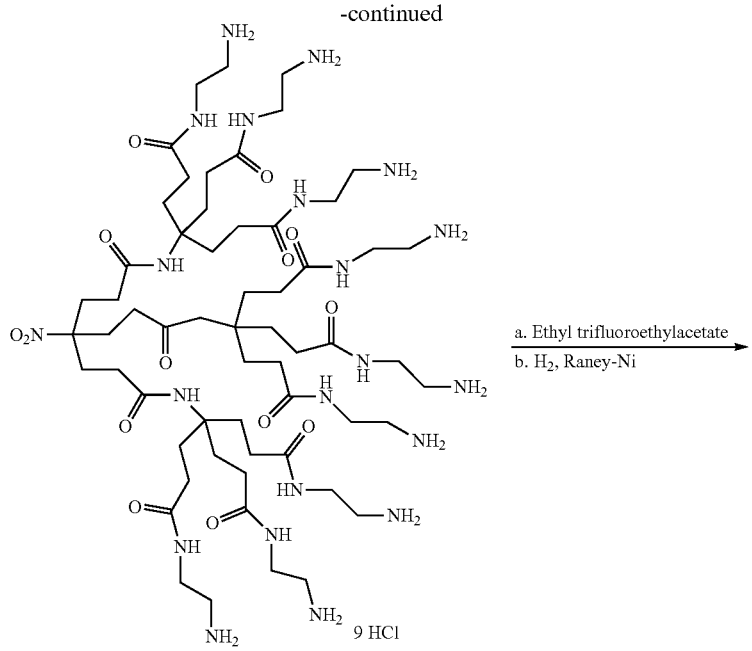
B5
a. Ethyl trifluoroethylacetate
b. H$_2$, Raney-Ni
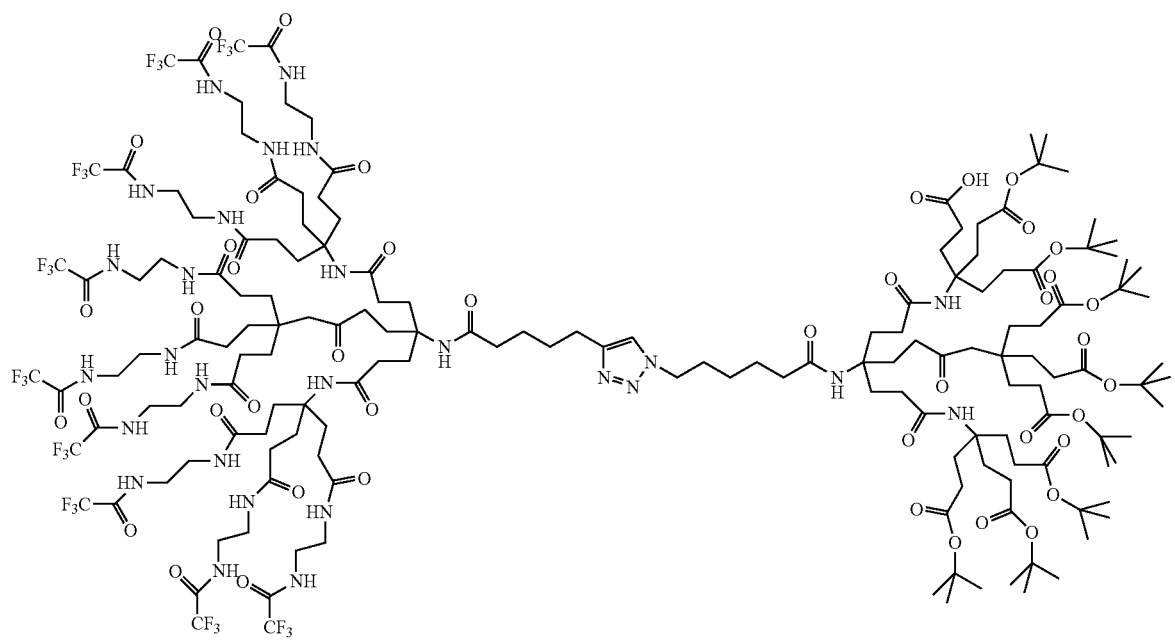
B16
Further Functionalization for Synthesis of Cell-Permeable Multi-Drug Carrier Conjugates:
a. HCOOH
b. N—Boc-ethylenediamine DCC, HOBt

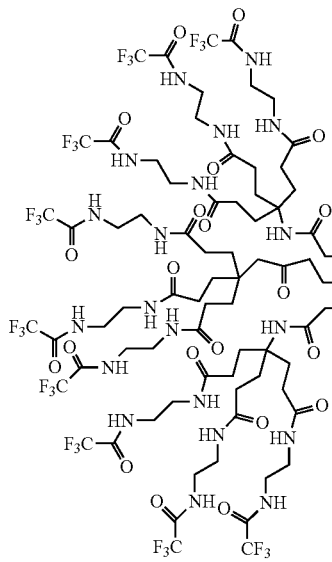
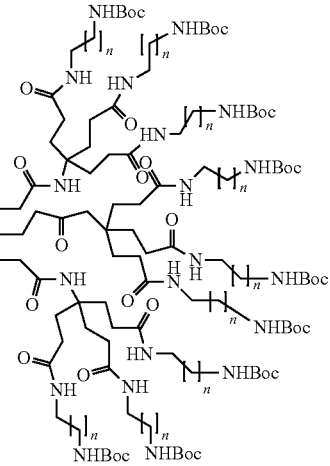
B17, n = 1
B18, n = 5
a. K₂CO₃, MeOH/H₂O
b. DCC, HOBt
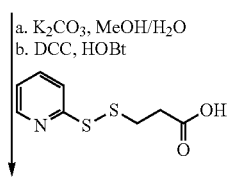
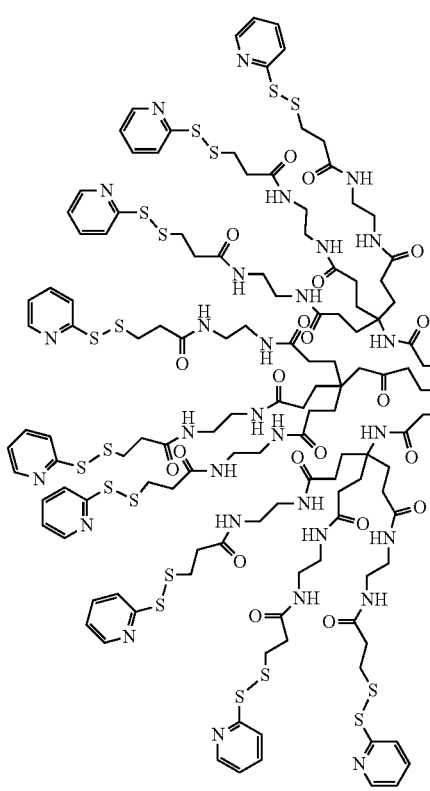
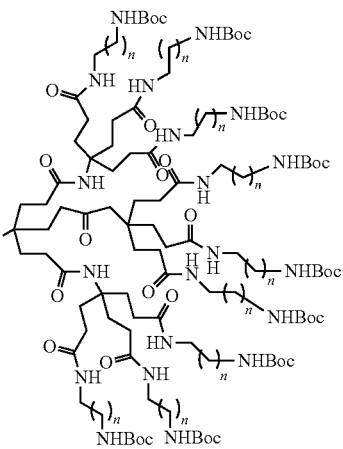
B19, n = 1
B20, n = 5
a. 2M HCl in Dioxane
b. diBoc-triflylguanidine
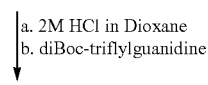

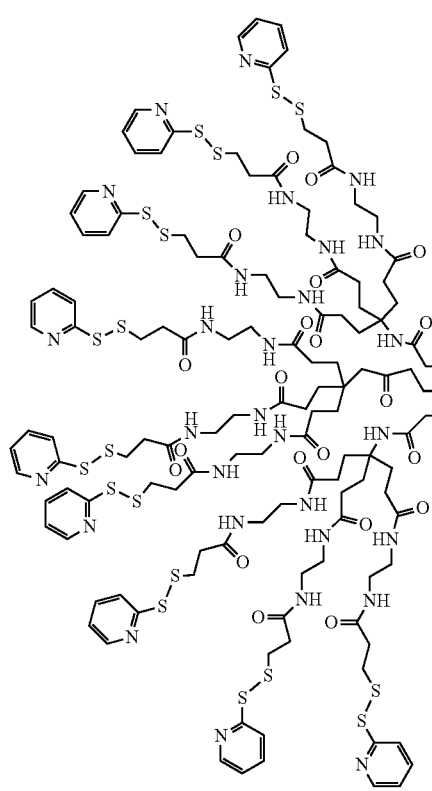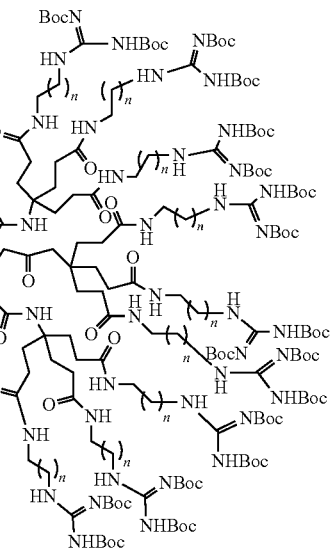
B21, n = 1
B22, n = 5
↓ 2M HCl in Dioxane
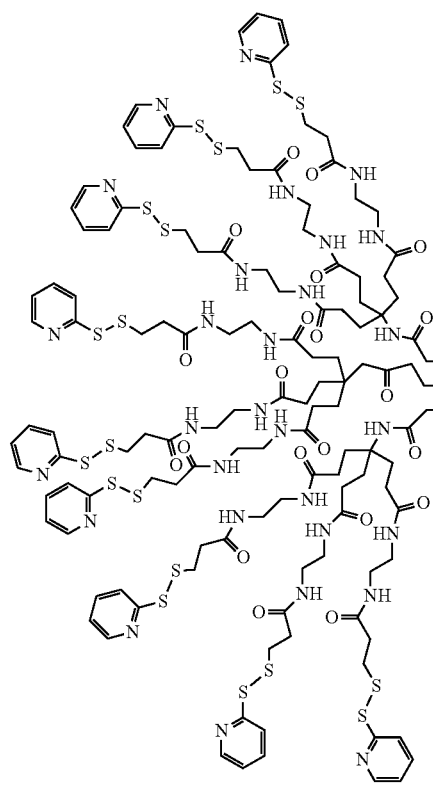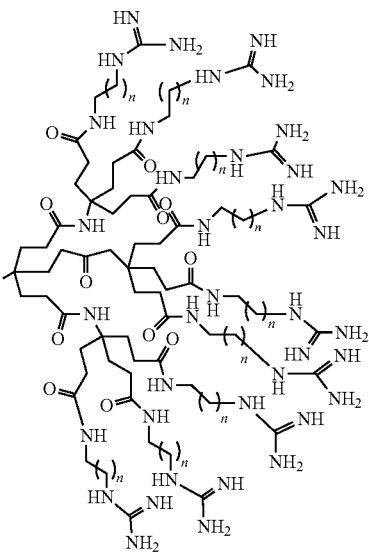
B23, n = 1
B24, n = 5

In one aspect, the invention relates to compounds comprising the structure:

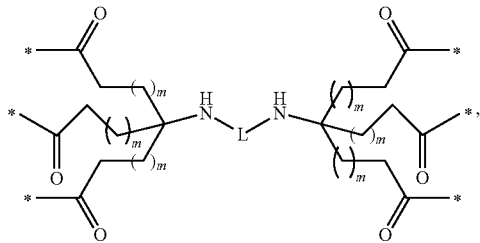

wherein each m is independently zero or a positive integer, and wherein L is a linking moiety comprising optionally substituted alkyl, optionally substituted alkoxyl, optionally substituted heteroalkyl, or optionally substituted heteroaryl.

In a further aspect, L comprises a structure:

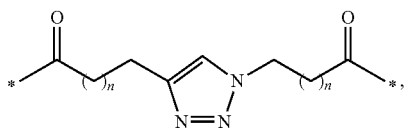

wherein each n is independently selected from 0-8. That is, L can comprise the reaction product of a "click" reaction.

In a further aspect, the compound can comprise a structure

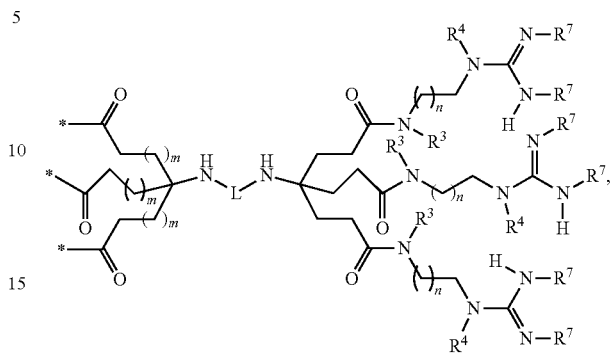

wherein n is an integer from 1 to 9; wherein $R^3$ is hydrogen or alkyl; wherein $R^4$ is hydrogen, or alkyloxycarbonyl, alkyl, or acyl; and wherein $R^7$ is hydrogen or alkyloxycarbonyl.

In a yet further aspect, the compound can comprise the structure:

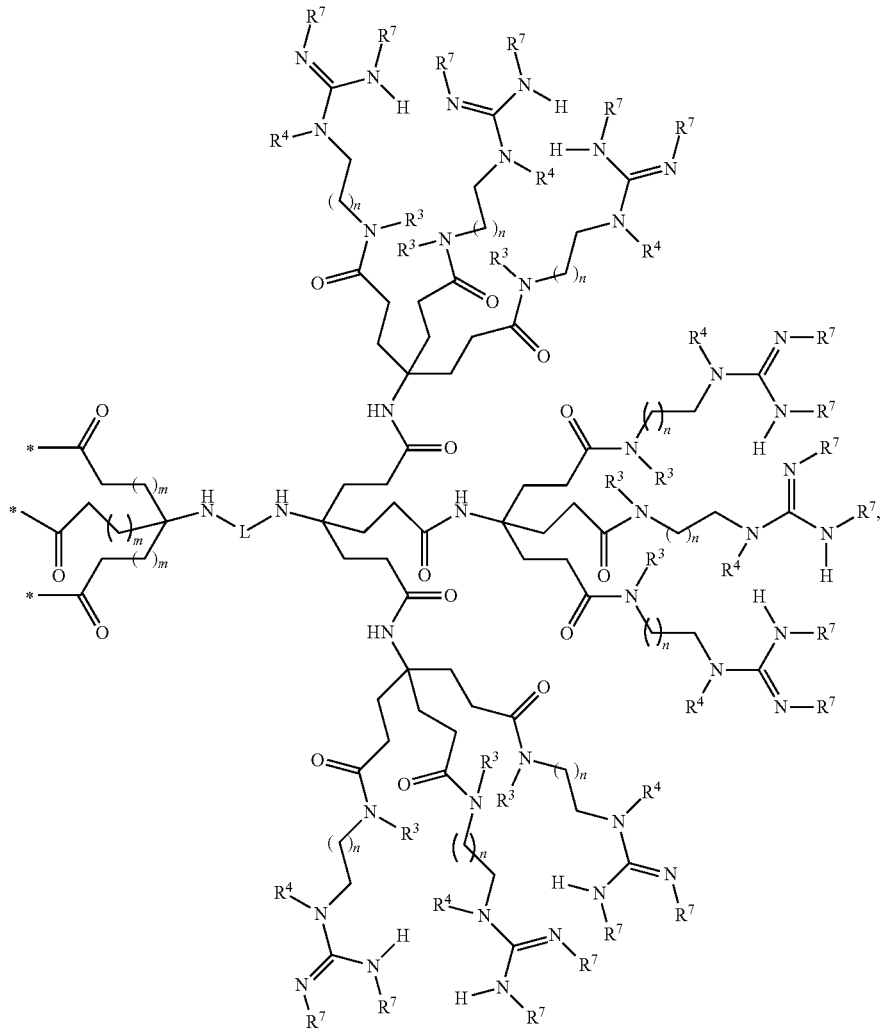

wherein n is an integer from 1 to 9; wherein $R^3$ is hydrogen or alkyl; wherein $R^4$ is hydrogen, or alkyloxycarbonyl, alkyl, or acyl; and wherein $R^7$ is hydrogen or alkyloxycarbonyl.

In a still further aspect, the compound can comprise the structure:
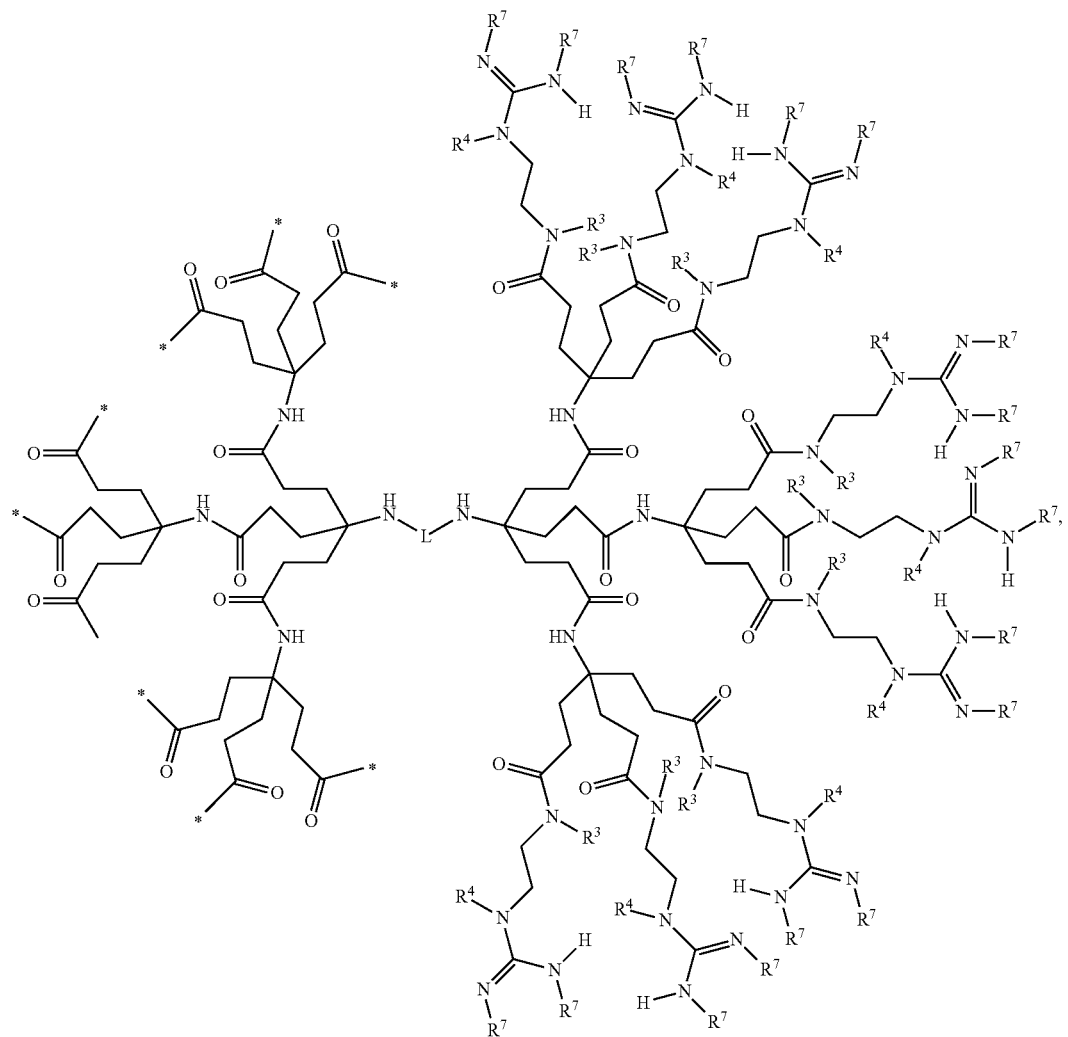
wherein n is an integer from 1 to 9; wherein $R^3$ is hydrogen or alkyl; wherein $R^4$ is hydrogen, or alkyloxycarbonyl, alkyl, or acyl; and wherein $R^7$ is hydrogen or alkyloxycarbonyl.

In an even further aspect, the compound can comprise the structure:

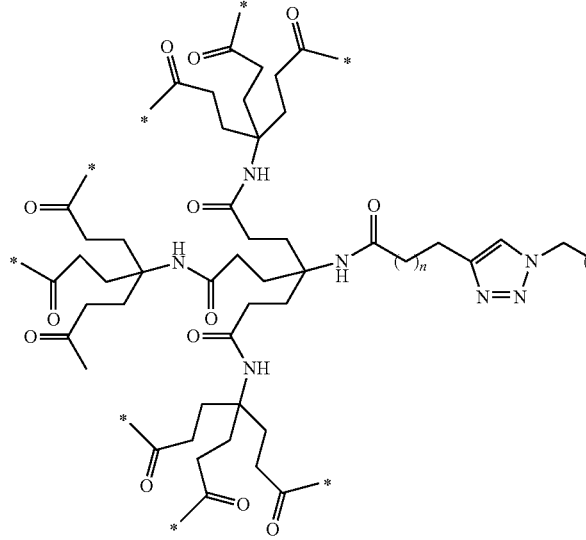
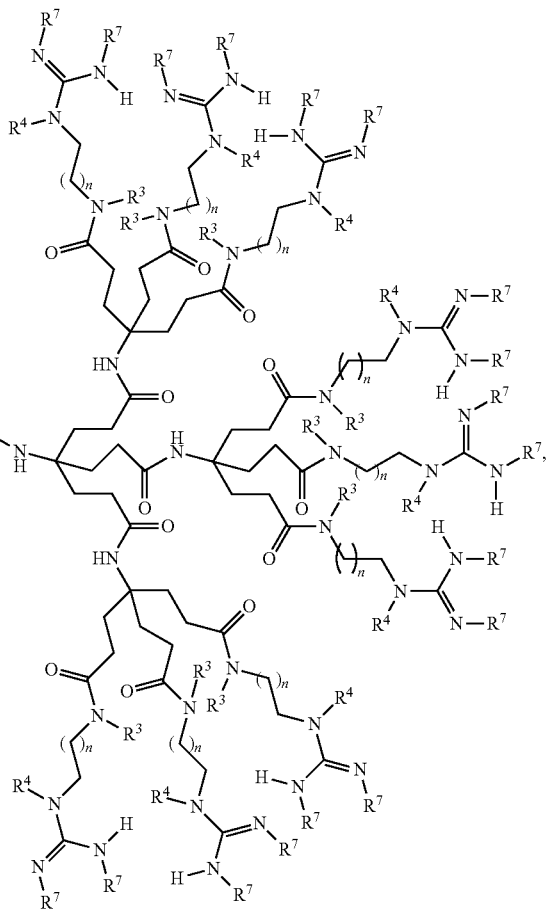

wherein each n is independently an integer from 0 to 9; wherein $R^3$ is hydrogen or alkyl; wherein $R^4$ is hydrogen, or alkyloxycarbonyl, alkyl, or acyl; and wherein $R^7$ is hydrogen or alkyloxycarbonyl.

Figure 32:
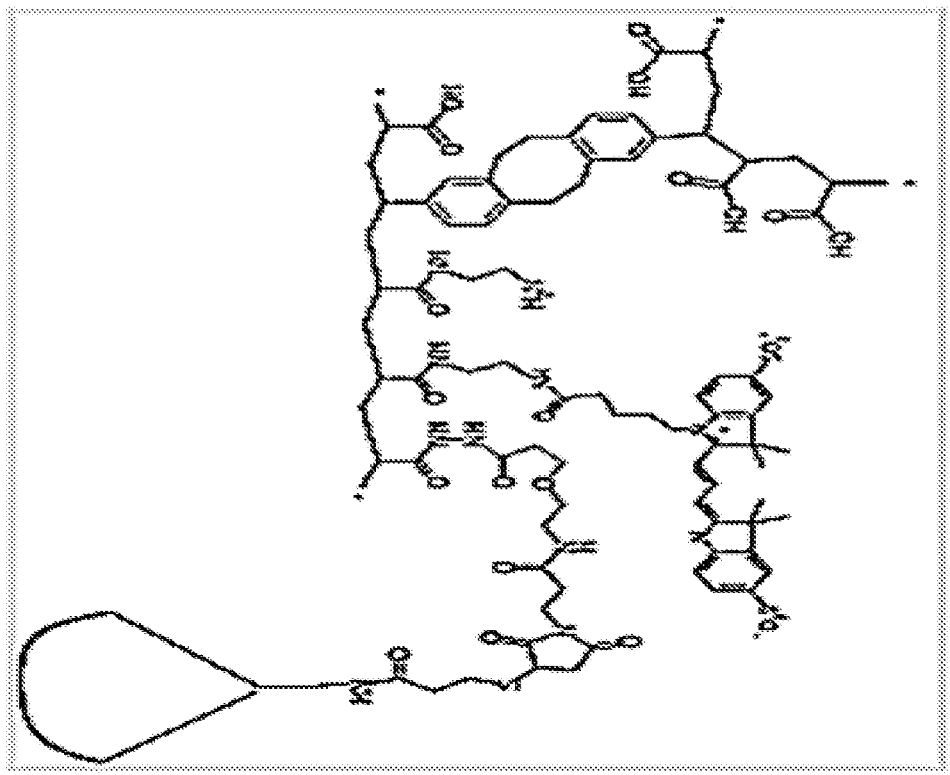
FIG. 32 demonstrates the flexibility of assembly of the disclosed delivery systems.
Figure 32:
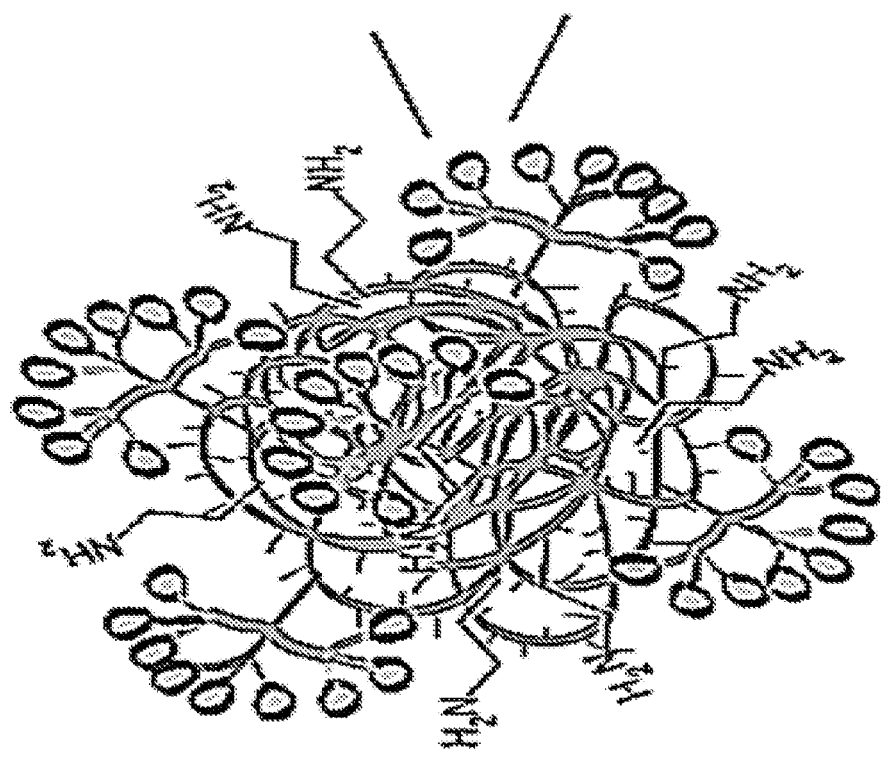
Figure 33:
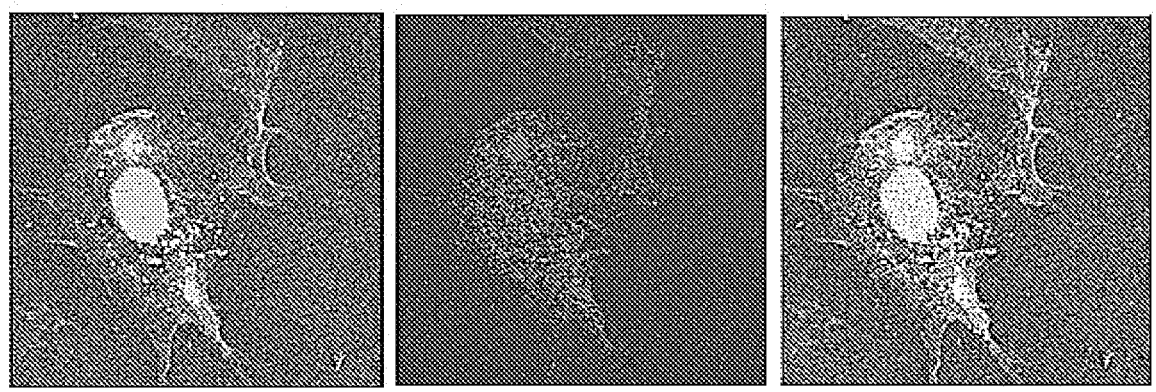
FIG. 33 shows micrographs of HeLa cells exposed 10 µM FD-1 for 1 h, fixed with 3.3% paraformaldehyde, stained with 100 nM Mitotracker® Red 580 FM. The illuminated regions show cell penetration (left), mitochondria location (center), and overlap (right).
Figure 34:
FIG. 34 shows micrographs of HeLa cells exposed 20 µM FD-2 for 1 h, fixed with 3.3% paraformaldehyde, stained with 100 nM Mitotracker® Red 580 FM. The illuminated regions show cell penetration (left), mitochondria location (center), and overlap (right).
Figure 35:
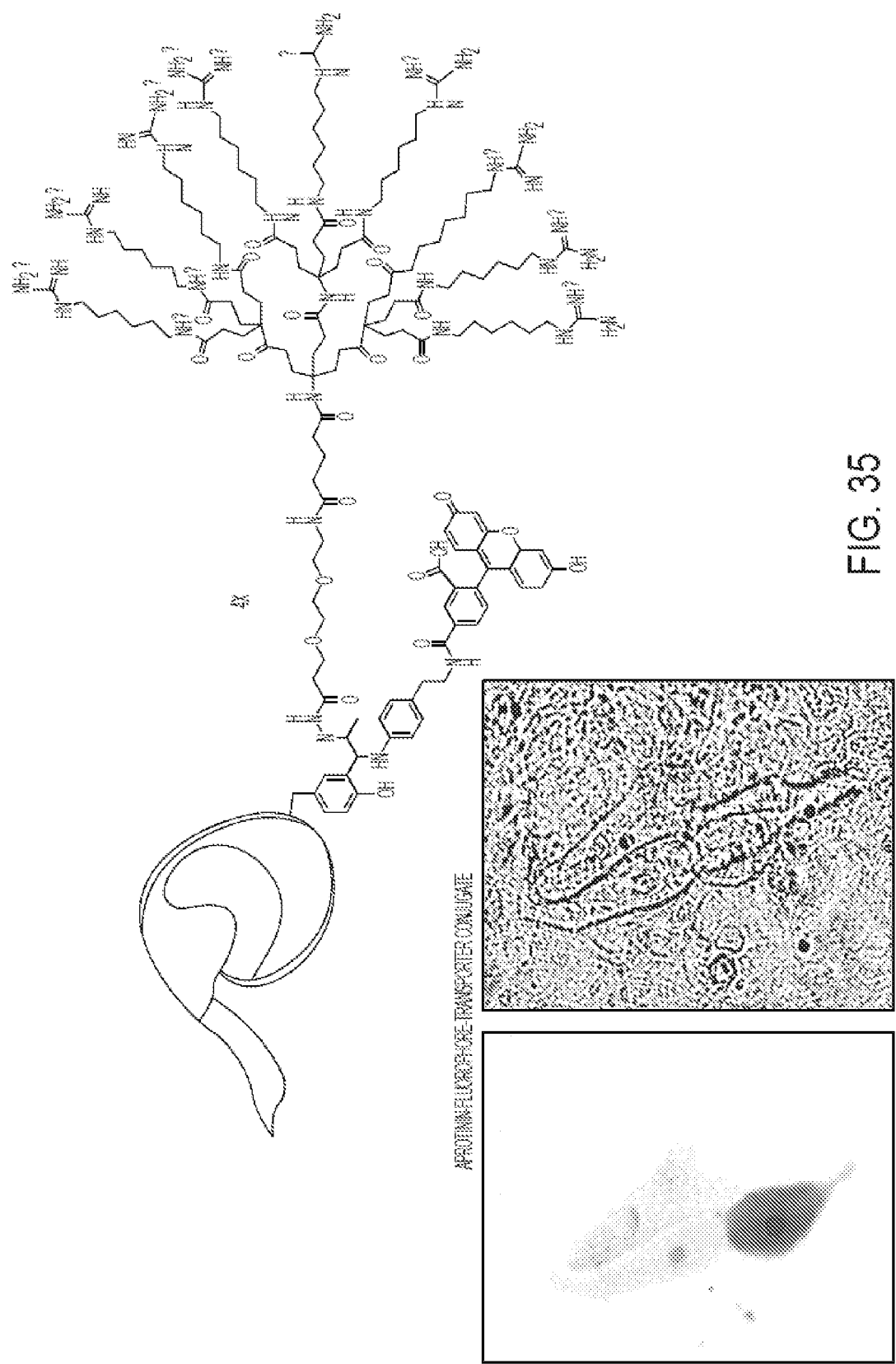
FIG. 35 shows micrographs demonstrating intercellular transport of an aprotinin-fluorophore-transporter conjugate (FD-1, illustrated) into HAEC cells.
Figure 36:
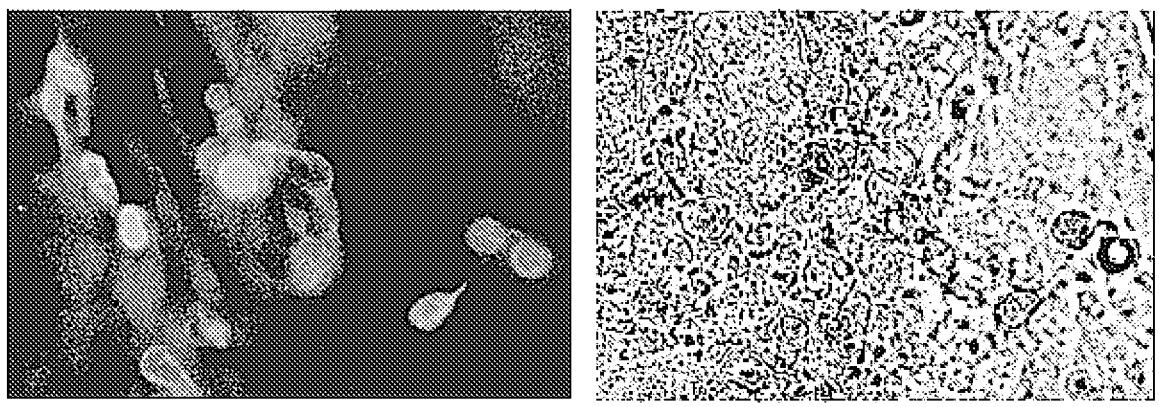
FIG. 36 shows micrographs demonstrating intercellular transport of an aprotinin-fluorophore-transporter conjugate (FD-2) into HAEC cells.
Figure 37:
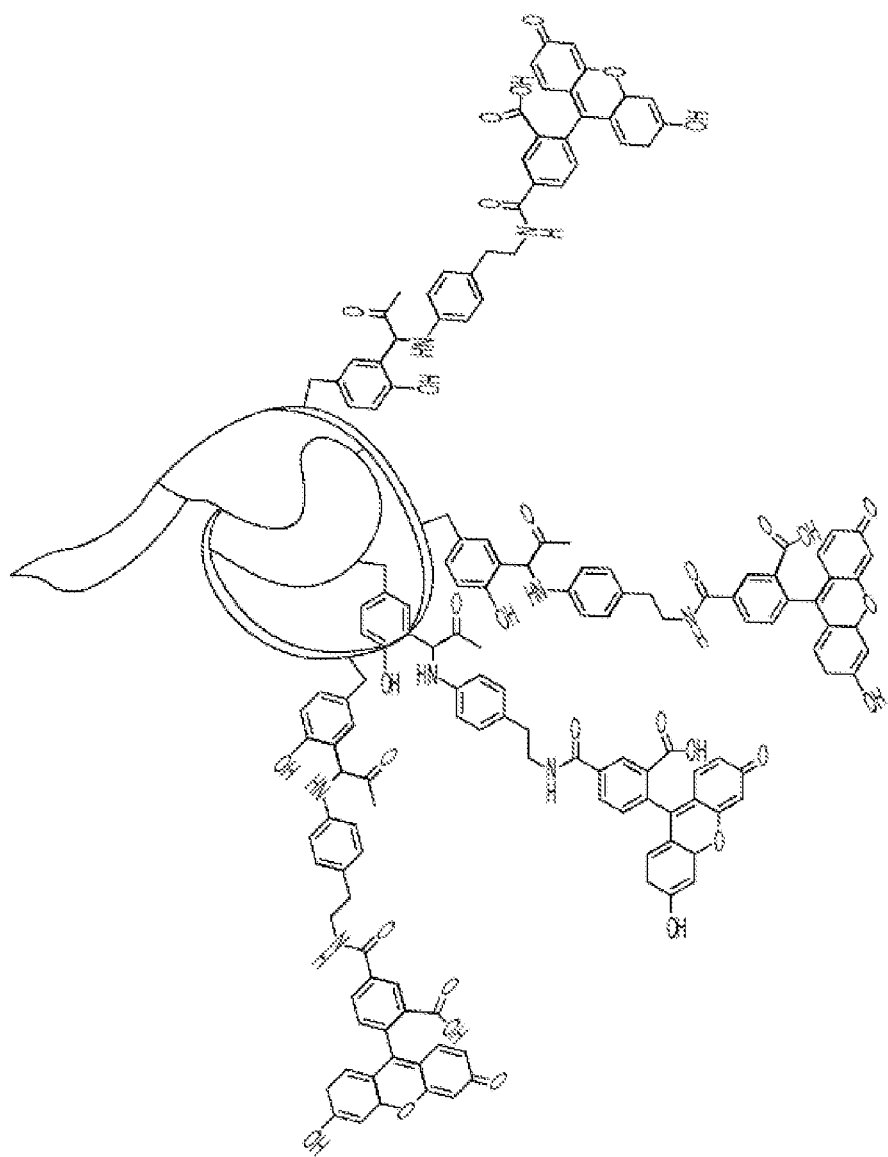
FIG. 37 shows micrographs demonstrating no uptake (i.e., no intercellular transport into HAEC cells) of a control aprotinin-fluorophore conjugate (illustrated).
Figure 37:
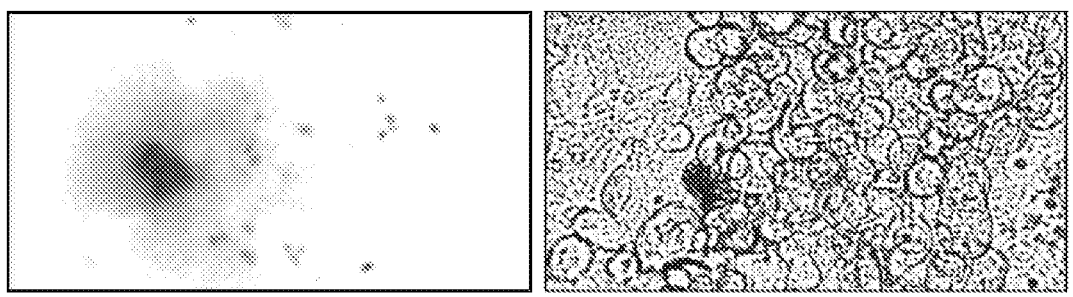
Figure 38:
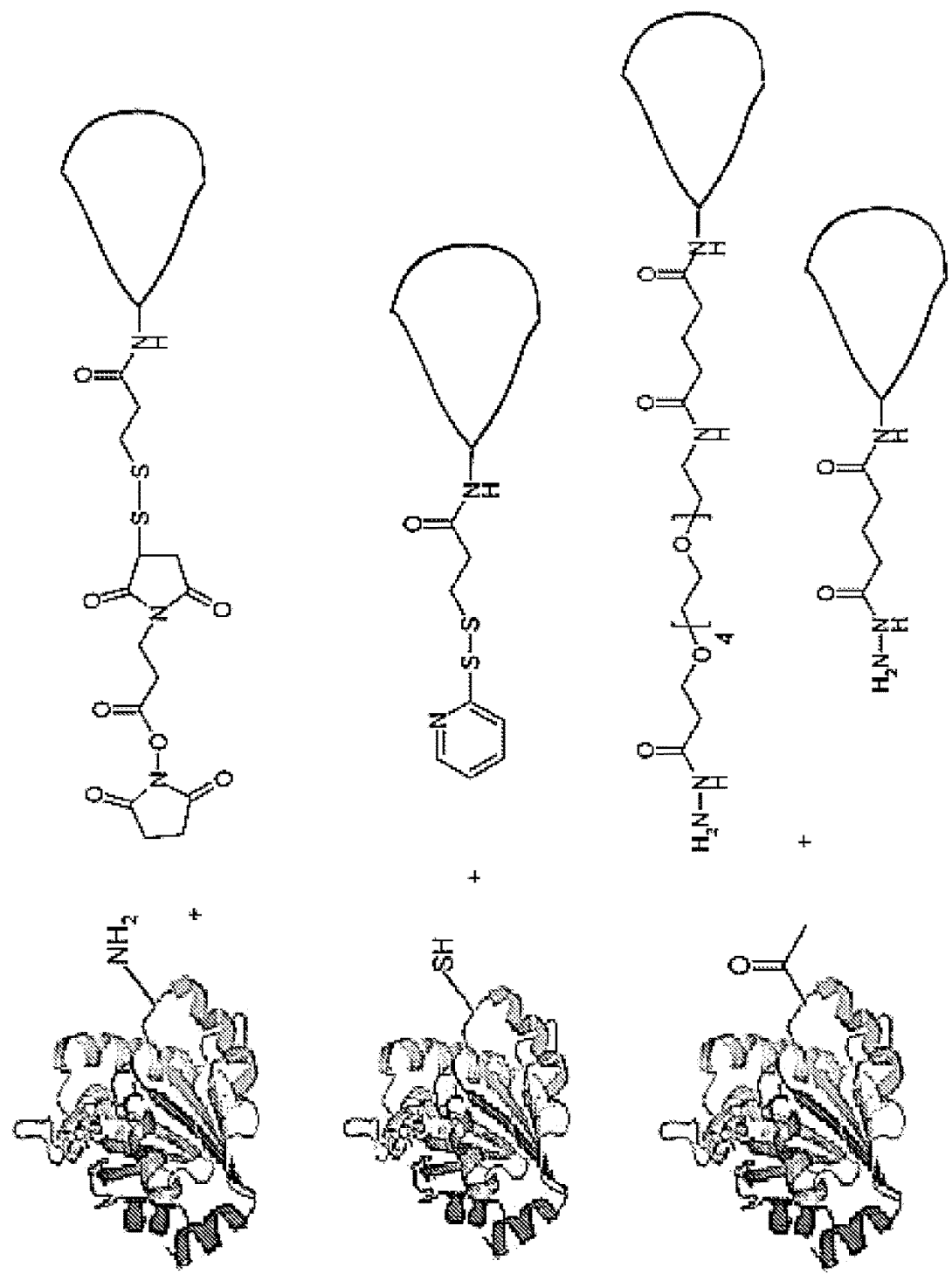
FIG. 38 illustrates several chemical strategies for binding transporter moieties to various protein functional groups (e.g., amine, thiol, carbonyl).
Figure 39:
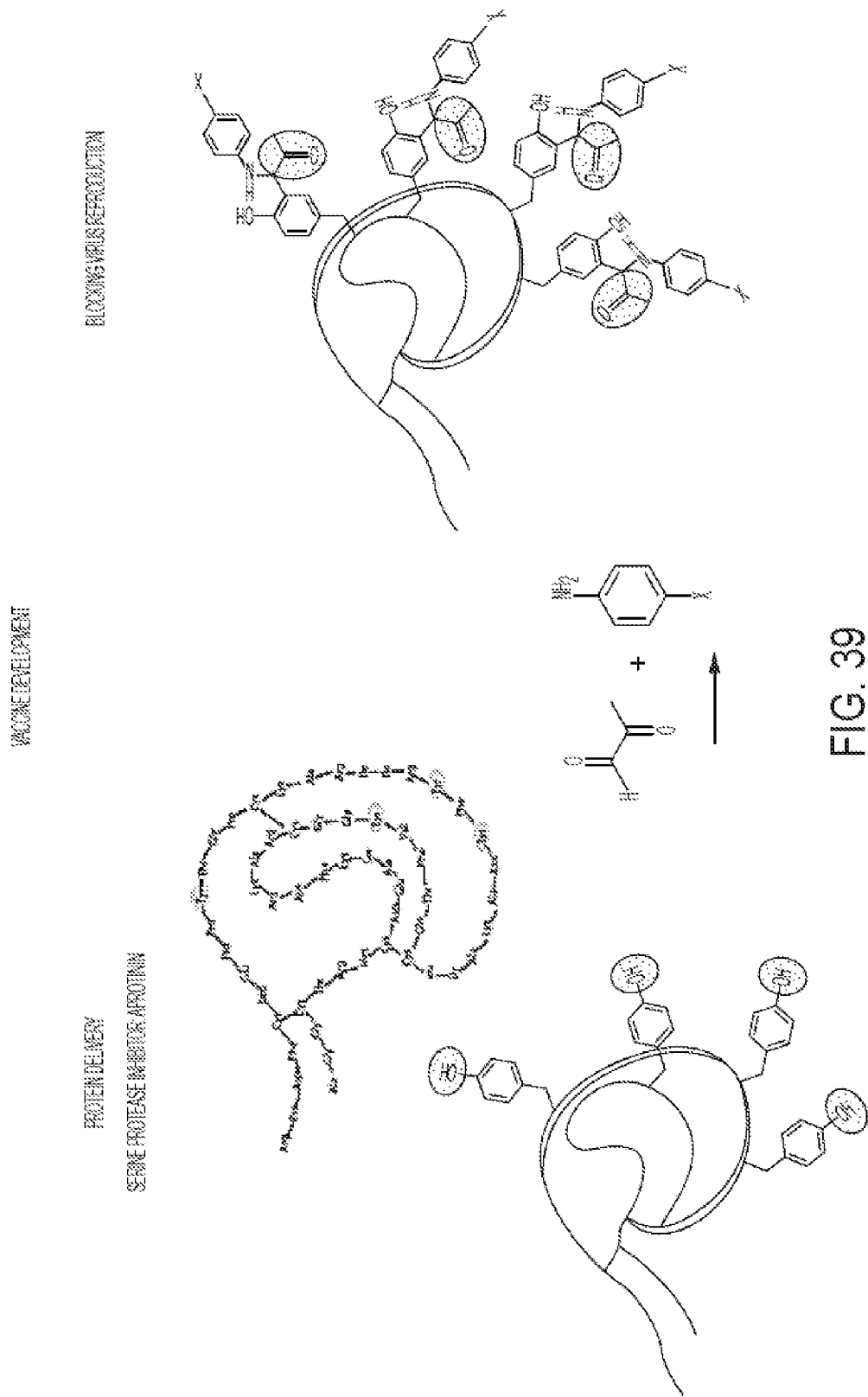
FIG. 39 presents strategies for vaccine development by incorporation of aprotinin through conjugation to carbonyl-functionalized proteins (e.g., tyrosine residues) by Mannich reaction.
Figure 40:
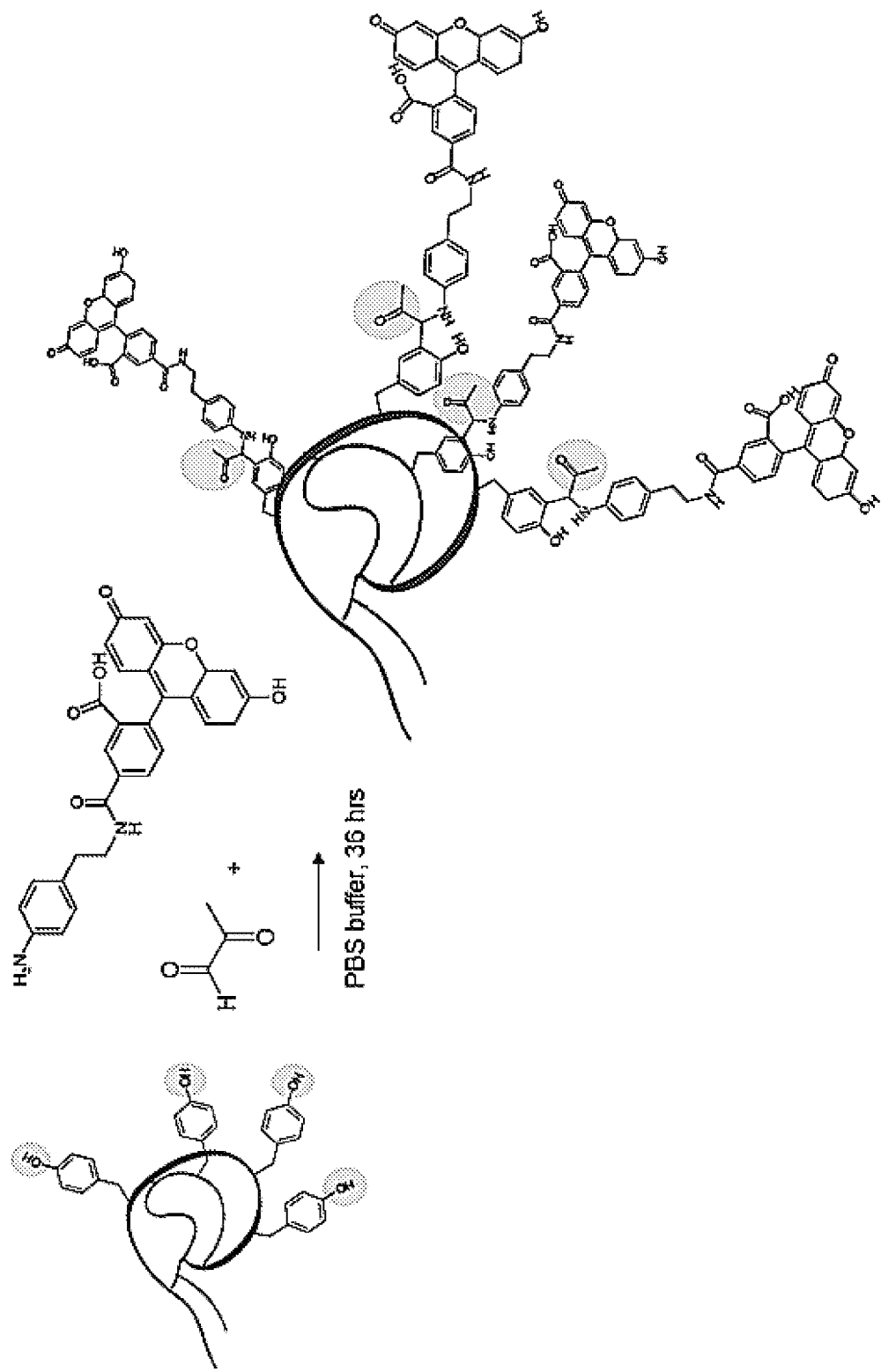
FIG. 40 illustrates incorporation of fluorophores through conjugation to carbonyl-functionalized proteins (e.g., tyrosine residues) by Mannich reaction.

It is demonstrated that the disclosed transporter (e.g., FD-2, hexyl linker) shows selectivity towards the mitochondria of a cell. (see FIG. 33) The FD-1 shows selectivity towards the cell nucleus (see FIG. 32). A common obstacle in macromolecular drug delivery is the cellular uptake into cell compartments that do not release the drug delivery vector into the cytosol or mitochondria in which the drug becomes effective. Most other delivery pathways into the cell end up in the lysosome and do not get released (endocytosis). The therapeutic efficacy of drug molecules typically depends on its ability to reach desired target tissues, cells and intracellular organelles.

The mitochondria play a key role in apoptosis (cancer therapy), familial amyotrophic lateral sclerosis (ALS, Lou Gehrig's disease), Leber hereditary optic neuropathy (LHON), lactic acidosis, strokelike syndrome (MELAS) Huntington's disease, and Alzheimer's disease, Kearns-Sayre Syndrome (KSS), myoclonic epilepsy, ragged-red fibers (MERRF), cluster of metabolic diseases (SyndromeX), progressive external ophthalmophlegia (PEO) and antioxidants. By targeting the mitochondria, the disclosed compounds, compositions, and methods can play a role in therapy or prevention of disease processes relating to mitochondria function.

When the disclosed transporter is attached to the disclosed nanoparticle, it can enter the cell and also can achieve localization in the entire cell, including the mitochondria. The nanoparticle allows delivering a high drug load and, thus, can facilitate delivery of small and other molecules, such as peptides, nucleotides and such. The structures can be further modified with amines to allow complexation with plasmic DNA and covalent attachment s though covalent approaches. (See FIGS. 34-39).

A nanoparticle with a number of molecular transporter moieties conjugated to the periphery crosses the plasmic membrane and localizes in the cytosol and, particularly, in the mitochondria of the cells. Techniques are disclosed that allow the attachment of the molecular transporter the scaffolds that increase the drug load significantly. Attachment to the "bow-tie" structure and/or the attachment to nanoparticles from intramolecular chain collapse techniques also increase the drug load significantly.

The dendritic transporter allows the conjugation of nine bioactive conjugates and the drug load is increased nine fold by attaching a dendric molecule to the focal point of the dendritic molecular transporter (bow-tie). A well-defined macromolecule is designed, that is "clicked" together in a Huisgen type reaction. The deprotection of the basic/acidic protecting groups allows the modification to a delivery system with a short ethyl linker or hexyl linker before guanidylation to maintain uptake into specific subcellular locations. The disulfide linker is only one of the examples of a linker chemistry attached to the drug part of the bow-tie structure. All other linkers presented can be applied as well.

The drug load can be increased nine-fold by attaching a dendric molecule to the focal point of the dendritic molecular transporter (bow-tie). A well-defined macromolecule is designed, that is "clicked" together in a Huisgen type reaction. The deprotection of the basic/acidic protecting groups allows the modification to a delivery system with a short ethyl linker or hexyl linker before guanidylation to maintain uptake into specific subcellular locations.

Here, the drug load can be increased to a theoretical amount of 100-300 positions to conjugate small molecule drugs, peptides, oligonucleotides and more. The functionalization of the particle with a varied amount of amines allows together with the attachment of transporter allows the development of a gene delivery system. A "drug" can also be conjugated though a disulfide bond in a covalent conjugation approach. For example, proteins can be delivered. (See FIGS. 47, 48, 50, and 51).

F. Crosslinked Degradable Polymeric Nanoparticles

Traditional polyester nanoparticle delivery systems are typically self-assembled from linear polyesters chains driven by the polarity of the solvent, emulsion composition and addition techniques. These procedures predetermine the drug loading during nanoparticle formation and limit post-modification chemistries in organic and aqueous solutions. Furthermore, the result of this self-assembly process is mirrored in the morphology and degradation properties of the release systems. It has been recognized that the degradation behavior of the nanoparticles and release profile of the entrapped drug molecules are factors to establish predictable pharmacokinetic profiles in effective multidrug cancer therapies. So far, release kinetics are challenged by a rapid release of the drug molecules in the first 24-48 h followed by a slower release, referred to as a "burst-effect." These release profiles typically prevent the establishment of reliable dosages and contribute to developing multidrug resistance, often times the result of non-optimized drug concentrations at tumor sites.

In contrast, actively targeted drug delivery carriers can entrap high concentrations of hydrophobic therapeutics and maintain a linear release profile, which can be tuned to the demands of the tumor type as a result of the adjustable supramolecular architecture accomplished through an intermolecular cross-linking technique. The disclosed methods of preparing polyester particles utilize a controlled cross-linking mechanism of linear polyester precursors that contain pendant functional groups as one of the cross-linking units with a difunctionalized linker that acts as the second cross-linking partner. To achieve control over a series of different nanoparticle size dimensions, the amount of the difunctionalized linker is added in a series of varying equivalencies to the pendant functionalities of the linear polyester precursor. Nanoparticles can be produced, depending on the linker amount present in the reaction, with unique sizes and standard deviations of only 10%. These "nanonetworks," depending on their nanoparticle size and cross-linking density, influence their crystallinity, but the particles are amorphous at the temperature of use (37° C.). To determine if the amorphous properties of poly(valerolactoneepoxyvalerolactone), poly(vl-evl) particles have a positive effect on the degradation behavior, a series of degradation studies in buffer at pH 7.4 at 37° C. were performed, investigating particles from a completed series of linear precursors and increasing amounts of difunctionalized cross-linkers with controlled nanoscopic dimensions (FIG. 1).

Degradation of the particles was monitored by the change of the absolute molecular weight, as determined through static light scattering (SLS). Linear degradation profiles were observed for all particles investigated, with the highest loss of molecular weight for the 725 nm nanoparticle with 17.5% of its total molecular mass remaining after 10 days. Smaller particles with a slightly higher degree of crystallinity of 20.6% were degraded to 26% of the original molecular weight. The observed linear degradation kinetics are a parameter that determines the quality of the developed particles towards applications as controlled release systems.

The capacity to encapsulate small molecule drugs, such as paclitaxel (taxol), can also be evaluated. Traditional polyester particles, produced with salting-out or nanoprecipitation methods, typically do not exceed a drug loading over 5% that is facilitated during nanoparticle formation. However, the disclosed nanoparticles consist of crosslinked supramolecular structures that are readily soluble in organic solvents without affecting the 3-D architecture. This property provides the opportunity to load the particles after formation by dissolving the particles in dimethyl sulfoxide (DMSO) together with cancer therapeutics, such as paclitaxel (taxol), and precipitating into water.

Figure 3:
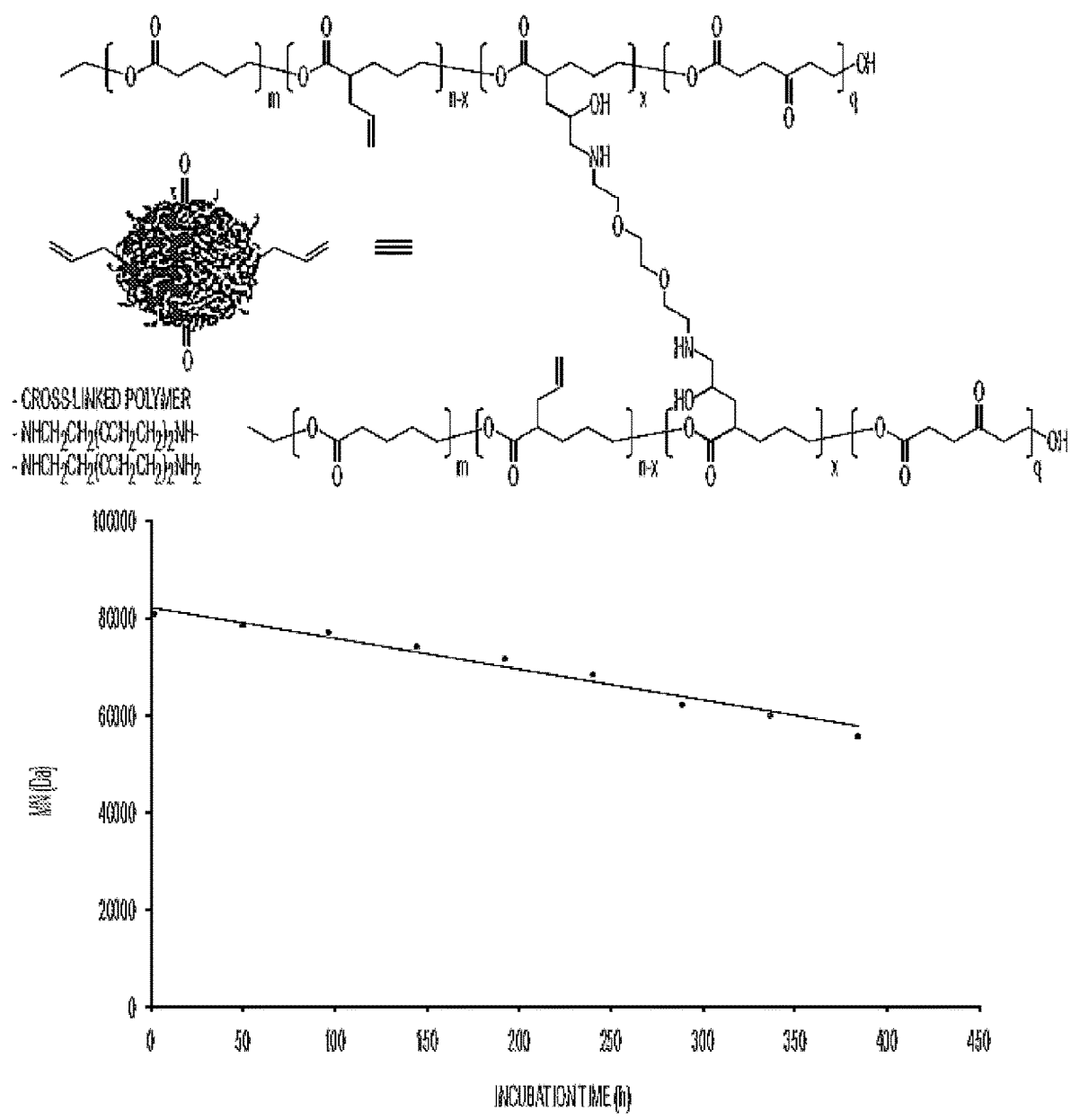
FIG. 3 shows in vitro degradation profile of vitamin E TPGS formulated poly(vl-evl-avl-opd) nanoparticles of 53 nm in DPBS at pH 7.4 and 37° C. over a period of 384 h (16 days).

Determination of drug loading capacity was performed with particles of 53 nm in diameter from linear precursors, poly(-valerolactone-epoxyvalerolactone-allylvalerolactone-oxepanedione), poly(vl-evl-avl-opd), containing 11% epoxide and crosslinked with 2 equivalents of diamines per epoxide (FIG. 3). In preparation for in vivo experiments, the encapsulation method was designed to also increase the homogenity of the particle dispersion in water for a practical administration of the drug loaded particles by injection. An emulsification process with vitamin E TPGS (D-a-tocopherol polyethylene glycol 1000 succinate) was used, which achieves a homogenous dispersion of the loaded or un-loaded particles in water or buffer. The resulting particles are analyzed by UV-Vis with a NanoDrop Spectrophotometer at 254 nm, and along with a calibration curve, the drug loading with paclitaxel was found to be 15.7% for an aimed 20% drug load and 11.3% for a 15% drug load, respectively. With this process, it is not only possible to load therapeutic drug molecules to a higher degree into prepared nanoparticles, but it is also possible to solubilize hydrophobic cancer therapeutics in aqueous solutions.

Figure 2:
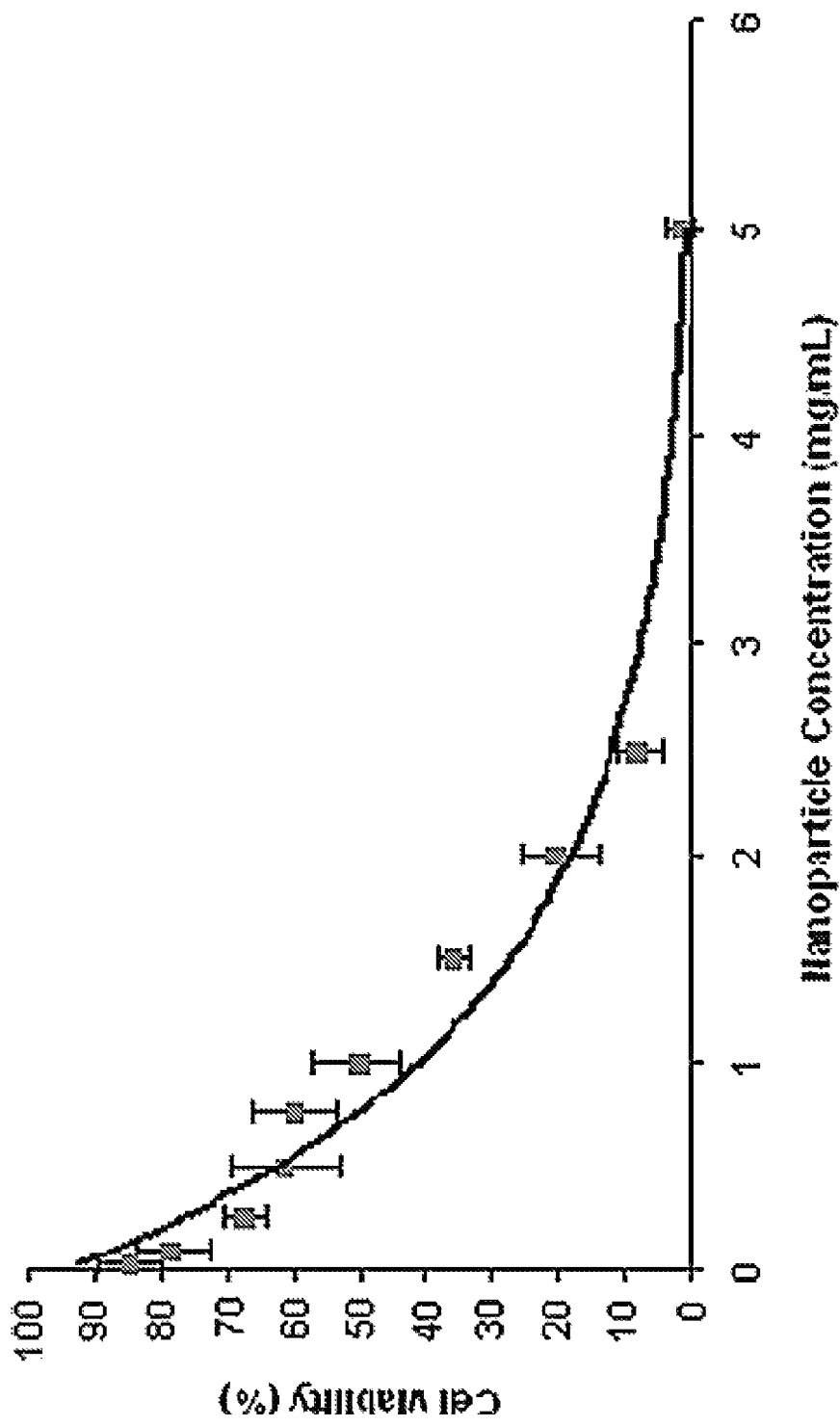
FIG. 2 shows cytotoxicity of vitamin E TPGS formulated nanoparticles on HeLa cells after 24 h incubation using the MTT assay. Fitted curve shows cell viability of the HeLa cell line.

Side effects known to be caused by adjuvant agents, such as Cremophor EL (50:50 ethanol-polyoxyethylated castor oil) to solubilize hydrophobic drug molecules for intravenous injections, can be avoided. To ensure that no cellular toxicity is caused by the vitamin E TPGS formulated particles prior to drug loading, the cell viability was assessed by utilizing a MTT assay (FIG. 2). The cellular toxicity was determined by incubating HeLa cells with varying concentrations of particles in triplicate ranging from 5 mg/ml to 0.001 mg/ml. Following 24 h of incubation with particles, cell viability was assessed. As seen in FIG. 2, the nanoparticles did not cause significant cytotoxicity against the HeLa cell line. The experimental TC50 value for the formulated particles was found to be 1.0 mg/ml. Moreover, emulsification had an effect on the degradation profile and was found to correlate with the in vitro release studies. Over the period of 16 days, the particles experienced a low controlled degradation, as seen by the linear degradation profile, finishing with 70% of its original molecular weight remaining (FIG. 3). Without wishing to be bound by theory, it is believed that the slower degradation rate can be attributed to the well-defined structure of the nanoparticle and the vitamin E TPGS that remains at the surface to stabilize the particles. Consequently, this gradual constant degradation profile of the particles is a desirable feature, as it translates into the controlled and sustained release of therapeutics.

Figure 4:
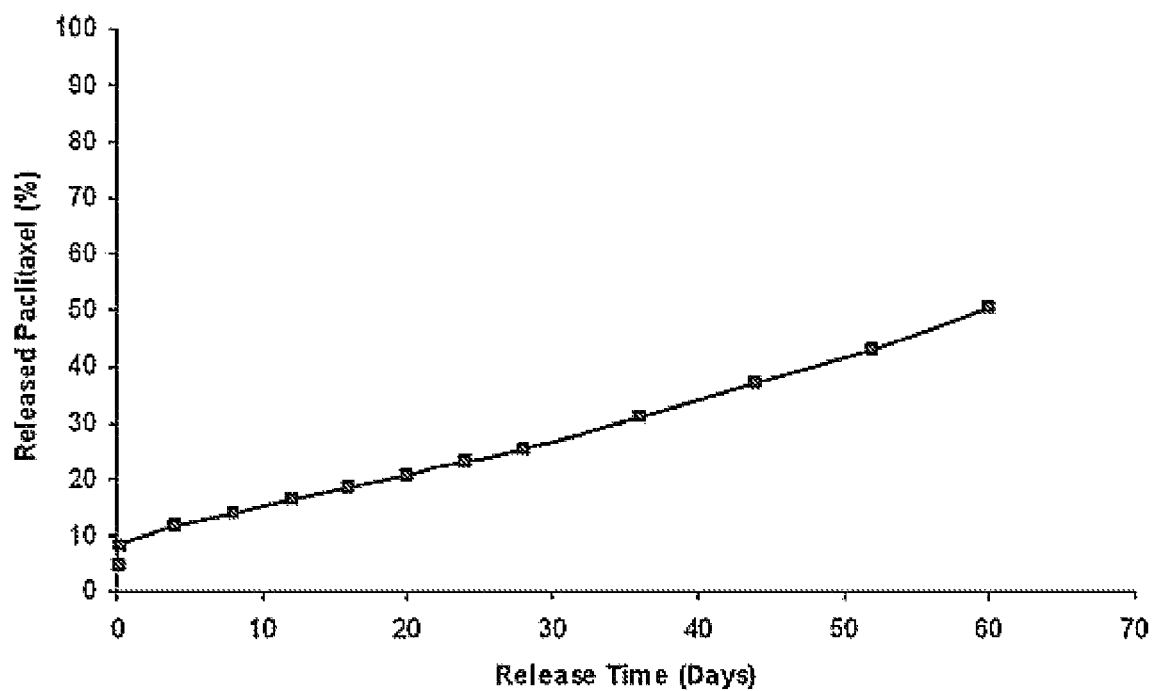
FIG. 4 shows in vitro release profile of paclitaxel from particles loaded with 11.3% paclitaxel prepared with the emulsification process. The drug release was performed in DPBS at pH 7.4 and 37° C. for 60 days. The cumulative release profile shows a desirable controlled and sustained release of paclitaxel from the nanoparticles.

The paclitaxel release kinetics from vitamin E TPGS formulated nanoparticles were assessed by monitoring the cumulative release of taxol at 37° C. in DPBS at pH 7.4. At particular time intervals, the samples were centrifuged, and the supernatant was taken for analysis of paclitaxel concentration by NanoDrop spectrophotometry (254 nm). FIG. 4 depicts the cumulative release of paclitaxel from the particles. The profile shows a collective release of 4.4% and 7.4% taxol in the first 2 and 6 h respectively, followed by a slow and sustained release over 60 days, which again confirmed the efficient encapsulation of paclitaxel within the cross-linked nanoparticles. Without wishing to be bound by theory, it is believed that the initial instant release of paclitaxel in the first several hours is due to the dissolution or diffusion of the drug that was absorbed onto the nanoparticle surface, while the linear slow continuous release is attributed to the diffusion of the drug encapsulated in the nanoparticle during degradation. In contrast, traditional poly (lactic-co-glycolic acid) (PLGA) nanoparticles experience an erratic nonlinear drug release, that includes a "burst-effect" in which about 40% of taxol is released in the first day, followed by a fast release of about 10-30% in the next 2-5 days and then finally a slow release till no paxlitaxel (taxol) remains. In is noteworthy that the release kinetics can be adjusted to faster or slower release, governed by the density of cross-linking and the particle size.

Figure 5:
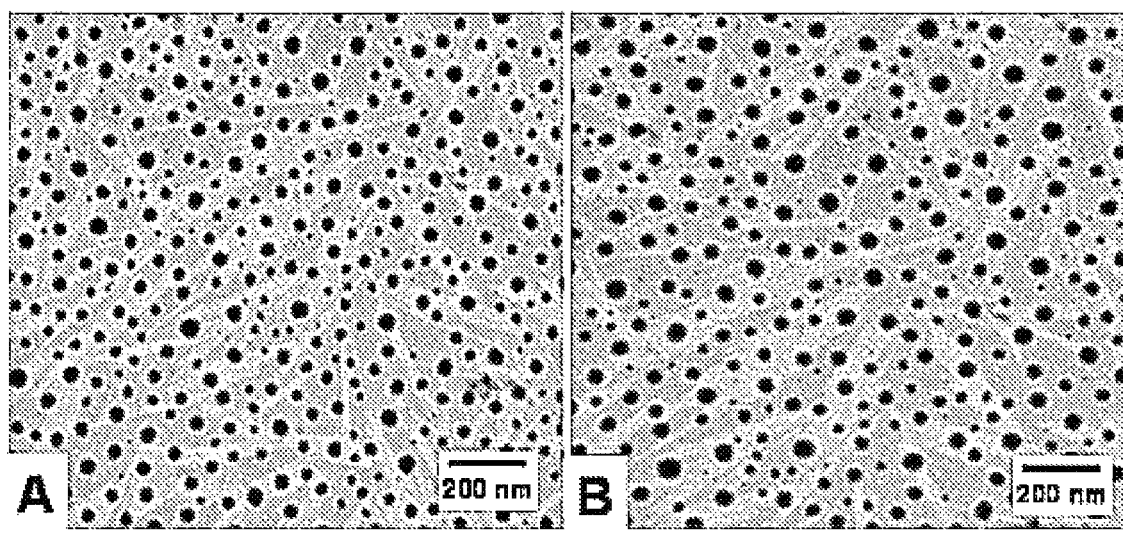
FIG. 5 shows transmission electron microscopy (TEM) images of (A) nanoparticles without taxol with a size of 53 nm and (B) nanoparticles encapsulated with 11.3% taxol with a size dimension of 57 nm.
Figure 8:
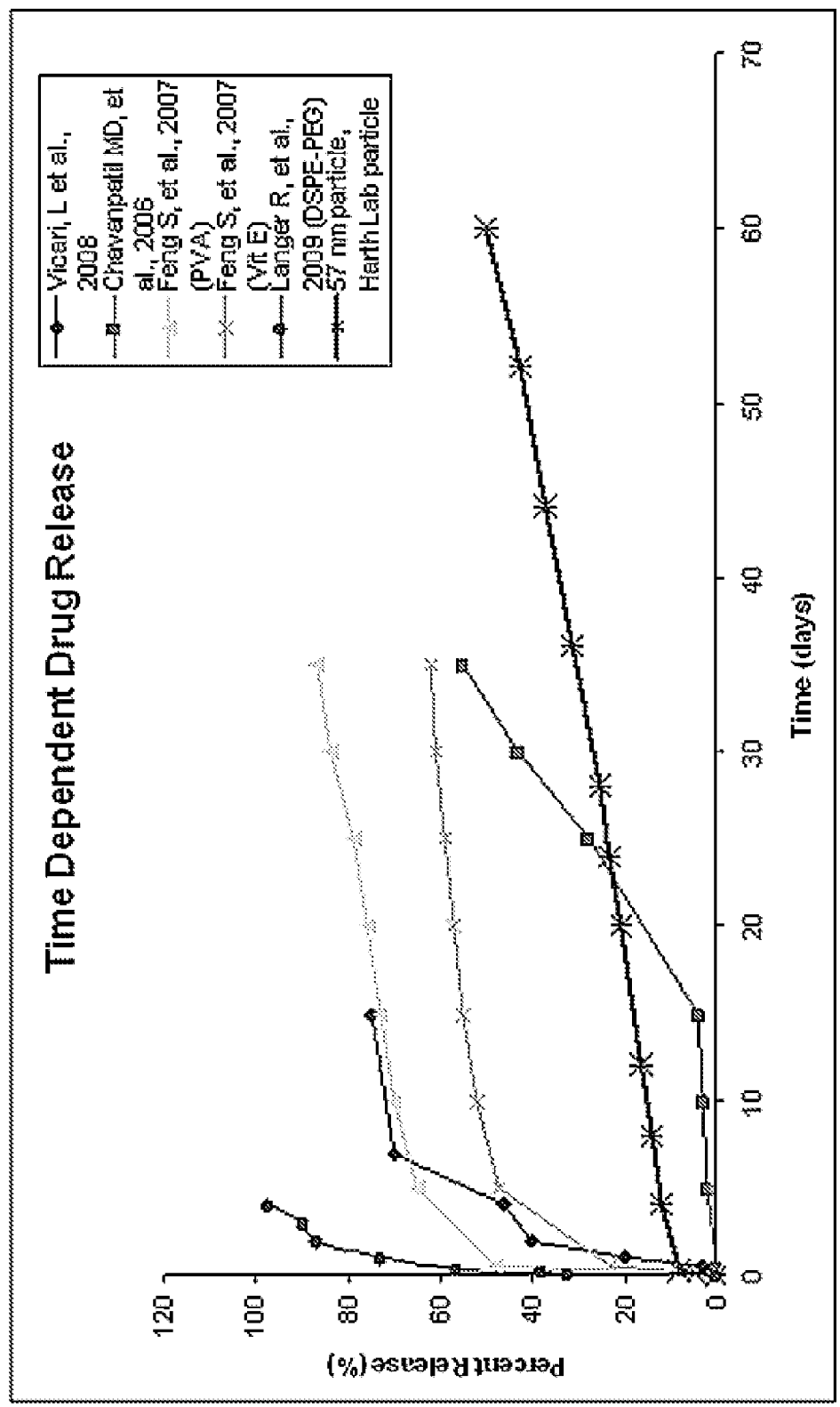
FIG. 8 shows drug release of disclosed nanoparticles in comparison to other polyester based nanoparticle systems.

In preparation for in vivo studies, in which the particle sizes can play an role in the interaction with the tumor vasculature, the influence of formulation and encapsulation of small molecule drugs to the diameter of the nanoparticles was evaluated. It was found that based on the 3-D cross-linked network structure, the size dimension slightly changes from 53 nm to 57 nm and indicates the conformity of the 3-D network structure upon encapsulation, as seen by transmission electron microscopy (TEM), (FIG. 5), with 2-8 times more drug incorporated compared to traditional polyester nanoparticle systems. Drug release profiles for conventional polyester based nanoparticle systems, compared to the disclosed nanoparticle systems, are shown in FIG. 8.

Figure 6:
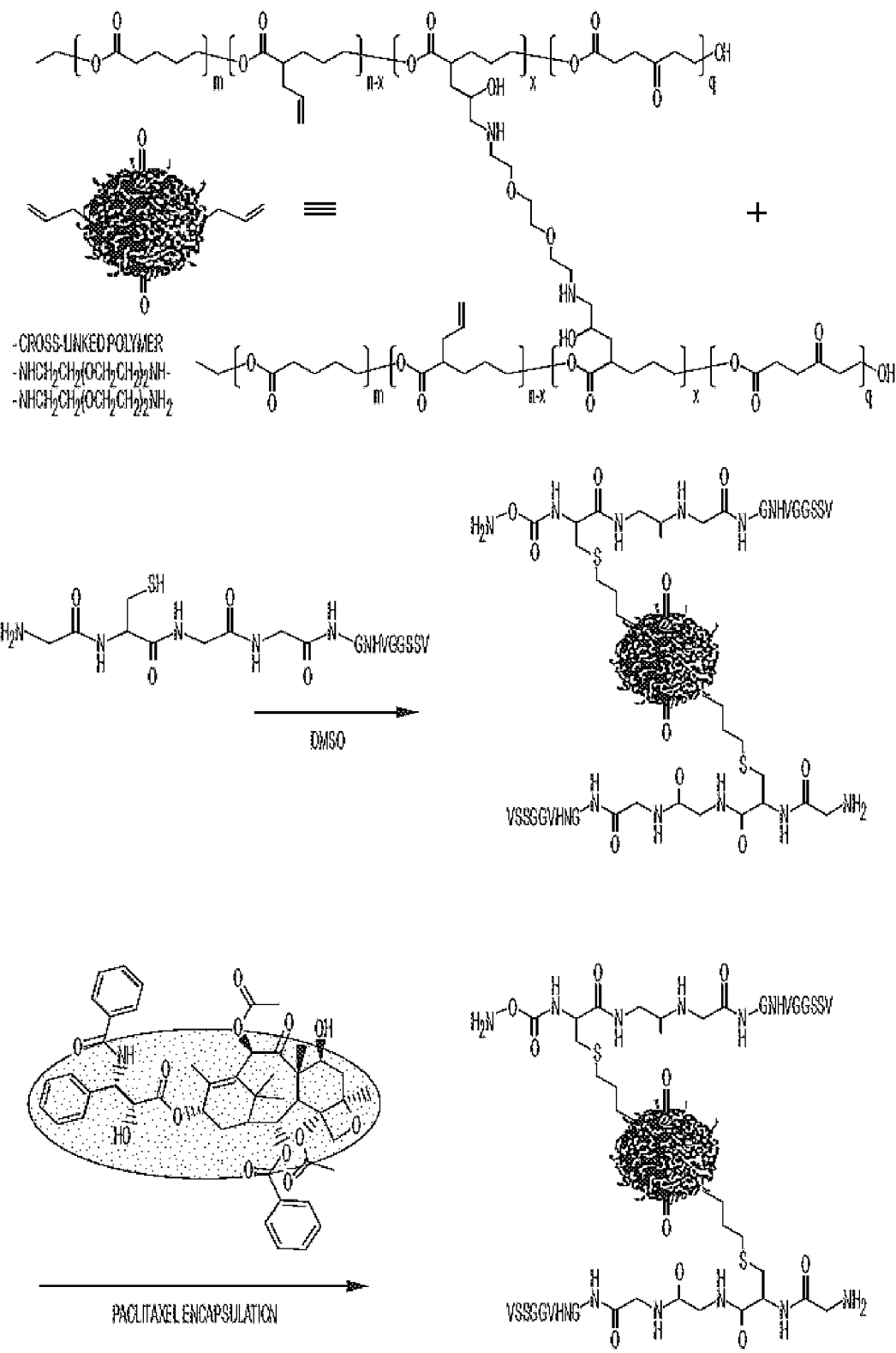
FIG. 6 shows synthesis of a targeted, water-soluble nanoparticle drug delivery system involving thiol-ene "click" chemistries and drug loading via developed emulsification process after post-modification.
Figure 7:
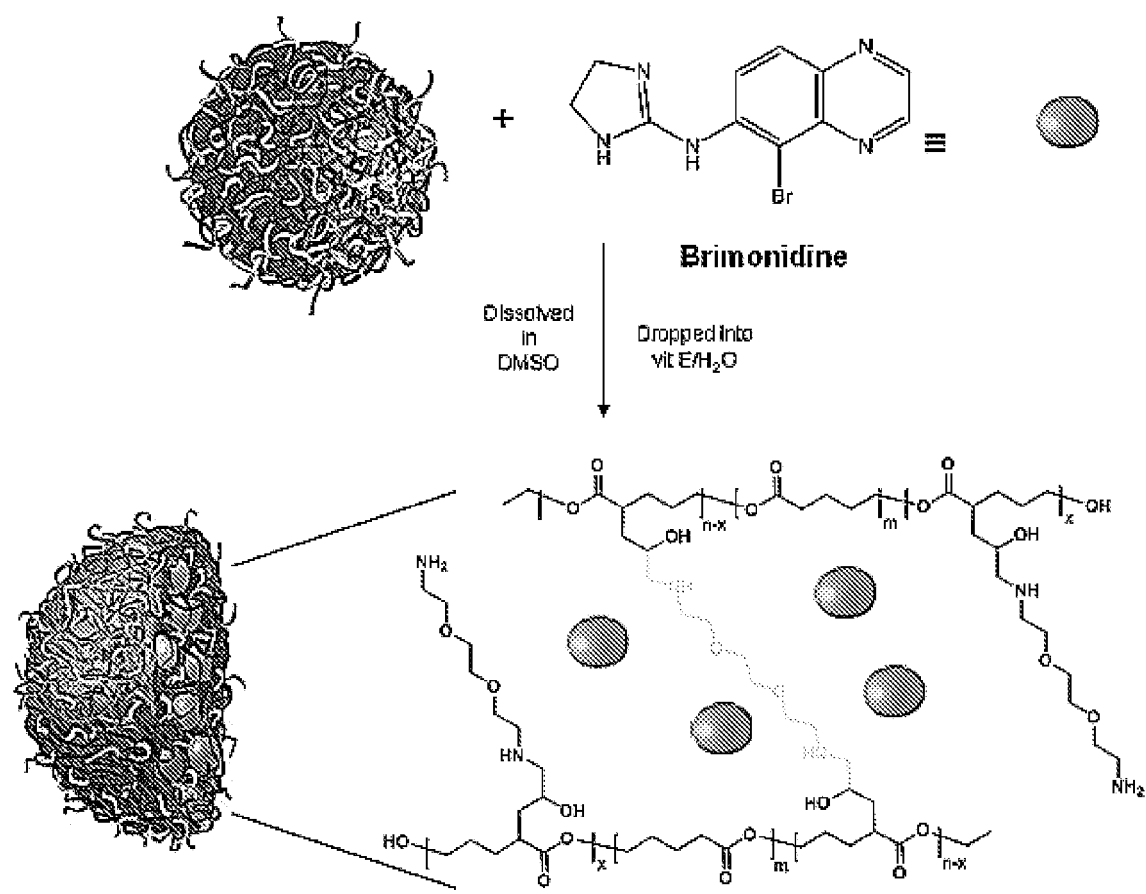
FIG. 7 shows encapsulation of brimonidine in nanoparticles.

Thus, the disclosed nanoparticle synthesis pathways allow for the introduction of functional groups, such as alkyne, allyl or keto functionalities, that are not affected by the cross-linking reactions and nanoparticle formation. In particular, thiol-ene "click" reactions allow for the conjugation of peptides with integrated cysteines added to the sequence near the N-terminus. Such mild reaction conditions do not require the addition of radical starters and use slightly elevated temperatures of 37° C. To synthesize the drug delivery systems, the linear poly(vl-evl-avl-opd) precursor was prepared, which was cross-linked with 2 equivalents of diamines per epoxide to form a nanoparticle of 53 nm in size. The remaining allyl groups were then functionalized with peptides to target radiated and nonradiated tumor vasculature, such as the reported peptides with recognition units HVGGSSV and cRGD, respectively (FIG. 6). The bioconjugates were analyzed via NMR, DLS and SLS and were then loaded with paclitaxel and formulated with vitamin E. Using UV-Vis, the loading capacity was found to be 11%, aiming for a 15% drug load.

Figure 9:
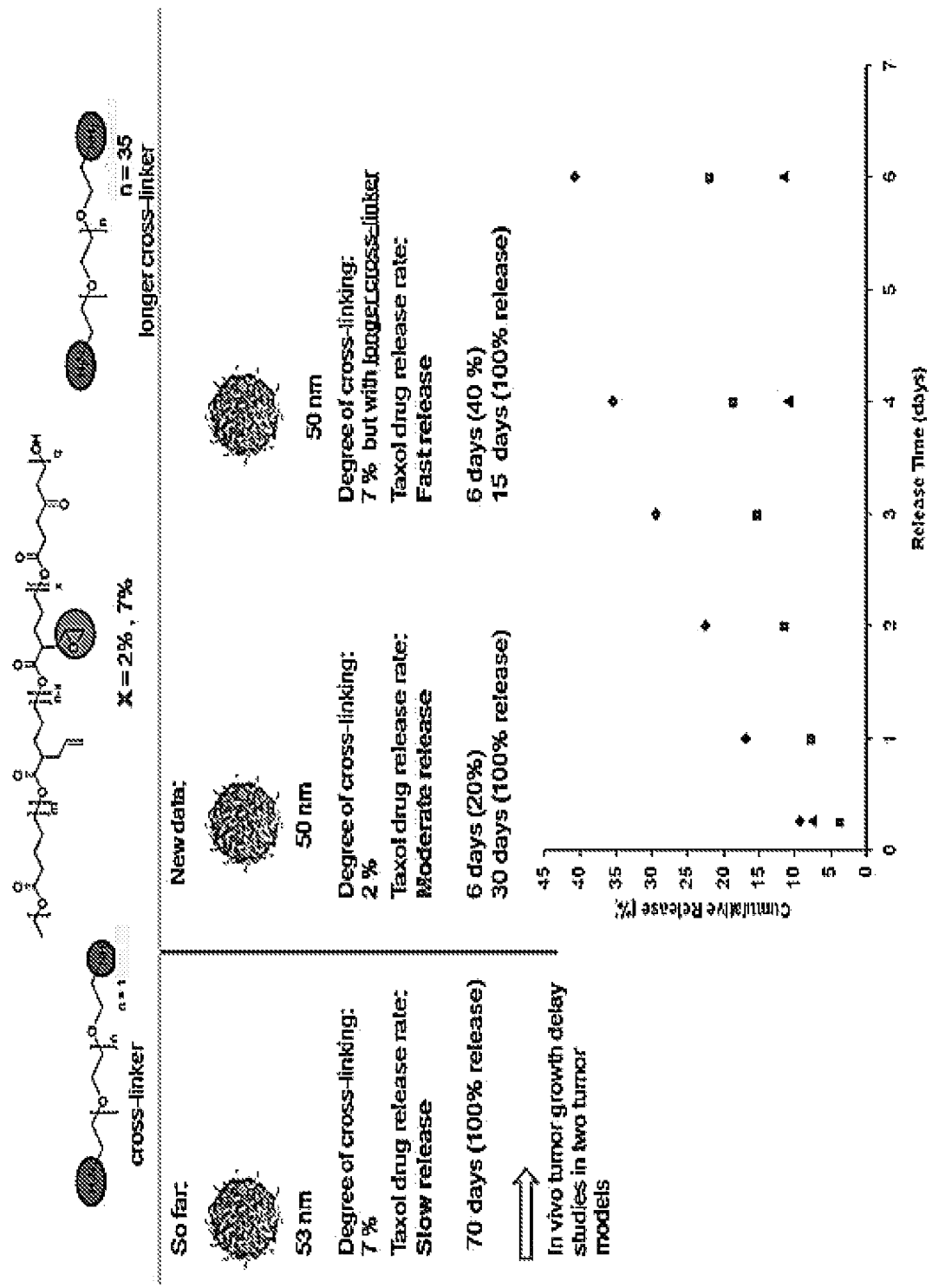
FIG. 9 shows synthesis and validation of optimized nanoparticles differentiated by size, release kinetics, incorporated drug, targeting parameter, and/or imaging modality.

It can also be demonstrated that the linear release kinetics are in fact adjustable. With decreasing cross-linking density, the drug molecule is released at a higher rate. By decreasing the cross-linking density (~50%), from 7% to 2%, the release rate increased by around 50%. These data point indicate that a 15% cross-linking can decrease the release by another 50% with 140 days for 100% release and would afford a very slow release rate. To afford a faster release of the drug molecule than the 2% cross-liking, a longer cross-linker (MW 2003) can be used to prepare a particle with a wider network architecture for an even faster release profile. With a 7% cross-linking density, 40% of the drug is released in 6 days. It is understood that with the decrease of the cross-linking density to 2%, the release can be increased to 3 days (40%). This is represented schematically in FIG. 9.

1. Polymers

It is understood that the disclosed polymers can be used in connection with the disclosed nanoparticles and disclosed methods. Unless stated to the contrary, the disclosed structures can be used in connection with the disclosed methods, the disclosed polymers, and the disclosed nanoparticles.

a. Epoxide-Functionalized Polymers

In one aspect, the invention relates to a polymer comprising at least one monomer residue having an optionally substituted structure represented by a formula:

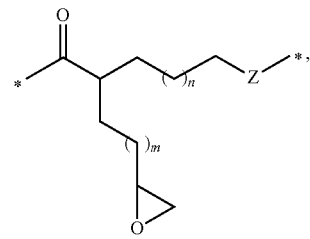

wherein Z is O or NR, wherein R is H or C1 to C6 alkyl; wherein m is an integer from 0 to 6; wherein n is an integer from 0 to 2; and wherein the monomer residue comprises less than about 10% by weight of the monomer residue of halogen selected from chlorine, bromine, and iodine. In further aspects, the monomer residue can comprise less than about 8%, less than about 5%, less than about 4%, less than about 3%, less than about 2%, or less than about 1% of halogen selected from chlorine, bromine, and iodine, by weight of the monomer residue.

In a further aspect, an epoxide-functionalized polymer can further comprise at least one monomer residue selected from a propargyl-functionalized monomer residue having an optionally substituted structure represented by a formula:

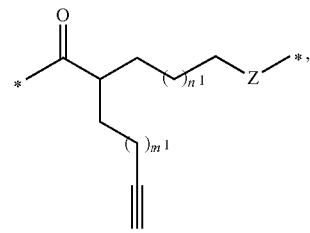

wherein Z is O or NR, wherein R is H or C1 to C6 alkyl, wherein $m^1$ is an integer from 0 to 6, and wherein $n^1$ is an integer from 0 to 2; a monomer residue having an optionally substituted structure represented by a formula:

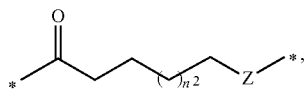

wherein Z is O or NR, wherein R is H or C1 to C6 alkyl, and wherein $n^2$ is an integer from 0 to 2; and a keto-functionalized monomer residue having an optionally substituted structure represented by a formula:

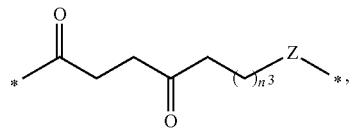

wherein Z is O or NR, wherein R is H or C1 to C6 alkyl, and wherein $n^3$ is an integer from 0 to 2.

In one aspect, Z is O. That is, the polymer residue can be a polyester residue. In a further aspect, the polymer is a polyester. In a further aspect, the polymer is a co-polyester.

In a further aspect, the Z is NR, wherein R is H or C1 to C6 alkyl. In one aspect, the polymer residue can be a polyamide residue. In a further aspect, the polymer is a polyamide. In a further aspect, the polymer is a co-polyamide. The alkyl can be optionally further substituted. R can be C1 to C6, C2 to C6, C1 to C5, C2 to C5, C1 to C4, C2 to C4, C1, C2, C3, C4, C5, or C6 alkyl.

In one aspect, the polymer comprises at least one monomer residue having an optionally substituted structure represented by a formula:

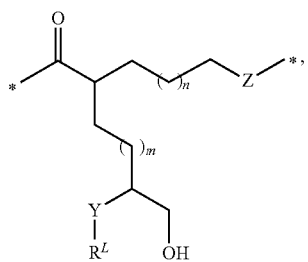

wherein Z is O or NR, wherein R is H or C1 to C6 alkyl; wherein Y is O, S, or NR, wherein R is H or C1 to C6 alkyl; wherein $R^L$ is selected from optionally substituted alkyl and optionally substituted alkoxylene; wherein m is an integer from 0 to 6; and wherein n is an integer from 0 to 2.

In a further aspect, the polymer further comprises at least one monomer residue selected from a propargyl-functionalized monomer residue having an optionally substituted structure represented by a formula:

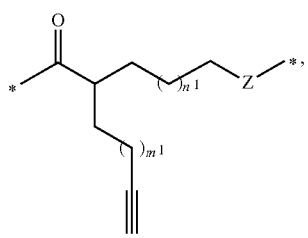

wherein Z is O or NR, wherein R is H or C1 to C6 alkyl, wherein $m^1$ is an integer from 0 to 6, and wherein $n^1$ is an integer from 0 to 2; a monomer residue having an optionally substituted structure represented by a formula:

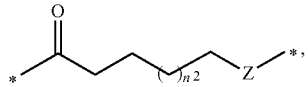

wherein Z is O or NR, wherein R is H or C1 to C6 alkyl, and wherein $n^2$ is an integer from 0 to 2; and a keto-functionalized monomer residue having an optionally substituted structure represented by a formula:

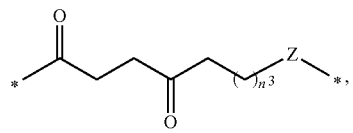

wherein Z is O or NR, wherein R is H or C1 to C6 alkyl, and wherein $n^3$ is an integer from 0 to 2.

In a further aspect, the polymer comprises an optionally substituted structure represented by a formula:

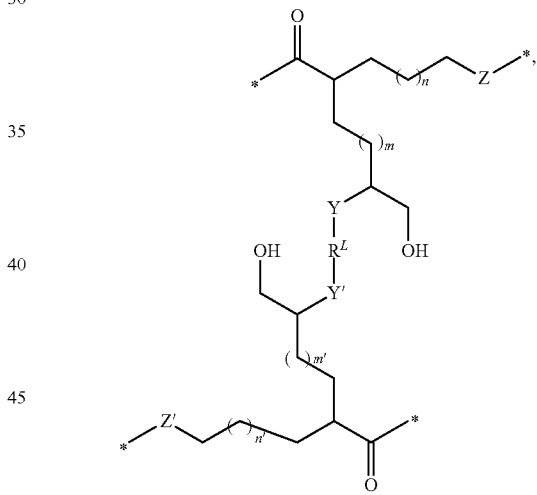

wherein m and m' are independently integers from 0 to 6; wherein n and n' are independently integers from 0 to 2; and wherein Z and Z' are independently O or NR, wherein R is H or C1 to C6 alkyl; wherein Y and Y' are independently O. S, or NR, wherein R is H or C1 to C6 alkyl; and wherein $R^L$ is selected from optionally substituted alkyl and optionally substituted alkoxylene.

In various aspects, m can be an integer from 0 to 6, from 1 to 6, from 0 to 5, from 1 to 5, from 0 to 4, from 1 to 4, from 0 to 3, from 1 to 3, from 0 to 2, from 1 to 2, 0, 1, 2, 3, 4, 5, or 6. In various aspects, m' can be an integer from 0 to 6, from 1 to 6, from 0 to 5, from 1 to 5, from 0 to 4, from to 4, from 0 to 3, from 1 to 3, from 0 to 2, from 1 to 2, 0, 1, 2, 3, 4, 5, or 6. In various aspects, m' can be an integer from 0 to 6, from 1 to 6, from 0 to 5, from 1 to 5, from 0 to 4, from 1 to 4, from 0 to 3, from 1 to 3, from 0 to 2, from 1 to 2, 0, 1, 2, 3, 4, 5, or 6.

In various aspects, n can be an integer from 0 to 2, from 1 to 2, from 0 to 1, 0, 1, or 2. In various aspects, n' can be an integer from 0 to 2, from 1 to 2, from 0 to 1, 0, 1, or 2. In various aspects, $n^1$ can be an integer from 0 to 2, from 1 to 2, from 0 to 1, 0, 1, or 2. In various aspects, $n^2$ can be an integer from 0 to 2, from 1 to 2, from 0 to 1, 0, 1, or 2. In various aspects, $n^3$ can be an integer from 0 to 2, from 1 to 2, from 0 to 1, 0, 1, or 2.

$R^L$ can be selected from optionally substituted alkyl and optionally substituted alkoxylene. Suitable alkyls include divalent organic radicals selected from ethyl, propyl, butyl, pentyl, hexyl, heptyl, octyl, decyl, dodecyl, hexadecyl, and higher alkyl. Suitable alkoxylene include divalent organic radicals selected from groups having a structure represented by a formula:

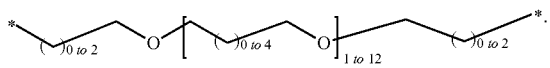

Further suitable alkoxylene include divalent organic radicals selected from groups having a structure represented by a formula:

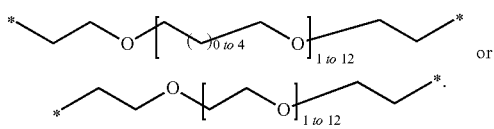

Further suitable alkoxylene include a divalent organic radical having a structure represented by a formula:

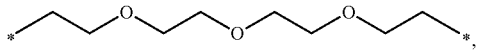

which can be derived from 2,2-(ethylenedioxy)bis(ethylamine).

The polymers and copolymers typically have a number average molecular weight (Mn) of from about 3500-4800 Daltons with a narrow polydispersity of from about 1.17 to about 1.27. It is understood that the molecular weight can be higher or lower and that one of skill in the art can readily manipulate reaction conditions to achieve a different desired molecular weight.

b. Multifunctional Polymers

In one aspect, a polymer can be a multifunctional polymer. That is, the polymer comprises monomer residues selected from two or more of an epoxide-functionalized monomer residue having an optionally substituted structure represented by a formula:

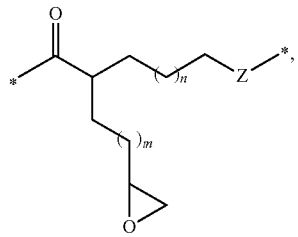

wherein Z is O or NR, wherein R is H or C1 to C6 alkyl; wherein m is an integer from 0 to 6; wherein n is an integer from 0 to 2; and a propargyl-functionalized monomer residue having an optionally substituted structure represented by a formula:

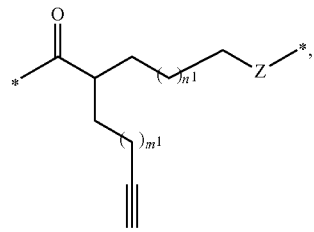

wherein Z is O or NR, wherein R is H or C1 to C6 alkyl, wherein $m^1$ is an integer from 0 to 6, and wherein $n^1$ is an integer from 0 to 2; and a keto-functionalized monomer residue having an optionally substituted structure represented by a formula:

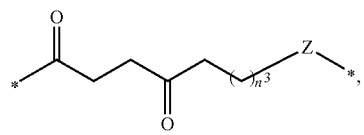

wherein Z is O or NR, wherein R is H or C1 to C6 alkyl, and wherein $n^3$ is an integer from 0 to 2.

In one aspect, the epoxide-functionalized monomer residue is present and comprises less than about 10% by weight of the monomer residue of halogen selected from chlorine, bromine, and iodine. In further aspects, the monomer residue can comprise less than about 8%, less than about 5%, less than about 4%, less than about 3%, less than about 2%, or less than about 1% of halogen selected from chlorine, bromine, and iodine, by weight of the monomer residue.

In a further aspect, the polymer further comprises at least one monomer residue having an optionally substituted structure represented by a formula:

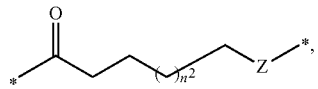

wherein Z is O or NR, wherein R is H or C1 to C6 alkyl, and wherein $n^2$ is an integer from 0 to 2.

In one aspect, a polymer comprises at least one monomer residue having an optionally substituted structure represented by a formula:

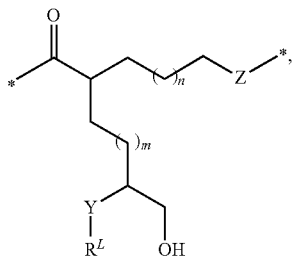

wherein Z is O or NR, wherein R is H or C1 to C6 alkyl, wherein Y is O, S, or NR, wherein R is H or C1 to C6 alkyl, wherein $R^L$ is selected from optionally substituted alkyl and optionally substituted alkoxylene, wherein m is an integer from 0 to 6, and wherein n is an integer from 0 to 2; and one or more of:
a propargyl-functionalized monomer residue having an optionally substituted structure represented by a formula:

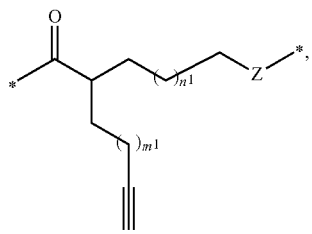

wherein Z is O or NR, wherein R is H or C1 to C6 alkyl, wherein $m^1$ is an integer from 0 to 6, and wherein $n^1$ is an integer from 0 to 2; and
a keto-functionalized monomer residue having an optionally substituted structure represented by a formula:

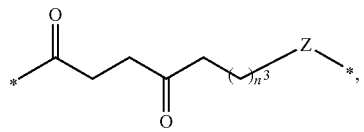

wherein Z is O or NR, wherein R is H or C1 to C6 alkyl, and wherein $n^3$ is an integer from 0 to 2. In a further aspect, the polymer further comprises at least one monomer residue having an optionally substituted structure represented by a formula:

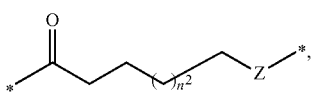

wherein Z is O or NR, wherein R is H or C1 to C6 alkyl, and wherein $n^2$ is an integer from 0 to 2. In one aspect, the at least one monomer residue has an optionally substituted structure represented by a formula:

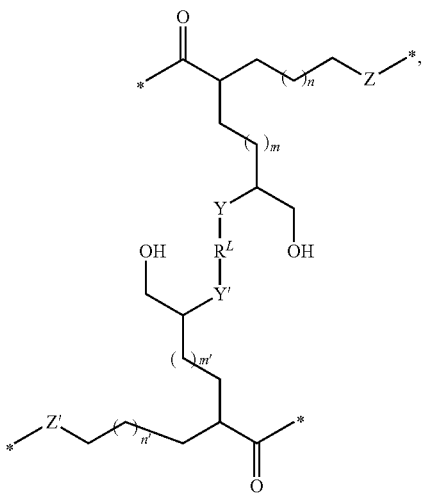

wherein m and m' are independently integers from 0 to 6; wherein n and n' are independently integers from 0 to 2; and wherein Z and Z' are independently O or NR, wherein R is H or C1 to C6 alkyl; wherein Y and Y' are independently O, S, or NR, wherein R is H or C1 to C6 alkyl; and wherein $R^L$ is selected from optionally substituted alkyl and optionally substituted alkoxylene.

In one aspect, at least one monomer residue has an optionally substituted structure represented by a formula:

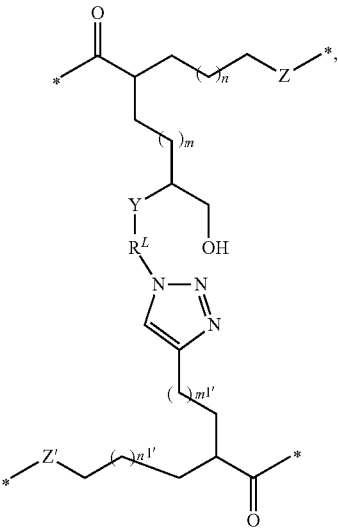

wherein m and $m^{1'}$ are independently integers from 0 to 6; wherein n and $n^{1'}$ are independently integers from 0 to 2; and wherein Z and Z' are independently O or NR, wherein R is H or C1 to C6 alkyl; wherein Y is O, S, or NR, wherein R is H or C1 to C6 alkyl; and wherein $R^L$ is selected from optionally substituted alkyl and optionally substituted alkoxylene.

In various aspects, m can be an integer from 0 to 6, from 1 to 6, from 0 to 5, from 1 to 5, from 0 to 4, from 1 to 4, from 0 to 3, from 1 to 3, from 0 to 2, from 1 to 2, 0, 1, 2, 3, 4, 5, or 6. In various aspects, m' can be an integer from 0 to 6, from 1 to 6, from 0 to 5, from 1 to 5, from 0 to 4, from 1 to 4, from 0 to 3, from 1 to 3, from 0 to 2, from 1 to 2, 0, 1, 2, 3, 4, 5, or 6. In various aspects, m' can be an integer from 0 to 6, from 1 to 6, from 0 to 5, from 1 to 5, from 0 to 4, from 1 to 4, from 0 to 3, from 1 to 3, from 0 to 2, from 1 to 2, 0, 1, 2, 3, 4, 5, or 6. In various aspects, m' can be an integer from 0 to 6, from 1 to 6, from 0 to 5, from 1 to 5, from 0 to 4, from 1 to 4, from 0 to 3, from 1 to 3, from 0 to 2, from 1 to 2, 0, 1, 2, 3, 4, 5, or 6.

In various aspects, n can be an integer from 0 to 2, from 1 to 2, from 0 to 1, 0, 1, or 2. In various aspects, n' can be an integer from 0 to 2, from 1 to 2, from 0 to 1, 0, 1, or 2. In various aspects, $n^1$ can be an integer from 0 to 2, from 1 to 2, from 0 to 1, 0, 1, or 2. In various aspects, $n^{1'}$ can be an integer from 0 to 2, from 1 to 2, from 0 to 1, 0, 1, or 2. In various aspects, $n^2$ can be an integer from 0 to 2, from 1 to 2, from 0 to 1, 0, 1, or 2. In various aspects, $n^3$ can be an integer from 0 to 2, from 1 to 2, from 0 to 1, 0, 1, or 2.

$R^L$ can be selected from optionally substituted alkyl and optionally substituted alkoxylene. Suitable alkyls include divalent organic radicals selected from ethyl, propyl, butyl, pentyl, hexyl, heptyl, octyl, decyl, dodecyl, hexadecyl, and higher alkyl. Suitable alkoxylene include divalent organic radicals selected from groups having a structure represented by a formula:

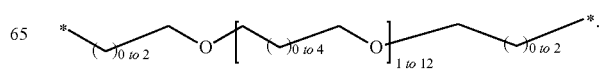

Further suitable alkoxylene include divalent organic radicals selected from groups having a structure represented by a formula:

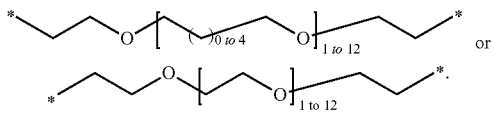

Further suitable alkoxylene include a divalent organic radical having a structure represented by a formula:

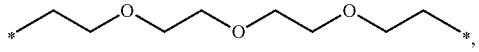

which can be derived from 2,2-(ethylenedioxy)bis(ethylamine) or 2,2-(ethylenedioxy)bis(ethylazide).

In one aspect, a polymer can comprise at least one monomer residue having an optionally substituted structure represented by a formula:

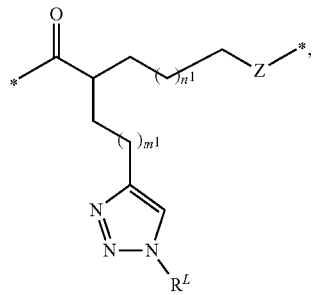

wherein Z is O or NR, wherein R is H or C1 to C6 alkyl, wherein $R^L$ is selected from optionally substituted alkyl and optionally substituted alkoxylene, wherein m is an integer from 0 to 6, and wherein $n^1$ is an integer from 0 to 2; and one or more of an epoxide-functionalized monomer residue having an optionally substituted structure represented by a formula:

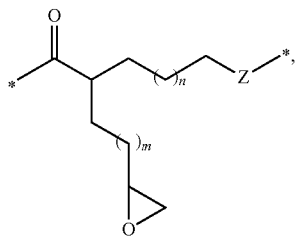

wherein Z is O or NR, wherein R is H or C1 to C6 alkyl; wherein m is an integer from 0 to 6; wherein n is an integer from 0 to 2; and a keto-functionalized monomer residue having an optionally substituted structure represented by a formula:

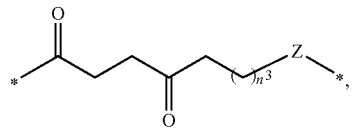

wherein Z is O or NR, wherein R is H or C1 to C6 alkyl, and wherein $n^3$ is an integer from 0 to 2. In a further aspect, the epoxide-functionalized monomer residue is present and comprises less than about 10% by weight of the monomer residue of halogen selected from chlorine, bromine, and iodine.

In one aspect, the polymer further comprises at least one monomer residue having an optionally substituted structure represented by a formula:

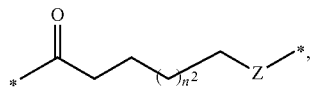

wherein Z is O or NR, wherein R is H or C1 to C6 alkyl, and wherein $n^2$ is an integer from 0 to 2.

In a further aspect, at least one monomer residue has an optionally substituted structure represented by a formula:

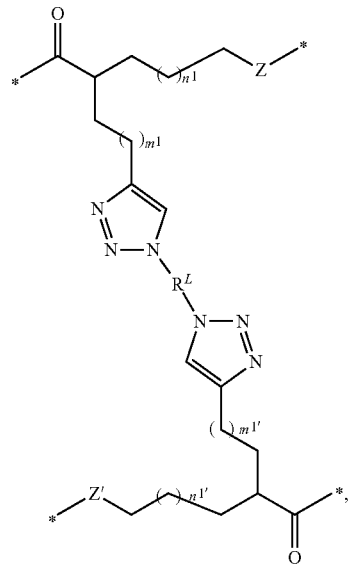

wherein $m^1$ and $m^{1'}$ are independently integers from 0 to 6; wherein $n^1$ and $n^{1'}$ are independently integers from 0 to 2; and wherein Z and Z' are independently O or NR, wherein R is H or C1 to C6 alkyl; and wherein $R^L$ is selected from optionally substituted alkyl and optionally substituted alkoxylene.

In one aspect, at least one monomer residue has an optionally substituted structure represented by a formula:

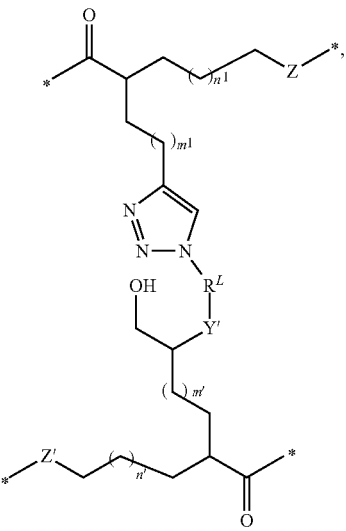

wherein $m^1$ and m' are independently integers from 0 to 6; wherein $n^1$ and n' are independently integers from 0 to 2; and wherein Z and Z' are independently O or NR, wherein R is H or C1 to C6 alkyl; and wherein Y' is O, S, or NR, wherein R is H or C1 to C6 alkyl; wherein $R^L$ is selected from optionally substituted alkyl and optionally substituted alkoxylene.

2. Nanoparticles

It is understood that the disclosed nanoparticles can be used in connection with the disclosed polymers and disclosed methods. Unless stated to the contrary, the disclosed structures can be used in connection with the disclosed methods, the disclosed polymers, and the disclosed nanoparticles.

In one aspect, the invention relates to a degradable polymeric nanoparticle comprising at least one monomer residue having an optionally substituted structure represented by a formula:

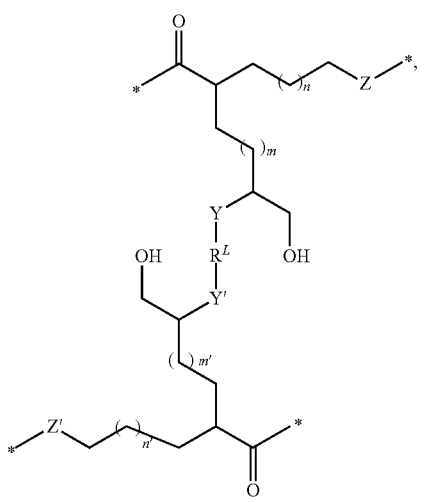

wherein m and m' are independently integers from 0 to 6; wherein n and n' are independently integers from 0 to 2; and wherein Z and Z' are independently O or NR, wherein R is H or C1 to C6 alkyl; wherein Y and Y' are independently O, S, or NR, wherein R is H or C1 to C6 alkyl; and wherein $R^L$ is selected from optionally substituted alkyl and optionally substituted alkoxylene, wherein the nanoparticle has a particle size of from about 5 nm to about 850 nm.

In one aspect, the nanoparticle further comprises at least one monomer residue selected from a propargyl-functionalized monomer residue having an optionally substituted structure represented by a formula:

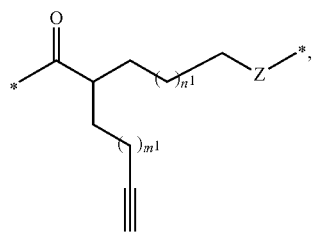

wherein Z is O or NR, wherein R is H or C1 to C6 alkyl, wherein $m^1$ is an integer from 0 to 6, and wherein $n^1$ is an integer from 0 to 2; a keto-functionalized monomer residue having an optionally substituted structure represented by a formula:

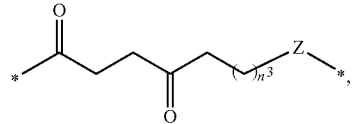

wherein Z is O or NR, wherein R is H or C1 to C6 alkyl, and wherein $n^3$ is an integer from 0 to 2; and a monomer residue having an optionally substituted structure represented by a formula:

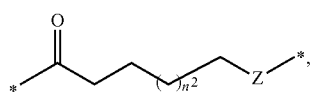

wherein Z is O or NR, wherein R is H or C1 to C6 alkyl, and wherein $n^2$ is an integer from 0 to 2. In a further aspect, Z and Z' are O.

In one aspect, the nanoparticle further comprises at least one epoxide-functionalized monomer residue having an optionally substituted structure represented by a formula:

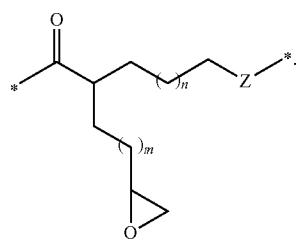

In a further aspect, the nanoparticle further comprises at least one functionalized monomer residue having an optionally substituted structure represented by a formula:

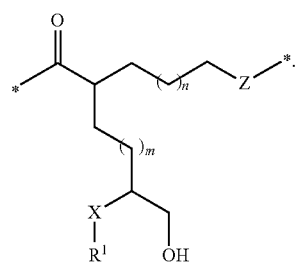

wherein X is OH, SH, $NH_2$, or NHR, wherein R is H or C1 to C6 alkyl; and wherein $R^1$ is an optionally substituted organic radical comprising 1 to 24 carbon atoms.

In a further aspect, $R^1$ is further substituted with at least one biologically active agent, at least one pharmaceutically active agent, and/or at least one imaging moiety.

In one aspect, the nanoparticle further comprises at least one nucleophile-functionalized monomer residue having an optionally substituted structure represented by a formula:

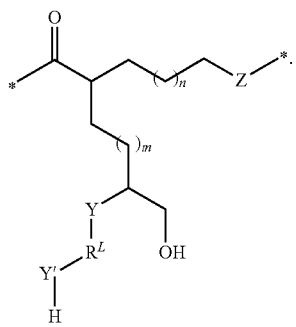

In a further aspect, the nanoparticle further comprises at least one functionalized monomer residue having an optionally substituted structure represented by a formula:

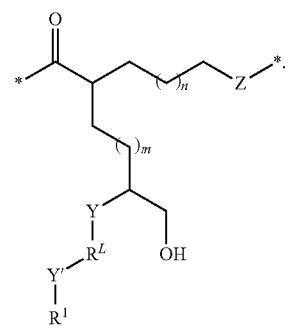

wherein $R^1$ is an optionally substituted organic radical comprising 1 to 24 carbon atoms.

In a further aspect, $R^1$ is further substituted with at least one biologically active agent, at least one pharmaceutically active agent, and/or at least one imaging moiety.

In one aspect, the invention relates to a degradable polymeric nanoparticle comprising at least one monomer residue having an optionally substituted structure represented by a formula:

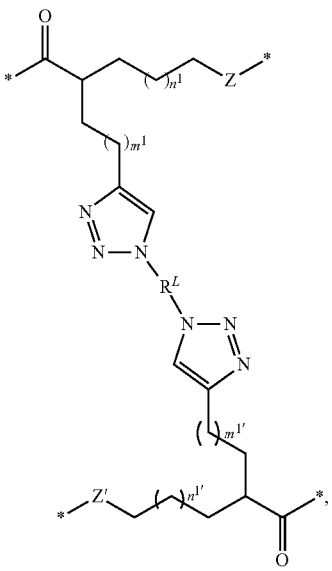

wherein $m^1$ and $m^{1'}$ are independently integers from 0 to 6; wherein $n^1$ and $n^{1'}$ are independently integers from 0 to 2; and wherein Z and Z' are independently O or NR, wherein R is H or C1 to C6 alkyl; and wherein $R^L$ is selected from optionally substituted alkyl and optionally substituted alkoxylene, wherein the nanoparticle has a particle size of from about 5 nm to about 850 nm.

In a further aspect, the nanoparticle further comprises at least one monomer residue selected from: an epoxide-functionalized monomer residue having an optionally substituted structure represented by a formula:

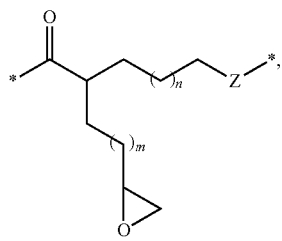

wherein Z is O or NR, wherein R is H or C1 to C6 alkyl; wherein m is an integer from 0 to 6; wherein n is an integer from 0 to 2; a keto-functionalized monomer residue having an optionally substituted structure represented by a formula:

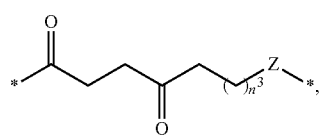

wherein Z is O or NR, wherein R is H or C1 to C6 alkyl, and wherein $n^3$ is an integer from 0 to 2; and a monomer residue having an optionally substituted structure represented by a formula:

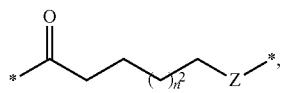

wherein Z is O or NR, wherein R is H or C1 to C6 alkyl, and wherein $n^2$ is an integer from 0 to 2. In a further aspect, Z and Z' are O.

In a further aspect, the nanoparticle further comprises at least one propargyl-functionalized monomer residue having an optionally substituted structure represented by a formula:

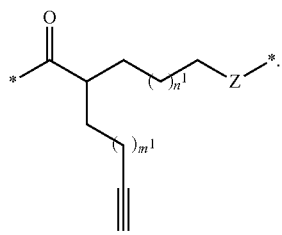

In a further aspect, the nanoparticle further comprises at least one functionalized monomer residue having an optionally substituted structure represented by a formula:

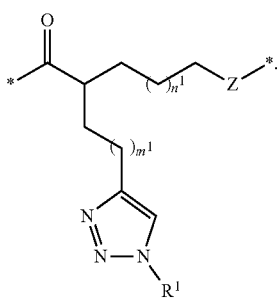

wherein $R^1$ is an optionally substituted organic radical comprising 1 to 24 carbon atoms. In a further aspect, $R^1$ is further substituted with at least one biologically active agent, at least one pharmaceutically active agent, and/or at least one imaging moiety.

In a further aspect, the nanoparticle further comprises at least one azide-functionalized monomer residue having an optionally substituted structure represented by a formula:

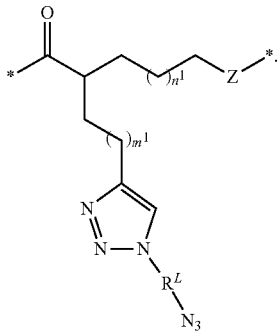

In a further aspect, the nanoparticle further comprises at least one functionalized monomer residue having an optionally substituted structure represented by a formula:

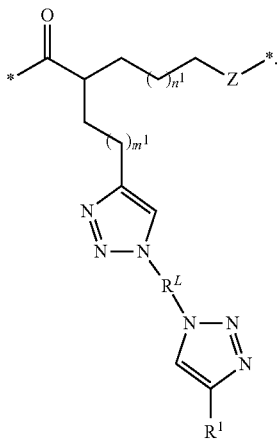

wherein $R^1$ is an optionally substituted organic radical comprising 1 to 24 carbon atoms. In a further aspect, $R^1$ is further substituted with at least one biologically active agent, at least one pharmaceutically active agent, and/or at least one imaging moiety.

In one aspect, the invention relates to crosslinked degradable nanoparticles having a polyester backbone and one or more crosslinks having a structure selected from:

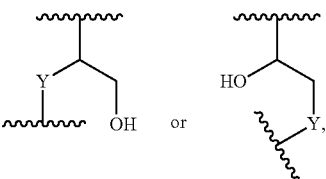

wherein Y is O, S, or N—R, wherein R is C1-C4 alkyl;

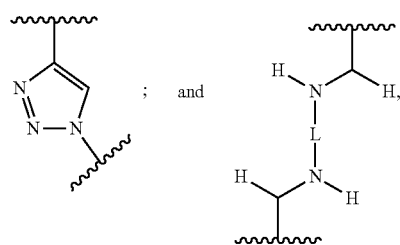

wherein L is a divalent alkyl chain or alkyloxyalkyl chain.

In a further aspect, the one or more crosslinks are produced by a nucleophilic epoxide ring opening reaction. In a further aspect, the one or more crosslinks are produced by a reductive amination reaction. In a further aspect, the one or more crosslinks are produced by an azide alkyne cycloaddition.

In a further aspect, the nanoparticle further comprises one or more biologically active agents or pharmaceutically active agents.

In a further aspect, the nanoparticle is produced by crosslinking a polymer comprising at least one monomer residue having an optionally substituted structure represented by a formula:

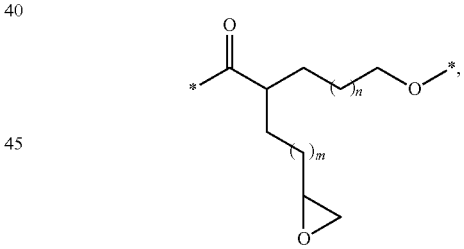

wherein m is an integer from 0 to 6, and wherein n is an integer from 0 to 2; or at least one propargyl-functionalized monomer residue having an optionally substituted structure represented by a formula:

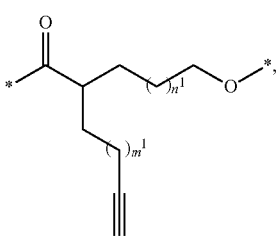

wherein $m^1$ is an integer from 0 to 6, and wherein $n^1$ is an integer from 0 to 2; or at least one monomer residue having an optionally substituted structure represented by a formula:

wherein $n^2$ is an integer from 0 to 2; or at least one keto-functionalized monomer residue having an optionally substituted structure represented by a formula:

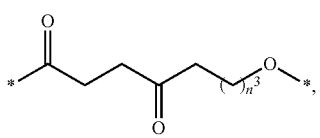

wherein $n^3$ is an integer from 0 to 2.

In one aspect, the invention relates to compositions comprising a degradable polyester nanoparticle and, encapsulated therein, a biologically active agent, a pharmaceutically active agent, or an imaging agent. In a further aspect, the biologically active agent is encapsulated within the nanoparticle. In a further aspect, the pharmaceutically active agent is encapsulated within the nanoparticle. In a further aspect, the imaging agent is encapsulated within the nanoparticle.

In a further aspect, the degradable polyester nanoparticle comprises a crosslinked degradable nanoparticle having a polyester backbone and one or more crosslinks having a structure selected from:

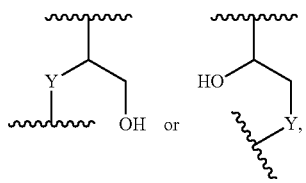

wherein Y is O, S, or N—R, wherein R is C1-C4 alkyl;

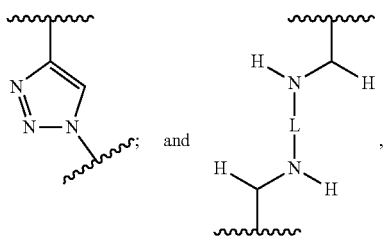

wherein L is a divalent alkyl chain or alkyloxyalkyl chain.

G. Preparation Methods

It is understood that the disclosed methods can be used in connection with the disclosed polymers and disclosed nanoparticles. Unless stated to the contrary, the disclosed structures can be used in connection with the disclosed methods, the disclosed polymers, and the disclosed nanoparticles.

1. Methods of Making Polymer

To address the deficiencies of conventional nanoparticle compositions and methods, the availability of novel functional polyesters that allow orthogonal modification approaches was addressed. Additionally, controlled chain cross-linking strategies for obtaining distinct nanoparticles in a variety of nanoscopic dimensions are disclosed. In contrast to investigating emulsification-solvent techniques [Hans, M. L.; Lowman, A. M. Curr. Opin. Solid State Mater. Sci. 2002, 6, 319-327.] or emulsion diffusion methods [Kallinteri, P.; Higgins, S.; Hutcheon, G. A.; St. Pourcain, C. B.; Garnett, M. C. Biomacromolecules 2005, 6, 1885-1894.] that need surfactants or salts, the disclosed methods and compositions involve controlled cross-linking techniques.

A clean and non-toxic cross-linking entity can be provided from epoxide groups that react with dinucleophiles (e.g., diamines) to form alkane —OH groups. While this crosslinking unit has been employed to form acrylate based microparticles [Burke, S. K.; Slatopolsky, E. A.; Goldberg, D. I., Nephrol. Dial. Transplant. 1997, 12, (8), 1640-1644.], it has been never investigated in the formation of degradable nanoparticles due to the lack of suitable linear precursors.

Figure 10:
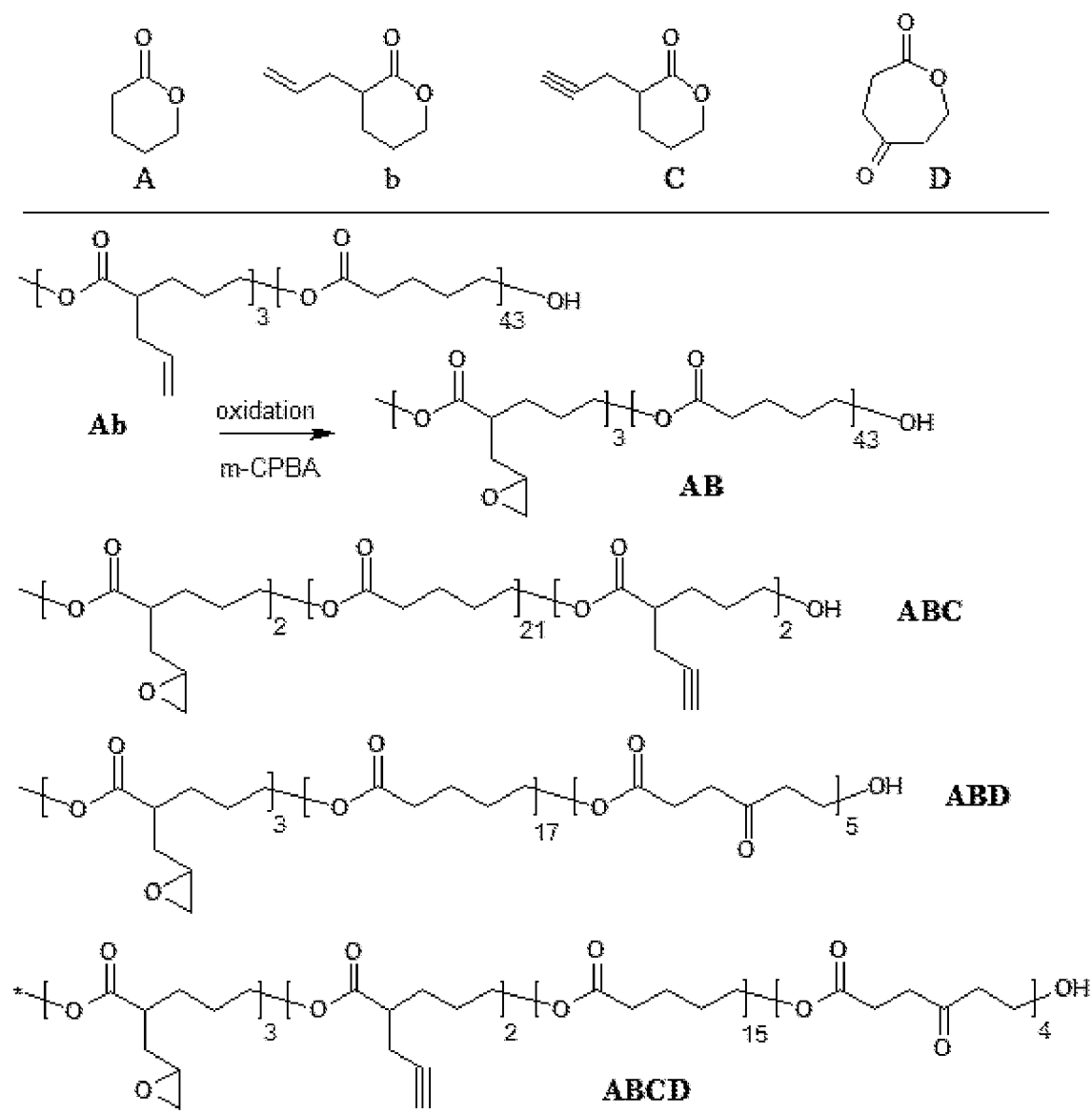
FIG. 10 shows multifunctional linear polyester precursors with epoxide cross-linking entity.

The epoxide entity for the formation of discrete cross-linked nanoparticles can be integrated by polymerization of a low molecular weight linear copolymer, Ab, with pendant allyl groups. See FIG. 10. Pendant allyl groups represent valuable intermediates to many functional groups and can be incorporated into the polymer backbone by copolymerizing α-allyl-δ-valerolactone, (b), and commercially available δ-valerolactone, (A), via ring-opening polymerization (ROP). [Parrish, B.; Quansah, J. K.; Emrick, T. J. Polym. Sci. Part A: Polym. Chem. 2002, 40, 1983-1990.] Upon copolymerization, the pendant allyl groups can be oxidized by a Baeyer-Villiger oxidation with meta-chloroperbenzoic acid (m-CPBA) to convert the double bonds to epoxide rings, which then became a coupling group in the preparation of the nanoparticles. [(a) Mecerreyes, D.; Miller, R. D.; Hedrick, J. L.; Detrembleur, C.; Jerome, R. J. Polym. Sci. Part A: Polym. Chem. 2000, 38, 870-875. (b) Latere, J. P.; Lecomte, P.; Dubois, P.; Jérôme, R. Macromolecules 2002, 35, 7857-7859.] To introduce additional functional groups into the nanoparticle, additional monomers can be synthesized, for example α-propargyl-δ-valerolactone, (C), and 2-oxepane-1,5-dione, (D). These monomers can then be individually copolymerized with (B) and δ-valerolactone, (A), in a similar manner as Ab, to give rise to linear polyesters with additional propargyl or keto functionalities respectively. To increase the number of functionalities that allow orthogonal modification approaches, (C) and (D) were copolymerized together with (b) and δ-valerolactone (A), as summarized in FIG. 10. The copolymers were typically obtained in molecular weight ranges of 3500-4800 Da with narrow polydispersities of 1.17-1.27.

In one aspect, the invention relates to a method of preparing a polymer comprising the step of copolymerizing a mixture of two or more of an alkene-functionalized monomer providing a residue having an optionally substituted structure represented by a formula:

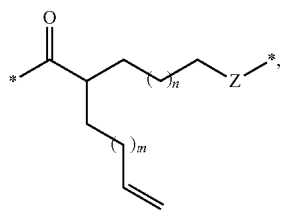

wherein Z is O or NR, wherein R is H or C1 to C6 alkyl; wherein m is an integer from 0 to 6; wherein n is an integer from 0 to 2; a propargyl-functionalized monomer providing a residue having an optionally substituted structure represented by a formula:

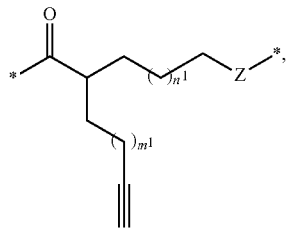

wherein Z is O or NR, wherein R is H or C1 to C6 alkyl, wherein $m^1$ is an integer from 0 to 6, and wherein $n^1$ is an integer from 0 to 2; and a keto-functionalized monomer providing a residue having an optionally substituted structure represented by a formula:

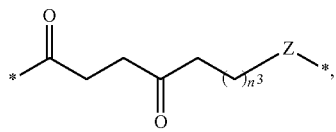

wherein Z is O or NR, wherein R is H or C1 to C6 alkyl, and wherein $n^3$ is an integer from 0 to 2.

In a further aspect, the mixture further comprises at least one monomer providing a residue having an optionally substituted structure represented by a formula:

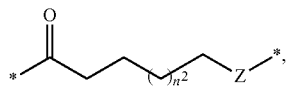

wherein Z is O or NR, wherein R is H or C1 to C6 alkyl, and wherein $n^2$ is an integer from 0 to 2.

In one aspect, the alkene-functionalized monomer is present and the method further comprises the step of oxidizing the resultant polymer to provide an epoxide-functionalized monomer residue having an optionally substituted structure represented by a formula:

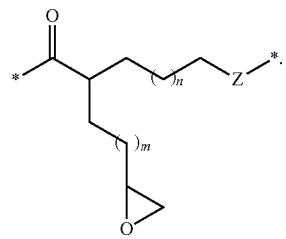

In a further aspect, the alkene-functionalized monomer is present and has an optionally substituted structure represented by a formula:

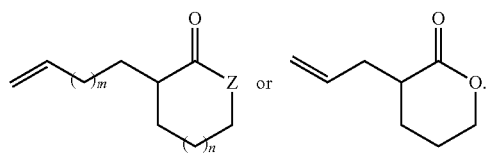

In a further aspect, the propargyl-functionalized monomer is present and has an optionally substituted structure represented by a formula:

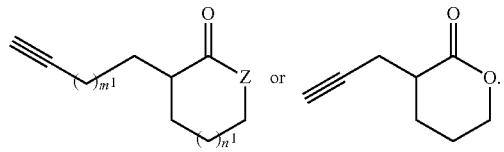

In a further aspect, the keto-functionalized monomer is present and has an optionally substituted structure represented by a formula:

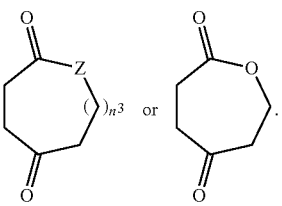

In a further aspect, the monomer providing a residue having an optionally substituted structure represented by a formula:

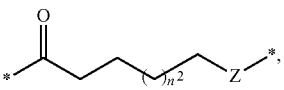

has an optionally substituted structure represented by a formula:

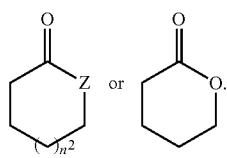

In one aspect, the invention relates to a method of preparing an epoxide-functionalized polymer comprising the step of oxidizing a polymer having at least one monomer residue having an optionally substituted structure represented by a formula:

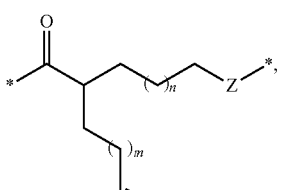

wherein Z is O or NR, wherein R is H or C1 to C6 alkyl, wherein m is an integer from 0 to 6, and wherein n is an integer from 0 to 2.

In a further aspect, the polymer further comprises at least one monomer residue selected from:

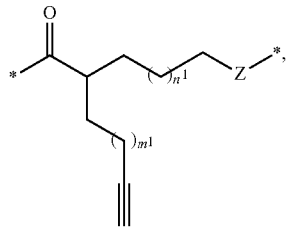

wherein Z is O or NR, wherein R is H or C1 to C6 alkyl, wherein $m^1$ is an integer from 0 to 6, and wherein $n^1$ is an integer from 0 to 2;

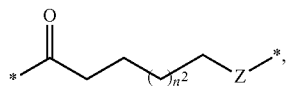

wherein Z is O or NR, wherein R is H or C1 to C6 alkyl, wherein $n^2$ is an integer from 0 to 2; and

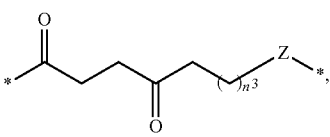

wherein $n^3$ is an integer from 0 to 2.

In a further aspect, at least one monomer residue has an optionally substituted structure represented by a formula:

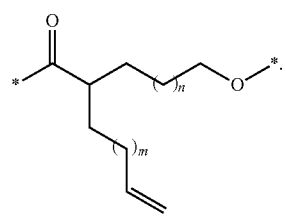

wherein m is an integer from 0 to 6, and wherein n is an integer from 0 to 2. For example, in one aspect, m is 1, and n is 0, providing an optionally substituted structure represented by a formula:

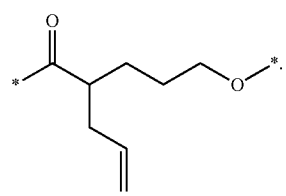

In a further aspect, the epoxide-functionalized polymer has an optionally substituted structure represented by a formula:

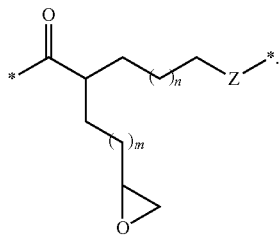

2. Methods of Crosslinking

In one aspect, the invention relates to a method of crosslinking a polymer comprising the step of reacting a polymer comprising at least one monomer residue selected from an epoxide-functionalized monomer residue having an optionally substituted structure represented by a formula:

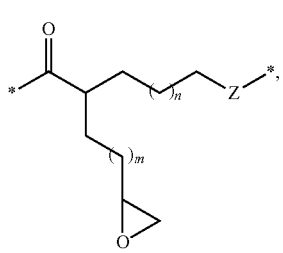

wherein Z is O or NR, wherein R is H or C1 to C6 alkyl; wherein m is an integer from 0 to 6; wherein n is an integer from 0 to 2; and a propargyl-functionalized monomer residue having an optionally substituted structure represented by a formula:

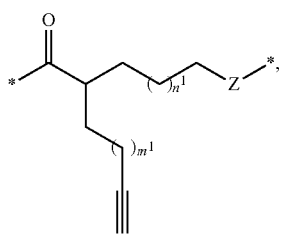

wherein Z is O or NR, wherein R is H or C1 to C6 alkyl, wherein $m^1$ is an integer from 0 to 6, and wherein n' is an integer from 0 to 2; with a cross-linker having a structure represented by a formula X—$R^L$—X', wherein X and X' are independently $N_3$, OH, SH, $NH_2$, or NHR, wherein R is H or C1 to C6 alkyl, and wherein $R^L$ is selected from optionally substituted alkyl and optionally substituted alkoxylene.

In one aspect, the linker groups can be bis-nucleophilic (e.g., diamine) compounds derived from alkylene oxides (e.g., diamino poly(ethylene oxides)) and/or alkyls (e.g., 1,8-diaminooctane; Jeffamines) and their derivatives.

In a further aspect, the linker groups can be thiols. For example, the dinucleophile can have a structure X—$R^L$—X', wherein X and X' are each SH, wherein R is H or C1 to C6 alkyl, and wherein $R^L$ is selected from optionally substituted alkyl, optionally substituted alkoxylene, and optionally substituted esters.

Thiols suitable for crosslinking include mono- and di-thiol analogues of compounds derived from alkylene oxides (e.g., diamino poly(ethylene oxides)) and/or alkyls (e.g., 1,8-diaminooctane; Jeffamines) and their derivatives. Other suitable dithiols for cross-linking include:

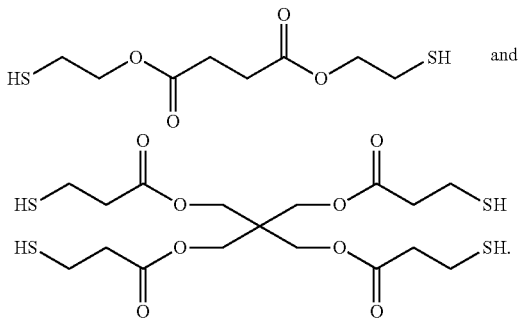

Figure 59:
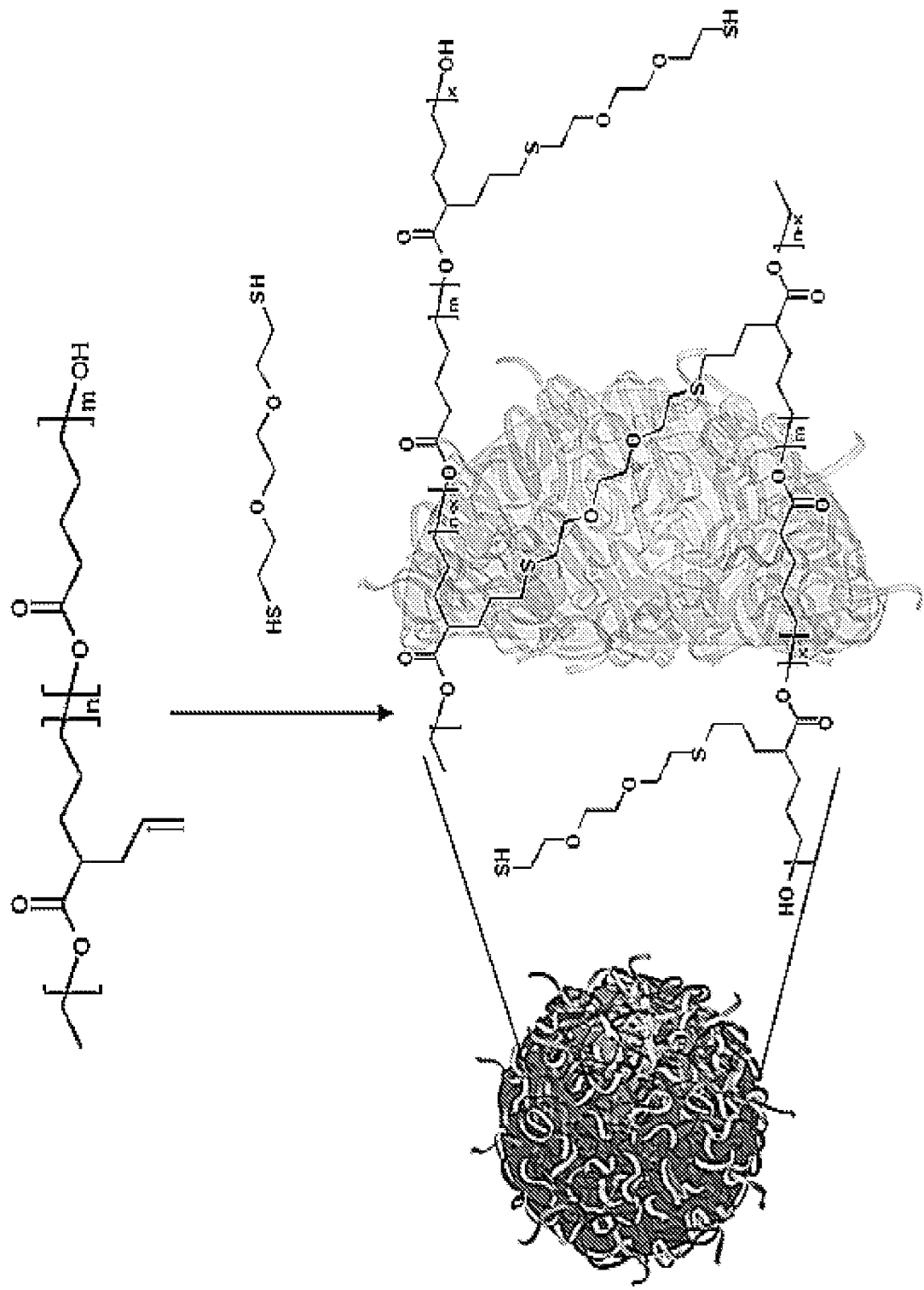
FIG. 59 shows an example crosslinking reaction, and example product thereof.

An example crosslinking reaction, and example product thereof, is shown in FIG. 59.

In one aspect, the cross-linker reacts with two polymer strands. In a further aspect, X—$R^L$—X' reacts with two epoxide-functionalized monomer residues. In a further aspect, X—$R^L$—X' reacts with two propargyl-functionalized monomer residues. In a further aspect, X—$R^L$—X' reacts with one epoxide-functionalized monomer residue and one propargyl-functionalized monomer residue. In a further aspect, X=X'. In a further aspect, X=X'=$NH_2$. In a further aspect, $R^L$ comprises two or more residues of ethylene oxide or trimethylene oxide. In a further aspect, X—$R^L$—X' is 2,2-(ethylenedioxy)bis(ethylamine). In a further aspect, X=X'=$N_3$.

In one aspect, the polymer comprises at least one monomer residue having an optionally substituted structure represented by a formula:

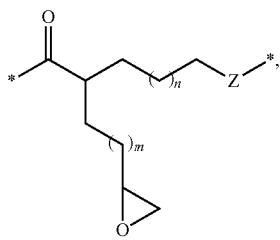

and wherein X=X'=$NH_2$. In one aspect, the polymer and the crosslinker are reacted in a ratio of about 1:1 (polymer:cross-linker). In a further aspect, the polymer and the crosslinker are reacted in a ratio of about >1:1 (polymer:cross-linker) to provide a polymer with excess epoxide-functionalization. In a further aspect, the polymer and the crosslinker are reacted in a ratio of about <1:1 (polymer:cross-linker) to provide a polymer with excess amino-functionalization.

In one aspect, the polymer comprises at least one monomer residue having an optionally substituted structure represented by a formula:

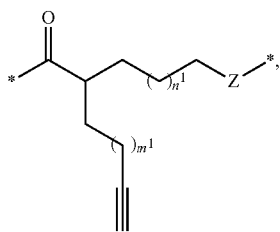

and wherein X=X'=$N_3$. In a further aspect, the polymer and the crosslinker are reacted in a ratio of about 1:1 (polymer:cross-linker). In a further aspect, the polymer and the crosslinker are reacted in a ratio of about >1:1 (polymer:cross-linker) to provide a polymer with excess alkyne-functionalization. In a further aspect, the polymer and the crosslinker are reacted in a ratio of about <1:1 (polymer:cross-linker) to provide a polymer with excess azide-functionalization.

In a further aspect, the polymer further comprises a keto-functionalized monomer providing a residue having an optionally substituted structure represented by a formula:

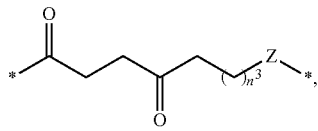

wherein Z is O or NR, wherein R is H or C1 to C6 alkyl, and wherein $n^3$ is an integer from 0 to 2.

In a further aspect, the polymer further comprises at least one monomer providing a residue having an optionally substituted structure represented by a formula:

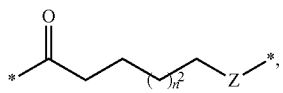

wherein Z is O or NR, wherein R is H or C1 to C6 alkyl, and wherein $n^2$ is an integer from 0 to 2.

3. Methods of Functionalizing Polymers

In one aspect, the invention relates to a method of functionalizing a polymer comprising the step of reacting an epoxide-functionalized monomer residue having an optionally substituted structure represented by a formula:

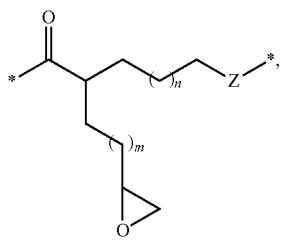

wherein Z is O or NR, wherein R is H or C1 to C6 alkyl; wherein m is an integer from 0 to 6; wherein n is an integer from 0 to 2; with a nucleophile having a structure represented by a formula X—$R^1$, wherein X is OH, SH, $NH_2$, or NHR, wherein R is H or C1 to C6 alkyl; and wherein $R^1$ is an optionally substituted organic radical comprising 1 to 24 carbon atoms.

Organic radicals suitable for use as $R^1$ include substituted or unsubstituted monovalent organic radicals selected from ethyl, propyl, butyl, pentyl, hexyl, heptyl, octyl, decyl, dodecyl, hexadecyl, and higher alkyl. The alkyl can be linear or branched and can be cyclic or acyclic. In a further aspect, $R^1$ can comprise an optionally substituted alkoxylene. Suitable alkoxylene include substituted or unsubstituted monovalent organic radicals selected from groups having a structure represented by a formula:

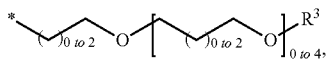

wherein $R^3$ comprises C1 to C6 alkyl.

In a further aspect, $R^1$ is further substituted with at least one biologically active agent, at least one pharmaceutically active agent, and/or at least one imaging moiety, thus providing a convenient method for functionalizing the polymer with one or more biologically active agents, pharmaceutically active agents, and/or imaging moieties via a nucleophilic substitution reaction. That is, $R^1$ can comprise at least one biologically active agent, at least one pharmaceutically active agent, and/or at least one imaging moiety. In a further aspect, $R^1$ can comprise a portion of the at least one biologically active agent, at least one pharmaceutically active agent, and/or at least one imaging moiety. In a further aspect, $R^1$ can be covalently bonded to at least one biologically active agent, at least one pharmaceutically active agent, and/or at least one imaging moiety.

In one aspect, the invention relates to a method of functionalizing a polymer comprising the step of reacting a propargyl-functionalized monomer residue having an optionally substituted structure represented by a formula:

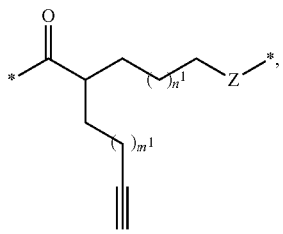

wherein Z is O or NR, wherein R is H or C1 to C6 alkyl, wherein m' is an integer from 0 to 6, and wherein n' is an integer from 0 to 2; with an azide having a structure represented by a formula $N_3$—$R^1$, wherein $R^1$ is an optionally substituted organic radical comprising 1 to 24 carbon atoms. In a further aspect, $R^1$ is further substituted with at least one biologically active agent, at least one pharmaceutically active agent, and/or at least one imaging moiety.

In one aspect, the invention relates to a method of functionalizing a polymer comprising the steps of reacting a keto-functionalized monomer providing a residue having an optionally substituted structure represented by a formula:

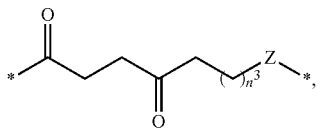

wherein Z is O or NR, wherein R is H or C1 to C6 alkyl, and wherein $n^3$ is an integer from 0 to 2; with an amine having a structure represented by a formula $H_2N$—$R^1$, wherein $R^1$ is an optionally substituted organic radical comprising 1 to 24 carbon atoms; and reducing the resulting imine. In a further aspect, the reacting step and the reducing step are performed simultaneously. In a further aspect, $R^1$ is further substituted with at least one biologically active agent, at least one pharmaceutically active agent, and/or at least one imaging moiety.

In one aspect, the invention relates to a method of functionalizing a polymer comprising the step of reacting a nucleophile-functionalized monomer residue having an optionally substituted structure represented by a formula:

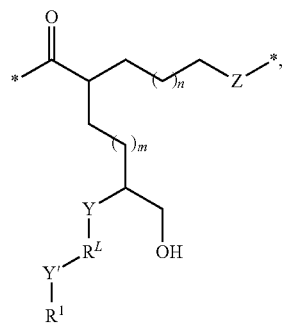

wherein Z is O or NR, wherein R is H or C1 to C6 alkyl; wherein m is an integer from 0 to 6; wherein n is an integer from 0 to 2; wherein Y and Y' are independently O, S, or NR, wherein R is H or C1 to C6 alkyl; and wherein $R^L$ is selected from optionally substituted alkyl and optionally substituted alkoxylene; with an electrophile having a structure represented by a formula E-$R^1$, wherein E is an electrophilic moiety; and wherein $R^1$ is an optionally substituted organic radical comprising 1 to 24 carbon atoms.

In a further aspect, Y' is $NH_2$ or NHR. In a further aspect, wherein Y=Y'. In a further aspect, the electrophilic moiety is selected from alkyl halide, alkyl pseudohalide, and carboxyl derivative. In a further aspect, $R^1$ is further substituted with at least one biologically active agent, at least one pharmaceutically active agent, and/or at least one imaging moiety.

4. Methods of Making Nanoparticles

The formation of nanoparticles in controlled size dimensions can proceed from linear polymers containing pendant epoxide groups which crosslink with 2,2'-(ethylenedioxy)bis(ethylamine). To evaluate the particle formation under controlled conditions, reactions in which the equivalents of diamine cross-linker were linearly increased with respect to the reactive epoxide groups of the polymers were studied.

To achieve a high degree of cross-linking between the individual polyester chains, the polymer solution with the pendant expoxide entities can be added in a dropwise fashion to a refluxing solution of different equivalents of dinucleophile (e.g., diamine) in dichloromethane. In this strategy, the difunctional amine is in high excess during the addition (13 mL/min) of the linear polymer solution (0.5 M) and thus provides optimum cross-linking reactions (Table 1; particle size reported in nm diameter by dynamic light scattering (DLS) in relation to varying amine ratios).

TABLE 1

| | Nanoparticle Size Dimensions (nm) | | |
|---|---|---|---|
| Amine/1 Epoxide | Diameter (nm) Poly(vl-evl) AB | Diameter (nm) Poly(vl-evl-opd) ABD | Diameter (nm) Poly(vl-evl-pvl) ABC |
| 1 | 30.71 ± 2.21 | 34.29 ± 3.22 | 21.40 ± 2.90 |
| 2 | 58.06 ± 6.20 | 63.46 ± 7.68 | 41.70 ± 5.36 |

TABLE 1-continued

| Nanoparticle Size Dimensions (nm) | | | |
|---|---|---|---|
| 3 | 82.1 ± 5.73 | 118.3 ± 13.6 | 114.9 ± 8.9 |
| 4 | 115.6 ± 25.4 | 164.9 ± 65.7 | 148.3 ± 25.2 |
| 5 | 255.7 ± 60.3 | 297.7 ± 80.3 | 186.1 ± 37.5 |
| 6 | 342.2 ± 52.2 | 341.0 ± 86.6 | 253.9 ± 41.4 |
| 8 | 425.1 ± 100 | 525.0 ± 100 | 472.1 ± 103.1 |
| 10 | 725.1 ± 94.3 | 800.0 ± 135 | 675.0 ± 126.1 |

| Amine/1 Epoxide | Diameter (nm) $AB_1$ nanoparticles[a] | MW, RI (g/mol)[b] | PDI[c] | MW (kg/mol)[d] |
|---|---|---|---|---|
| 1 | 30.71 ± 2.21 | 3403 | 1.16 | 60.5 ± 3.5 |
| 2 | 58.06 ± 6.20 | 3445 | 1.16 | 81.5 ± 4.6 |
| 3 | 82.61 ± 5.73 | 3544 | 1.17 | 96.1 ± 4.9 |
| 4 | 115.6 ± 12.5 | 3860 | 1.18 | 112 ± 6 |
| 5 | 255.7 ± 26.9 | 4005 | 1.18 | 187 ± 8 |
| 6 | 342.2 ± 42.2 | 4267 | 1.21 | 222 ± 11 |
| 8 | 425.1 ± 44.6 | 4470 | 1.21 | 328 ± 15 |
| 10 | 725.1 ± 94.3 | 4887 | 1.22 | 525 ± 28 |

Figure 11:
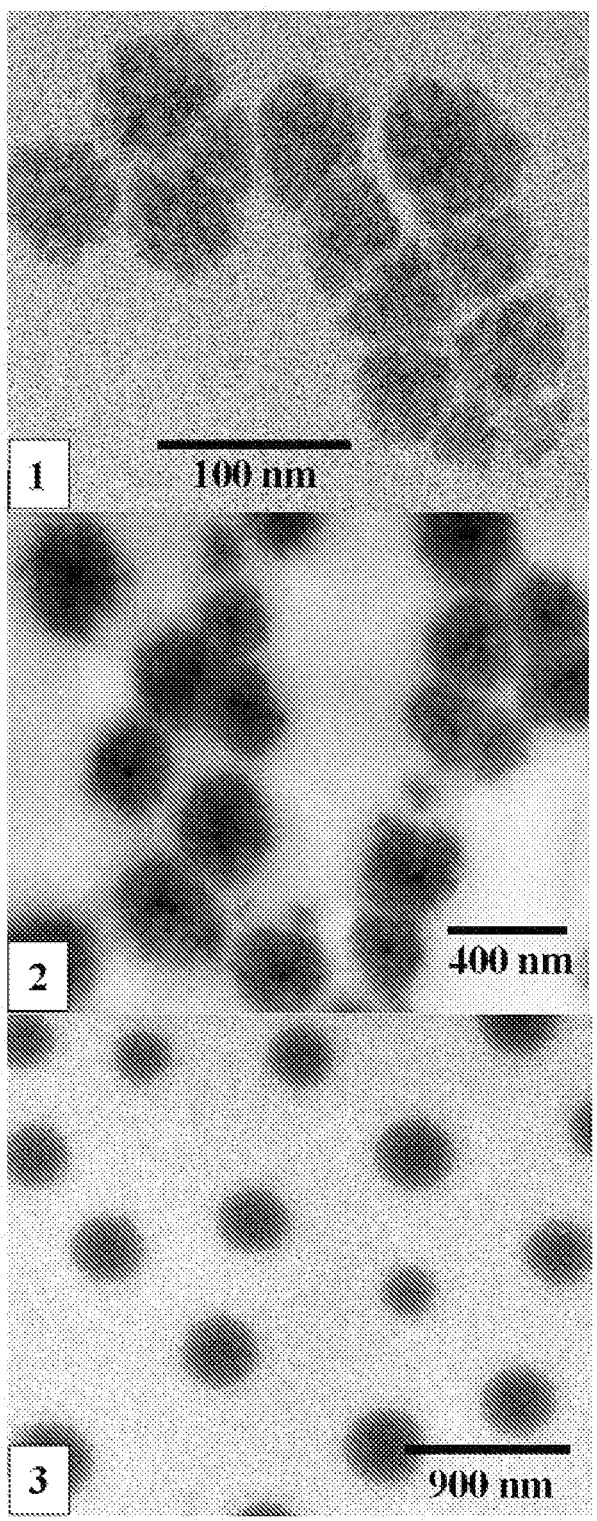
FIG. 11 shows TEM images of AB nanoparticles; (1) 2 equivalents of amine; (2) 5 equivalents of amine; (3) 8 equivalents of amine.

The first trial was employed with polymer (AB) and implemented 1 to 10 equivalents of amine functionalities to the pendant epoxide cross-linking entity. The resulting particles were characterized by transmission electron microscopy (TEM) that provides the actual size, and by dynamic light scattering (DLS), to obtain the hydrodynamic diameter as a representative measure of the particle under physiological conditions. Micrographs of representative nanoparticles are shown in FIG. 11. It is also contemplated that reaction stoichiometry can be selected to utilitze in excess of ten (10) equivalents, thereby providing microparticles, materials for us in tissue engineering and biogels in biomedical applications and devices.

Figure 12:
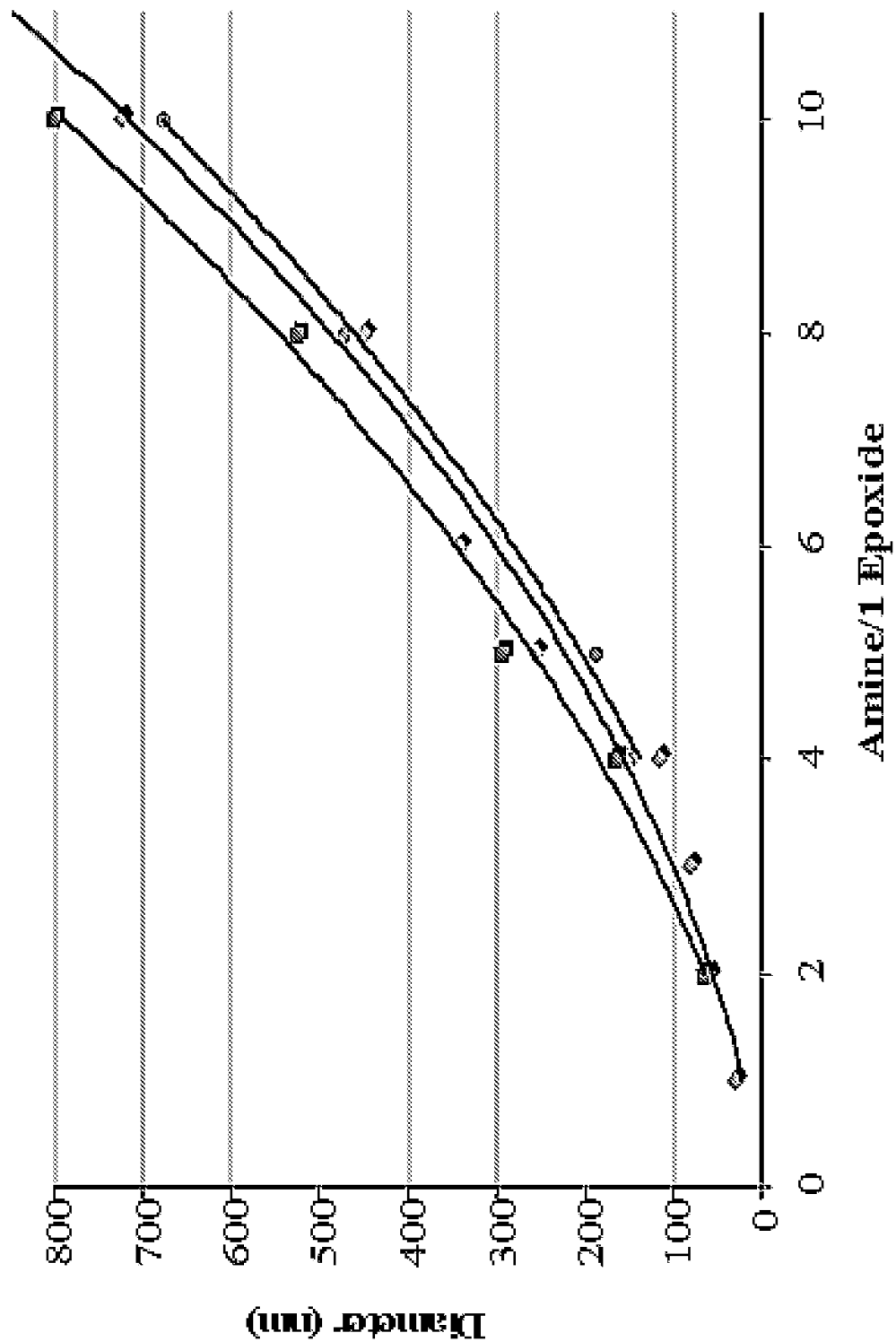
FIG. 12 shows polynomial increase of nanoparticle diameter (nm) with increase of diamine cross-linker; (■) ABD nanoparticles; (♦) AB nanoparticles; (●) ABC nanoparticles.
Figure 13:
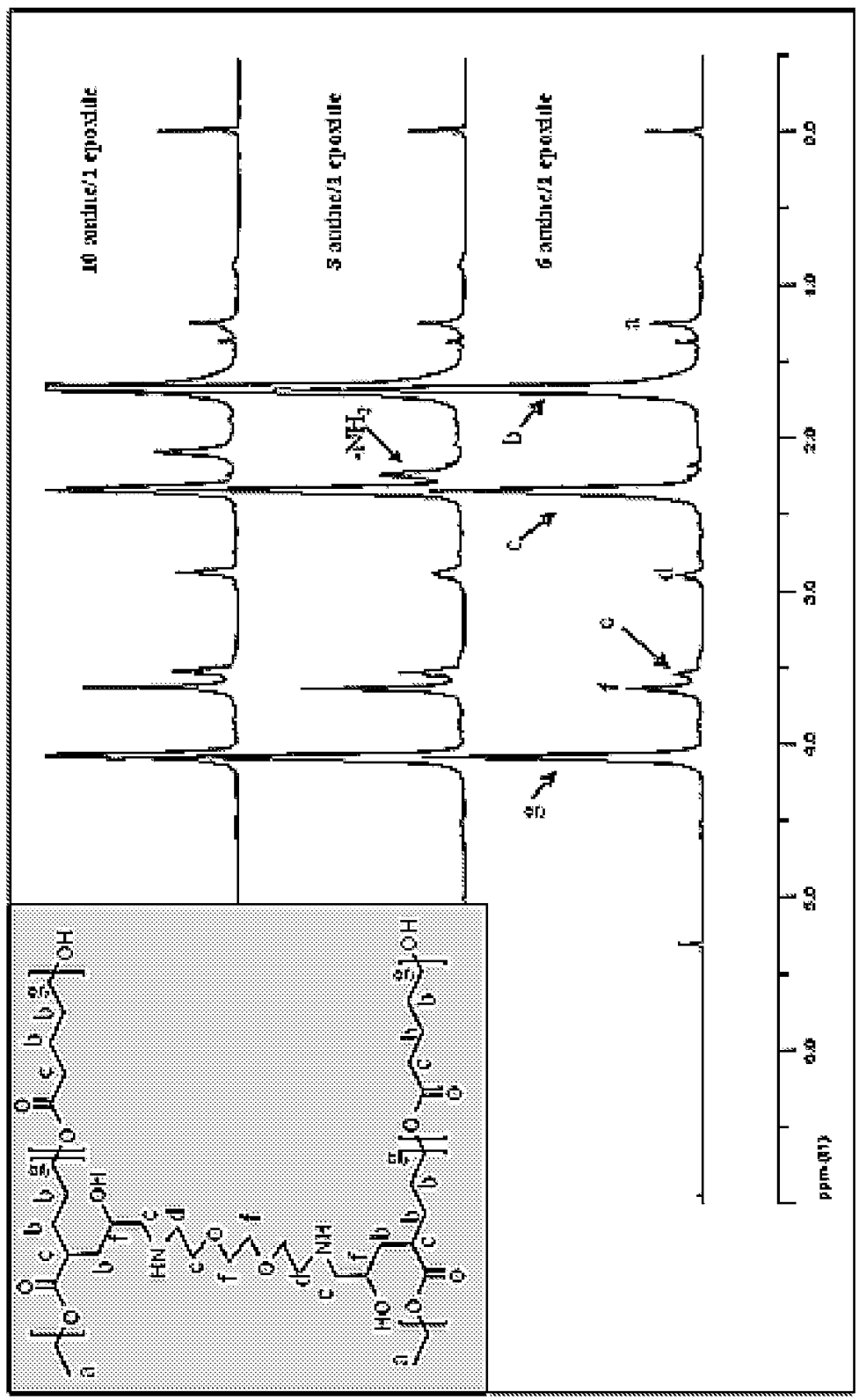
FIG. 13 shows $^1$H NMR overlay for poly(vl-evl) nanoparticles with increasing cross-linking.
Figure 14:
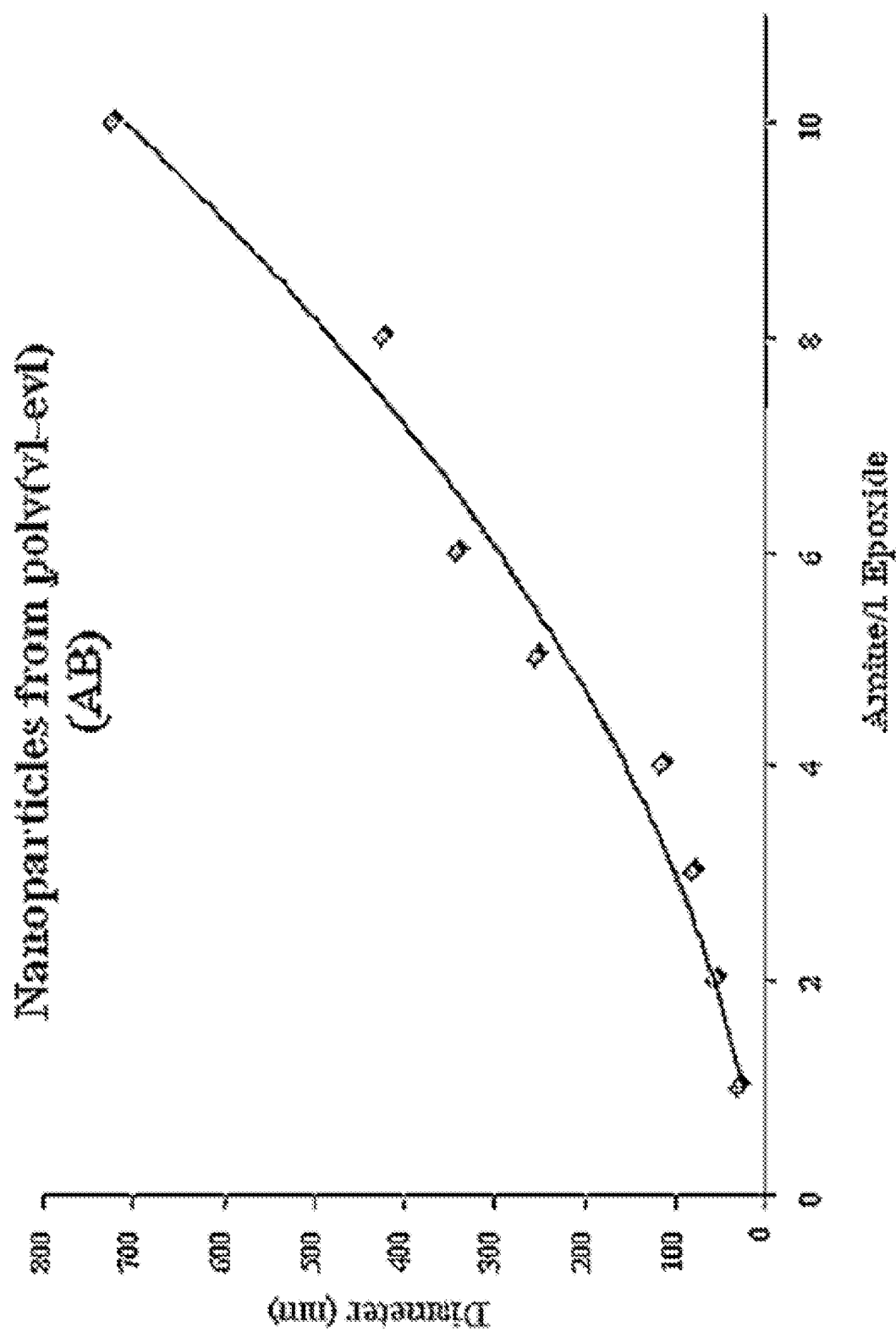
FIG. 14 shows polynomial increase of nanoparticle diameter (nm) with increase of diamine cross-linker for (♦) AB nanoparticles from FIG. 12.
Figure 15:
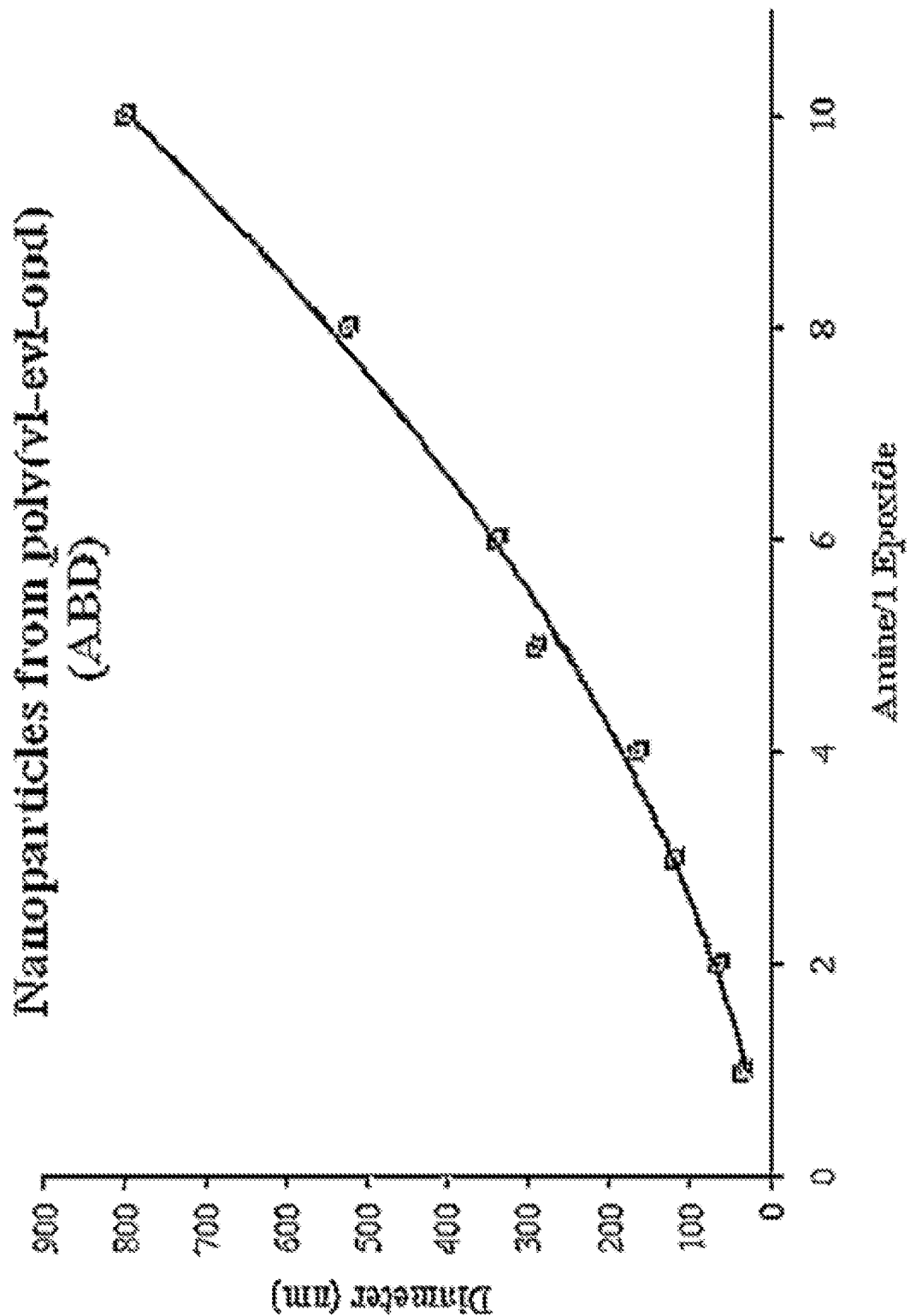
FIG. 15 shows polynomial increase of nanoparticle diameter (nm) with increase of diamine cross-linker for (■) ABD nanoparticles from FIG. 12.
Figure 16:
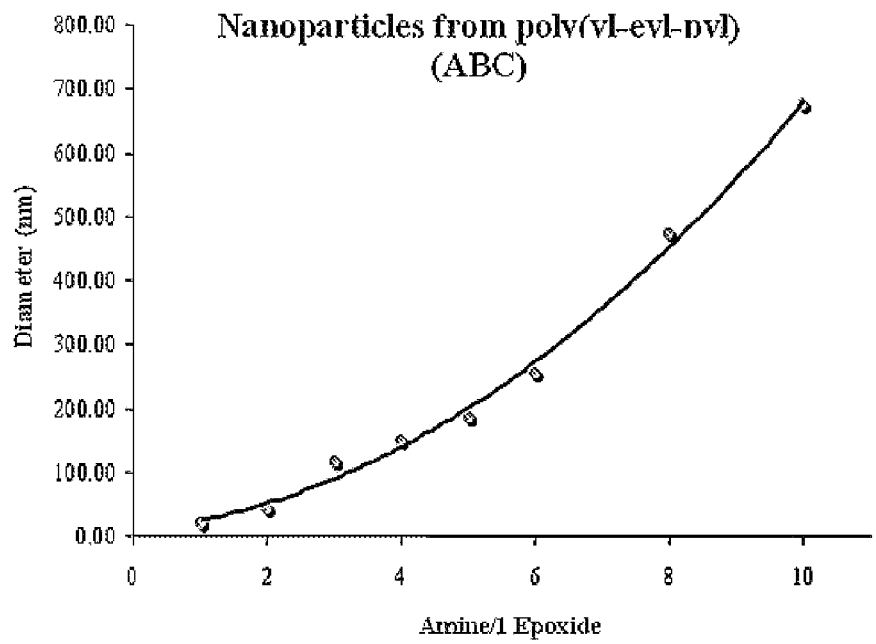
FIG. 16 shows polynomial increase of nanoparticle diameter (nm) with increase of diamine cross-linker for (●) ABC nanoparticles from FIG. 12.

As illustrated in FIG. 12, the particle size increase with a polynominal trend as the equivalents of amine rises. For example, two equivalents of amine yielded 58 nm particles, and five equivalents produced particles with 255 nm dimensions (Table 1). Synthesized linear polymers containing additional functionalities (ABC and ABD) were found to respond in the same way to the controlled intermolecular chain crosslinking conditions, as with polymer (AB) from the original trial, and well-defined nanoparticles were obtained (Table 1). As shown in FIG. 13, characterization of the particles with $^1$H NMR confirmed the nanoparticle formation for each trial with an increase of signals at 3.5 and 2.89 ppm corresponding to protons neighboring the secondary amine of the polyethylene glycol (PEG)-linker after successful crosslinking event. In particular, a shift in resonance from 2.86 to 2.89 ppm was observed due to the change of the primary amine to the secondary amine after cross-linking. As a consequence, the continuous increase in amine cross-linker equivalents not only extends the particle size, but it also introduces additional amine functionalities connected to short PEG linker that are available for further modification strategies.

In one aspect, the invention relates to a method of preparing a degradable nanoparticle comprising the step of adding a polymer comprising at least one monomer residue having a structure represented by a formula:

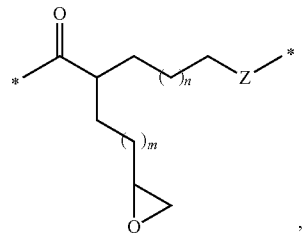

wherein Z is O or NR, wherein R is H or C1 to C6 alkyl, wherein m is an integer from 0 to 6, and wherein n is an integer from 0 to 2; to a solution of from about 1 to about 10 molar equivalents of a dinucleophile (nucleophilic moiety:epoxide functionality) having a structure X—$R^L$-X', wherein X and X' are independently OH, SH, $NH_2$, or NHR, wherein R is H or C1 to C6 alkyl, and wherein $R^L$ is selected from optionally substituted alkyl and optionally substituted alkoxylene. In a further aspect, the monomer residue comprises less than about 10% by weight of the monomer residue of halogen selected from chlorine, bromine, and iodine. In a further aspect, Z is O.

In one aspect, the solution comprises from about 1 molar equivalent of a dinucleophile (nucleophilic moiety:epoxide functionality) and the resultant nanoparticle has a particle size of from about 5 nm to about 55 nm. In a further aspect, the solution comprises from about 1 molar equivalent of a dinucleophile (nucleophilic moiety:epoxide functionality) and the resultant nanoparticle has a particle size of from about 5 nm to about 55 nm. In a further aspect, the solution comprises from about 2 molar equivalents of a dinucleophile (nucleophilic moiety:epoxide functionality) and the resultant nanoparticle has a particle size of from about 30 nm to about 80 nm. In a further aspect, the solution comprises from about 3 molar equivalents of a dinucleophile (nucleophilic moiety:epoxide functionality) and the resultant nanoparticle has a particle size of from about 70 nm to about 120 nm. In a further aspect, the solution comprises from about 4 molar equivalents of a dinucleophile (nucleophilic moiety:epoxide functionality) and the resultant nanoparticle has a particle size of from about 110 nm to about 170 nm. In a further aspect, the solution comprises from about 5 molar equivalents of a dinucleophile (nucleophilic moiety:epoxide functionality) and the resultant nanoparticle has a particle size of from about 175 nm to about 300 nm. In a further aspect, the solution comprises from about 6 molar equivalents of a dinucleophile (nucleophilic moiety:epoxide functionality) and the resultant nanoparticle has a particle size of from about 250 nm to about 350 nm. In a further aspect, the solution comprises from about 8 molar equivalents of a dinucleophile (nucleophilic moiety:epoxide functionality) and the resultant nanoparticle has a particle size of from about 400 nm to about 550 nm. In a further aspect, the solution comprises from about 10 molar equivalents of a dinucleophile (nucleophilic moiety:epoxide functionality) and the resultant nanoparticle has a particle size of from about 650 nm to about 850 nm. It is also contemplated that reaction stoichiometry can be selected to utilitze in excess of ten (10) molar equivalents, thereby providing higher particle sizes.

In one aspect, the invention relates to a method of preparing a degradable nanoparticle comprising the step of adding a polymer comprising at least one monomer residue having a structure represented by a formula:

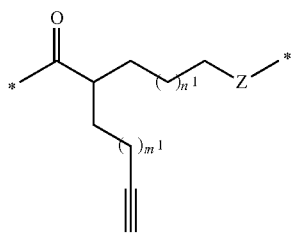

wherein Z is O or NR, wherein R is H or C1 to C6 alkyl, wherein $m^1$ is an integer from 0 to 6, and wherein $n^1$ is an integer from 0 to 2; to a solution of from about 1 to about 10 molar equivalents of a bis-azide (azide moiety:alkyne functionality) having a structure $N_3$—$R^L$—$N_3$, wherein $R^L$ is selected from optionally substituted alkyl and optionally substituted alkoxylene. In a further aspect, the monomer residue comprises less than about 10% by weight of the monomer residue of halogen selected from chlorine, bromine, and iodine. In a further aspect, Z is O.

In one aspect, the invention relates to a method of controlling particle size during the preparation of a degradable nanoparticle comprising the step of adding an epoxide-functionalized polymer to a solution of a dinucleophilic cross-linker, wherein the stoichiometry of the cross-linker (ratio of nucleophilic moiety:epoxide functionality) is selected to provide a desired particle size according to one or more of the graphs shown in FIG. 14-FIG. 19.

5. Methods of Functionalizing Nanoparticles

In one aspect, the invention relates to a method of functionalizing a nanoparticle comprising the step of reacting a nanoparticle comprising at least one epoxide-functionalized monomer residue having an optionally substituted structure represented by a formula:

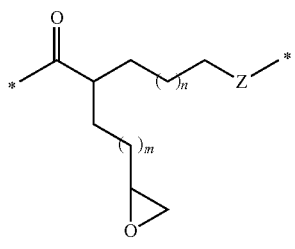

wherein Z is O or NR, wherein R is H or C1 to C6 alkyl; wherein m is an integer from 0 to 6; wherein n is an integer from 0 to 2; with a nucleophile having a structure represented by a formula X—$R^1$, wherein X is OH, SH, $NH_2$, or NHR, wherein R is H or C1 to C6 alkyl; and wherein $R^1$ is an optionally substituted organic radical comprising 1 to 24 carbon atoms. In a further aspect, $R^1$ is further substituted with at least one biologically active agent, at least one pharmaceutically active agent, and/or at least one imaging moiety.

In one aspect, the invention relates to a method of functionalizing a nanoparticle comprising the step of reacting a nanoparticle comprising at least one propargyl-functionalized monomer residue having an optionally substituted structure represented by a formula:

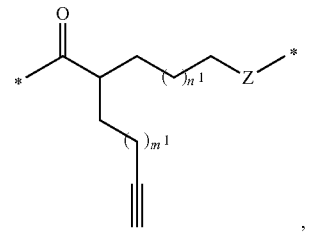

wherein Z is O or NR, wherein R is H or C1 to C6 alkyl, wherein $m^1$ is an integer from 0 to 6, and wherein $n^1$ is an integer from 0 to 2; with an azide having a structure represented by a formula $N_3$—$R^1$, wherein $R^1$ is an optionally substituted organic radical comprising 1 to 24 carbon atoms. In a further aspect, $R^1$ is further substituted with at least one biologically active agent, at least one pharmaceutically active agent, and/or at least one imaging moiety.

In one aspect, the invention relates to a method of functionalizing a nanoparticle comprising the steps of reacting a nanoparticle comprising at least one keto-functionalized monomer providing a residue having an optionally substituted structure represented by a formula:

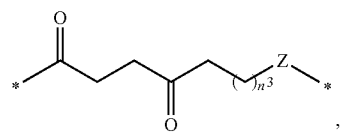

wherein Z is O or NR, wherein R is H or C1 to C6 alkyl, and wherein $n^3$ is an integer from 0 to 2; with an amine having a structure represented by a formula $H_2N$—$R^1$, wherein $R^1$ is an optionally substituted organic radical comprising 1 to 24 carbon atoms; and reducing the resulting imine. In a further aspect, the reacting step and the reducing step are performed simultaneously. In a further aspect, $R^1$ is further substituted with at least one biologically active agent, at least one pharmaceutically active agent, and/or at least one imaging moiety.

In one aspect, the invention relates to a method of functionalizing a nanoparticle comprising the step of reacting a nanoparticle comprising at least one nucleophile-functionalized monomer residue having an optionally substituted structure represented by a formula:

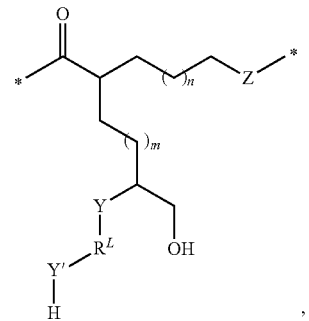

wherein Z is O or NR, wherein R is H or C1 to C6 alkyl; wherein m is an integer from 0 to 6; wherein n is an integer from 0 to 2; wherein Y and Y' are independently O, S, or NR, wherein R is H or C1 to C6 alkyl; and wherein $R^L$ is selected from optionally substituted alkyl and optionally substituted alkoxylene; with an electrophile having a structure represented by a formula E-R$^1$, wherein E is an electrophilic moiety; and wherein R$^1$ is an optionally substituted organic radical comprising 1 to 24 carbon atoms. In a further aspect, Y' is NH$_2$ or NHR. In a further aspect, Y=Y'. In a further aspect, the electrophilic moiety is selected from alkyl halide, alkyl pseudohalide, and carboxyl derivative. In a further aspect, R$^1$ is further substituted with at least one biologically active agent, at least one pharmaceutically active agent, and/or at least one imaging moiety.

6. Methods of Degrading Nanoparticles

In one aspect, the invention relates to a method of degrading a degradable nanoparticle comprising subjecting the nanoparticle to reaction conditions sufficient to hydrolyze an ester. In a further aspect, the conditions are biological conditions. In a further aspect, the conditions involve exposure to an esterase. In a further aspect, the conditions exist within an organism.

In one aspect, the invention relates to a method of degrading a degradable polymer comprising subjecting the polymer to reaction conditions sufficient to hydrolyze an ester. In certain aspects, the degradable polymer is a disclosed polymer or a product of a disclosed method.

H. Functionalized Polymers and Nanoparticles

In one aspect, the disclosed nanoparticles can be functionalized with, for example, the disclosed dendrimeric compounds. That is, in one aspect, the invention relates to a nanoparticle-dendrimer conjugate. In a further aspect, the nanoparticle can be a disclosed organic quantum dots via intramolecular chain collapse. In a further aspect, the nanoparticle can be a disclosed degradable nanoparticle. In a further aspect, the dendrimer can be a disclosed intracellular delivery composition.

As disclosed herein, certain nanoparticles can bear electrophilic (e.g., ketone) functionalities. Vinylsulfonyl functionality can be introduced to the disclosed nanoparticles.

Figure 60:
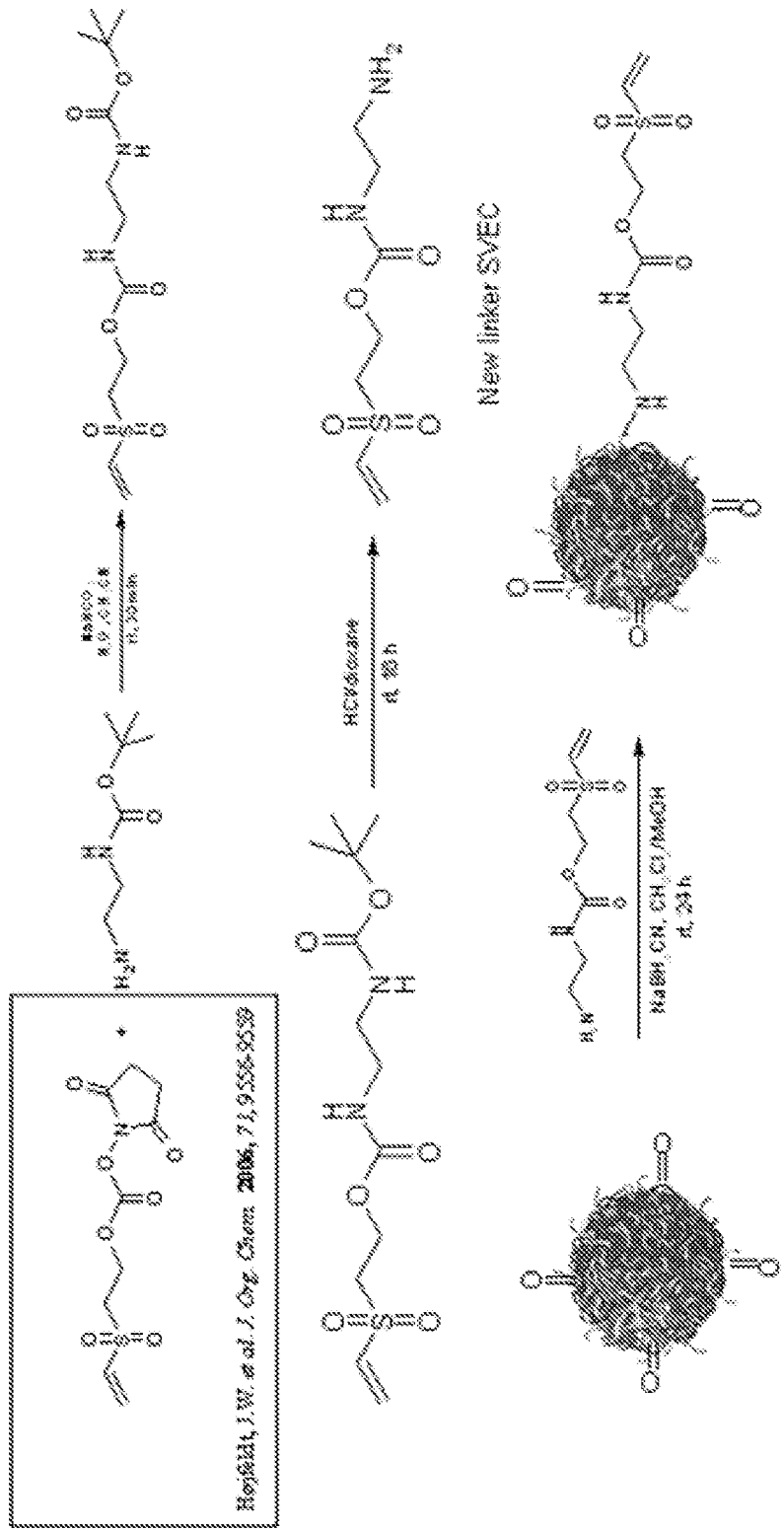
FIG. 60 shows the synthesis of a SVEC linker and attachment to the particle.

Thus, a vinylsulfonyl linker moiety was prepared that can be attached in a reductive amination procedure to a keto groups of the particle. The synthesis of such a linker appears in Scheme 1 in FIG. 60. It is understood that the alkyl chain can be homologated by selection of appropriate reagents.

The vinylsulfonyl moiety readily reacts with a nucleophile (e.g., a thiol) to form a covalent bond, thereby further functionalizing a nanoparticle. These linkers can be used to attach peptides that are labeled with dye molecules at the focal point of the peptide or other amines groups of the peptide. The thiol groups of cysteines can be used to attach to the vinyl function of the vinyl sulfonyl linker. Also, the thiol group in the focal point of the disclosed dendritic molecular transporters can be attached to the vinyl sulfonyl (or allyl) group, thus allowing a transporter to be attached to any post-modified nanoparticle.

The same reaction can be used to attach peptides that are not labeled with dye. In such cases, the particle can be labeled with dye or not labeled.

Figure 61:
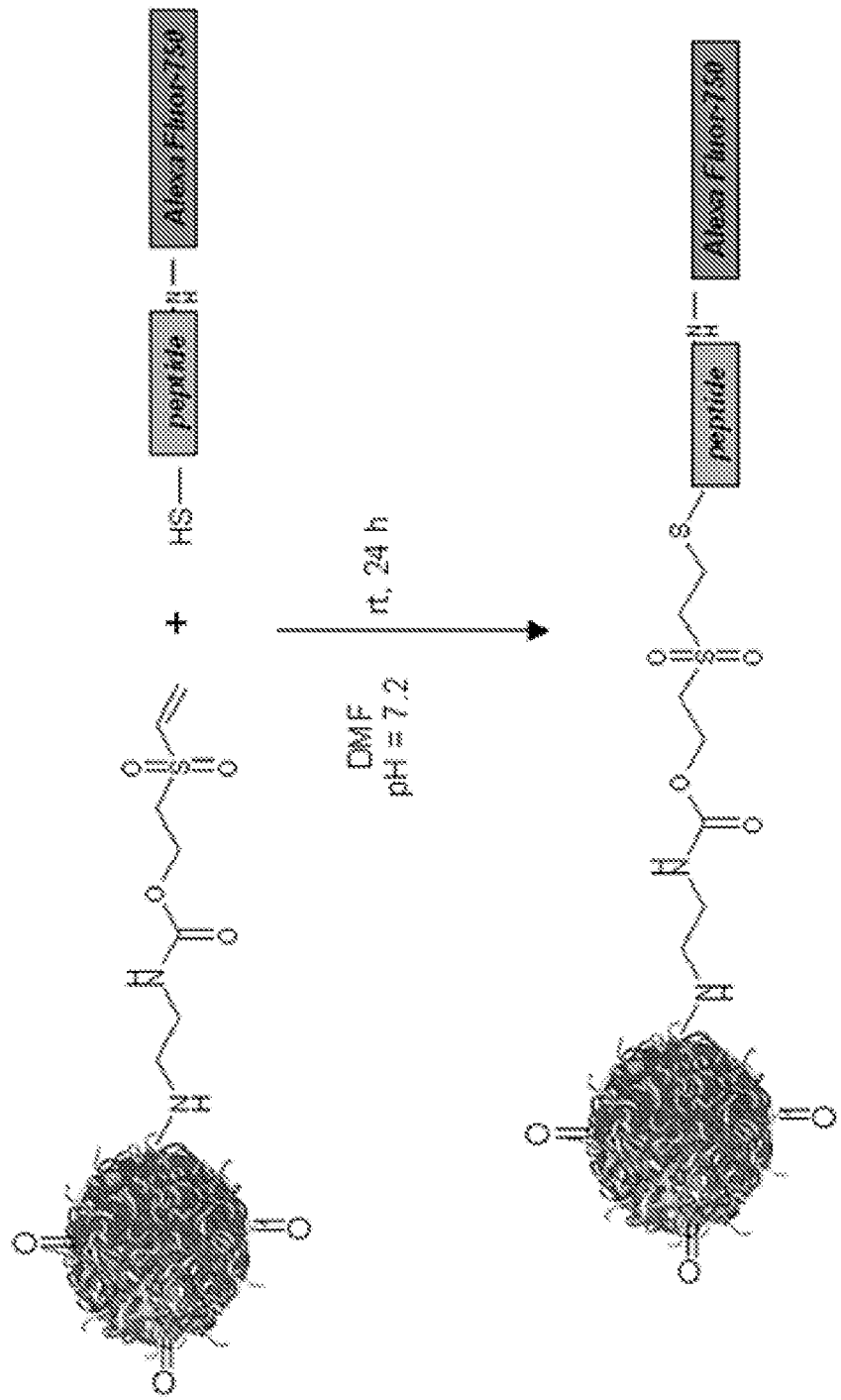
FIG. 61 shows the attachment of a peptide with an integrated thiol group from a cysteine residue to a linker-modified particle.
Figure 62:
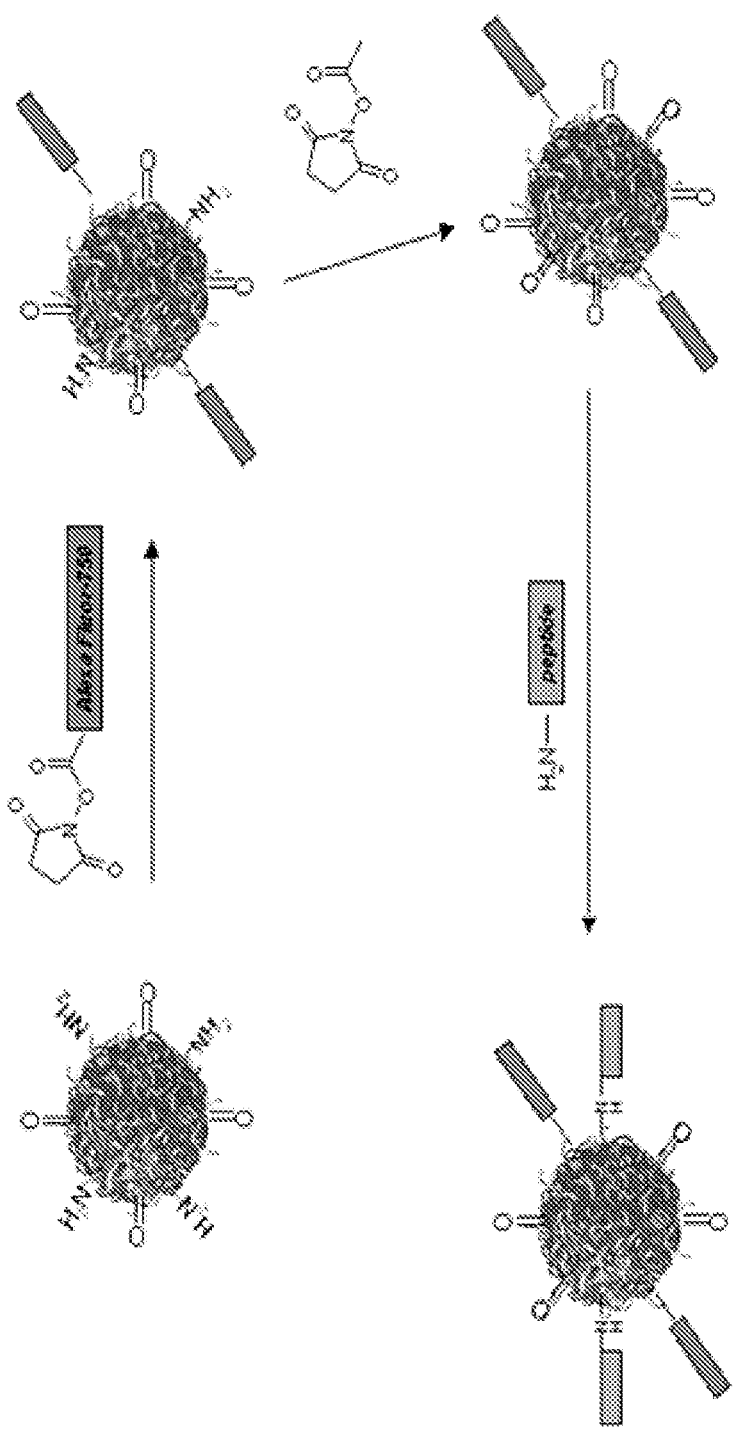
FIG. 62 shows the attachment of Alex Fluor dye to the free amine groups of the particle (NHS ester to amine) and quenching of the residual amines before reductive amination of amines of peptides (bioactive compounds) to the keto groups of the particle.

Peptides (or other amines) can also be attached directly through the amine terminus of the peptide to the keto group through reductive amination. See Scheme 2 in FIG. 61. Here, it is preferred that the peptide contains only one amine group. Before the reductive amination is performed, the particle can be labeled with a dye that adds to the amine functionality of the particle. After the reaction, residual dyes can be quenched so as to not interfere with the following reductive amination.

Similar systems can be constructed with particles from intramolecular cross-linking reactions. Replacing N-BED with an ethylenoxide equivalent enhances the solubility of the system.

Another approach that can enable formation of nanoparticle-dendrimer conjugate involves direct attachment of nucleophile-functionalized moieties (e.g., peptides or disclosed intracellular delivery compositions) to an allylic function on disclosed degradable nanoparticles. As shown in Scheme 4, direct attachment of a thiol with an allyl functionalized polymer or nanoparticle can bypass use of the disclosed SVEC linker.

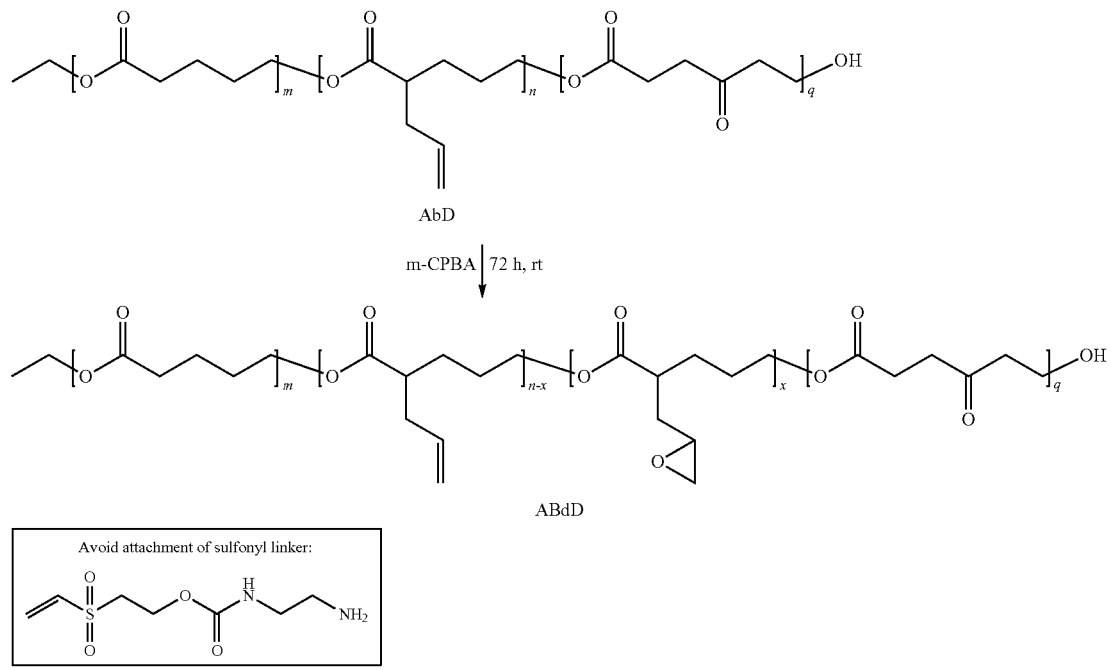

In one aspect, an allylic function on disclosed degradable nanoparticles can be provided via incomplete oxidation of epoxide functionalities, as shown in Scheme 5a.
Scheme 5a. Linear precursor.
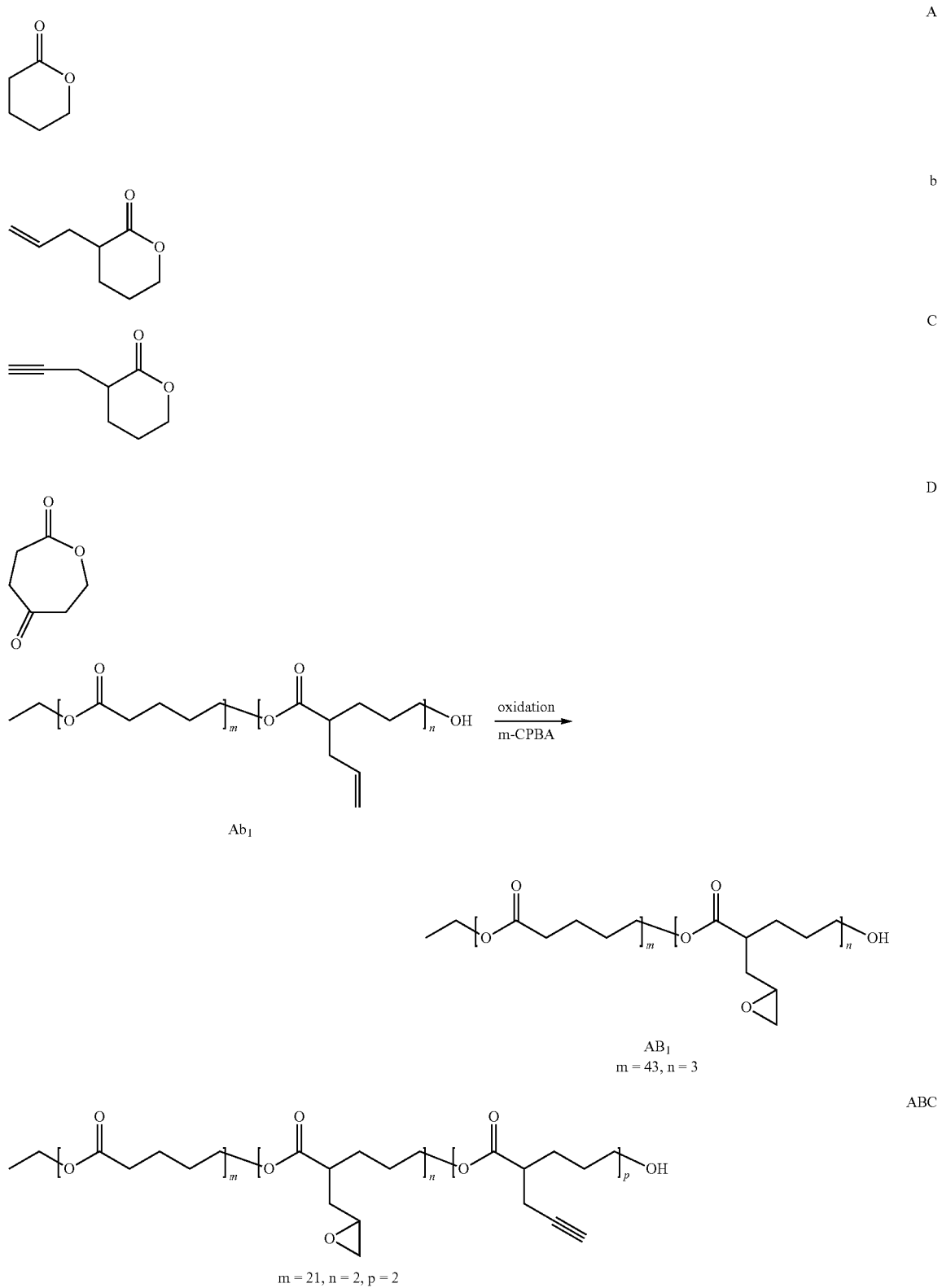

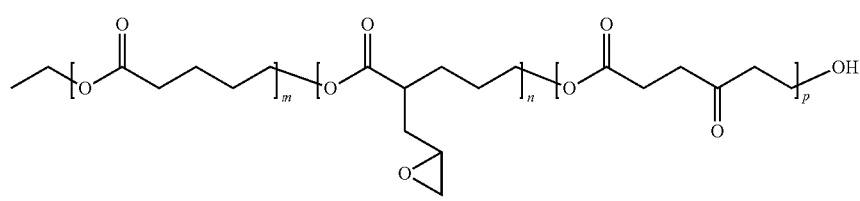
m = 17, n = 3, q = 5
ABD
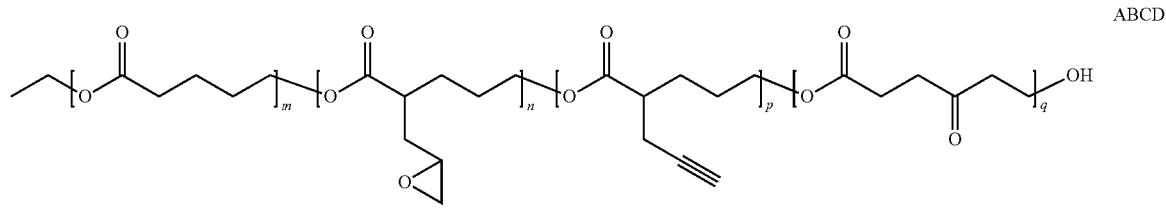
m = 15, n = 3, p = 2, q = 4
ABCD
Still other examples of linear precursors can be prepared according to Scheme 5b.
Scheme 5b. Linear precursor.
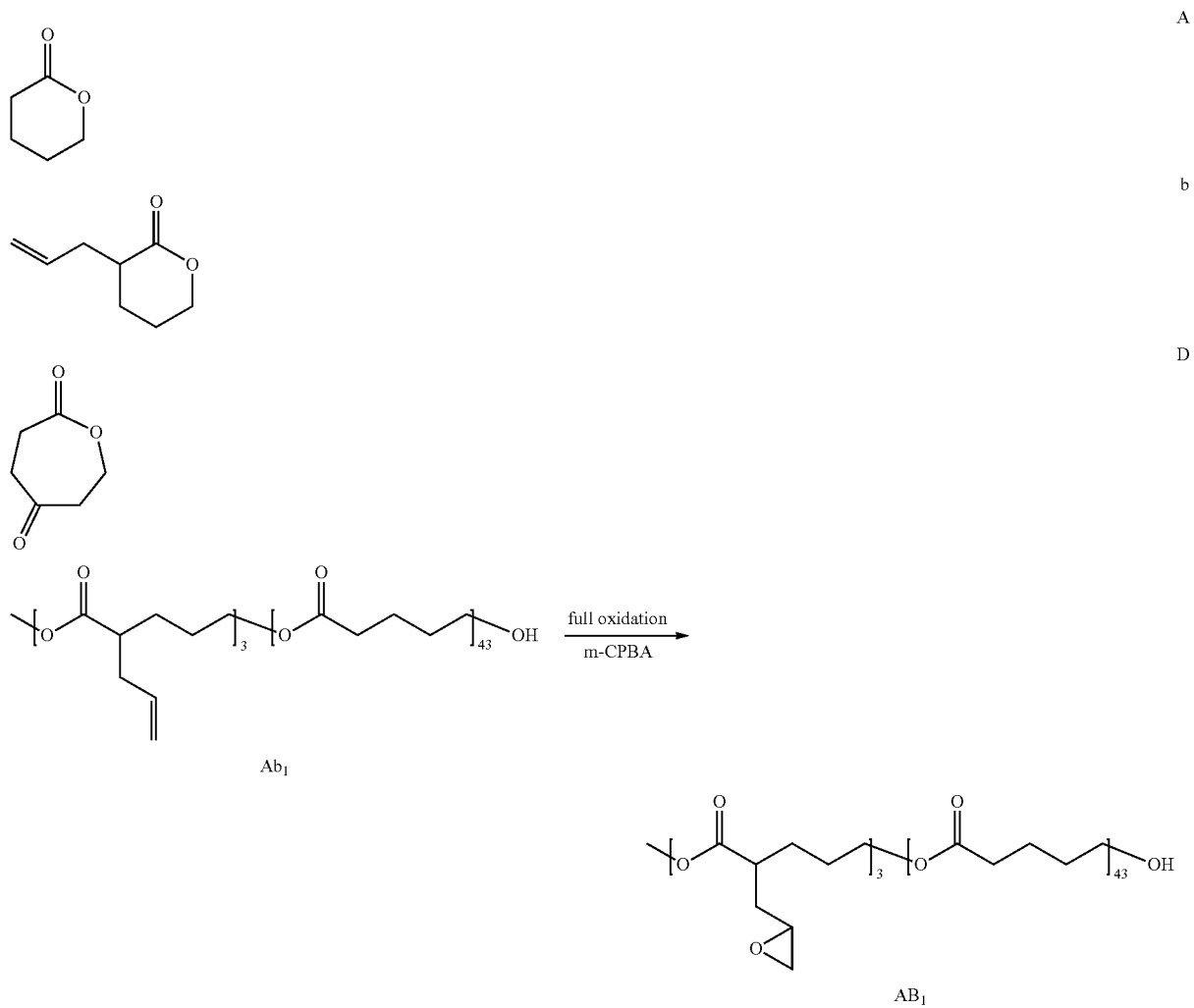

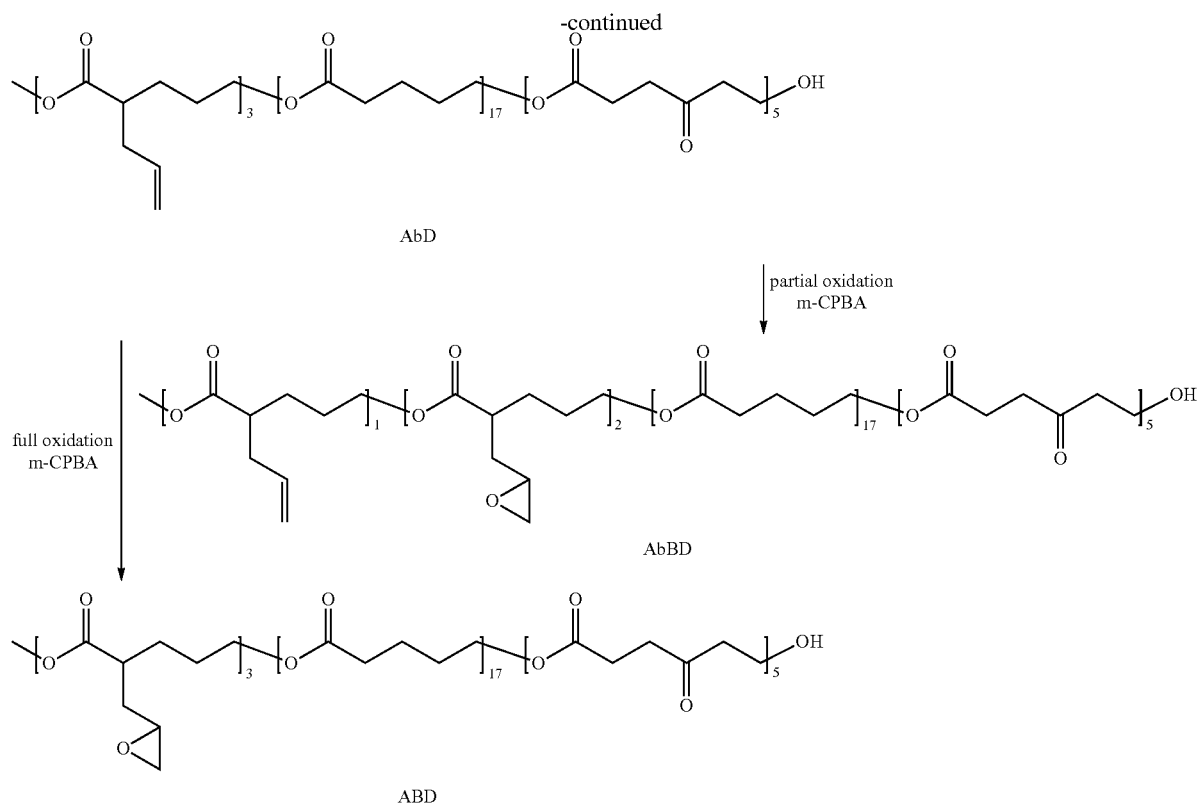

An allyl functionality is thus available for functionalization and allows very mild conditions for the attachment of peptides and other moieties that contain nucleophilic (e.g., thiol) groups. The allyl groups from Ab linear precursors can be partially preserved by partial oxidation to the epoxide that is needed for cross-linking to the nanoparticle to from AbB linear polymer. This chemistry is also compatible with the keto-group-containing ABD linear precursor to from AbBD.

Figure 63:
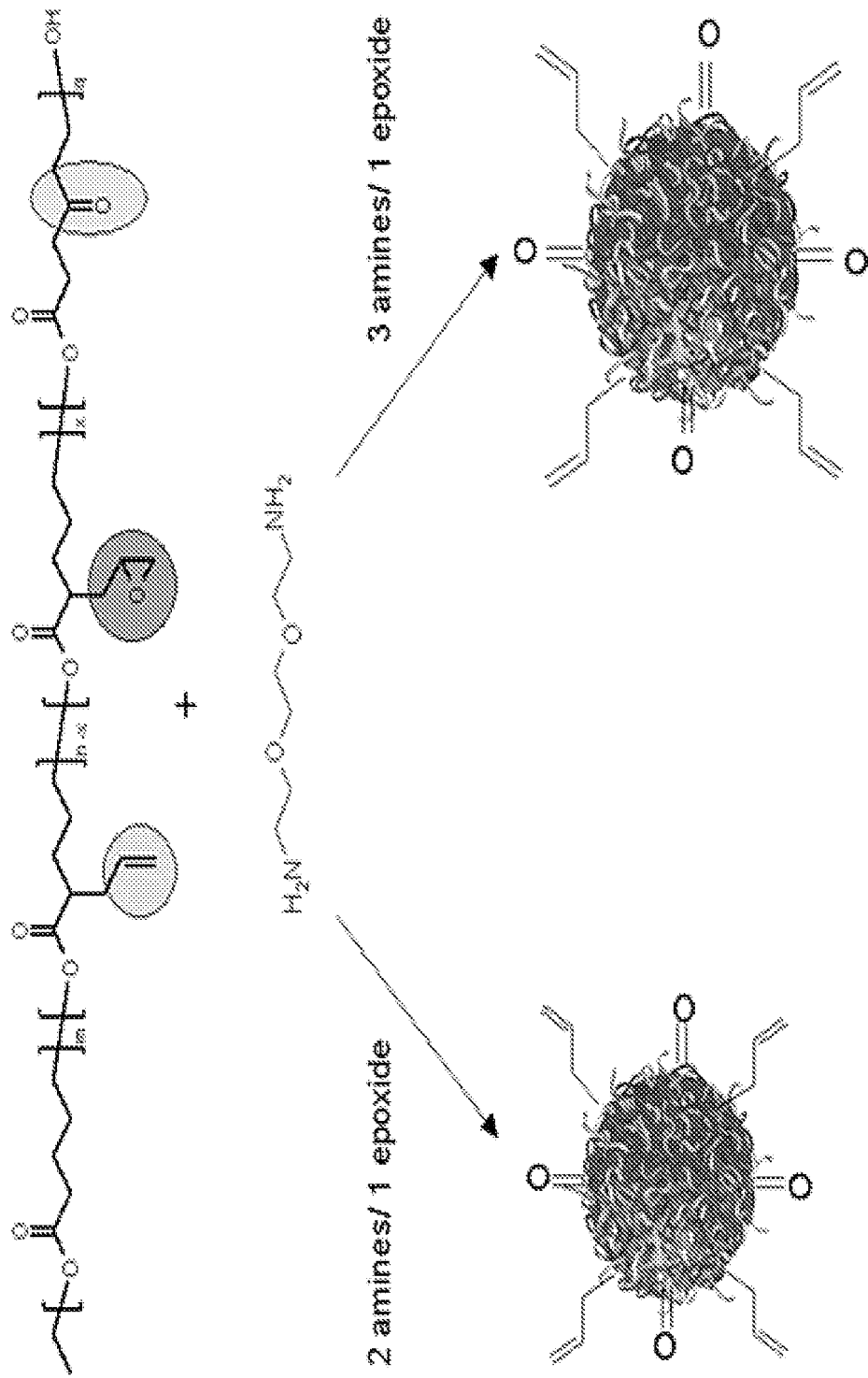
FIG. 63 shows nanoparticle formation from an allyl-functionalized ABbD linear precursor with diamines.

The nanoparticle formation does not take part in the cross-linking reaction and is therefore available for further modification. The allyl group is inert under the conditions used during the cross-linking process. The crosslinking reaction is illustrated in Scheme 6 in FIG. 63.

Again, the thiol group of the focal point of the dendritic molecular transporter can be attached to the ally group. One advantage of such attachment is that it requires no other reagent. This can permit the transporter to be attached to any already post-modified nanoparticle because of the mild reaction conditions.

Figure 64:
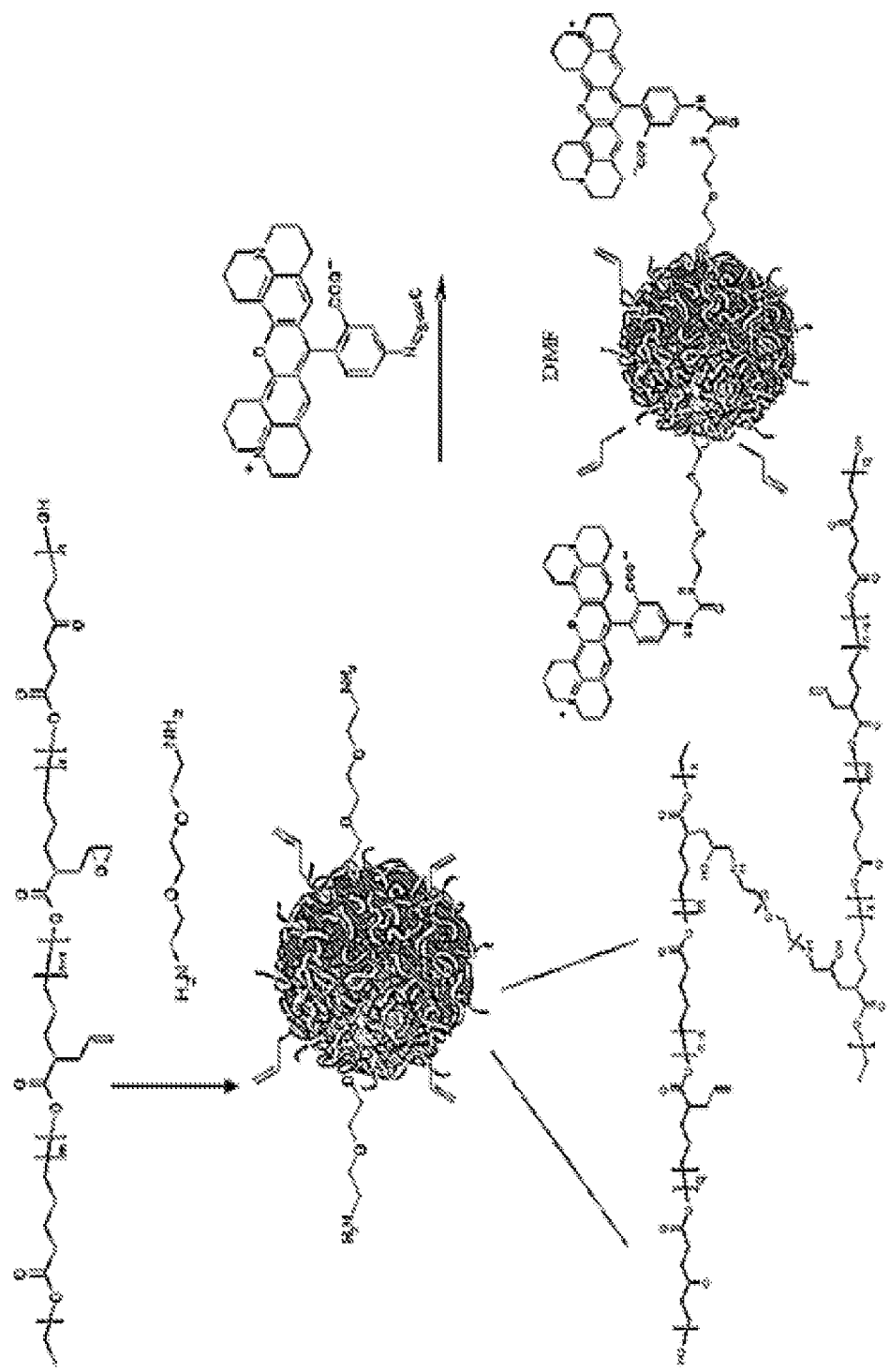
FIG. 64 shows nanoparticle formation from an allyl-functionalized ABbD linear precursor with diamines, followed by attachment to an isothiocyanate.

In order to track the drug delivery system and study the uptake into tissues, an imaging moiety (e.g., a dye molecule such as rodamine or other dye) that has functionality to react with amines such as NHS-ester or isothiocyanates can be attached to the free amine groups that result from the cross-linking reaction, as shown in Scheme 7 in FIG. 64. The allyl groups or all other groups introduced are not affected.

Figure 65:
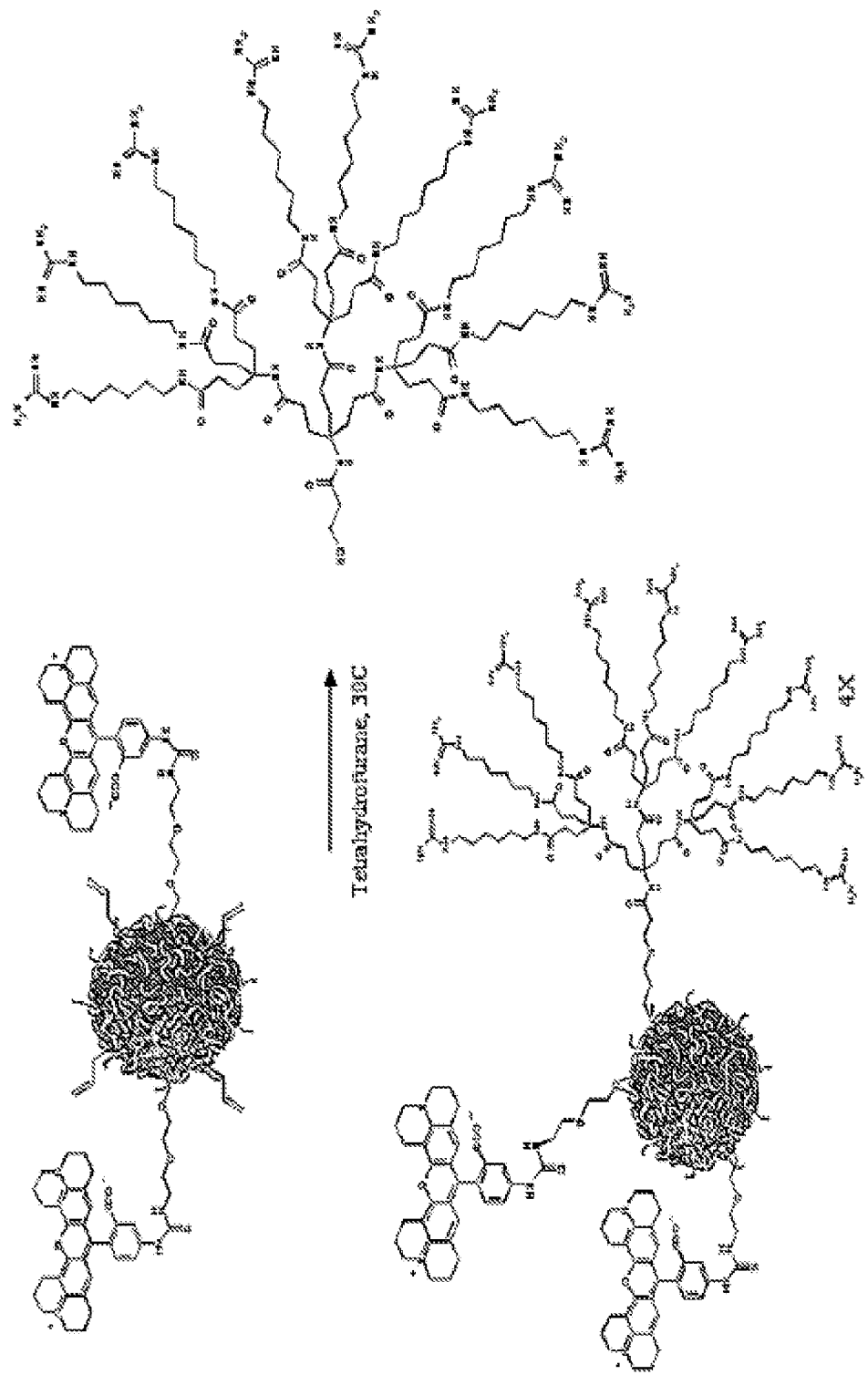
FIG. 65 shows nanoparticle formation from an allyl-functionalized ABbD linear precursor with diamines, thereby providing multiply functionalized degradable nanoparticles.

The allyl groups can then be reacted with thiol groups of the focal point of the dendritic transporter, as illustrated in Scheme 8a in FIG. 65, thereby providing multiply functionalized degradable nanoparticles.

The number of molecular transporter(s) bonded to the nanoparticle can be selected by varying the stoichiometry of the reagents added to the allyl groups. The same reaction can be performed with thiol groups attached to peptides. It was found that elevated temperatures such as 37° C. speed up the reaction but do not destroy the peptide.

Figure 66:
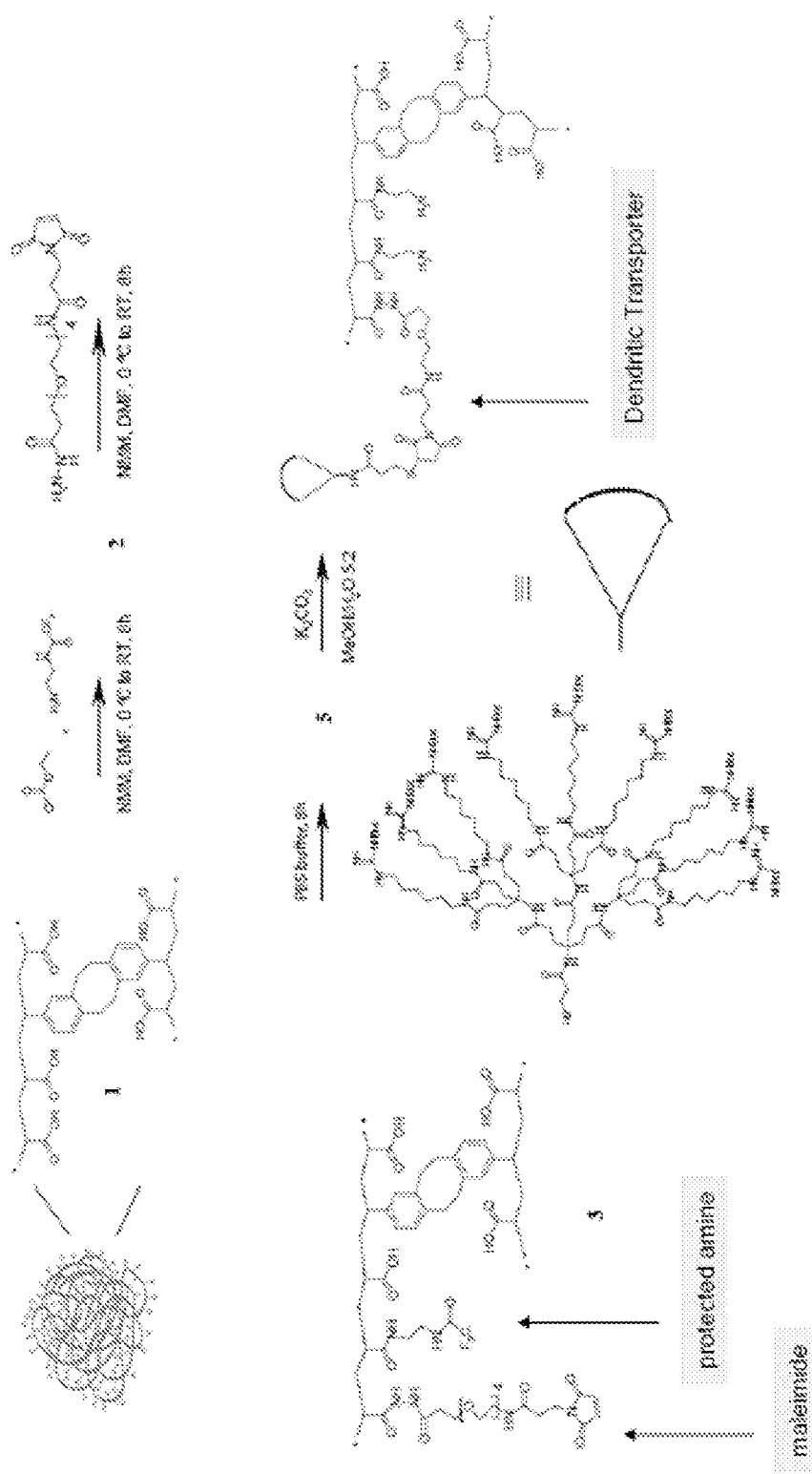
FIG. 66 shows a strategy for attaching dendritic transporter to nanoparticle.

In a further aspect, a nanoparticle can be attached to a disclosed dendritic molecular transporter through an exemplary strategy shown in Scheme 8b in FIG. 66.

Figure 67:
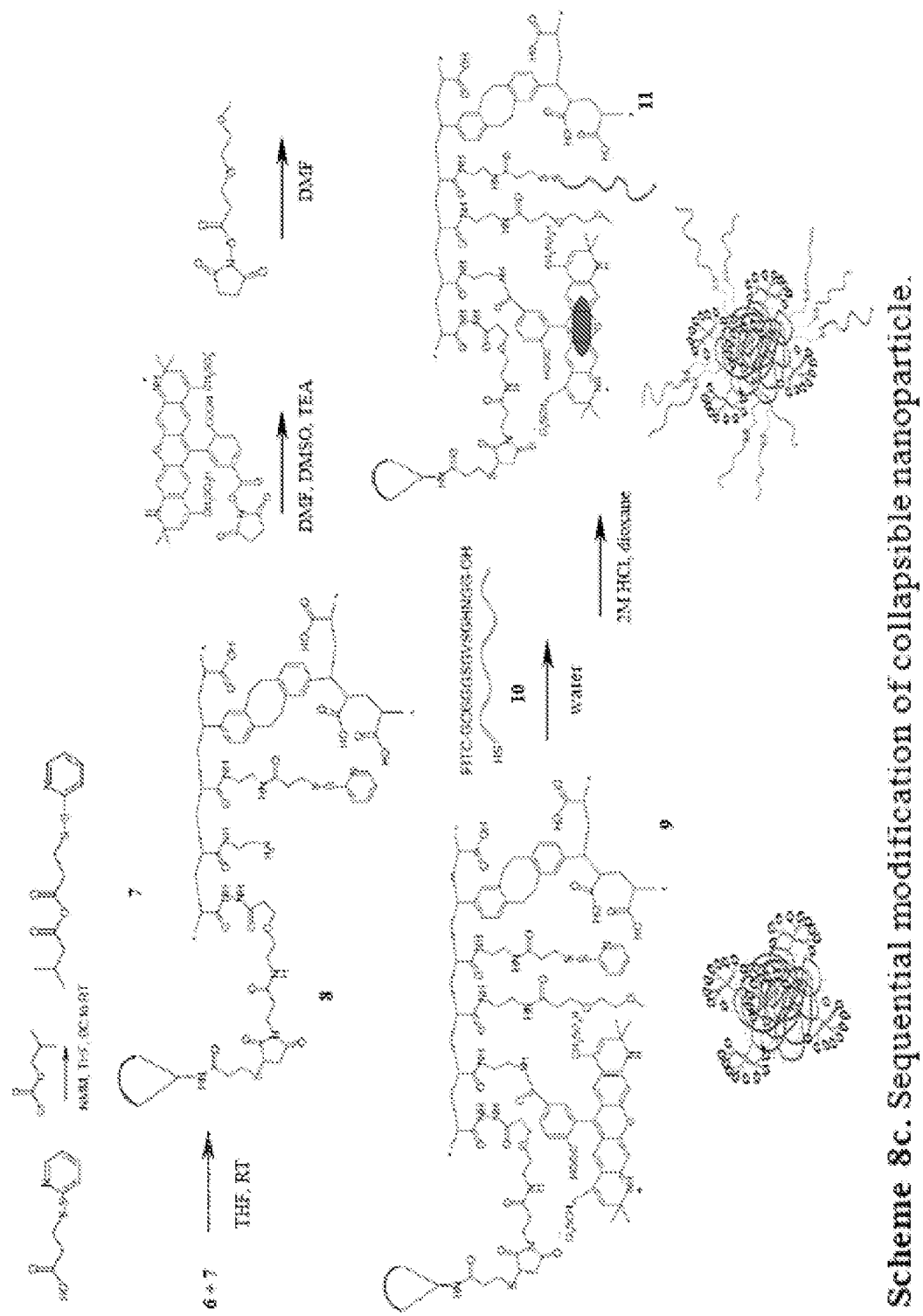
FIG. 67 shows sequential modification of collapsible nanoparticles.

The dendritic transporter shown in Scheme 8 can be further functionalized according to Scheme 8c in FIG. 67.

Figure 68:
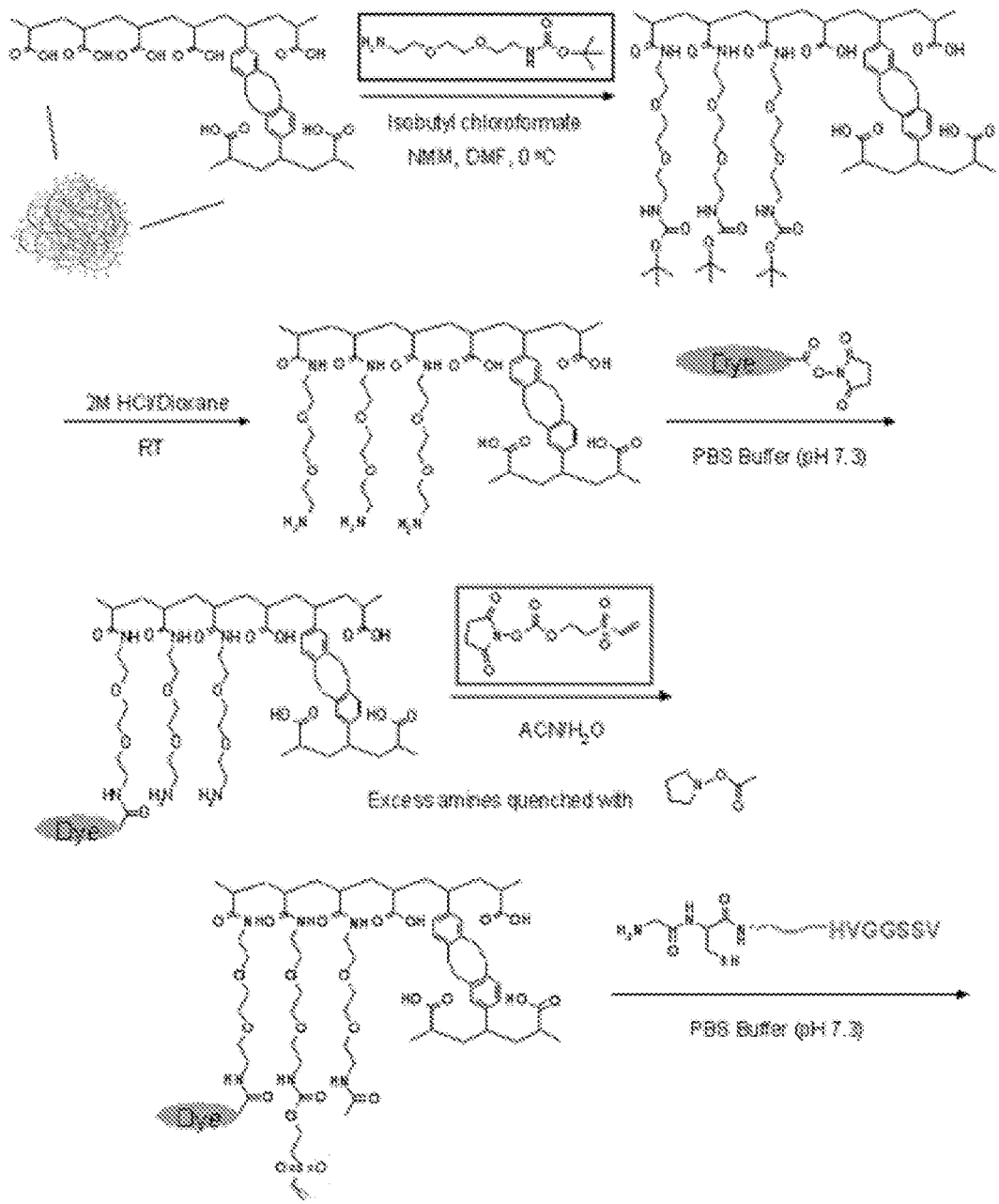
FIG. 68 shows attachment of a targeting peptide to the SVEC system. The peptide shown is Seq. I.D. 1.

The nanoparticle of the intramolecular chain collapse reaction can be reacted with the commercially available N-Boc ethylenoxide amine. The amine can be deprotected via acid cleavage with HCl or formic acid. Some of the free amines can be labeled with dye via NHS-ester reaction or thioisocyanide reaction. An SVEC moiety can then be connected trough an NHS ester reaction. After the reaction the residual amine groups are being quenched. The thiol groups are attached to the vinylsulfone groups of the SVEC. The thiol groups of the molecular transporter can also be attached in the same fashion as the peptides, as shown in Scheme 9a in FIG. 68.

Figure 69:
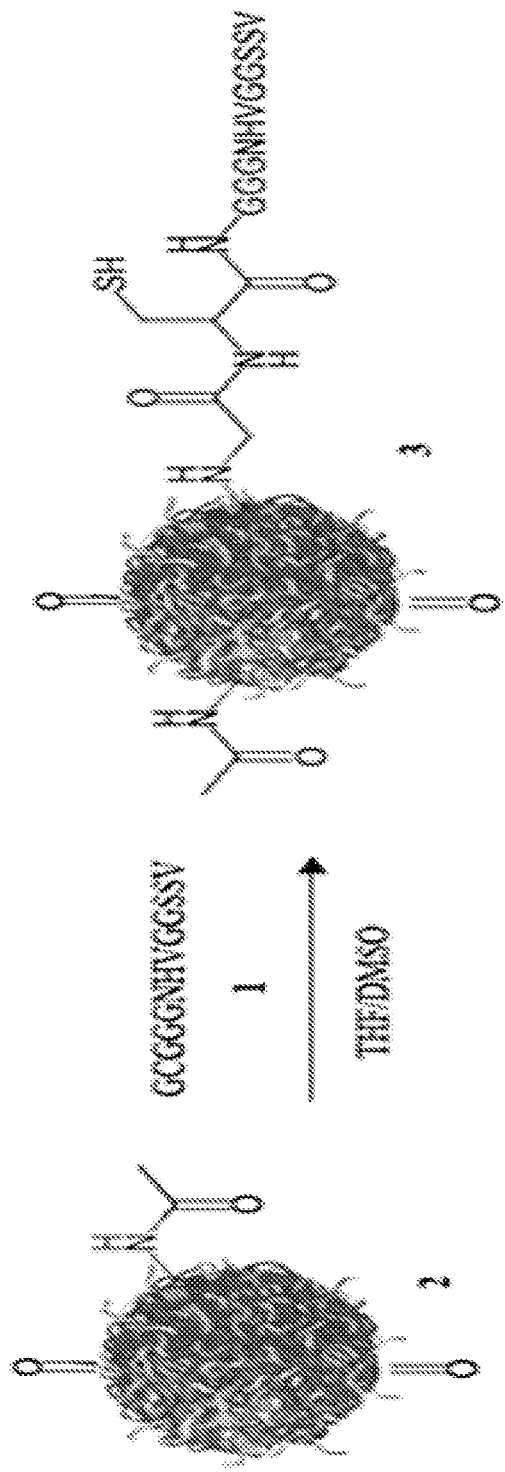
FIG. 69 shows attachment of a targeting peptide to a nanoparticle system. The peptide shown is Seq. I.D. 2.

Another example of attaching a peptide to a nanoparticle core is shown in Scheme 9b in FIG. 69.

Figure 70:
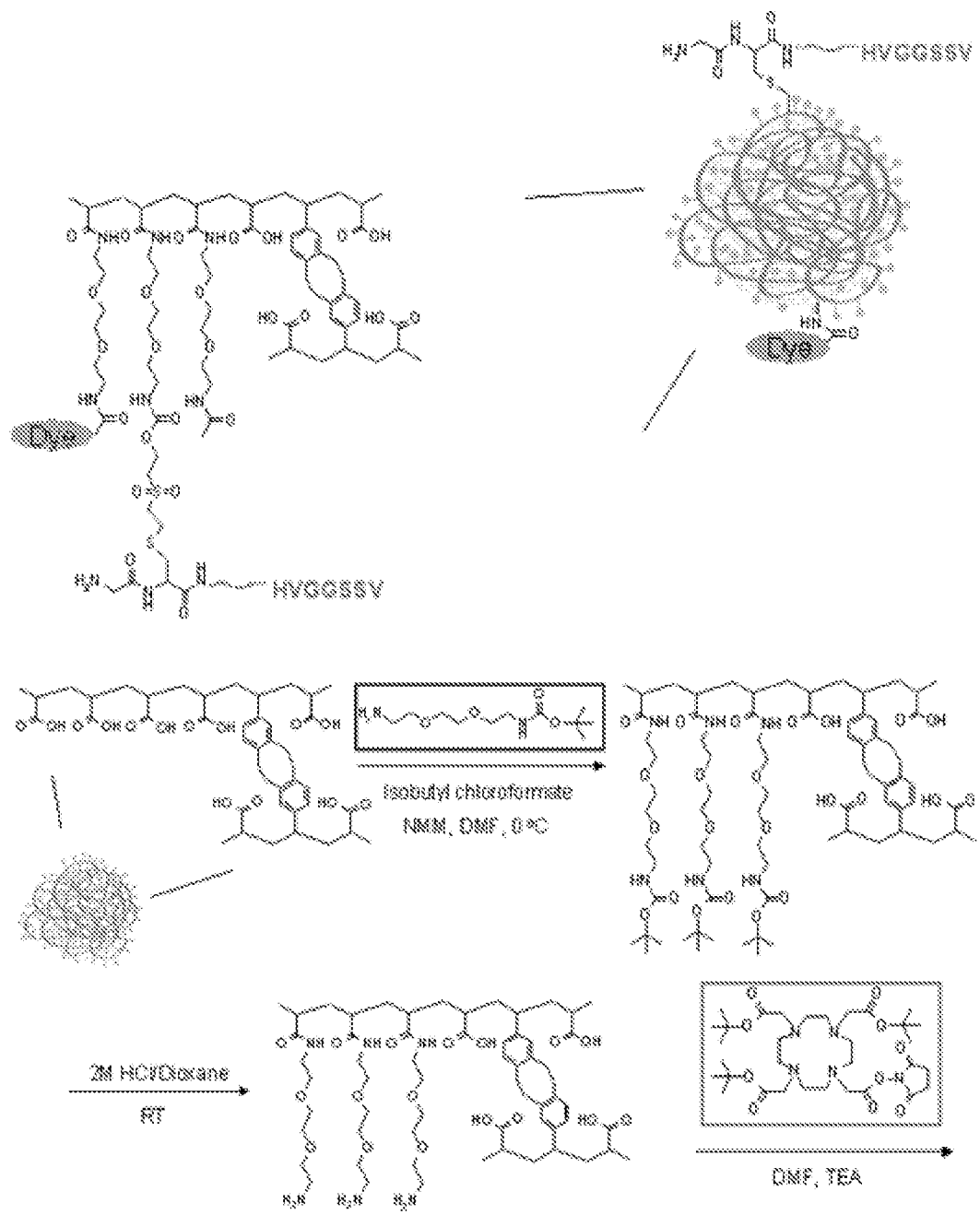
FIG. 70 shows functionalization of organic quantum dots via intramolecular chain collapse. The peptide shown is Seq. I.D. 1.
Figure 71:
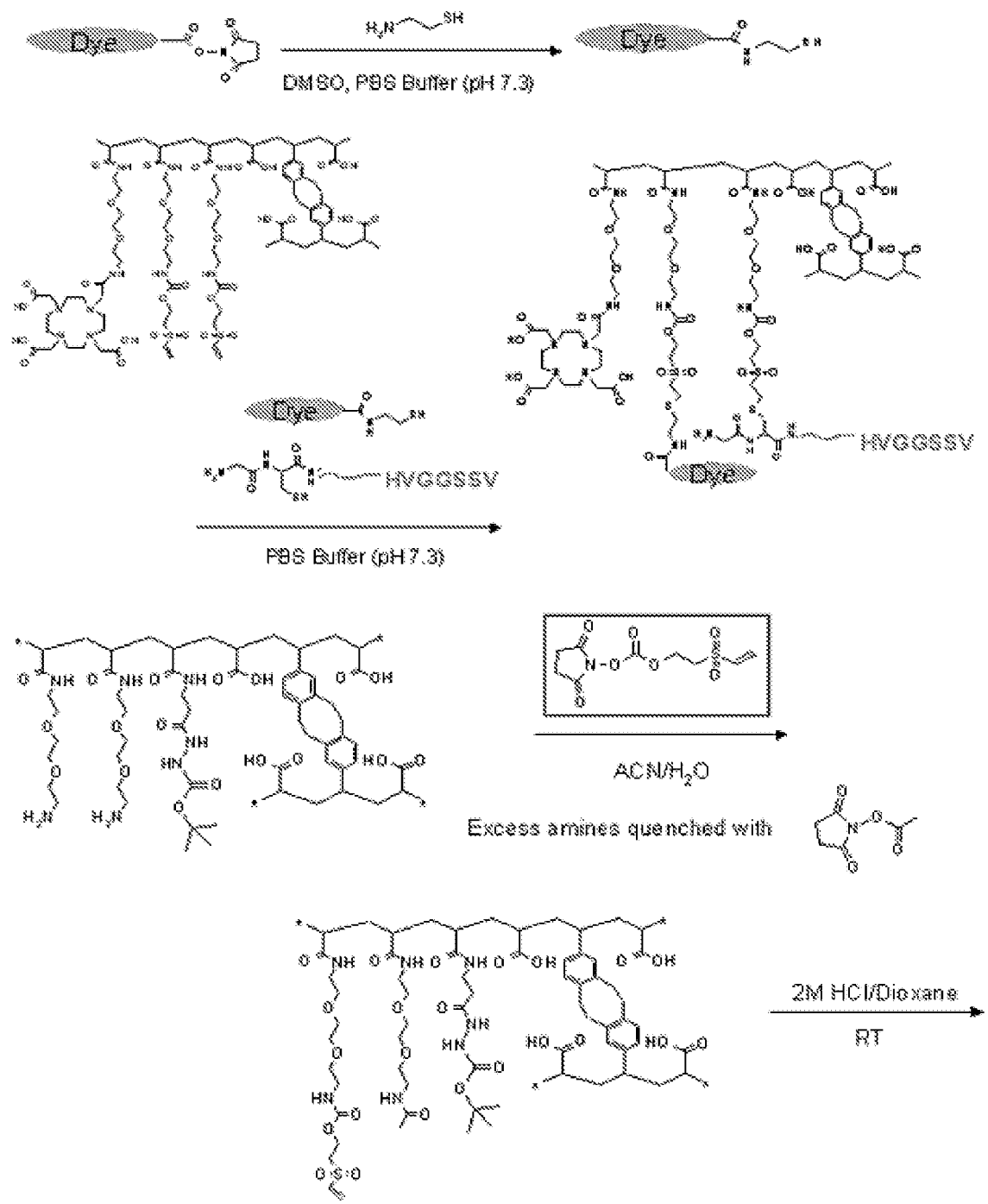
FIG. 71 shows deprotection of triflate with a base and attachment of SVEC followed by the deprotection of the acylhydrazone linker. The peptide shown is Seq. I.D. 1.
Figure 72:
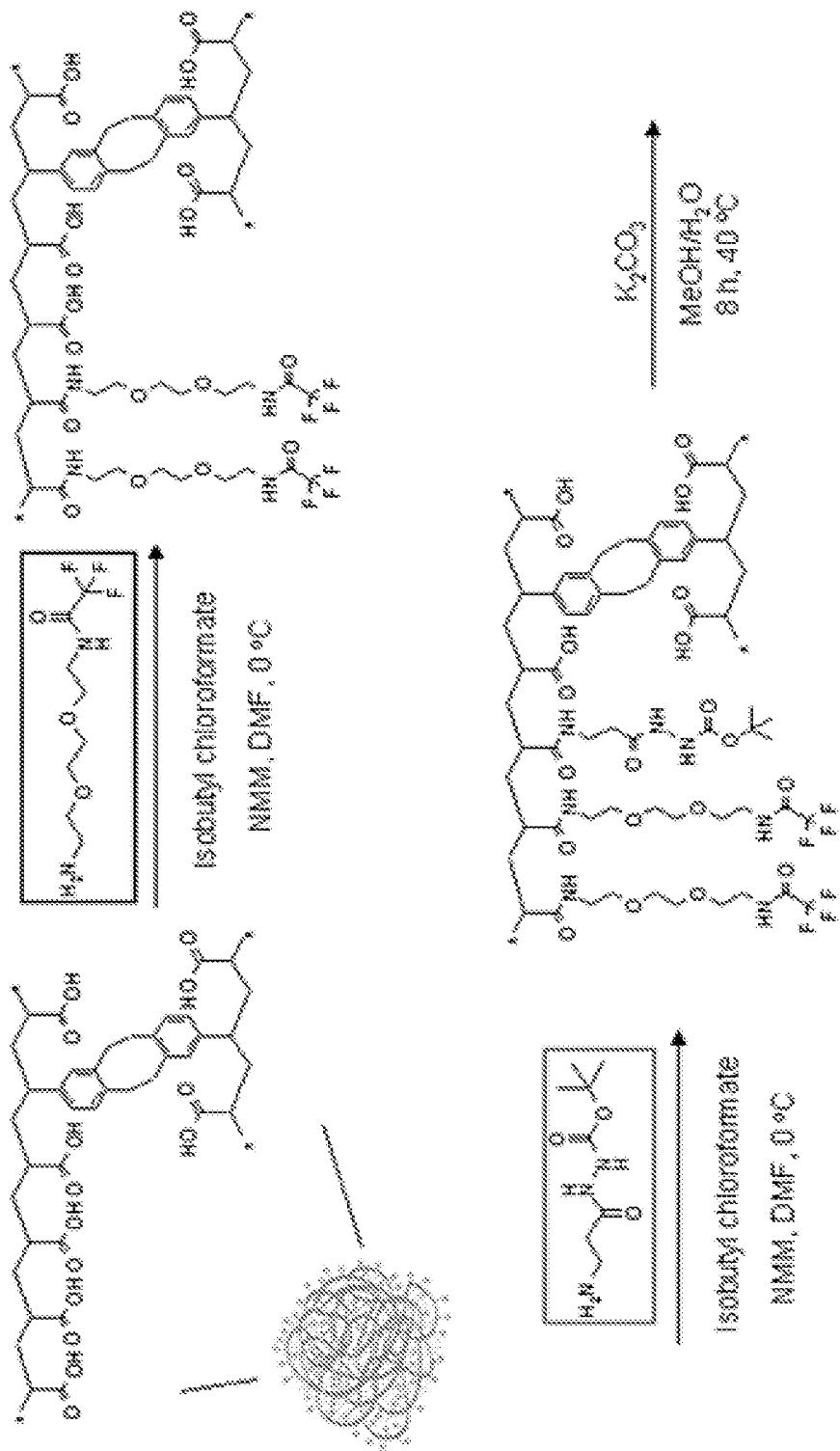
FIG. 72 shows the attachment of DOTA.

Imaging moieties (e.g., dyes or DOTA moieties) that can function as therapeutic and tracking units can also be attached via a nucleophilic functionality, as shown in Scheme 10 in FIG. 70.

Figure 73:
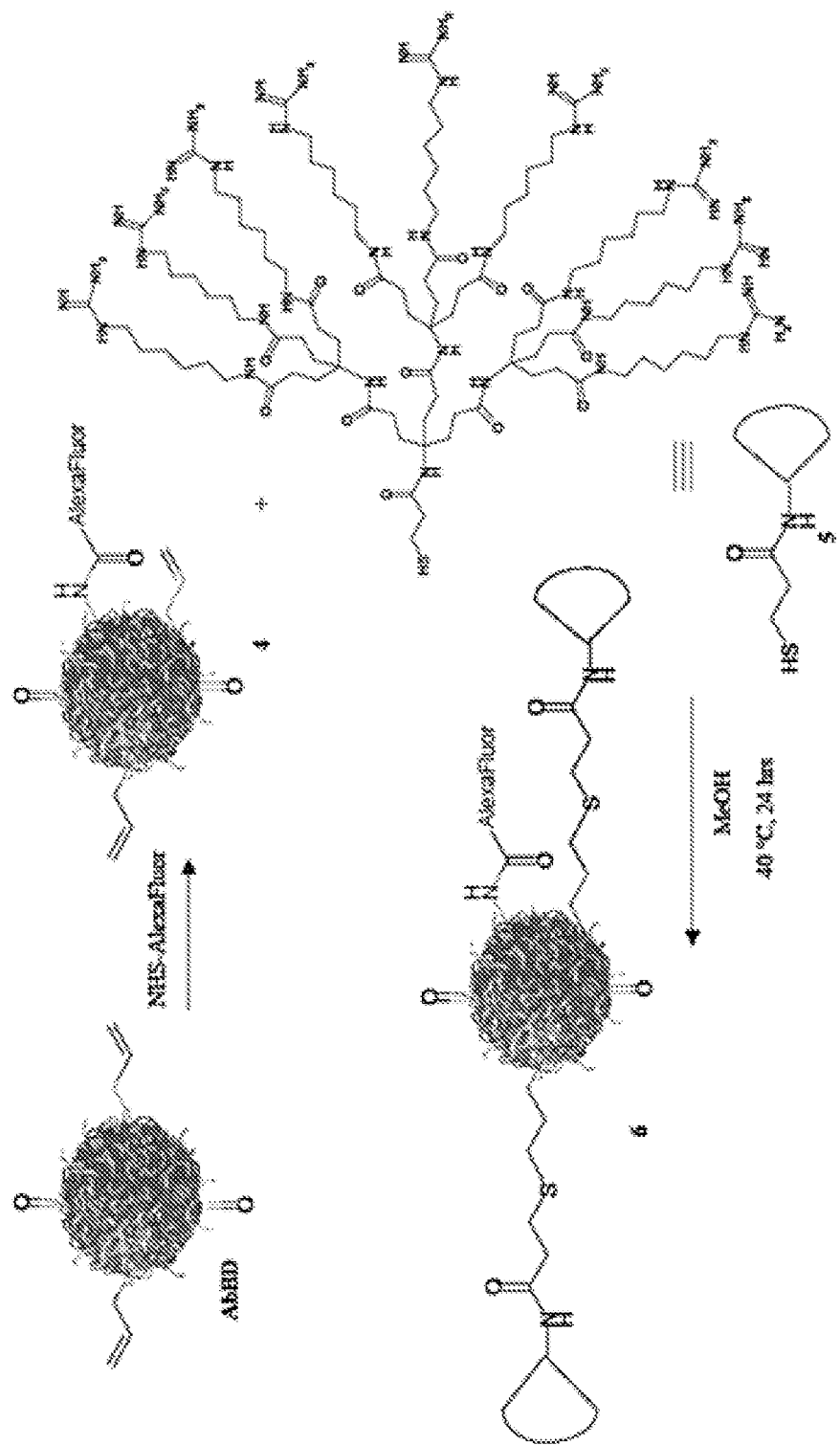
FIG. 73 shows functionalization of a nanoparticle with a dye for imaging the eye for testing.

In a further aspect, a disclosed nanoparticle can be functionalized with a dye for imaging the eye in a subject. For example, such a method can be accomplished conveniently by Scheme 12b in FIG. 73.

Figure 74:
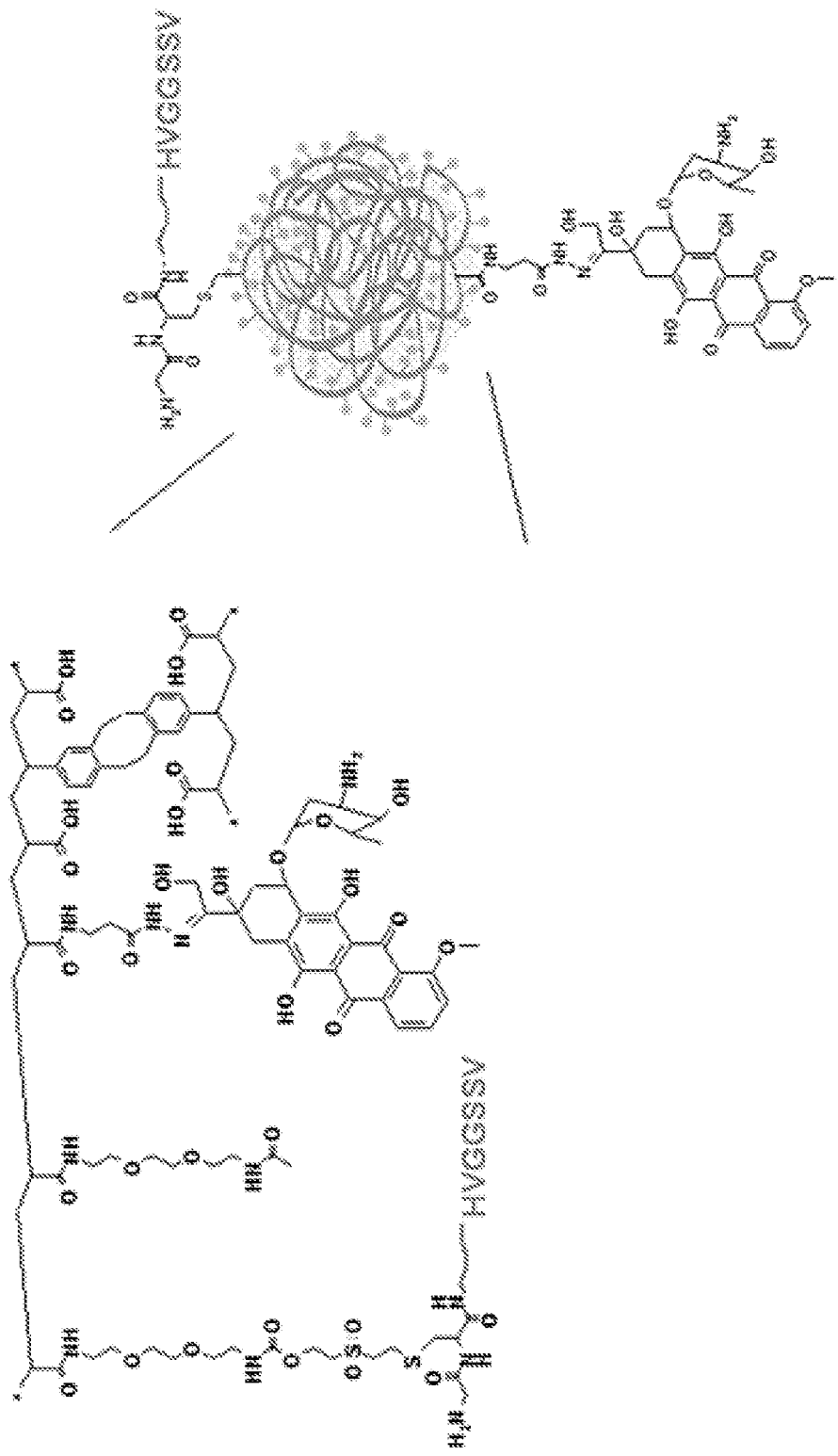
FIG. 74 shows attachment of a targeting unit; also c-RGD. The peptide shown is Seq. I.D. 1.

In a further aspect, analogous chemistry can be used to prepare a drug delivery system comprising a drug molecule that is attached to a pH sensitive linker and includes a hydrazide linker and doxorubicin. The synthesis is illustrated in Schemes 13 and 14 and in Scheme 15 in FIG. 74.

Scheme 13. Attachment of two types of β-alanyl (Boc)hydrazide; and N-Tfa-ethyleneoxide diamine.
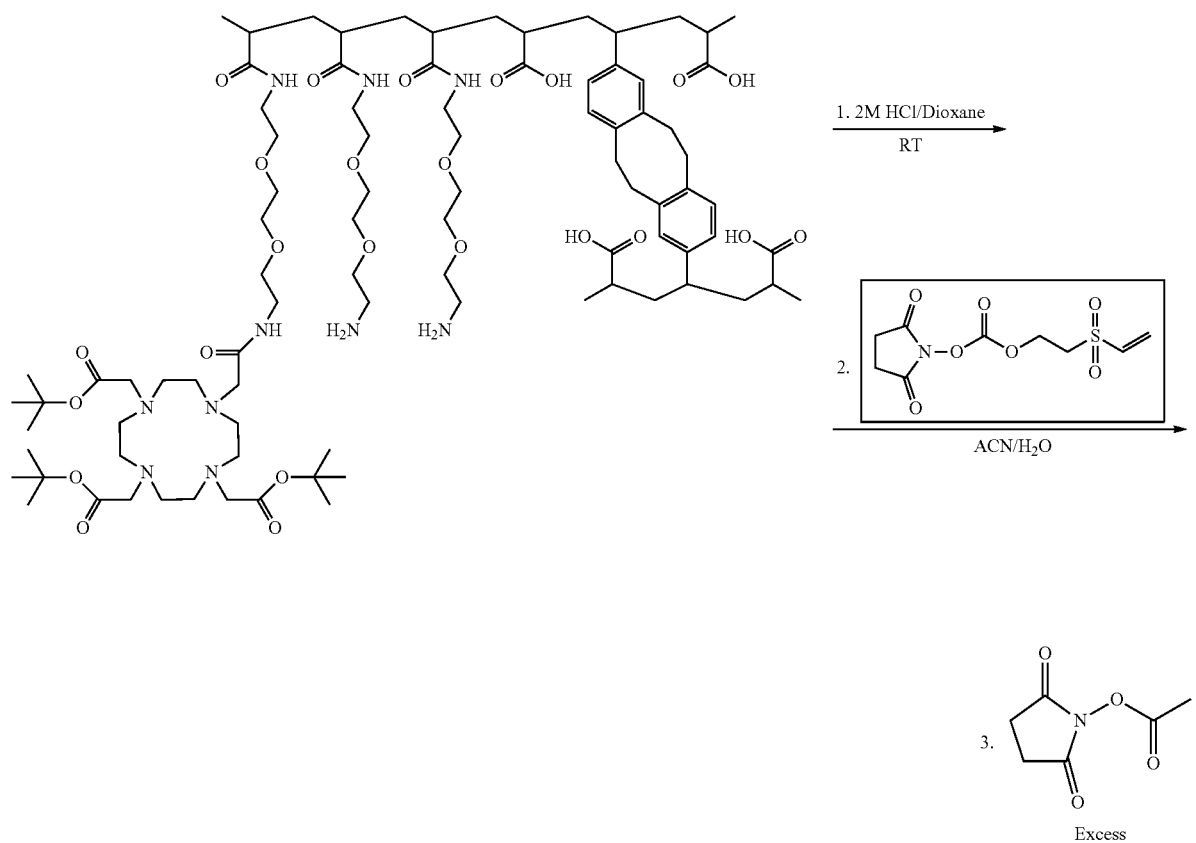
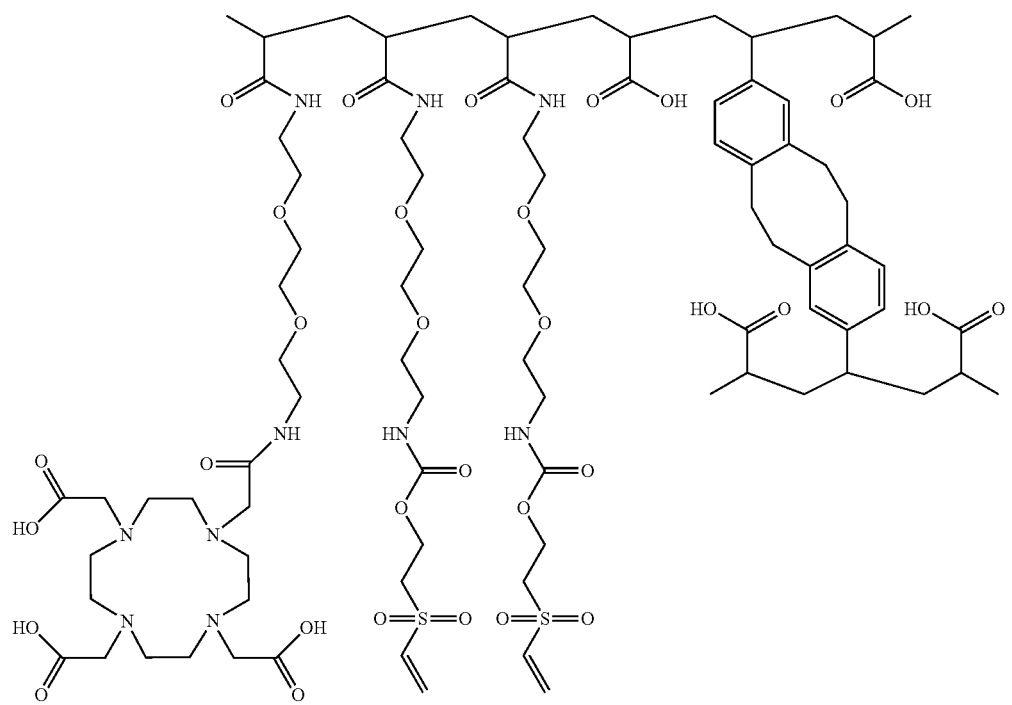

Scheme 14. Hydrazide linker formation of doxorubicine

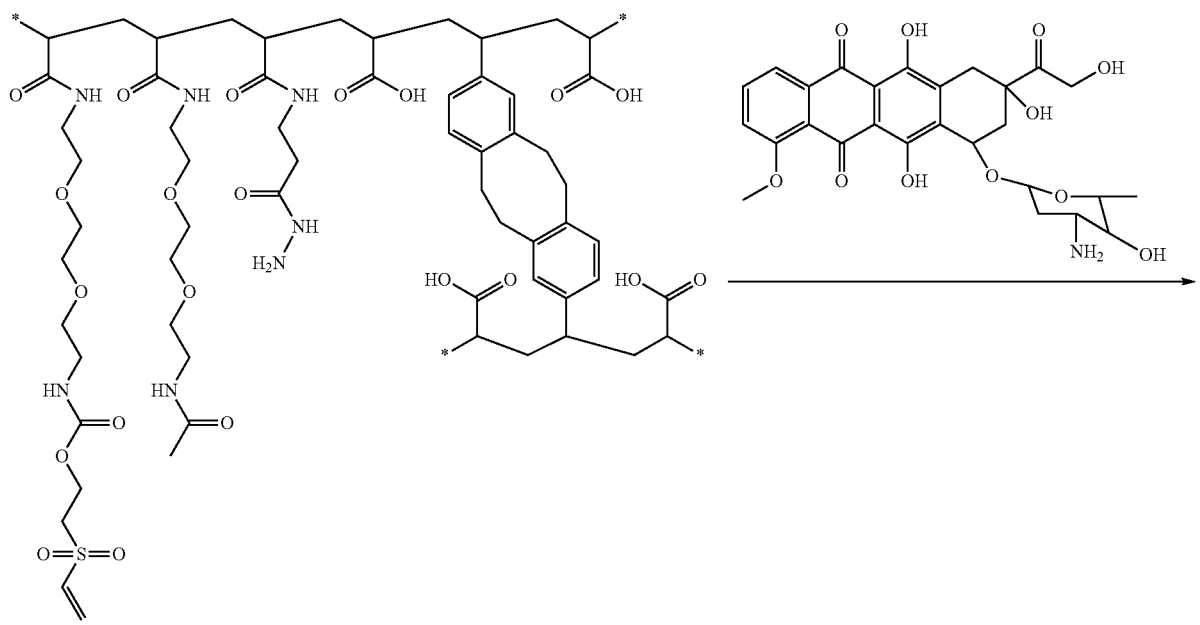

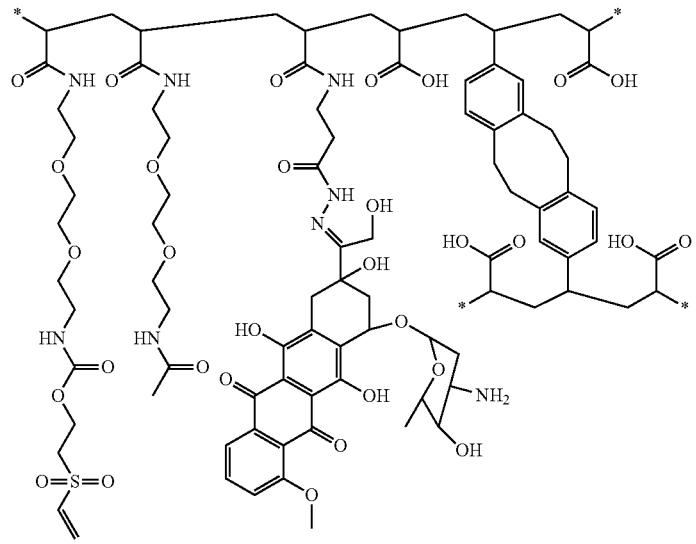

Figure 75:
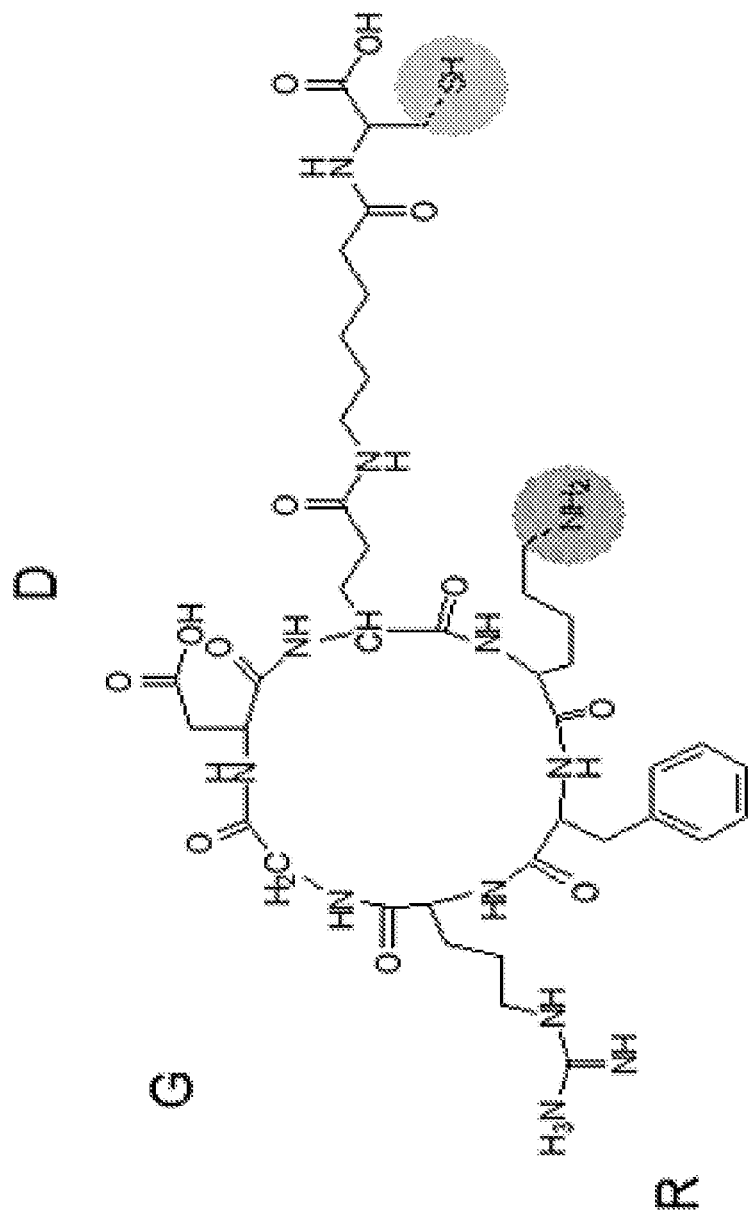
FIG. 75 shows c-RGD.

A novel c-RGD has been prepared and can be attached to the nanoparticles and used for targeting of the disclosed delivery systems (See Scheme 16 in FIG. 75).

Figure 76:
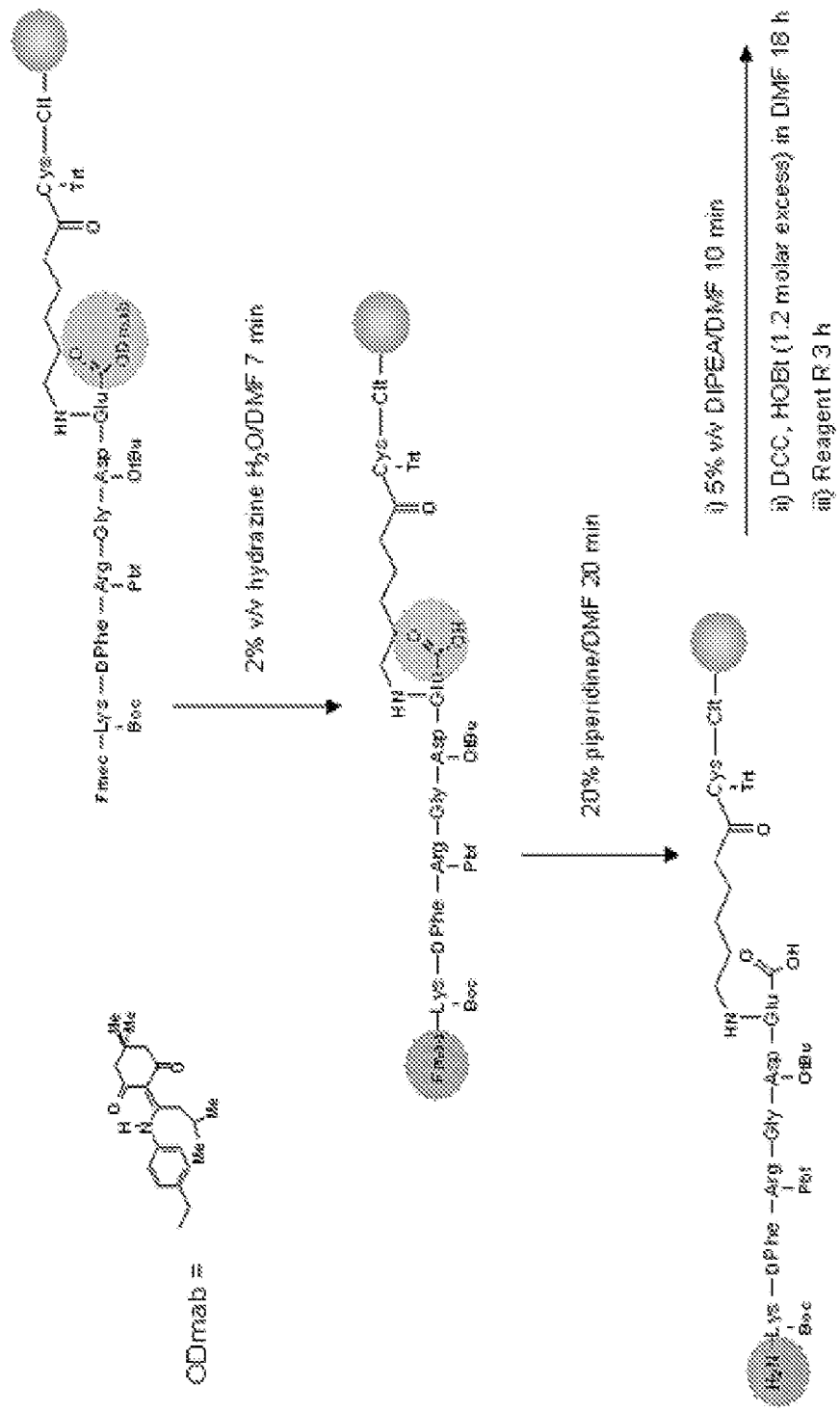
FIG. 76 shows the synthesis of C-RGD.

The synthesis of the c-RGD that contains free amine and thiol unit for attachment to SVEC of the particle from the intra-molecular chain collapse and the SVEC or the allyl group of the polyester particles is detailed in Scheme 17 in FIG. 76.

The attachment of the molecular transporter to the maleiminde of the intra-molecular chain collapse particle has also been investigated to create a system that transports peptides to intracellular location and across biological barriers. See Scheme 18.

Scheme 18. Attachment of N-Tfa-ethylenedioxide diamine linker and maleimide hydrazide to the nanoparticle.

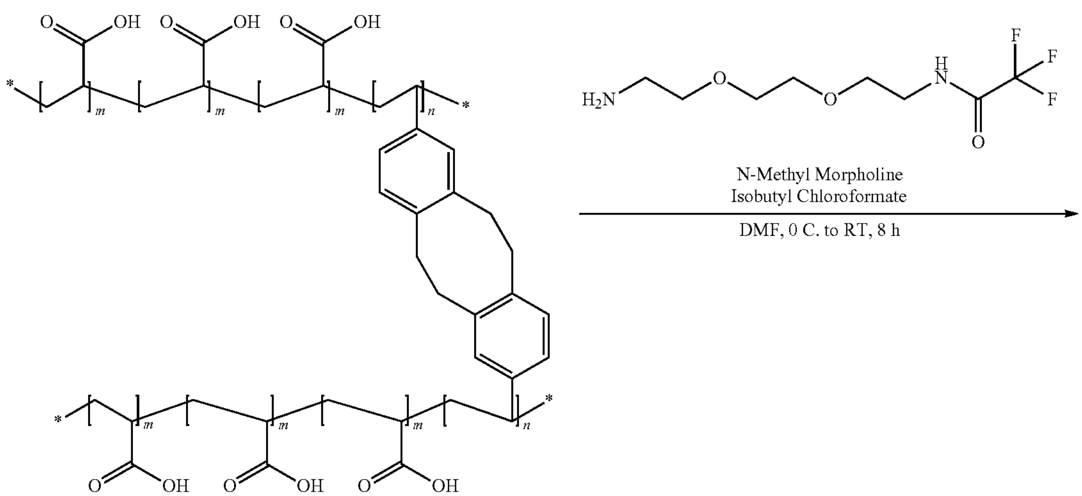

-continued
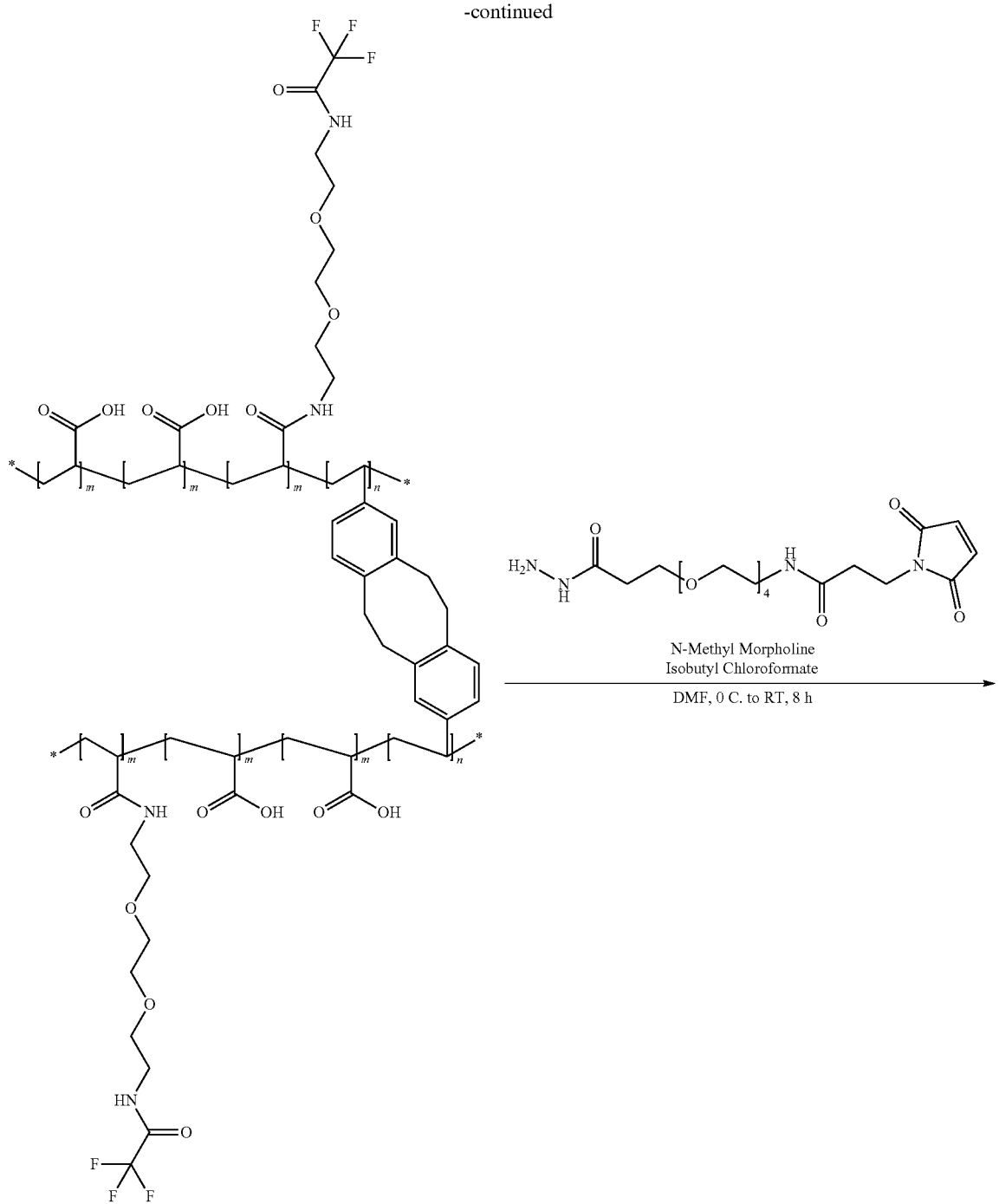
Further modifications of the nanoparticle-dendrimer conjugate systems have also been investigated. See Schemes 19-20. The disclosed modifications, as well as analogous transformations, results in a collection of compounds available for use in intracellular transport.

Scheme 19. Attachment of dendritic moieties to organic quantum dots.
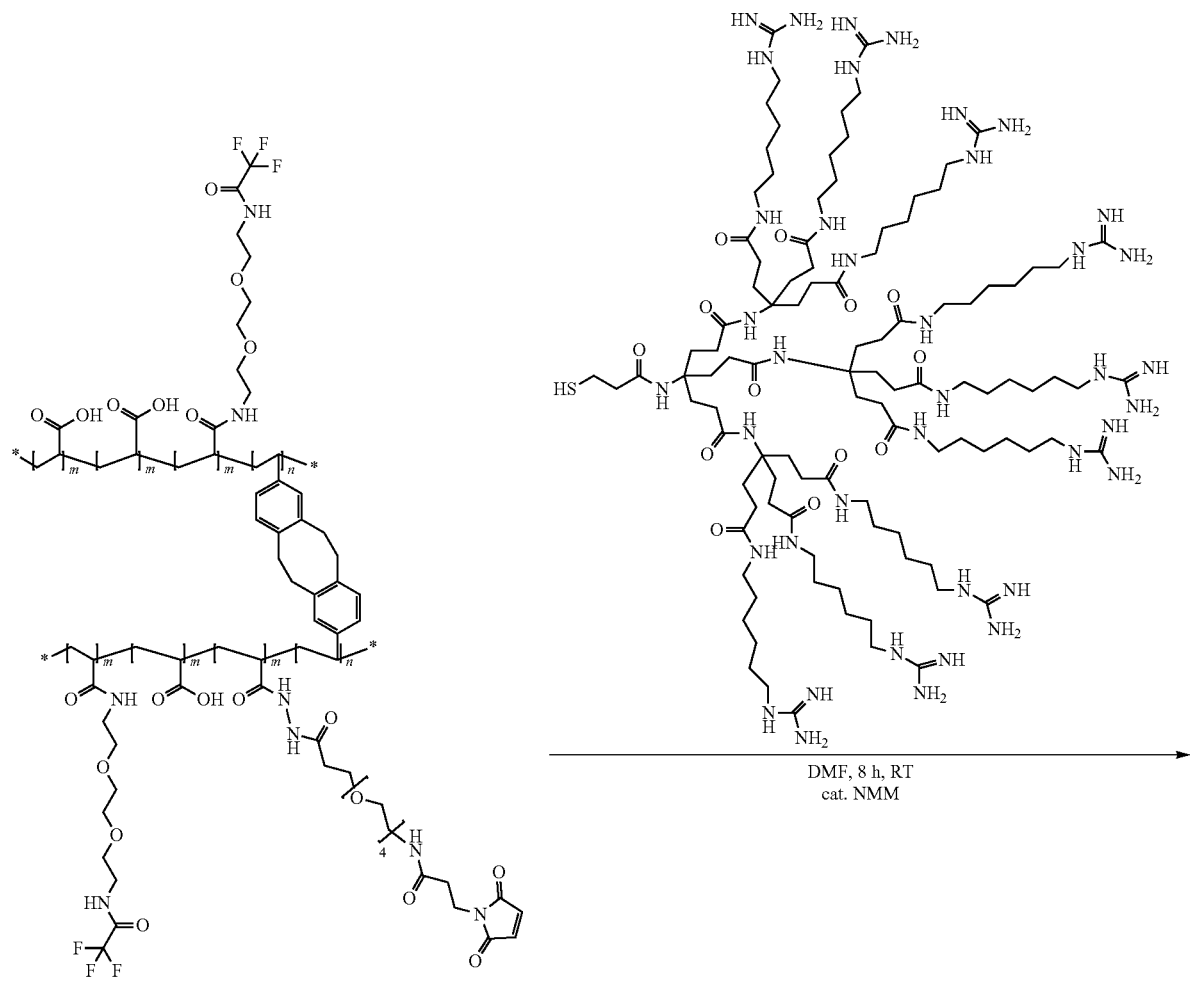

-continued
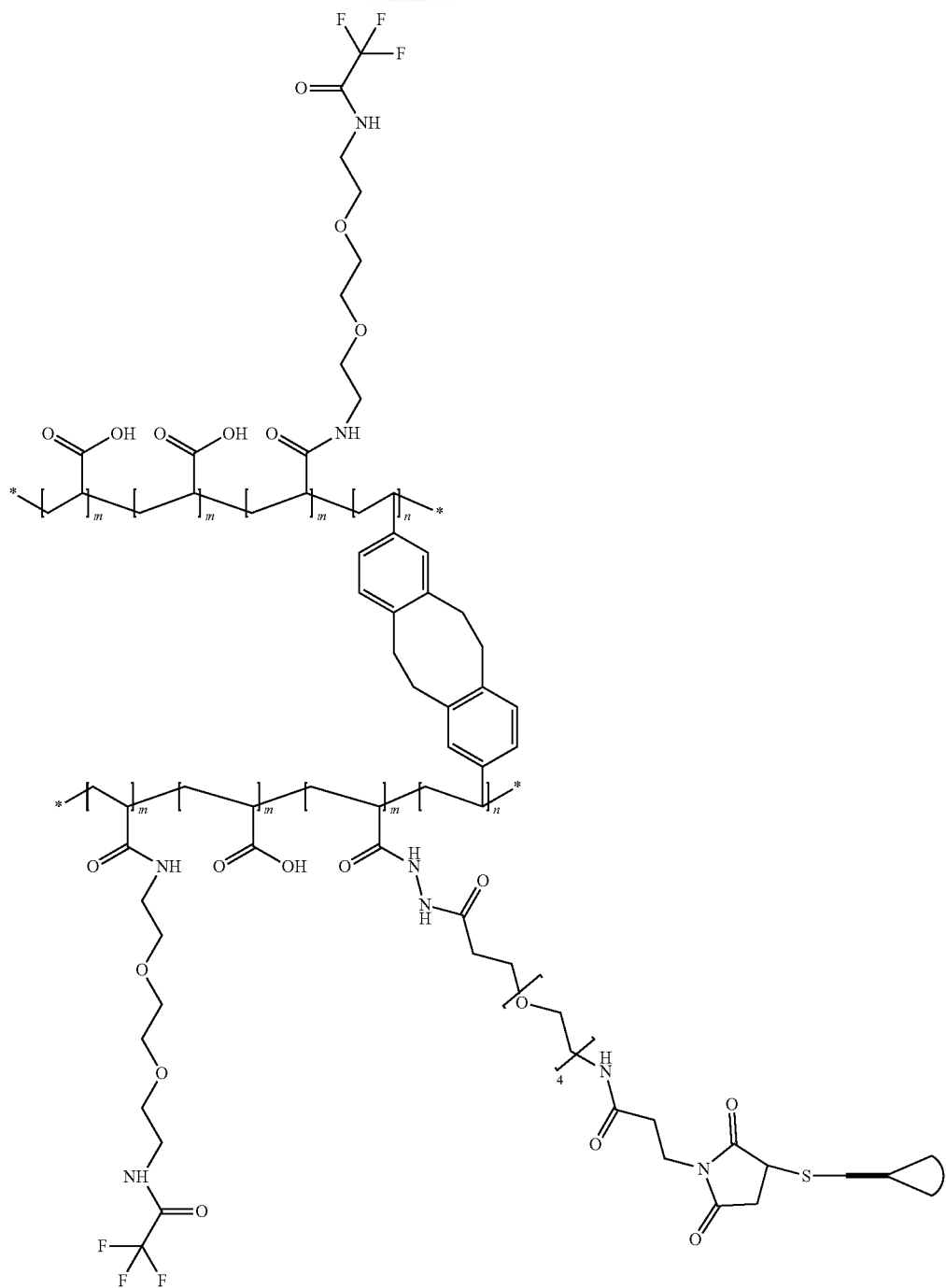

Scheme 19. Attachment of dendritic moieties to organic quantum dots.
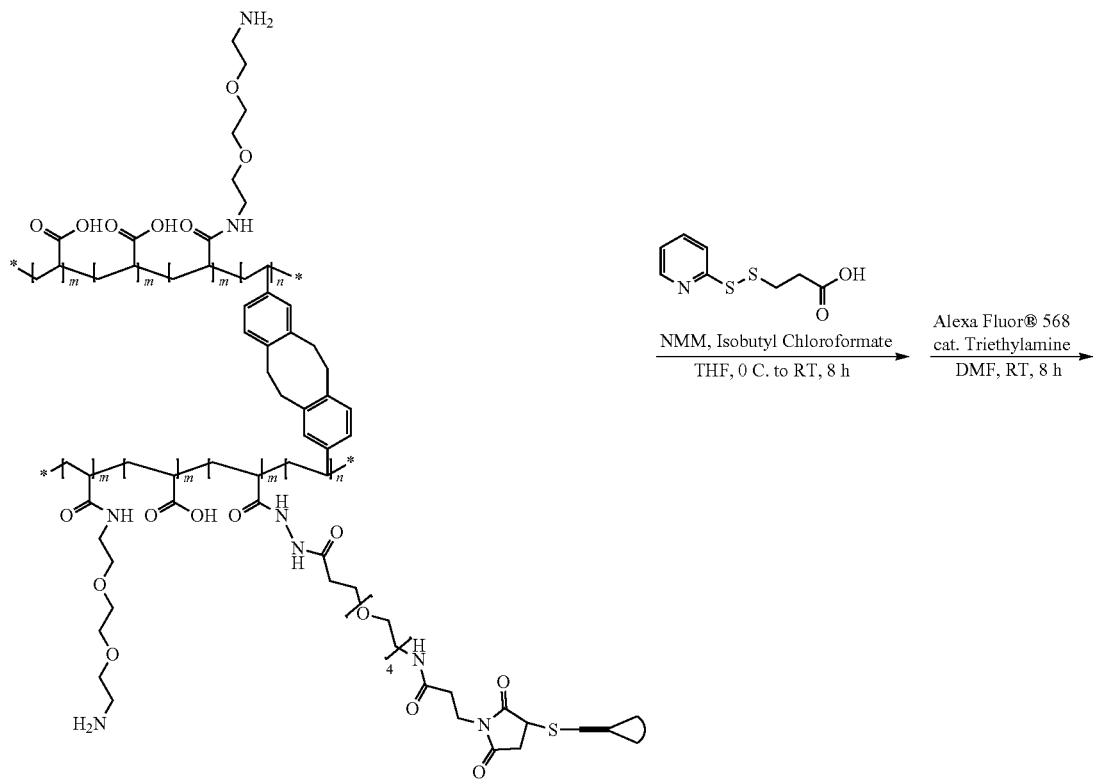

-continued

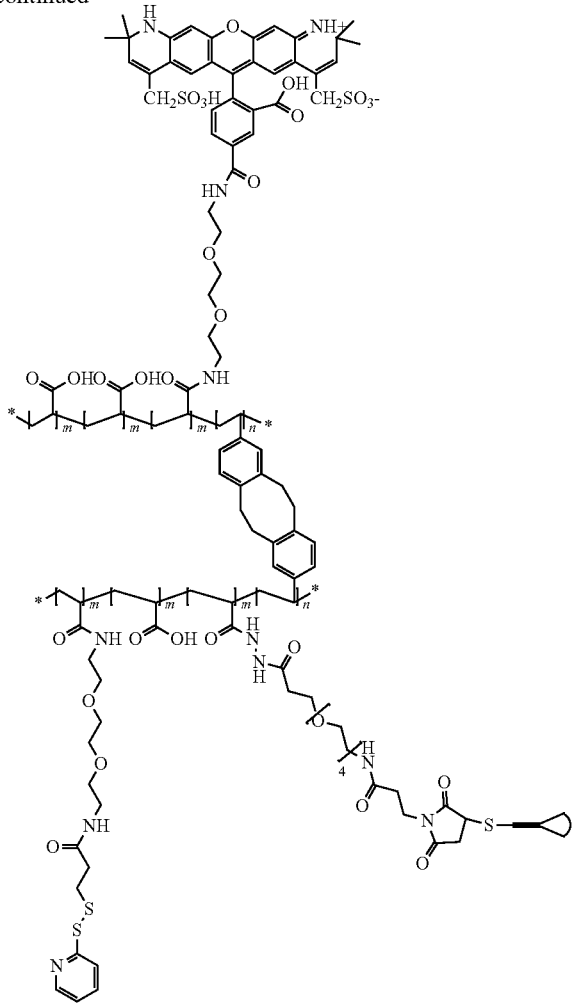

I. Nanosponges

In one aspect, the invention relates to intravitreal drug-delivery nanoparticles ("nanosponges"), which are three-dimensional nano-networks formed from degradable materials, in particular, formed by crosslinking degradable linear polyesters. In various aspects, nanosponges can refer to compositions comprising one or more disclosed compounds of the invention or one or more products of the disclosed methods. In particular, nanosponges can refer to disclosed compounds or products encapsulating one or more pharmaceutically active agent or biologically active agent, for example, agents disclosed herein.

In a further aspect, a nanosponge is an ocular delivery platform (degradable polyester nanoparticle pharmaceutical or biologically active agent complex, which can be also referred to as a nanoparticle complex, and can comprise one or more degradable crosslinked polyester nanoparticles and one or more biologically active agents, one or more pharmaceutically active agents, and/or one or more imaging agents, as disclosed herein. In a particular aspect, a nanosponge is an ocular delivery platform for treatment and/or prevention of eye diseases (e.g., glaucoma) and cancer (e.g., intraocular melanoma).

Nanosponges can offer significant advantages over conventional drug delivery systems. For example, nanosponges can be prepared using practical synthetic methods in suitable nanoscopic dimensions. In one aspect, nanosponges can be prepared for treatment of eye disease (e.g., 400 nm and 700 nm) or for treatment of cancer (e.g., 50 nm and, optionally, modified with targeting unit that only targets cancer site).

In one aspect, nanosponges can encapsulate hydrophobic, potent drugs as well as solubilize them in high concentrations. This leads to a larger pool of drugs available for drug discovery efforts. It is observed that there is no accumulation of nanosponges in other organs. As disclosed herein, nanosponges can be tailored to facilitate treatment of cancer type and disease stage. For example, drug release can be tailored (e.g., fast, medium, slow), which can be important for fast and slow growing cancer types (e.g., beast, prostate, lung, and brain). Nanosponges can be prepared for release of the encapsulated drug at a constant rate, which can be important for the development of clinical protocols.

In one aspect, the disclosed nanosponges can be used in connection with treatment of eye diseases such as glaucoma (4th major cause of blindness): Inter Ocular Pressure (IOP) can be controlled over a period of two months with ONE treatment, so far limited or no treatment possible.

J. Methods of Administration

The disclosed compositions are useful for the deposition of pharmaceutical agents encapsulated within the degradable polyester nanoparticle. Thus, disclosed herein are methods of administering a pharmaceutical or biologically active agent to a cell comprising contacting the cell with a degradable polyester nanoparticle-pharmaceutical or biologically active agent complex (nanoparticle complex) thereby administering the pharmaceutical biologically active agent to the cell. It is contemplated herein that the nanoparticles can release the pharmaceutical agents over time as the particle degrades resulting in the time release of the agent.

It is understood the nanoparticle-pharmaceutical agent complex can be administered to any cell type desired. For example, the cell can be a neuron (e.g., a photoreceptor neuron), ganglion cell, cone cell, rod cell, epithelial cell, muscle cell, adipose cell, hepatic cell, erythrocyte, leukocyte, mast cell, fibroblast (e.g., a comeal fibroblast). Such cells can be part of a larger tissue such as neuronal, fibrous, blood, gangloid, dermal, muscular, amacrine, bipolar, horizontal, connective, epithelial, and vitreal fluid. It is further understood that the cells to which the nanoparticle-pharmaceutical agent complex is applied can be located in a region of an organ such as the eye. Examples of such regions include by are not limited to a region of the eye selected from the group consisting of sclera, cornea, retina, vitrius fluid, rods, cones, iris, zonular fibers, aqueous humour, choroid, ciliary muscle, optic disc, dura mater, optic nerve, fovea, and macula. Because the nanoparticle-pharmaceutical agent complex can be delivered to living tissue, organs, or cells, it is further contemplated herein that said complexes have particular uses for administration of a pharmaceutical agent to a subject.

Due to the size of the nanoparticle complexes disclosed herein, it is understood that the degradable polyester nanoparticles can be used to deliver a pharmaceutical agent directly to the interior of a cell. Thus contemplated herein are methods of administration, wherein the nanoparticle complex is administered to anorganelle of a cell such as for example mitochondria, the nucleus, the golgi apparatus, endoplasmic reticulum, ribosomes, lysosomes, or centrioles. Thus, for example, disclosed herein are methods of administering a pharmaceutical or biologically active agent to the nucleus comprising contacting a cell with a degradable polyester nanoparticle-pharmaceutical or biologically active agent complex. It is understood that the complex can be taken up by the cell or can pass through a molecular channel such that the pharmaceutical or biologically active agent is internalized into the cell. It is further understood that the nanoparticle complex can further pass through organelle membranes to enter mitochondria or the nucleus of the cell.

It is understood that there are circumstances where one of skill in the art would want to monitor the deposition of the pharmaceutical or biologically active agent following the administration of the degradable polyester nanoparticle pharmaceutical or biologically active complexes. Therefore, it is contemplated herein that the nanoparticle complexes can further comprise a mechanism for detection. Detection can occur the use of imaging agents such as labels and dyes, but can also occur through the measure of physical characteristics such as measuring interocular pressure (IOP) or visualization such as electron microscopy. Where a dye or label is used, the means of detection can employ any method known in the art including but not limited to microscopy such as immunofluorescence, radioimmunoassay, ELISAs, ELISpot, and flow cytometry. As used herein, a label can include radiolabels, pigment dyes, a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Fluorophores are compounds or molecules that luminesce. Typically fluorophores absorb electromagnetic energy at one wavelength and emit electromagnetic energy at a second wavelength. Representative fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO™-1; BOBO™-3; Bodipy492/515; Bodipy493/503; Bodipy500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue: Calcium Crimson-; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM 1 Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DiD (DilC18(5)); DIDS; Dihydorhodamine 123 (DHR); Dil (DilC18(3)); I Dinitrophenol; DiO (DiOC18(3)); DiR; DiR (DilC18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genaciyl Pink 3G; Genacryl Yellow SGF; GeneBlazer; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Neuro DiO; Nile Red; Nitrobenzoxedidole; Noradrenaline; Nuclear Fast Red; i Nuclear Yellow; Nylosan Brilliant lavin E8G; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3 sulfopropyl) quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodaminelsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO 3; YOYO-1; YOYO-3; Sybr Green; Thiazole orange (interchelating dyes); semiconductor nanoparticles such as quantum dots; or caged fluorophore (which can be activated with light or other electromagnetic energy source), or a combination thereof.

A modifier unit such as a radionuclide can be incorporated into or attached directly to any of the compounds described herein by halogenation. Examples of radionuclides useful in this embodiment include, but are not limited to, tritium, iodine-125, iodine-131, iodine-123, iodine-124, astatine-210, carbon-11, carbon-14, nitrogen-13, fluorine-18. In another aspect, the radionuclide can be attached to a linking group or bound by a chelating group, which is then attached to the compound directly or by means of a linker. Examples of radionuclides useful in the apset include, but are not limited to, Tc-99m, Re-186, Ga-68, Re-188, Y-90, Sm-153, Bi-212, Cu-67, Cu-64, and Cu-62. Radiolabeling techniques such as these are routinely used in the radiopharmaceutical industry.

The radiolabeled compounds are useful as imaging agents to diagnose neurological disease (e.g., a neurodegenerative disease) or a mental condition or to follow the progression or treatment of such a disease or condition in a mammal (e.g., a human). The radiolabeled compounds described herein can be conveniently used in conjunction with imaging techniques such as positron emission tomography (PET) or single photon emission computerized tomography (SPECT).

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex. ELISAs use this type of indirect labeling.

As another example of indirect labeling, an additional molecule (which can be referred to as a binding agent) that can bind to either the molecule of interest or to the antibody (primary antibody) to the molecule of interest, such as a second antibody to the primary antibody, can be contacted with the immunocomplex. The additional molecule can have a label or signal-generating molecule or moiety. The additional molecule can be an antibody, which can thus be termed a secondary antibody. Binding of a secondary antibody to the primary antibody can form a so-called sandwich with the first (or primary) antibody and the molecule of interest. The immune complexes can be contacted with the labeled, secondary antibody under conditions effective and for a period of time sufficient to allow the formation of secondary immune complexes. The secondary immune complexes can then be generally washed to remove any non-specifically bound labeled secondary antibodies, and the remaining label in the secondary immune complexes can then be detected. The additional molecule can also be or include one of a pair of molecules or moieties that can bind to each other, such as the biotin/avadin pair. In this mode, the detecting antibody or detecting molecule should include the other member of the pair.

Other modes of indirect labeling include the detection of primary immune complexes by a two step approach. For example, a molecule (which can be referred to as a first binding agent), such as an antibody, that has binding affinity for the molecule of interest or corresponding antibody can be used to form secondary immune complexes, as described above. After washing, the secondary immune complexes can be contacted with another molecule (which can be referred to as a second binding agent) that has binding affinity for the first binding agent, again under conditions effective and for a period of time sufficient to allow the formation of immune complexes (thus forming tertiary immune complexes). The second binding agent can be linked to a detectable label or signal-generating molecule or moiety, allowing detection of the tertiary immune complexes thus formed. This system can provide for signal amplification.

Immunoassays that involve the detection of as substance, such as a protein or an antibody to a specific protein, include label-free assays, protein separation methods (i.e., electrophoresis), solid support capture assays, or in vivo detection. Label-free assays are generally diagnostic means of determining the presence or absence of a specific protein, or an antibody to a specific protein, in a sample. Protein separation methods are additionally useful for evaluating physical properties of the protein, such as size or net charge. Capture assays are generally more useful for quantitatively evaluating the concentration of a specific protein, or antibody to a specific protein, in a sample. Finally, in vivo detection is useful for evaluating the spatial expression patterns of the substance, i.e., where the substance can be found in a subject, tissue or cell.

Provided that the concentrations are sufficient, the molecular complexes ([Ab-Ag]n) generated by antibody-antigen interaction are visible to the naked eye, but smaller amounts may also be detected and measured due to their ability to scatter a beam of light. The formation of complexes indicates that both reactants are present, and in immunoprecipitation assays a constant concentration of a reagent antibody is used to measure specific antigen ([Ab-Ag]n), and reagent antigens are used to detect specific antibody ([Ab-Ag]n). If the reagent species is previously coated onto cells (as in hemagglutination assay) or very small particles (as in latex agglutination assay), "clumping" of the coated particles is visible at much lower concentrations. A variety of assays based on these elementary principles are in common use, including Ouchterlony immunodiffusion assay, rocket immunoelectrophoresis, and immunoturbidometric and nephelometric assays. The main limitations of such assays are restricted sensitivity (lower detection limits) in comparison to assays employing labels and, in some cases, the fact that very high concentrations of analyte can actually inhibit complex formation, necessitating safeguards that make the procedures more complex. Some of these Group 1 assays date right back to the discovery of antibodies and none of them have an actual "label" (e.g. Ag-enz). Other kinds of immunoassays that are label free depend on immunosensors, and a variety of instruments that can directly detect antibody-antigen interactions are now commercially available. Most depend on generating an evanescent wave on a sensor surface with immobilized ligand, which allows continuous monitoring of binding to the ligand. Immunosensors allow the easy investigation of kinetic interactions and, with the advent of lower-cost specialized instruments, may in the future find wide application in immunoanalysis.

The deposition of the nanoparticle-pharmaceutical agent complex can be direct or indirect depending on the needs of the particular situation. For example, the nanoparticle-pharmaceutical agent complexes disclosed herein can be applied directly to the sclera of an eye. Also, by way of example, the nanoparticle-pharmaceutical agent complexes can be injected into the vitreal fluid whereby the complexes can then come into contact with cells on the retina. One of skill in the art understands that the particle method of applying the nanoparticle-pharmaceutical agent complex depends In one aspect, the invention relates to a method of intracellular delivery comprising administering an effective amount of a disclosed nanoparticle to a subject. In a further aspect, the nanoparticle is further substituted with at least one biologically active agent, at least one pharmaceutically active agent, and/or at least one imaging moiety. In a further aspect, the method further comprises the step of degrading the nanoparticle.

In a further aspect, the invention relates to a method of intracellular delivery comprising administering an effective amount of a disclosed polymer or product of a disclosed method to a subject. In a further aspect, the polymer or product of a disclosed method is further substituted with at least one biologically active agent, at least one pharmaceutically active agent, and/or at least one imaging moiety. In a further aspect, the method further comprises the step of degrading the polymer or product of a disclosed method.

K. Methods of Treatment

It is contemplated herein that degradable polyester nanoparticles disclosed herein will slowly release any agent encapsulated within the nanoparticle at a rate equivalent to the degradation of the particle. Such release over time is particularly useful for the time release of pharmaceutical or biologically active agents that can be used to treat various diseases or conditions. Such diseases and conditions can include but are not limited to ophthalmic disorders. Thus, disclosed herein are method of treating any of the ophthalmic disorder disclosed herein (e.g., glaucoma) comprising administering to a subject a degradable polyester nanoparticle pharmaceutical or biologically active agent complex (nanoparticle complex).

The disclosed treatment methods may be used with any pharmaceutical or biologically active agent known for use as a treatment for the given ophthalmic disorder to be treated. Thus, for example, the pharmaceutical or biologically active agent can be an aptamer, an antibody, an alpha agonist, beta blocker, prostaglandin analog, carbonic anhydrase inhibitor, cholinergic, or any other agent disclosed herein.

Such agents are well known to those of skill in the art, but can include for example, triamcinolone, ranibizumab, bevacizumab, pegaptanib (MACUGEN®), travoprost, bimatoprost, methazolamide, brinzolamide, Dorzolamide HCl, Acetazolamide, Timolol Maleate, Betaxolol HCl, Levobunolol HCl, Metipranolol, Timolol hemihydrate, Pilocarpine HCl, Carbachol, brimonidine tartrate, memantine, Apraclonidine HCl, or latanoprost (XALATAN®). It is understood that the particular agent used will be suited to the medicinal purpose of the skilled artisan. For example, for treatment of macular degeneration, one or more pharmaceutical or biologically active agent such as ranibizumab or bevacizumab can be used. For the treatment of diabetic related disorders, triamcinolone can be used. For the treatment of glaucoma, one or more agents such as pegaptanib (MACUGEN®), travoprost, bimatoprost, methazolamide, brinzolamide, Dorzolamide HCl, Acetazolamide, Timolol Maleate, Betaxolol HCl, Levobunolol HCl, Metipranolol, Timolol hemihydrate, Pilocarpine HCl, Carbachol, brimonidine tartrate, Apraclonidine HCl, memantine, or latanoprost (XALATAN®) can be used in the disclosed methods. Thus, disclosed herein are methods of treating an ophthalmic disorder comprising administering to a subject one or more of the pharmaceutical or biologically active agents selected from the group consisting of triamcinolone, ranibizumab, bevacizumab, pegaptanib (MACUGEN®), travoprost, bimatoprost, methazolamide, brinzolamide, Dorzolamide HCl, Acetazolamide, Timolol Maleate, Betaxolol HCl, Levobunolol HCl, Metipranolol, Timolol hemihydrate, Pilocarpine HCl, memantine, Carbachol, brimonidine tartrate, Apraclonidine HCl, and latanoprost (XALATAN®).

It is disclosed herein that the treatment of any of the ophthalmic disorders disclosed herein may be treated by the use of more than one pharmaceutical or biologically active agent used in combination in the nanoparticle complexes. For example, disclosed herein are methods of treating glaucoma comprising administering to a subject a degradable polyester nanoparticle pharmaceutical agent complex wherein the complex comprises at least two pharmaceutical agents. It is understood that the disclosed methods of treatment or modulating receptor or enzymatic treatment can utilize within the nanoparticle complex any comprising a combination of at least two or more pharmaceutical or biologically active agents disclosed herein. For example, a combination of pharmaceutical agents may comprise an alpha agonist and a beta blocker such as Brimonidine Tartrate and Timolol Maleate or a beta blocker and a carbonic anhydrase inhibitor such as Dorzolomide HCl and Timolol Maleate. Other combinations contemplated herein include two or more alpha agonists, two or more beta blockers, two or more cholinergics, two or more carbonic anhydrases, two or more prostaglandin analogs, two or more antibodies, an alpha agonist and a beta blocker, an alpha agonist and a carbonic anhydrase inhibitor, an alpha agonist and a cholinergic, an alpha agonist and a carbonic anhydrase inhibitor, an alpha agonist and a prostaglandin analog, an alpha agonist an antibody, a beta blocker and a carbonic anhydrase inhibitor, a beta blocker and a prostaglandin analog, a beta blocker and an antibody, a beta blocker an a cholinergic, a carbonic anhydrase inhibitor and a prostaglandin analog, a carbonic anhydrase inhibitor and a cholinergic, a carbonic anhydrase inhibitor and an antibody, a cholinergic and a prostaglandin analog, a cholinergic and an antibody, and a prostaglandin analog and an antibody.

The mechanism by which the agents for use in the disclosed nanoparticles have their effect are known to those of skill in the art. For example, those of skill in the art know that the alpha agonist disclosed herein such as brimonidine tartrate and Apraclonidine HCl, function by interacting with a G coupled protein receptor known as the alpha adrenergic receptor. Similarly, the mechanism by which beta blockers function is two inhibit the functioning of a G coupled protein receptor referred to as the beta adrenergic receptor. Inhibitors of the beta adrenergic receptor include but are not limited to Timolol Maleate, Betaxolol HCl, Levobunolol HCl, Metipranolol, and Timolol hemihydrate. It is further understood that some agents which act as modulators of G coupled protein receptors are analogs to the natural ligand for the receptor. For example, latanoprost, travoprost, and bimatoprost are prostaglandin receptor analogs which modulate the activity of the prostaglandin F2 (FP) receptor. The activity of other receptors such as the acetylcholine receptor can also be modulated by the activity of the agents disclosed herein. For example, Pilocarpine HCl or Carbachol modulate acetylcholine receptor activity. Thus, disclosed herein are methods of modulating a receptor on a cell comprising contacting the receptor with a degradable polyester nanoparticle pharmaceutical biologically active agent complex (nanoparticle complex), wherein one or more pharmaceutical or biologically active agents is encapsulated by a degradable polyester nanoparticle. Also disclosed are methods of modulating a receptor wherein the receptor is a G coupled protein receptor such as the alpha adrenergic receptor, the beta adrenergic receptor, or prostaglandin F2 (FP) receptor comprising administering to a subject the nanoparticle complexes disclosed herein. Additionally, disclosed are methods of modulating a receptor wherein the receptor is the acetylcholine receptor comprising administering to a subject the nanoparticle complexes disclosed herein.

It is further contemplated herein that not all of the agents disclosed herein are known to those of skill in the art for use in the methods of treatment function by modulating the activity of a receptor. Some of the agents described herein have their medicinal effect through the ability to change the effect of an enzyme. For example, VEGF and in particular VEGF-A effects the outflow of vitreal fluid. Agents such as triamcinolone (a steroid) or pegaptanib (an aptamer) bind and inhibit VEGF whereas ranibizumab or bevacizumab are antibodies with a more specific action of inhibiting VEGF-A. Other agents such as methazolamide, brinzolamide, Dorzolamide HCl, and Acetazolamide inhibit carbonic anhydrase. Therefore disclosed herein are methods of modulating the activity of an enzyme such as VEGF, VEGF-A, or carbonic anhydrase comprising administering to a subject comprising administering to a subject the nanoparticle complexes disclosed herein. Due to the effect of enzyme activity on viteous outflow or other biological activity associated with ophthalmic disorders, disclosed herein are methods of treating an ophthalmic disorder (e.g., glaucoma, macular degeneration or diabetic odema) comprising administering to a subject a nanoparticle complex, wherein one or more pharmaceutical or biologically active agent encapsulated by the nanoparticle modulates that activity of VEGF, VEGF-A, or carbonic anhydrase.

L. Uses

Also provided are uses of the disclosed polymers, nanoparticles, and products. In one aspect, the invention relates to a use of a disclosed polymer or a disclosed nanoparticle to deliver a biologically active agent, a pharmaceutically active agent, and/or an imaging moiety. The disclosed compounds, compositions, and conjugates and practical synthesis of same provide approaches for applications in cancer treatment and drug delivery across biological barriers such as the cornea, tissues, skin, and the blood brain barrier.

These degradable polymers find application in controlled release technologies that have to penetrate tissues and cellular membranes. Thus, the nanoparticle-dendrimer conjugates comprising a disclosed degradable nanoparticle and a disclosed intracellular delivery composition can hold and deliver therapeutics ranging from small molecules to larger peptides, proteins, and antibodies.

In a further aspect, the invention relates to a use of a disclosed polymer or a disclosed nanoparticle for trancomeal delivery of a biologically active agent, a pharmaceutically active agent, and/or an imaging moiety.

Many regions of the eye are relatively inaccessible to systemically administered agents. For example, orally administered agents pass through the liver before reaching estrogen sensitive tissues. Because the liver contains enzymes that can inactivate the agent, the agent that eventually reaches tissue targeted for treatment can be virtually ineffective. Moreover, systemic administration risks production of undesirable side effects. It can also be problematic to deliver a biologically active agent, a pharmaceutically active agent, and/or an imaging moiety into the eye via invasive procedures such as injection. Further still, patient compliance can be low in cases of invasive administration.

As a result, topical drug delivery remains the preferred route of administration to the eye. There are a variety of factors that affect the absorption of drugs into the eye. These factors include: the instillation volume of the drug, the frequency of instilled drug administration, the structure and integrity of the cornea, the protein level in tears, the level of enzymes in tears, lacrimal drainage and tear turnover rate, as well the rate of adsorption and absorption of a drug by the conjunctiva, sclera, and eyelids. A potential way of reducing or even eliminating systemic side effects is to improve ocular targeting that would allow for the use of reduced doses of the biologically active agent in the ophthalmic drug formation.

A major barrier to ocular drug penetration is the cornea. The cornea is composed of three layers: a lipid-rich epithelium, a lipid-poor soma, and a lipid-rich endothelium. Therefore, an agent must possess both lipophilic-hydrophilic balance for adequate transcorneal penetration and, thus, ocular bioavailability (Akers, H. J., "Ocular bioavailability of topically applied ophthalmic drugs," Am Pharm, NS23: 33-36 (1983)).

Thus, in one aspect, the disclosed compounds provide improved physicochemical properties including, but not limited to, favorable ocular bioavailability and facile transcorneal penetration.

In another aspect, the disclosed compounds treat and/or protect against various ocular diseases. That is, the disclosed compounds can be used to diagnose, prevent, and/or treat ophthalmic disorders. Preferred disclosed compounds can be effective in treating and/or preventing maladies associated with vision-threatening intraocular damage due to pathophysiological predispositions. Preferred disclosed compounds include those which treat retinal infection, glaucoma, and/or macular degeneration.

M. Manufacture of a Medicament

Also provided is a method for the manufacture of a medicament. In one aspect, the invention relates to a method for the manufacture of a medicament for delivery of a biologically active agent, a pharmaceutically active agent, and/or an imaging moiety comprising combining at least one disclosed polymer or at least one disclosed nanoparticle with a pharmaceutically acceptable carrier.

In a further aspect, the pharmaceutical composition relates to a composition for preventing and/or treating ophthalmic disorders.

N. Pharmaceutical Compositions

In one aspect, the invention relates to pharmaceutical compositions comprising the disclosed compositions. That is, a pharmaceutical composition can be provided comprising a therapeutically effective amount of one or more disclosed polymer and/or one or more products of a disclosed method and/or one or more disclosed nanoparticle and a pharmaceutically acceptable carrier for administration in a mammal. In a further aspect, the one or more disclosed polymer and/or one or more products of a disclosed method and/or the one or more disclosed nanoparticle is further substituted with at least one biologically active agent, at least one pharmaceutically active agent, and/or at least one imaging moiety.

The disclosed pharmaceutical compositions can further comprise other therapeutically active compounds, which are usually applied in the treatment of the above mentioned pathological conditions. It is understood that the disclosed compositions can be employed in the disclosed methods of using.

O. Kits

Also provided are kits related to the disclosed compositions. In one aspect, the invention relates to a kit comprising at least one disclosed polymer, at least one disclosed nanoparticle or at least one product of a disclosed method. It is understood that the disclosed kits can be used in connection with the disclosed methods of using.

Thus, in one aspect, the invention related to kits comprising a first degradable polyester nanoparticle and a first biologically active agent, first pharmaceutically active agent, or first imaging agent encapsulated within the first nanoparticle, and one or more of: a second biologically active agent, second pharmaceutically active agent, or second imaging agent encapsulated within the first nanoparticle, wherein the first biologically active agent, first pharmaceutically active agent, or first imaging agent is different from the second biologically active agent, second pharmaceutically active agent, or second imaging agent; or a second degradable polyester nanoparticle and a second biologically active agent, second pharmaceutically active agent, or second imaging agent encapsulated within the second nanoparticle, wherein the first biologically active agent, first pharmaceutically active agent, or first imaging agent is different from the second biologically active agent, second pharmaceutically active agent, or second imaging agent; a pharmaceutically acceptable carrier; or instructions for treating a disorder known to be treatable by the first biologically active agent or first pharmaceutically active agent.

In a further aspect, at least one agent is brominidine tartrate. In a further aspect, at least one agent is an inhibitor of VEGF. In a further aspect, at least one agent is an inhibitor of VEGF-A. In a further aspect, at least one agent is a alpha agonist, beta blocker, prostaglandin analog, carbonic anhydrase inhibitor, antibody, aptamer, or cholinergic. In a further aspect, at least one agent is selected from triamcinolone, ranibizumab, bevacizumab, pegaptanib (MACUGEN®), travoprost, bimatoprost, methazolamide, brinzolamide, dorzolamide HCl, acetazolamide, memantine, timolol maleate, betaxolol HCl, levobunolol HCl, metipranolol, timolol hemihydrate, pilocarpine HCl, carbachol, brimonidine tartrate, apraclonidine HCl, and latanoprost (XALATAN®).

P. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Characterization Methods $^1$H NMR spectra were obtained from a Bruker AC300 Fourier Transform Spectrometer, with $CDCl_3$ in TMS as the solvent. $^{13}$C NMR spectra were obtained from a Bruker AC400 Fourier Transform Spectrometer with $CDCl_3$ as the solvent.

Gel-permeation chromatography (GPC) was performed on a Waters chromatograph equipped with a Waters 2414 refractive index detector, a Waters 2481 dual λ absorbance detector, a Waters 1525 binary HPLC pump, and four 5 mm Waters columns (300 mm×7.7 mm), connected in series with increasing pore size (100, 1000, 100,000 and 1,000,000 Å respectively). All runs were performed with tetrahydrofuran (THF) as the eluent at a flow rate of 1 mL/min.

For dynamic light scattering (DLS) a Zetasizer Nano Series instrument with a CGS-3 compact goniometer system by Malvern Instruments (Malvern Zetasizer Nanoseries, Malvern, UK) was employed at a fixed angle of 90° at 25° C., taking the average of three measurements. The particles were diluted with toluene to a concentration of 5-6 mg/mL, which gave the desired number of counts in order to obtain a good signal-to-noise ratio.

Samples for transmission electron microscopy (TEM) imaging were prepared by dissolving 0.5 mg nanoparticles in 1 mL isopropanol and 0.3 mL acetonitrile. The samples were sonicated for 5 min and were stained with 2 drops of 3% phosphotungstic acid. The carbon grids were prepared by placing a drop of dispersed particles onto an Ultrathin Carbon Type-A 400 Mesh Copper Grid (Ted Pella, Inc., Redding, Calif.) and drying at ambient temperature. A Philips CM20T transmission electron microscope operating at 200 kV in bright-field mode was used to obtain TEM micrographs of the polymeric nanoparticles.

Samples were centrifuged at 600 rpm on a Model CS International Centrifuge from International Equipment Company (Boston, Mass.).

2. Materials

Reagent chemicals were purchased from Aldrich (Milwaukee, Wis.), EMD, Alfa-Aesar, Fisher Scientific, and Acros and used as received, unless otherwise stated. Spectra/Por® Dialysis membrane and SnakeSkin® Pleated Dialysis Tubing, regenerated cellulose, were purchased from Spectrum Laboratories Inc. and Pierce Biotechnology, respectively. Analytical TLC was performed on commercial Merck plates coated with silica gel GF254 (0.24 mm thick). Silica gel for flash chromatography was Merck Kieselgel 60 (230-400 mesh, ASTM) or Sorbent Technologies 60 A (40-63 μm, technical grade). MAL-dPeg™$_4$-t-boc-hydrazide was obtained from Quanta Biodesign, Ltd. (Powell, Ohio) and used as received. Cy3 NHS dye and PD-10 Desalting columns were received from GE Healthcare (Piscataway, N.J.). Spectra/Por® Biotech Cellulose Ester (CE) Dialysis Membranes (1,000 MWCO) obtained from Spectrum Laboratories, Inc. (Rancho Dominguez, Calif.). SnakeSkin® Pleated Dialysis Tubing (10,000 MWCO) was obtained from Pierce Biotechnology, Inc. (Rockford, Ill.). Absolute molecular weight was determined with static light scattering.

3. Synthesis of a-allyl-Δ-valerolactone (avl)(B)

A 500 mL round bottom flask, equipped with stir bar, was sealed with a septum, purged with nitrogen for 30 min and cooled in a dry ice/acetone bath. A solution of lithium diisopropylamine (2.0 M in THF/heptane/ethyl benzene, 33 mL, 66 mmol) was added to the round bottom flask. A nitrogen purged solution of δ-valerolactone (5.43 mL, 60 mmol) in THF (60 mL) was added dropwise via syringe over 1.5 h. After an additional 30 min of stirring, a solution of allyl bromide (6.21 mL, 72 mmol) in hexamethylphosphoramide (12.51 mL, 72 mmol) was added dropwise via syringe over 30 min. The reaction mixture was warmed up to −40° C. using a dry ice/acetone bath and stirred for 3 h. The reaction was quenched with excess $NH_4Cl$ solution and warmed to room temperature. The crude product was washed twice with brine, dried with anhydrous magnesium sulfate and concentrated via rotary evaporator. Column chromatography using $CH_2Cl_2$ gave a viscous yellow product. Yield: 3.4262 g (41%). $^1$H NMR (300 MHz, $CDCl_3$/TMS, ppm) δ: 5.7 (m, 1H, $H_2C=CH-$), 5.08 (m, 2H, $H_2C=CH-$), 4.28 (m, 2H, $-C(O)OCH_2-$), 2.53-2.58 (m, 2H, $H_2C=CHCH_2-$), 2.27 (m, 1H, $H_2C=CHCH_2CH-$), 2.06 (m, 1H, $H_2C=CHCH_2CHCH_2-$), 1.89 (m, 2H, $C(O)OCH_2CH_2-$), 1.55 (m, 1H, $H_2C=CHCH_2CHCH_2-$); $^{13}$C NMR (400 MHz, $CDCl_3$, ppm) δ: 173.8 ($-C(O)O-$), 135.0 ($H_2C=CH-$), 117.4 ($H_2C=CH-$), 68.4 ($-C(O)OCH_2-$), 39.2 ($H_2C=CHCH_2CH-$), 35.4 ($H_2C=CHCH_2-$), 24.0 ($-CH_2CH_2CH_2-$), 21.9 ($-CH_2CH_2CH_2-$).

4. Synthesis of Copolymer Poly(vl-avl)(Ab)

A 50 mL 3-necked round bottom flask, equipped with stir bar, was sealed with two septa and a gas inlet. The flask was evacuated and refilled with nitrogen three times. Stock solutions of 1.7 M ethanol (EtOH) in THF and $3.7 \times 10^{-2}$ M tin(II) 2-ethylhexanoate ($Sn(Oct)_2$) in THF were made in sealed $N_2$ purged flasks. Solutions of EtOH (0.32 mL, $5.410 \times 10^{-1}$ mmol) and $Sn(Oct)_2$ (0.30 mL, $1.12 \times 10^{-2}$ mmol) were combined in the nitrogen purged 50 mL flask. After stirring the mixture for 30 min, α-allyl-δ-valerolactone (1.16 g, 8.32 mmol) and δ-valerolactone (vl, 2.5 g, 24.97 mmol) were added. The reaction vessel stirred in a 105° C. oil bath for 48 h. Residual monomer and catalyst were removed by dialyzing with Spectra/Por® dialysis membrane (MWCO=1000) against $CH_2Cl_2$ to give a golden brown polymer. Yield: 3.2398 g (88%). $M_w$=4834 Da, PDI=1.17; $^1$H NMR (300 MHz, $CDCl_3$/TMS, ppm) δ: 5.7 (m, $H_2C=CH-$), 5.09 (m, $H_2C=CH-$), 4.09 (m, $-CH_2-$ O—), 3.65 (m, CH$_3$CH$_2$O—), 2.35 (m, vl, —CH$_2$CH$_2$C(O)O—, avl, H$_2$C=CHCH$_2$CH—, H$_2$C=CHCH$_2$CH—), 1.68 (m, avl & vl, —CHCH$_2$CH$_2$—), 1.25 (t, CH$_3$CH$_2$O—); $^{13}$C NMR (400 MHz, CDCl$_3$, ppm) δ: 174.6 (avl, —C(O)—), 172.7 (vl, —C(O)—), 134.6 (H$_2$C=CH—), 116.4 (H$_2$C=CH—), 63.3, 44.3, 35.9, 33.1, 27.5, 25.9, 23.6, 20.9.

5. Synthesis of a-propargyl-Δ-valerolactone (pvl)(C)

A 250 mL round bottom flask, equipped with stir bar, was sealed with a septum, purged with nitrogen for 30 min and cooled in a dry ice/acetone bath. A solution of lithium diisopropylamine (2.0 M in THF/heptane/ethyl benzene, 22 mL, 44 mmol) was added to the flask. A nitrogen purged solution of 5-valerolactone (3.62 mL, 40 mmol) in THF (40 mL) was added dropwise via syringe over 1.5 h. After an additional 30 min of stirring, a solution of propargyl bromide (4.34 mL, 48 mmol) in hexamethylphosphoranide (8.4 mL, 48 mmol) was added dropwise via syringe over 20 min. The reaction mixture was warmed up to −30° C. using a dry ice/acetone bath and stirred for 3 h. The reaction was quenched with excess NH$_4$Cl solution and warmed to room temperature. The crude product was washed twice with brine, dried with anhydrous magnesium sulfate and concentrated via rotary evaporator. Column chromatography with CH$_2$Cl$_2$ gave a viscous yellow product. Yield: 2.8194 g (50.6%). $^1$H NMR (300 MHz, CDCl$_3$/TMS, ppm) δ: 4.35 (m, 2H, —C(O)OCH$_2$—), 2.69 (m, 2H, —C(O)CHCH$_2$C≡CH), 2.53 (m, 1H—C(O)CHCH$_2$C≡CH), 2.29 (m, 1H, —CHCH$_2$CH$_2$—), 2.05 (s, 1H, HC≡CCH$_2$—), 1.96 (m, 2H, —CHCH$_2$CH$_2$—), 1.74 (m, 1H, —CHCH$_2$CH$_2$—); $^{13}$C NMR (400 MHz, CDCl$_3$, ppm) δ: 172.8, 80.8, 70.1, 68.5, 38.5, 23.8, 21.7, 20.4.

6. Synthesis of Copolymer Poly (vl-avl-pvl) (AbC)

A 50 mL 3-necked round-bottom flask, equipped with stir bar, was sealed with two septa and a gas inlet. The flask was evacuated and refilled with nitrogen three times. Stock solutions of 1.7 M ethanol in THF and 3.7×10$^2$ M Sn(Oct)$_2$ in THF were made in sealed N$_2$ purged flasks. Solutions of ethanol (0.21 mL, 3.69×10$^{-1}$ mmol) and Sn(Oct)$_2$ (0.20 mL, 5.41×10$^{-3}$ mmol) were combined in the nitrogen purged 50 mL flask. After stirring the mixture for 30 min, α-allyl-δ-valerolactone (0.8 g, 5.7 mmol), δ-valerolactone (1.26 g, 12.6 mmol) and α-propargyl-δ-valerolactone (0.63 g, 4.6 mmol) were added. The reaction vessel stirred in a 105° C. oil bath for 48 h. Residual monomer and catalyst were removed by dialyzing with Spectra/Por® dialysis membrane (MWCO=1000) against CH$_2$Cl$_2$ to give a golden brown polymer. Yield: 2.25 g (84%). M$_w$=3500 Da, PDI=1.26; $^1$H NMR (300 MHz, CDCl$_3$/TMS, ppm) δ: 5.71 (m, H$_2$C=CH—), 5.03 (m, H$_2$C=CH—), 4.08 (m, —CH$_2$O—), 3.65 (m, CH$_3$CH$_2$O—), 2.55 (m, pvl, —C(O)CH—, —CHCH$_2$C≡CH), 2.45 (m, —CH$_2$C≡CH), 2.34 (m, vl, —CH$_2$CH$_2$C(O)O—, avl, H$_2$C=CHCH$_2$CH—, H$_2$C=CHCH$_2$CH—), 2.02 (m, pyl, —C≡CH), 1.68 (m, pvl, avl & vl, —CHCH$_2$CH$_2$—), 1.259 (t, CH$_3$CH$_2$O—); $^{13}$C NMR (400 MHz, CDCl$_3$, ppm) δ: 174.6, 172.7, 133.6, 117.2, 80.7, 69.9, 63.3, 44.3, 35.9, 33.1, 27.5, 25.9, 23.6, 20.9.

7. Synthesis of 2-oxepane-1,5-dione (opd)(D)

A 100 mL round bottom flask, equipped with stir bar, was charged with 1,4-cyclohexanedione (2.0 g, 17.84 mmol) and 3-chloroperoxybenzoic acid (4.5 g, 26.08 mmol). Dichloromethane (22 mL) was added and the reaction mixture stirred and refluxed for 3 h at 40° C. The reaction mixture was cooled to room temperature and dried with anhydrous MgSO$_4$. Solvent was removed via rotary evaporation. The crude product was washed three times with cold diethyl ether (100 mL for each wash) and dried in vacuo at room temperature. Yield: 1.4814 g (64.7%). $^1$H NMR (300 MHz, CDCl$_3$/TMS, ppm) δ: 4.4 (t, 2H, —C(O)OCH$_2$CH$_2$C(O)—), 2.84 (dd, 2H, —CH$_2$C(O)O—), 2.72 (m, 4H, —CH$_2$C(O)CH$_2$—); $^{13}$C NMR (400 MHz, CDCl$_3$, ppm) δ: 204.9 (—C(O)—), 173.3 (—C(O)O—), 63.3 (—CH$_2$O—), 44.7 (—OCH$_2$CH$_2$C(O)—), 38.6 (—C(O)CH$_2$CH$_2$C(O)—), 27.9 (—CH$_2$C(O)O—).

8. Synthesis of Copolymer Poly(vl-avl-opd) (AbD)

To a 50 mL 3-necked round bottom flask, equipped with stir bar, condenser, nitrogen purge and septa, 2-oxepane-1,5-dione (0.6987 g, 5.45 mmol) and dry toluene (4 mL) was added. The mixture stirred in an oil bath at 70° C. to dissolve the monomer. Upon dissolving, δ-valerolactone (1.5 g, 14.98 mmol), α-allyl-δ-valerolactone (0.9546 g, 6.81 mmol), absolute ethanol (0.0205 g, 4.4×10$^{-1}$ mmol) and Sn(Oct)$_2$ (0.0119 g, 2.73×10$^{-2}$ mmol) were then added to the reactor and the mixture was heated for 48 h at 110° C. Residual monomer and catalyst were removed by dialyzing with Spectra/Por® dialysis membrane (MWCO=1000) against CH$_2$Cl$_2$ to give a golden brown polymer. Yield: 2.6894 g (85%). M$_w$=4858 Da, PDI=1.27; $^1$H NMR (300 MHz, CDCl$_3$/TMS, ppm) δ: 5.72 (m, H$_2$C=CH—), 5.06 (m, H$_2$C=CH—), 4.34 (m, —CH$_2$CH$_2$C(O)CH$_2$CH$_2$O—), 4.08 (m, —CH$_2$O—), 3.67 (m, —OCH$_2$CH$_3$), 2.78 (m, opd, —OC(O)CH$_2$CH$_2$C(O)CH$_2$—), 2.58 (m, opd, —OC(O)CH$_2$CH$_2$C(O)CH$_2$—), 2.34 (m, vl, —CH$_2$CH$_2$C(O)O—, avl, H$_2$C=CHCH$_2$CH—, H$_2$C=CHCH$_2$CH—), 1.66 (m, avl & vl, —CHCH$_2$CH$_2$—), 1.25 (t, —CH$_2$CH$_3$); $^{13}$C NMR (400 MHz, CDCl$_3$, ppm) δ: 204.9, 175.2, 173.7, 173.2, 135.0, 117.0, 63.9, 44.8, 36.4, 33.6, 28.0, 26.3, 21.3.

9. Synthesis of Copolymer Poly(vl-avl-pvl-opd) (AbCD)

To a 25 mL 3-necked round bottom flask, equipped with stir bar, 2-oxepane-1,5-dione (0.2626 g, 2.05 mmol) was added and the flask was sealed with two septa and a gas inlet. The flask was evacuated and refilled with argon three times. Dry toluene (1.25 mL) was added and the mixture stirred in an oil bath at 70° C. to dissolve the monomer. Upon dissolving, Sn(Oct)$_2$ (0.0018 g, 4.41×10$^3$ mmol in 0.15 mL dry toluene), absolute ethanol (12.8 µL, 2.22×10$^{-1}$ mmol), δ-valerolactone (0.62 g, 6.2 mmol), α-allyl-δ-valerolactone (0.38 g, 2.69 mmol), and α-propargyl-δ-valerolactone (0.38 g, 2.73 mmol) were added. The temperature of the oil bath was increased to 105° C. and the mixture stirred for 50 h. Residual monomer and catalyst were removed by dialyzing with Spectra/Por® dialysis membrane (MWCO=1000) against CH$_2$Cl$_2$ to give a golden brown polymer. Yield: 1.31 g (80%). M$_w$=3525 Da, PDI=1.27; $^1$H NMR (300 MHz, CDCl$_3$/TMS, ppm) δ: 5.86 (m, H$_2$C=CH—), 5.09 (m, H$_2$C=CH—), 4.34 (m, opd, —CH$_2$CH$_2$C(O)CH$_2$CH$_2$O—), 4.08 (m, avl, pvl & vl, —CH$_2$O—), 3.65 (m, —OCH$_2$CH$_3$), 2.74 (m, opd, —OC(O)CH$_2$CH$_2$C(O)—), 2.60 (m, opd, —CH$_2$CH$_2$C(O)CH$_2$CH$_2$—, pvl, —OC(O)CH—, —CHCH$_2$C≡CH), 2.50 (m, CHCH$_2$C≡CH), 2.34 (m, vl, —CH$_2$CH$_2$C(O)O—, avl, H$_2$C=CHCH$_2$CH—, $H_2C=CHCH_2CH-$), 2.02 (m, $HC\equiv C-$), 1.68 (m, pvl, avl & vl, $-CHCH_2CH_2-$), 1.25 (m, $-CH_2CH_3$).

10. General Procedure for Oxidation of Copolymers

In a 200 mL round bottom flask, equipped with stir bar, poly(vl-avl) (2.7389 g, 6.12 mmol) was dissolved in 37 mL of $CH_2Cl_2$. To this solution, 3-chloroperoxybenzoic acid (2.0903 g, 12.11 mmol) was added slowly. The mixture was stirred for 72 h at room temperature and then concentrated via rotary evaporator. The crude product was dissolved in a minimal amount of THF (5 mL) and poured into a round-bottomed flask containing 1 L diethyl ether. The solution was kept overnight at 0° C. and a white solid was obtained. The solution was decanted off and the solid was dried in vacuo to obtain poly(vl-evl). Yield: 1,9467 g (71%). $^1$H NMR (300 MHz, $CDCl_3$/TMS, ppm) δ: The significant change is the disappearance of the allylic protons at 5.7 and 5.09 ppm and the appearance of small broad resonance peaks at 2.96, 2.75 and 2.47 ppm due to the formation of the epoxide ring. All other aspects of the spectrum are similar.

11. General Procedure for Nanoparticle Formation

In a 100 mL three-necked round bottom flask equipped with stir bar, condenser and septa, a solution of 2,2'-(ethylenedioxy)diethylamine (39.3 μL, 2.68×10$^{-4}$ mol) in 27.6 mL $CH_2Cl_2$. A solution of poly(vl-evl) (0.1330 g, $M_w$=4834 Da, PDI=1.17) dissolved in $CH_2C2$ (0.18 mL) was added dropwise via a peristaltic pump at 13 mL/min with vigorous stirring. The mixture was heated at reflux for a total of 12 h. Residual diamine was removed by dialyzing with SnakeSkin® Pleated Dialysis Tubing (MWCO=10,000) against dichloromethane. $^1$H NMR (300 MHz, $CDCl_3$/TMS, ppm) δ: The significant change is the disappearance of the epoxide protons at 2.96, 2.75 and 2.47 ppm and the appearance of signals at 3.5 and 2.89 ppm corresponding to the protons neighboring the secondary amine of the PEG linker after cross-linking. All other aspects of the spectrum are similar.

12. Determination of Amine Content

Nanoparticles can be titrated with a strong acid to determine amine content. As shown in Table 2, several poly(vl-evl) (AB) nanoparticle samples were titrated with perchloric acid to determine the weight percentages (wt %) of primary amine and secondary amine in the three samples that we analyzed with transmission electron microscopy. The three samples (shown in Table 2) titrated have the following size dimensions by DLS: 58.06, 255.7 and 425.1 nm.

TABLE 2

Correlation of particle size and amine content

| AB Nanoparticle size (nm) | Primary amine wt % | Secondary amine wt % |
|---|---|---|
| 58.06 | 0.008% | 0.031% |
| 255.7 | 0.025% | 0.098% |
| 425.1 | 0.055% | 0.20% |

13. Nanoparticles Formed by Co-Polymerization

While nanoparticles are typically prepared with a single type of polymer or copolymer, nanoparticles have also been successfully produced from a mixture of poly(vl-evl-pvl) and poly(vl-evl-opd). Such nanoparticles are tabulated in Table 3.

TABLE 3

Nanoparticles formed from two polymers

| Amine/1 Epoxide | Diameter (nm) Poly(vl-evl-pvl) with poly(vl-evl-opd) |
|---|---|
| 4 | 43.7 ± 4.50 |
| 8 | 94.15 ± 6.85 |

14. Varying Comonomer Content

The properties of nanoparticles can be further tailored by incorporating different percentages of epoxy-δ-valerolactone (evl) into the polymer backbone. The data summarized in Table 4, below, shows the nanoparticles made from the linear poly(vl-evl) with 2% evl, 7% evl, and 19% evl. These data show that, as the % evl is decreased to 2% in the linear polymer, smaller nanoparticles can be obtained. As the % evl is increase to 19%, the resulting nanoparticles are larger but have a small deviation in comparison to the larger nanoparticles made from poly(vl-evl) with 7% evl.

TABLE 4

| | Effect of varying comonomer content Diameter (nm) | | |
|---|---|---|---|
| Amine/1 Epoxide | Diameter (nm) Polyed-evl) 2% evl | Poly(vl-evl) 7% evl AB | Diameter (nm) Poly(vl-ev1) 19% evl |
| 3 | 7.02 ± 1.05 | 82.1 ± 5.73 | 179.9 ± 18.0 |
| 4 | 19.04 ± 1.32 | 115.6 ± 25.4 | 225.6 ± 22.5 |
| 5 | 33.55 ± 1.93 | 255.7 ± 60.3 | 299.0 ± 31.2 |
| 6 | 48.66 ± 3.18 | 342.2 ± 52.2 | 409.1 ± 42.7 |
| 8 | 84.89 ± 10.47 | 425.1 ± 100 | 843.3 ± 88.0 |

Figure 17:
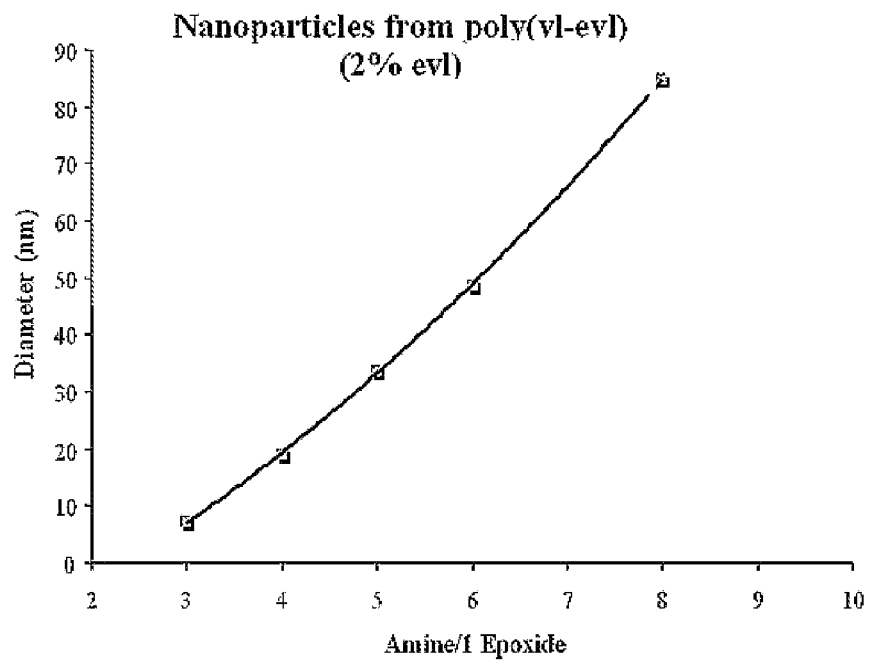
FIG. 17 shows polynomial increase of nanoparticle diameter (nm) with increase of diamine cross-linker for AB nanoparticles from poly(vl-evl) (2% evl) (■).
Figure 18:
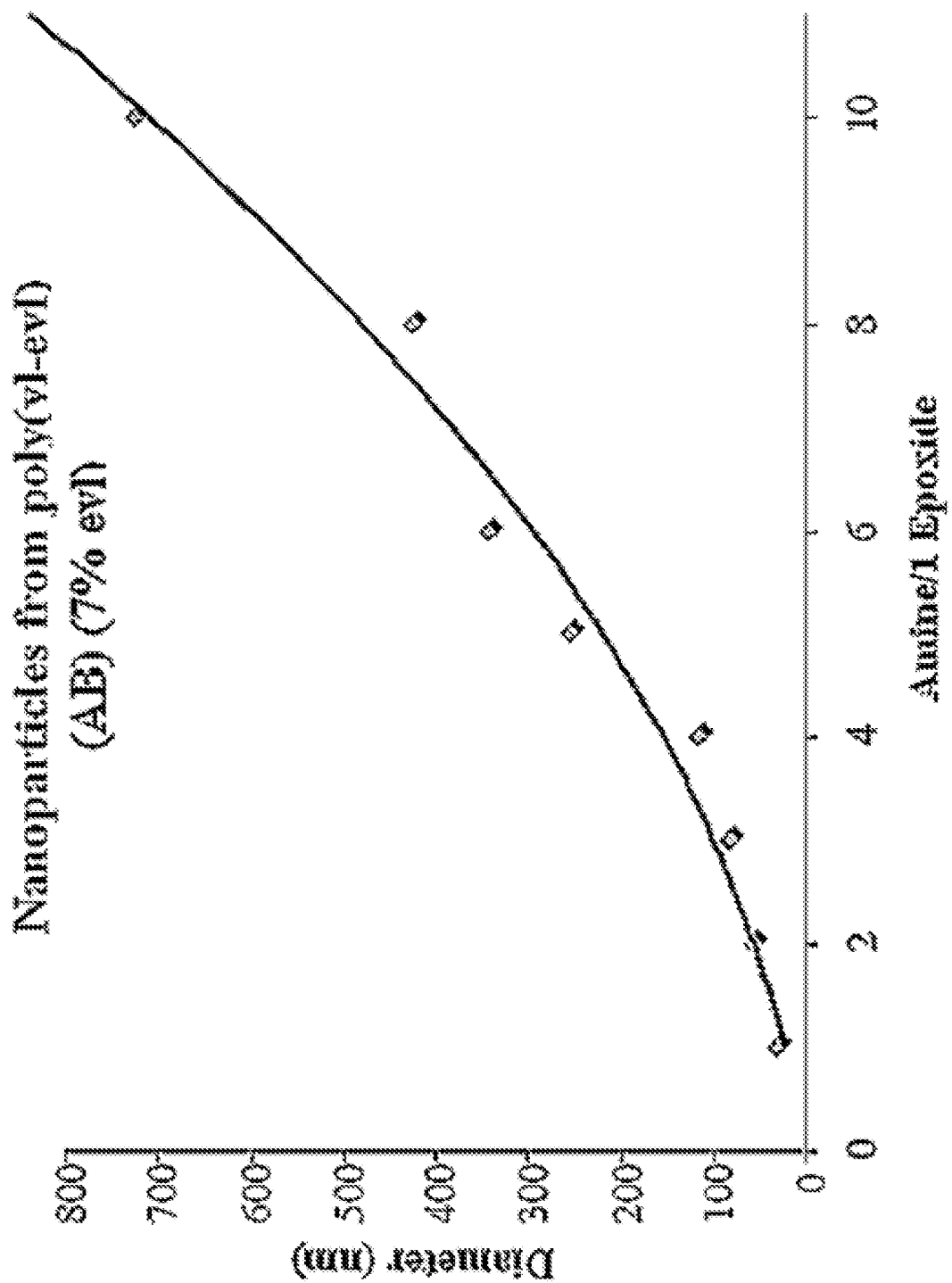
FIG. 18 shows polynomial increase of nanoparticle diameter (nm) with increase of diamine cross-linker for AB nanoparticles from poly(vl-evl) (7% evl) (♦).
Figure 19:
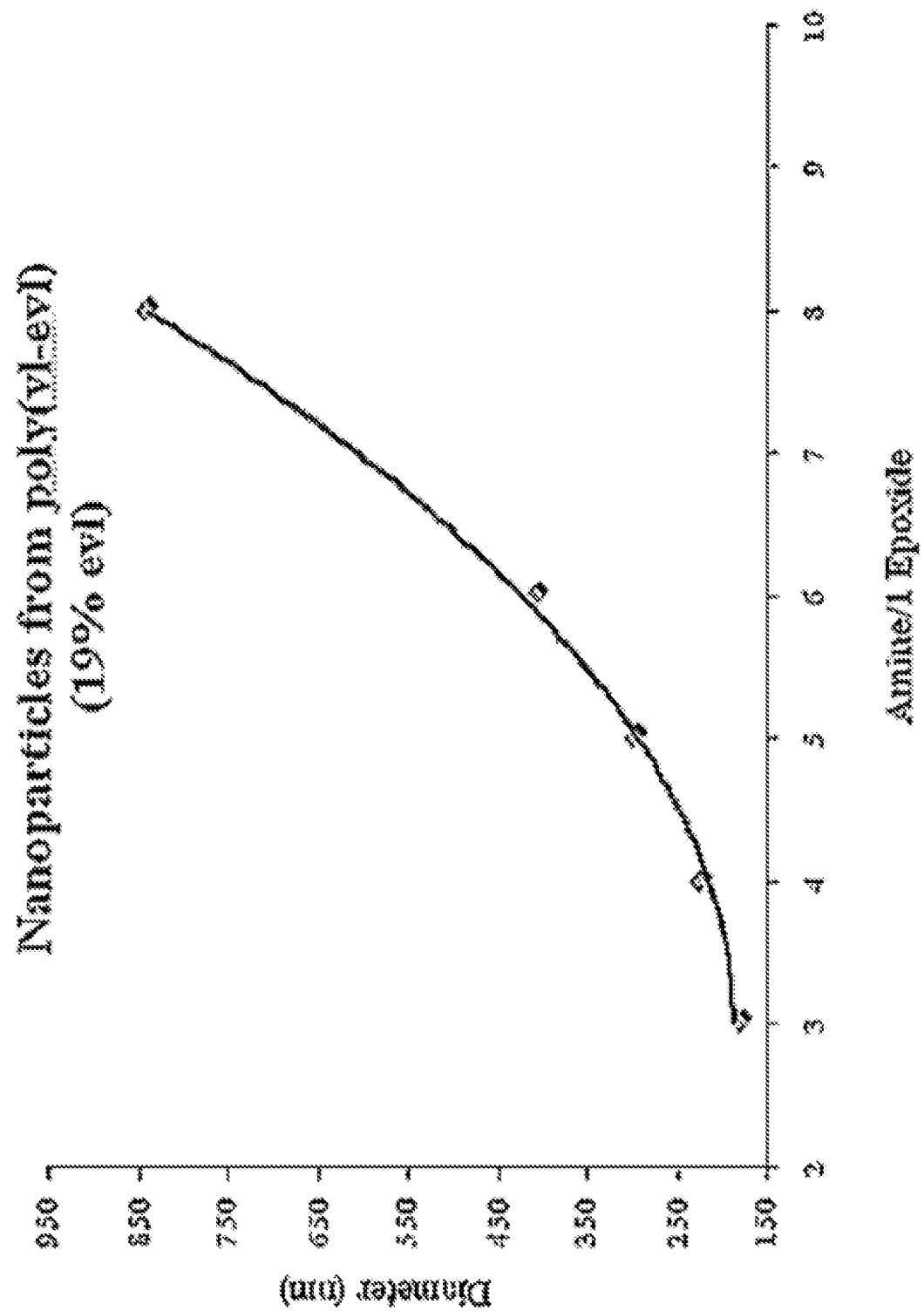
FIG. 19 shows polynomial increase of nanoparticle diameter (nm) with increase of diamine cross-linker for AB nanoparticles from poly(vl-evl) (19% evl) (♦).

The relationship between reaction stoichiometry and particle size for varying comonomer content is further illustrated in FIG. 17-FIG. 19.

15. Addition of ethylenediamine 2-vinylsulfonyl-ethyl Carbonate to ABD (poly(vl-evl-opd)) Nanoparticles In a 100 mL round bottom flask, equipped with stir bar, ABD nanoparticles (0.0846 g, 2.45×10$^{-4}$ mmol) were dissolved in 12.5 mL of $CH_2Cl_2$. To this solution, ethylenediamine 2-(vinylsulfonyl)-ethyl carbonate in methanol (0.0152 g in 69 μL methanol, 5.89×10$^{-2}$ mmol) was added. Sodium cyanoborohydride (0.0111 g, 1.76×10$^{-1}$ mmol) was dissolved in 12.5 mL methanol and added to the round bottom flask. The pH of the reaction mixture was adjusted to a pH of 6.5 with aqueous 1 M NaOH and 1 M HCl. The mixture was stirred for 25 h at room temperature and then dialyzed with SnakeSkin® Pleated Dialysis Tubing (MWCO=10,000) against 1:1 dichloromethane/methanol. Successful attachment of the linker was observed by the appearance of signals 6.7 ppm and 6.9 ppm ($^1$H NMR, 300 MHz, $CDCl_3$/TMS) due to the vinyl protons of the linker.

16. Attachment of GV-13-Alexafluor 750 to ABD Nanoparticles

In a small vial, equipped with a stir bar, linker modified nanoparticles (L-ABD) (29.9 mg) were dissolved in 800 μL PBS buffer (pH 7.2) and 700 μL dimethylformamide. To this solution, 251 μL GV-13-Alexafluor (0.44 mg in 150 μL PBS buffer and 26.5 μL DMF) was added to the vial via micropipette. After 45 min of stirring at room temperature, GV-13 (2.08 mg, $1.9 \times 10^{-3}$ mmol) dissolved in 200 μL PBS buffer was added. The reaction mixture stirred for 24 h in aluminum covered beaker. The resulting mixture was purified with concentrating tubes (MWCO=10,000) to remove excess GV-13 and GV-13-Alexafluor. The purified product was concentrated via rotary evaporator. Successful attachment of peptide and dye was observed by the presence of a bright blue color due to the dye. $^1$H NMR also shows the presence of the peptide.

General.

Commercial reagents were obtained from commercial sources (Aldrich, EMD, Alfa-Aesar, Fisher Scientific, and Acros) and used without further purification. Analytical TLC was performed on commercial Merck plates coated with silica gel GF254 (0.24 mm thick) and spots located by UV light (254 and 366 nm). Silica gel for flash chromatography was Merck Kieselgel 60 (230-400 mesh, ASTM) or Sorbent Technologies 60 Å (40-63 μm, technical grade). MAL-dPeg™$_4$-t-boc-hydrazide was obtained from Quanta Biodesign, Ltd. (Powell, Ohio) and used as received. Cy3 NHS dye and PD-10 Desalting columns were received from GE Healthcare (Piscataway, N.J.). Spectra/Por® Biotech Cellulose Ester (CE) Dialysis Membranes (1,000 MWCO) obtained from Spectrum Laboratories, Inc. (Rancho Dominguez, Calif.). SnakeSkin® Pleated Dialysis Tubing (10,000 MWCO) was obtained from Pierce Biotechnology, Inc. (Rockford, Ill.).

Instrumentation:

Samples were centrifuged at 600 rpm on a Model CS International Centrifuge from International Equipment Company (Boston, Mass.). Reverse-phase high performance liquid chromatography (RP-HPLC) was carried out with a Varian Prostar HPLC. The products were eluted using a solvent gradient (solvent A=0.05% TFA/H$_2$O; solvent B=0.05% TFA/CH$_3$CN). Nuclear magnetic resonance was performed on Bruker AC300 and AC400 Fourier Transform Spectrometers using deuterated solvents and the solvent peak as a reference. Gel permeation chromatography was performed in tetrahydrofuran (THF) with the eluent at a flow rate of 1 mL/min on a Waters chromatograph equipped with four 5 mm Waters columns (300 mm×7.7 mm) connected in series with increasing pore size (100, 1000, 100,000 and 1,000,000 Å respectively). A Waters 2487 Dual A Absorbance Detector and a 2414 Refractive Index Detector were employed. Dynamic light scattering was performed on a Malvern Zetasizer Nanoseries instrument with a CGS-3 compact goniometer system.

17. Synthesis of Compound 1

To a solution of dimethoxyethane (40 mL) was added MeNO$_2$ (11.37 mL, 200 mmol) followed by Triton B (2 mL). The mixture was heated to 67° C. and then tert-butyl acrylate (91.83 mL, 620 mmol) was added to maintain the temperature at 75° C. When the temperature started to decrease, additional Triton B (1 mL) was added. After the addition was completed, the solution was heated to maintain at 75° C. for 2 hours. The solvent was removed in vacuo and the residue was dissolved in CHCl$_3$ and the resulting organic solution was washed with 10% HCl, brine, and dried over anhydrous Na$_2$SO$_4$. Removal of the solvent in vacuo gave a crude solid that was further purified by recrystallization from EtOH to obtain a colorless crystal (95% yield). $^1$H NMR (CDCl$_3$): 51.44 (s, CH$_3$, 27H), 2.21 (m, CH$_2$, 12H). $^{13}$C NMR (CDCl$_3$): 27.93 (CH$_3$), 29.68 (CH$_2$CO), 30.22 (CCH$_2$), 81.02 (CCH$_3$), 92.09 (CNH$_2$), 170.97 (CO$_2$).

18. Synthesis of Compound 2

A solution of compound 1 (6.0 g, 0.0135 mol) in a mixture of ethanol (140 mL) and dichloromethane (20 mL) was added to a Parr hydrogenation bottle. Then, 4 grams of Raney-nickel was added. The mixture was hydrogenated at 50 psi and room temperature. The reaction was monitored by thin-layer chromatography (TLC) until the starting material disappeared. The catalyst was carefully filtered through Celite, and the solvent was removed in vacuo yielding a crude solid. The residue was dissolved in dichloromethane and washed with saturated NaHCO$_3$ and water, and then dried over anhydrous Na$_2$SO$_4$. Removal of dichloromethane gave a white solid (93%). $^1$H NMR (CDCl$_3$): δ1.44 (s, CH$_3$, 27H), 1.95 (t, CH$_2$, 6H), 2.43 (t, CH$_2$, 6H); $^{13}$C NMR (CDCl$_3$): 27.98 (CH$_3$), 29.46 (CH$_2$CO), 31.47 (CCH2), 56.99 (CNH$_2$), 80.96 (CCH3), 172.30 (CO$_2$).

19. Synthesis of Compound 4

To a solution of compound 3 (0.65 g, 2.35 mmol) in 50 mL dry THF the following reagents were added 1-hydrobenzotriazole (HOBt) (0.96 g, 7.10 mmol), DCC (1.46 g, 7.10 mmol) and then 2 (3.54 g, 8.5 mmol). The solution was stirred at room temperature and the reaction was monitored by TLC. After 40 hrs, the white precipitate was filtered and the solution was concentrated to yield a crude residue. The product was purified by column chromatography (silica gel, hexane:ethyl acetate=3:2) yielding a white solid (85%). $^1$H NMR (CDCl$_3$): δ1.44 (m, CH$_3$, 81H), 1.95 (m, CH$_2$, 18H), 2.21 (m, CH$_2$, 30H), 6.20 (s, NH, 3H); $^{13}$C NMR (CDCl$_3$): 28.04, 29.74, 29.85, 31.28, 57.56, 80.69, 92.47, 170.46, 172.76.

20. Synthesis of Compound 5

A solution of compound 4 (1.47 g, 1 mmol) in 15 mL of formic acid was stirred at room temperature overnight. After the solution was concentrated, toluene was added and the solution was evaporated to remove any residue of formic acid to give a white solid (100%). $^1$H NMR (DMSO): δ1.81 (m, CH$_2$, 18H), 2.11 (m, CH$_2$, 30H), 7.29 (s, NH, 3H), 12.10 (br, COOH); $^{13}$C NMR (DMSO): 28.03, 29.03, 30.08, 56.41, 93.31, 170.43, 174.42.

21. Synthesis of Compound 6

To a solution of compound 5 (2.12 g, 0.0022 mol) in DMF (30 mL), HOBt (2.68 g, 0.0198 mol) and DCC (4.09 g, 0.0198 mol) were added. The mixture was chilled to 0° C. with ice-water bath. Then, a solution of N-Boc-ethylenediamine (3.49 g, 0.0218 mol) in DMF (5 mL) was added dropwise at 0° C. The reaction mixture was stirred at room temperature for 48 hrs. The solution was then filtered and 200 mL of dichloromethane was added, and washed with 1N HCL, saturated NaHCO$_3$, and water. The organic phase was dried over anhydrous Na$_2$SO4 and evaporated to yield a crude residue. The product was purified by column chromatography (eluted first with 2% methanol in dichloromethane, then with 6% methanol in dichloromethane, followed by 10% methanol in dichloromethane) to obtain a white solid (51%). $^1$H NMR (CD$_3$OD): δ 1.44 (m, CH$_3$, 81H), 1.80-2.10 (m, CH$_2$, 48H), 3.0-3.2 (m, CH$_2$, 36H), 6.20 (m, NH, 3H), 6.46 (m, NH, 8H), 7.71 (m, NH, 8H); $^{13}$C NMR (CD$_3$OD): 28.40, 31.24, 31.44, 31.80, 32.09, 40.66, 40.97, 59.14, 80.13, 94.42, 158.48, 173.48, 175.91. This white solid was then dissolved in 40 mL of 1, 4-dioxane. At 0° C., 40 mL of 4 M HCl in dioxane was added to the solution under Ar atmosphere and stirred at room temperature for 1 hr. Removal of the solvent gave a white solid as the deprotected HCl salt (100%). $^1$H NMR (D$_2$O): δ 1.70-2.15 (m, CH$_2$, 48H), 3.30 (m, CH$_2$, 18H), 3.36 (m, CH$_2$, 18H); $^{13}$C NMR (D$_2$O): 27.61, 27.98, 28.86, 35.11, 37.41, 56.29, 92.01, 171.84, 174.98, 1.53 g (0.92 mmol) of the resulting HCl salt was dissolved in 80 mL of methanol. At 0° C., 3.5 mL of Et$_3$N was added to the solution, followed by the addition of N,N'-diBoc-N''-triflylguanidine (4.2 g, 10.73 mmol). The solution was stirred at room temperature for 24 hr. After removal of the solvent, the residue was dissolved in dichloromethane and washed with water, 1N HCl, saturated NaHCO$_3$, and water. The organic layer was dried over anhydrous Na$_2$SO$_4$ and removed in vacuo. The residue product was purified by column chromatography (eluted with 2% methanol in dichloromethane, then 10% methanol in dichloromethane) to give a white solid (90%) as compound 6. $^1$H NMR (CD$_3$OD): δ 1.45 (m, CH$_3$, 81H), 1.51 (m, CH$_3$, 81H), 1.90-2.25 (m, CH$_2$, 48H), 3.30-3.52 (m, CH$_2$, 36H); $^{13}$C NMR (CD$_3$OD): 28.37, 28.67, 31.32, 31.67, 32.06, 39.74, 41.24, 59.02, 80.23, 84.35, 94.31, 153.91, 157.737, 164.38, 173.33, 175.87.

22. Synthesis of Compound 7

To a solution of compound 5 (1.2, 0.001245 mol), HOBt (1.514 g, 0.0112 mol) and DCC (2.311 g, 0.0112 mol) were added in 20 mL of DMF. Then, N-Boc-1,6-diaminohexane (2.66 g, 0.0123 mol) was dissolved in 5 mL of DMF dropwise at 0° C. The solution was then stirred at room temperature for 48 hrs. The solution was then filtered and 200 mL of dichloromethane was added, and washed with 1N HCl, saturated NaHCO$_3$, and water. The organic phase was dried over anhydrous Na$_2$SO$_4$ and evaporated to yield a crude residue. The product was purified by column chromatography (eluted first with 2% methanol in dichloromethane, then with 5% methanol in dichloromethane, followed by 10% methanol in dichloromethane) to obtain a white solid (45%). $^1$H NMR (CD$_3$OD): δ 1.2-1.6 (m, CH$_3$, CH$_2$, 153H), 1.80-2.10 (m, CH$_2$, 48H), 3.0-3.2 (m, CH$_2$, 36H); $^{13}$C NMR (CD$_3$OD): 27.54, 28.85, 30.37, 30.90, 31.28, 31.60, 32.14, 40.58, 41.24, 59.13, 79.30, 94.30, 158.49, 173.50, 175.56. This white solid was then dissolved in 40 mL of 1, 4-dioxane. At 0° C., 40 mL of 4 M HCl in dioxane was added to the solution under Ar atmosphere and stirred at room temperature for 1 hr. Removal of the solvent gave a white solid as the deprotected HCl salt (100%). $^1$H NMR (D$_2$O): δ 1.10-1.60 (m, CH$_2$, 72H), 1.7-2.2 (m, CH$_2$, 48H), 3.30 (m, CH$_2$, 18H), 3.36 (m, CH$_2$, 18H). 0.838 g (0.385 mmol) of the resulting HCl salt was dissolved in 80 mL of methanol. At 0° C., 1.45 mL of Et$_3$N was added to the solution, followed by the addition of N,N'-diBoc-N''-triflylguanidine (1.765 g, 4.51 mmol). The solution was stirred at room temperature for 24 hr. After removal of the solvent, the residue was dissolved in dichloromethane and washed with water, 1N HCl, and water. The organic layer was dried over anhydrous Na$_2$SO$_4$ and removed in vacuo. The residue product was purified by column chromatography (eluted with 2% methanol in dichloromethane, then 10% methanol in dichloromethane) to give a white solid (90%) as compound 7. $^1$H NMR (CD$_3$OD): $^1$H NMR of 9 (CD$_3$OD): δ 1.15-1.55 (m, 234H), 1.70-2.15 (m, CH$_2$, 48H), 3.29-3.30 (m, CH$_2$, 36H); $^{13}$C NMR (CD$_3$OD): 27.70, 27.62, 28.33, 28.67, 30.08, 30.33, 31.30, 31.60, 40.48, 40.62, 41.27, 54.5, 59.14, 80.25, 84.40, 154.22, 157.49, 164.53, 173.50, 175.53.

23. Synthesis of Compound 8 and 9

Compound 6 (or 7, 0.10 mmol) was dissolved in 40 mL of ethanol and transferred into a hydrogenation bottle containing 5 g of Raney-Nickel catalyst. The solution was hydrogenated at room temperature at 65 psi and monitored by TLC. The catalyst was filtered through Celite. The solvent was removed in vacuo to give a white solid 8 or 9 (80%). $^1$H NMR of 8 (CD$_3$OD): δ 1.46 (m, CH$_3$, 81H), 1.51 (m, CH$_3$, 81H), 1.90-2.25 (m, CH$_2$, 48 H), 3.30-3.55 (m, CH$_2$, 36H); $^{13}$C NMR (CD$_3$OD): 28.37, 28.67, 31.40, 31.76, 39.76, 41.27, 54.0, 58.86, 80.32, 84.37, 153.97, 157.81, 164.4, 175.61, 176.02. $^1$H NMR of 9 (CD$_3$OD): δ 1.20-1.70 (m, 234H), 1.85-2.40 (m, CH$_2$, 48H), 3.10-3.50 (m, CH$_2$, 36H); $^{13}$C NMR (CD$_3$OD): 27.01, 27.18, 28.27, 28.53, 29.42, 29.71, 30.15, 30.88, 31.19, 40.03, 41.23, 54.3, 58.21, 79.93, 83.84, 153.62, 156.65, 163.83, 175.77.

24. Synthesis of Compound FD-1

FITC (0.14 g, 0.36 mmol), dissolved in 1 mL of DMF, was added to a solution of compound 8 (0.23 g, 0.066 mmol) in a mixture of DMF and dichloromethane. The solution was chilled to 0° C., to which Et$_3$N (0.092 mL, 0.66 mmol) was added. The mixture was stirred overnight at room temperature. After removal of DMF in vacuo, the residue was dissolved in dichloromethane and washed with 1N HCl and water. The dichloromethane layer was dried over anhydrous Na$_2$SO$_4$ and concentrated to obtain a yellow solid. $^1$H NMR (CD$_3$OD): δ 1.46 (m, CH$_3$, 81H), 1.51 (m, CH$_3$, 81H), 1.90-2.25 (m, CH$_2$, 48H), 3.30-3.55 (m, CH$_2$, 36H), 6.52-6.72 (br, 4H), 7.15 (br, 1H), 7.5 (br, 2H), 7.72 (br, 1H), 8.4 (br, 1H). The resulting yellow solid (200 mg. 0.052 mmol) was dissolved in 10 mL of 1, 4-dioxane. At 0° C., 10 mL of 4 M HCl in dioxane was added to the solution under Ar protection and stirred at room temperature overnight. After evaporation of the solvent in vacuo, the product was dissolved in water and the insoluble precipitate was filtered. Removal of water yielded a crude yellow solid, which was further purified by RP-HPLC using a solvent gradient (solvent A=0.05% TFA/H$_2$O; solvent B=0.05% TFA/CH$_3$CN) to obtain compound 10. $^1$H NMR (D$_2$O): δ 1.85-2.30 (m, CH$_2$, 48H), 3.10-3.30 (m, CH$_2$, 36H), 6.9 (br, 2H), 7.10-7.2 (m, 3H), 7.4 (s, 2H), 7.5 (br, 1K), 8.1 (s, 1H).

25. Synthesis of Compound FD-2

FITC (0.016 g, 0.0376 mmol), dissolved in 1 mL of DMF, was added to a solution of compound 9 (0.050 g, 0.0125 mmol) in a mixture of DMF and dichloromethane (1:1). The solution was chilled to 0° C., to which Et$_3$N (12 µL) was added. The mixture was stirred overnight at room temperature. After removal of DMF in vacuo, the residue was dissolved in dichloromethane and washed with 1N HCl and water. The dichloromethane layer was dried over anhydrous Na$_2$SO$_4$ and concentrated to obtain a solid. The product was dissolved in methanol and purified by dialysis with Spectro®Por Biotech RC membranes (MWCO 3500). After removal of the methanol, a yellow solid was obtained. $^1$H NMR (CD$_3$OD): δ 1.20-1.7 (m, CH$_3$, CH$_2$, 234H), 1.89-2.30 (m, CH$_2$, 48H), 3.10-3.40 (m, CH$_2$, 36H), 6.52-6.72 (br, 4H), 7.15 (br, 1H), 7.5-7.72 (br, 3H), 8.1 (br, 1H). The resulting yellow solid (200 mg, 0.052 mmol) was dissolved in 10 mL of 1, 4-dioxane. At 0° C., 10 mL of 4 M HCl in dioxane was added to the solution under Ar protection and stirred at room temperature overnight. The precipitate was filtered out and dried in vacuo. The obtained yellow solid was dissolved in water and lyophilized to yield compound 11. $^1$H NMR (D$_2$O): δ 1.1-1.50, (m, CH$_2$, 72H), 1.50-2.20 (m, CH$_2$, 48H), 3.10-3.30 (m, CH$_2$, 36H), 6.5-6.7 (br, 6H), 7.10 (m, 1H), 7.5 (br, 3H).

26. Examples FD-1 and FD-2

As examples of the compounds of the invention, two non-peptidic fluorescently labeled Newkome-type dendrimers, differentiated over a varied alkylspacer with guanidine end moieties, were designed and synthesized. The assessment of internalization into mammalian cells using NIH-3T3 fibroblasts and human microvascular endothelial cells (HMEC) showed that the spacer length at the terminal generation of the dendrimers can affect direction of cargo molecules precisely into specific subcellular compartments (e.g., nucleus or cytosol). Such direction can be particularly advantageous for the controlled intracellular delivery of bioactive cargo molecules into targeted locations.

Figure 21:
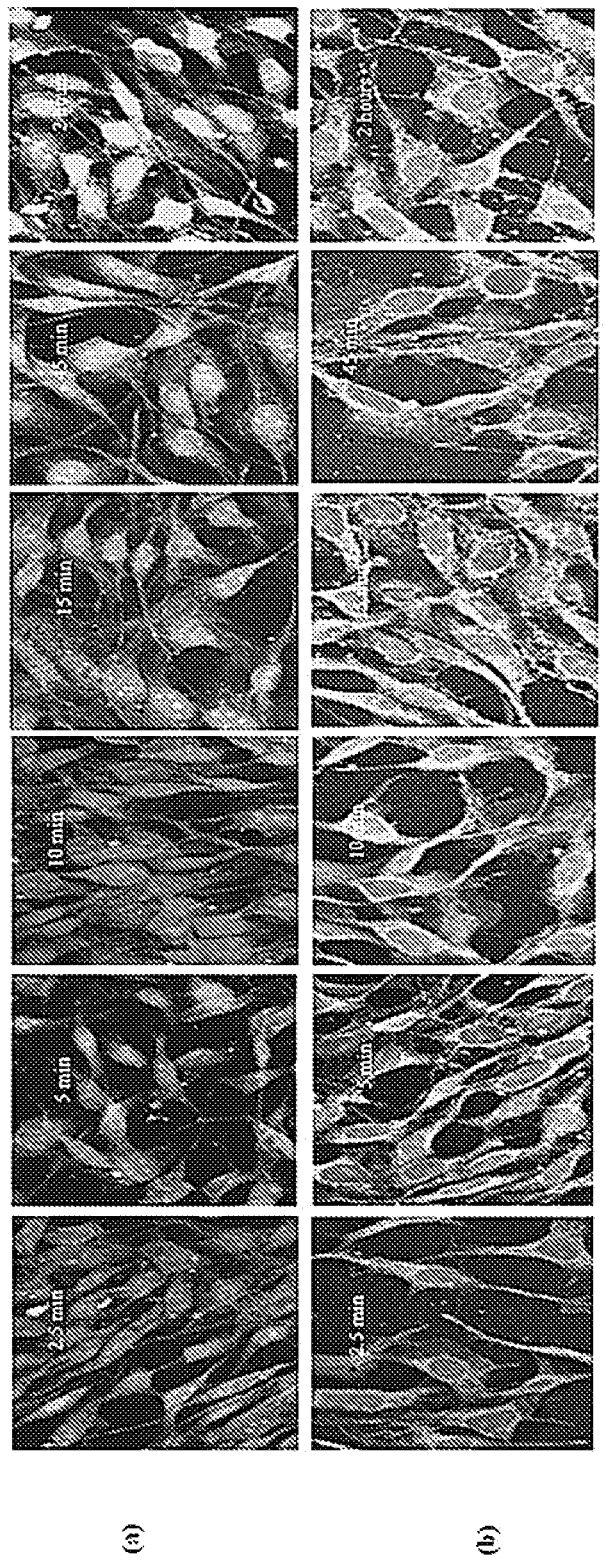
FIG. 21 shows time course of internalization of (a) FD-1 and (b) FD-2 into NIH-3T3 Fibroblasts at 37° C. The conjugate concentration was 10 µM.
Figure 22:
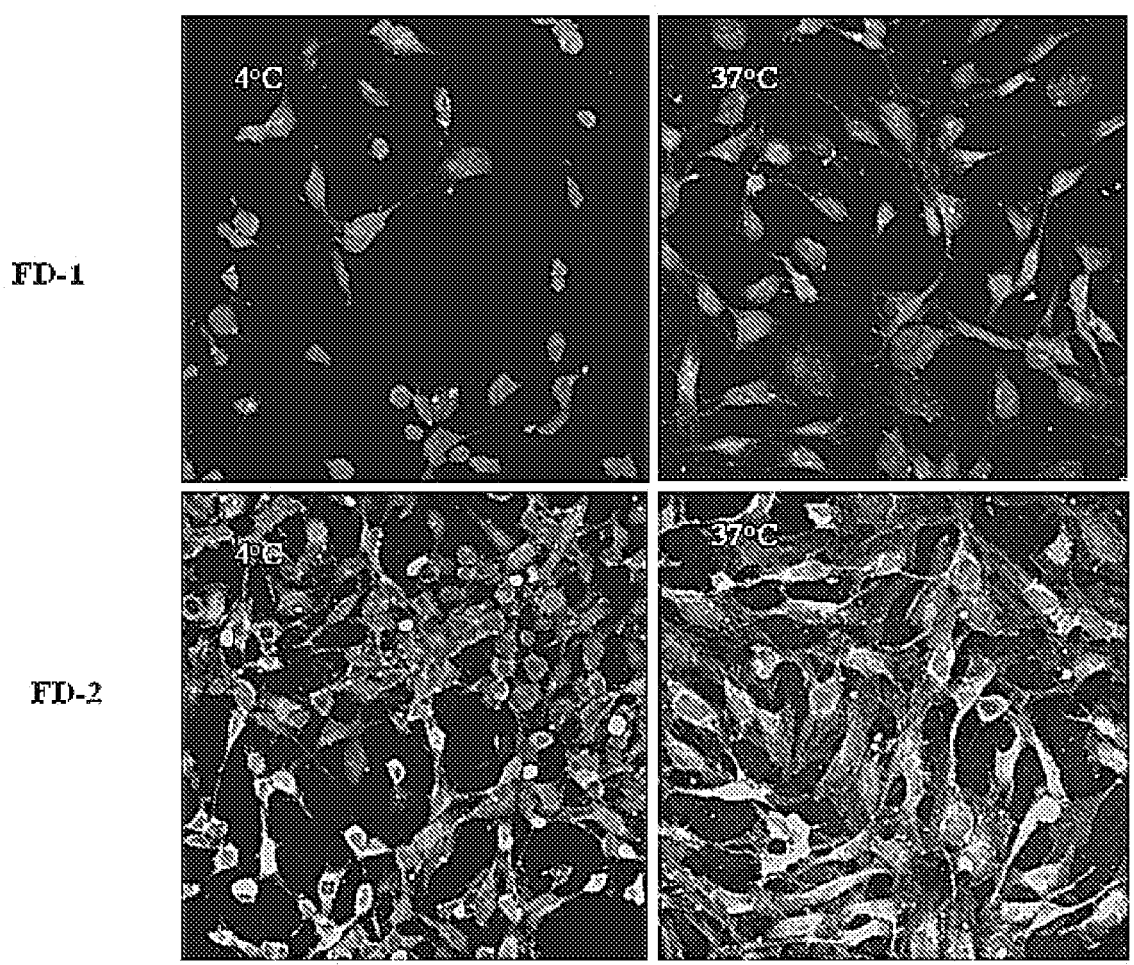
FIG. 22 shows the effect of temperature on (a) FD-1 and (b) FD-2 internalization. The human microvascular endothelial cells (HMEC) cells were incubated with conjugates (10 uM) for 2.5 min at 4° C. or at 37° C.
Figure 23:
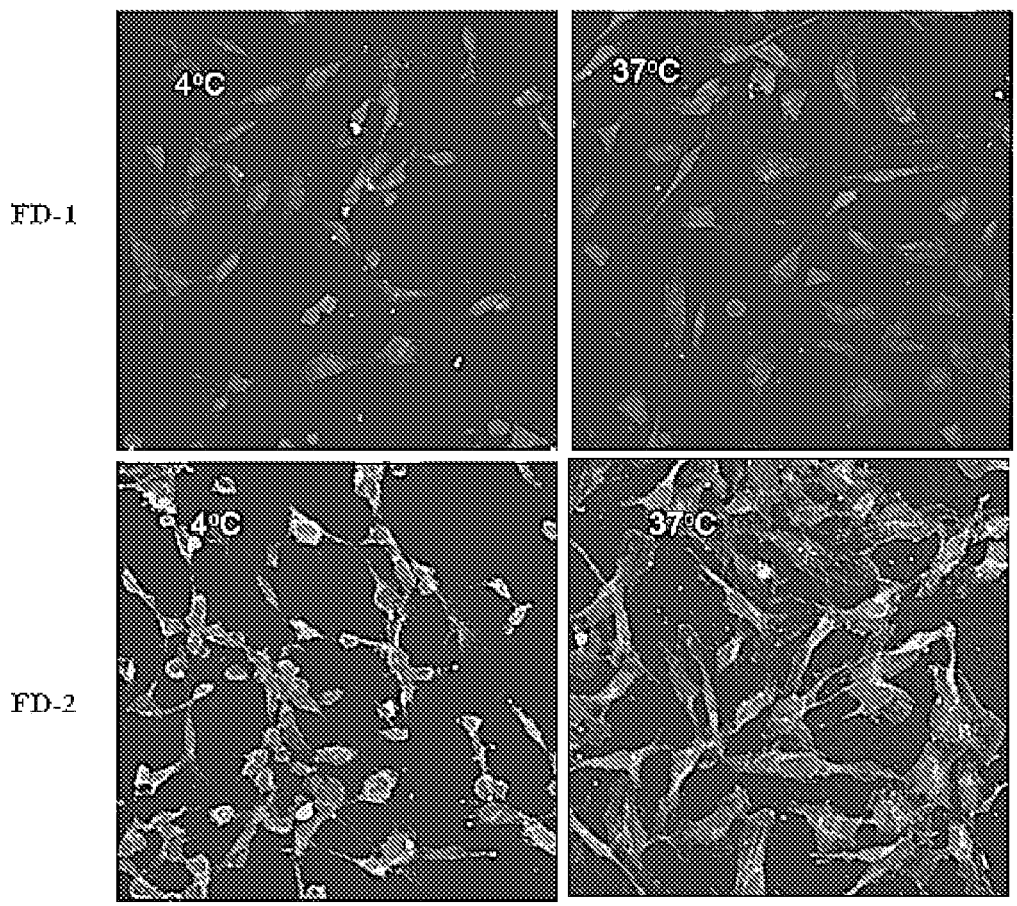
FIG. 23 shows the effect of temperature on (a) FD-1 and (b) FD-2 internalization. The HMEC cells were incubated with conjugates (1 uM) for 30 min at 4° C. or at 37° C.

The two exemplary FITC-dendrimer conjugates were found to be highly water soluble and were further investigated for their capability to translocate through the cell membrane. Internalization of FD-1 and FD-2 in mammalian cells was assessed using two different cell lines and a previously described method [Futaki, S.; Nakase, I.; Suzuki, T.; Youjun, Y.; Sugiura, Y. Biochemistry 2002, 41, 7925.] with NIH-3T3 fibroblasts and HMEC (human microvascular endothelial cells) and a Zeiss LSM 510 confocal microscope. FIG. 21 shows the time course of uptake of FD-1 and FD-2 into NIH-3T3 Fibroblasts at 37° C. The fluorescence was clearly observed within the cells 2.5 min after the addition of conjugates to the medium, which is comparable to the uptake rate of Tat-peptide. [Futaki, S.; Nakase, I.; Suzuki, T.; Youjun, Y.; Sugiura, Y. Biochemistry 2002, 41, 7925.; Vives, E.; Brodin, P.; Lebleu, B. J. Biol. Chem. 1997, 272, 16010.] Furthermore, the extent of internalization increased in an incubation time-dependent manner, and it was observed that after just 10 min, the fluorescence intensity of cells treated with FD-2 was near saturation. However, the fluorescence intensity of cells treated with FD-1 did not approach saturation until the longer time points (45 min~2 hr). Additionally, FD-1 and FD-2 exhibited differential patterns of subcellular localization, as FD-1 appeared to concentrate in the nucleus while FD-2 appeared to concentrate in the cytosol. Without wishing to be bound by theory, it is believed that the length of the spacer at the terminal generation of the dendrimer can not only control the uptake rate, [Wender, P. A.; Kreider, E.; Pelkey, E. T.; Steinman, L.; Rothbard, J. B.; VanDeusen, C. L. Org. Lett. 2005, 7, 4815.1 but also regulate the subcellular localization of the molecule and its putative cargo. For instance, the uptake levels of FD-2 appeared to be generally stronger than those of FD-1 after the same incubation time at the same concentration. Therefore, the dendrimer with a hexyl spacer crosses the cell membrane faster than the molecule with an ethyl chain. On the other hand, the localization patterns can also be controlled by the length of the spacer. FD-1 with the short spacer appeared to be localized everywhere in the cell, but highly concentrated in the nucleus. However, FD-2, with its longer spacer, was observed to reside mainly in the cytosol. These translocation features of guanidinlyated dendritic scaffolds as carriers can be important for intracellular delivery of cargo molecules to specific subcellular compartments (e.g., cytosol or nucleus). For example, a translocation approach that does not saturate the nucleus can be highly attractive as it can be both less cytotoxic and could afford cytosolic-targeted cargos with greater accuracy in delivery, and therefore higher efficacy. Without wishing to be bound by theory, it is believed that the differential uptake patterns by FD-1 and FD-2 are due to the presence of a hexyl spacing chain in FD-2, resulting in a greater hydrophobicity of the entire conjugate as compared with FD-1. Additionally, the uptake of FD-1 and FD-2 conjugates by HMEC was also conducted. Entry of the two conjugates into HMEC shows a similar internalization pattern to that seen in fibroblasts.

Figure 24:
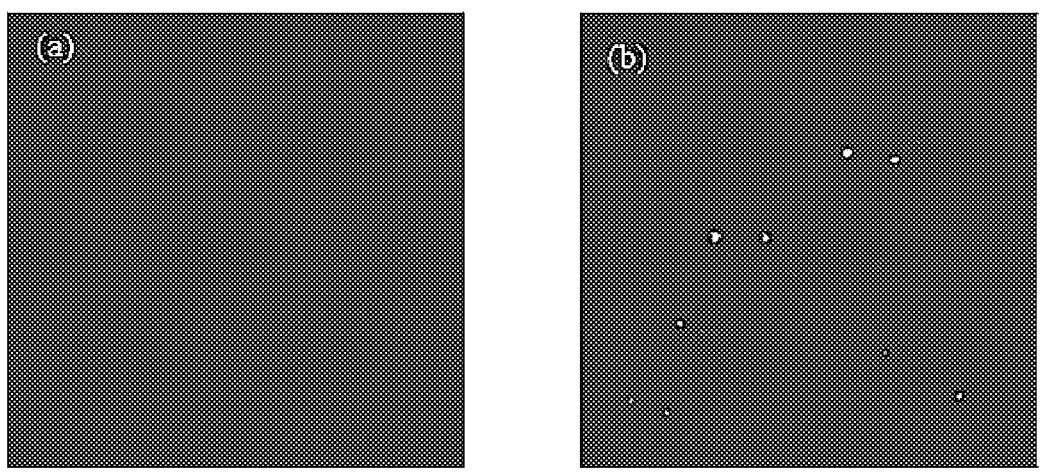
FIG. 24 shows control experiments: (a) The HMEC cells were incubated with free FITC conjugates (10 uM) for 60 min at 37° C. (b) The HMEC cells were incubated with Boc-protected guanidinylated FD-2 (10 uM) for 60 min at 37° C.
Figure 25A:
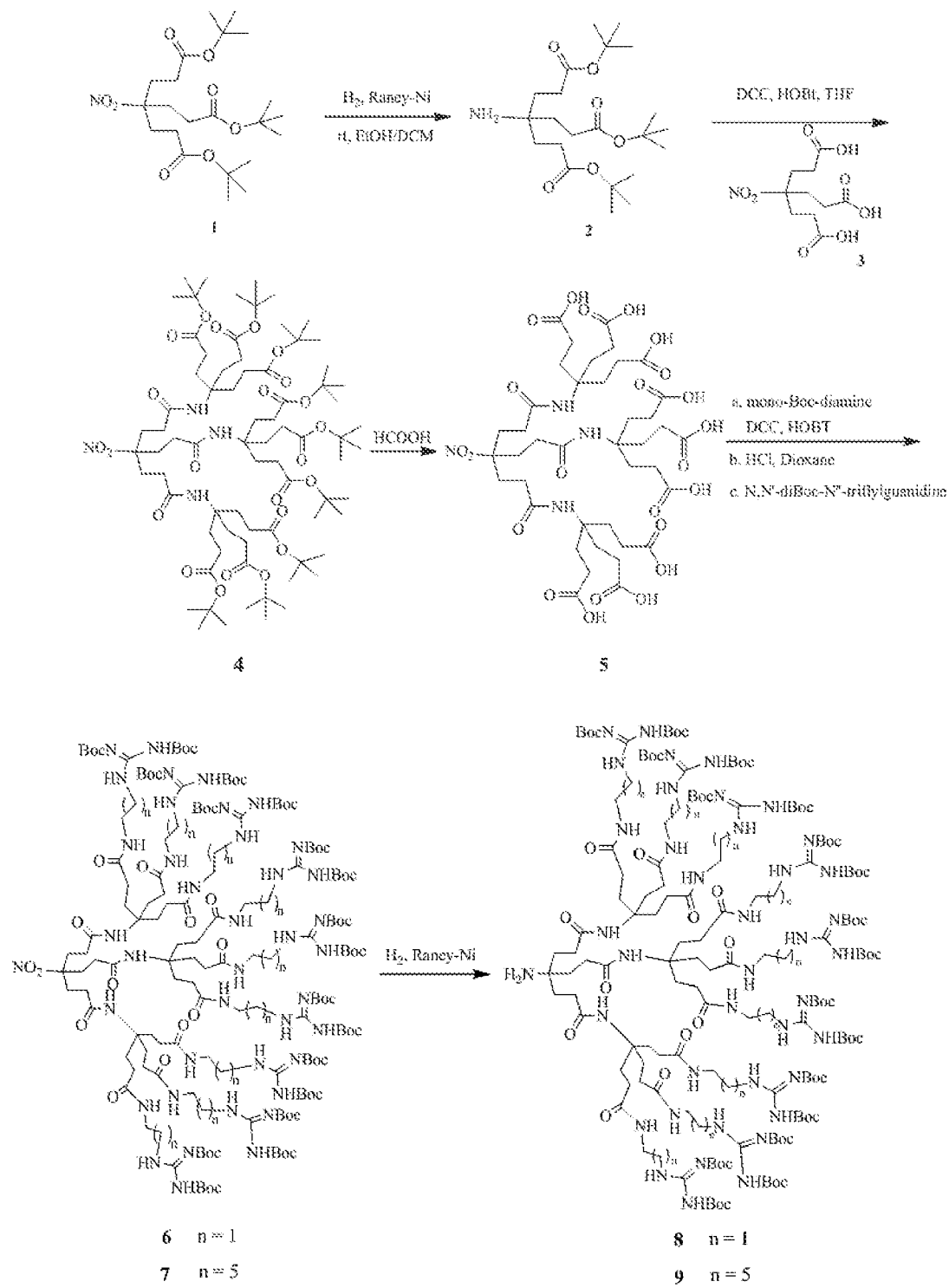
FIG. 25A and FIG. 25B show an exemplary synthetic scheme for the preparation of FD-1, FD-2, and intermediates thereof.
Figure 25B:
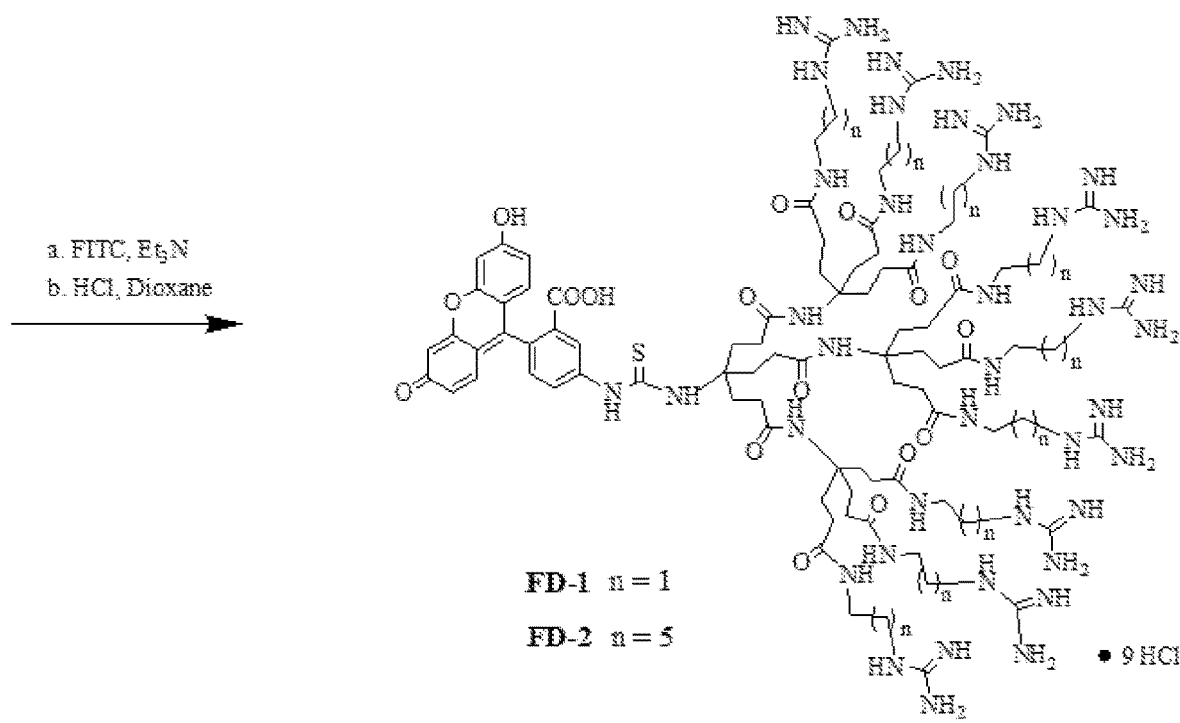
Figure 26:
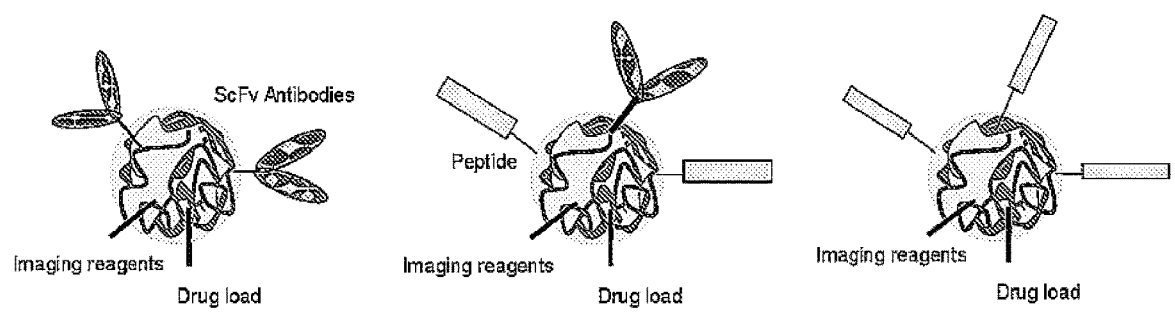
FIG. 26 shows a schematic of exemplary multimodal nanoparticles.
Figure 27:
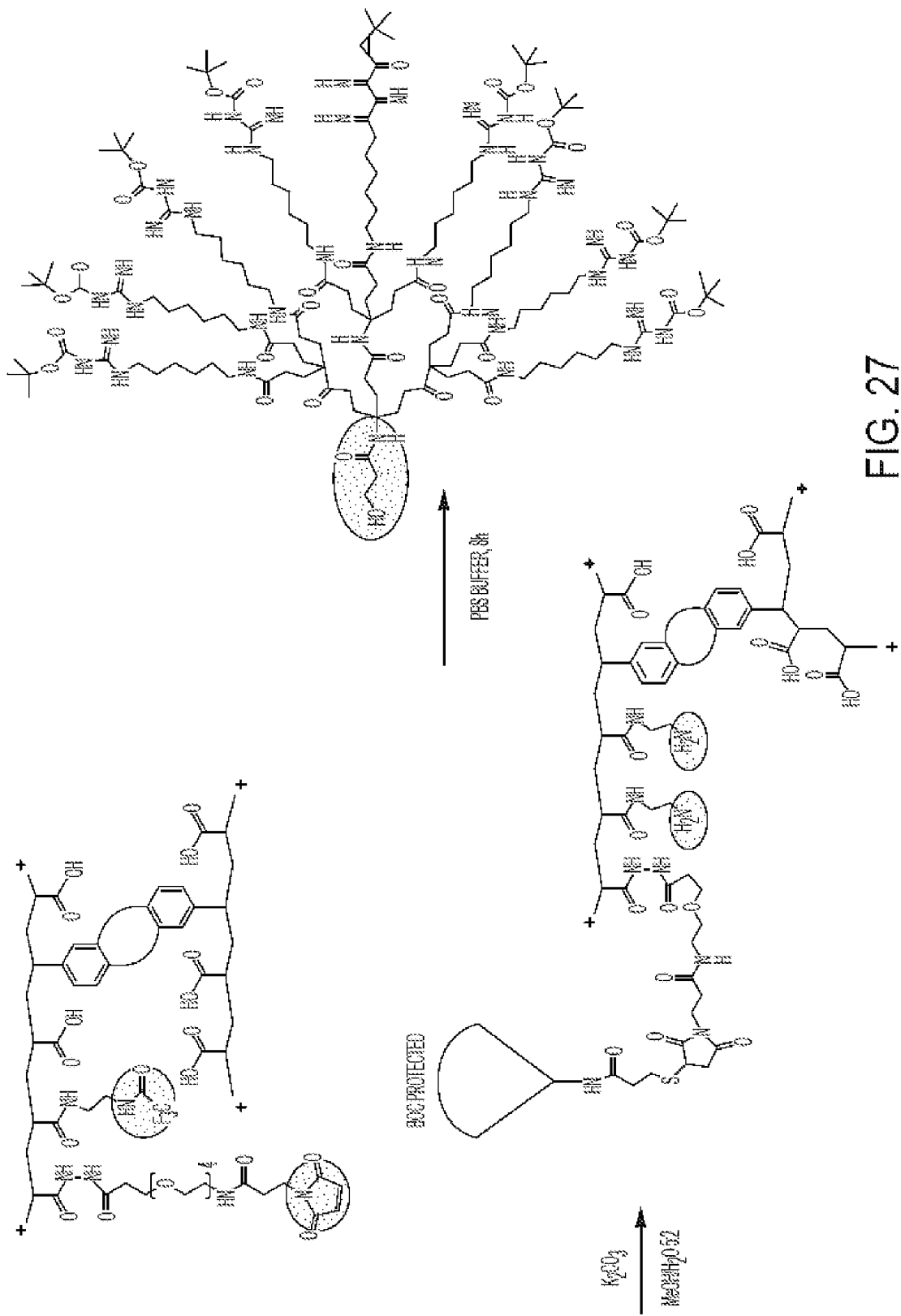
FIG. 27 shows an exemplary conjugation of a disclosed dendrimeric material with a disclosed cross-linked organic nanoparticle.
Figure 28:
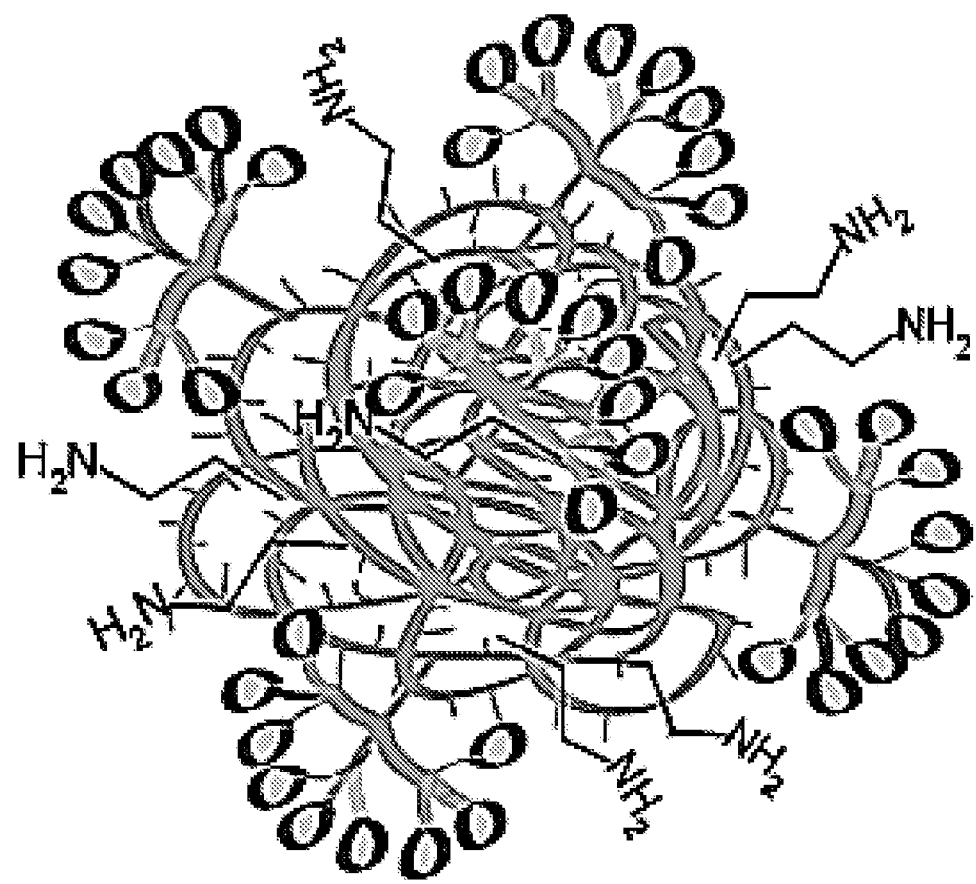
FIG. 28 shows a schematic illustrating a disclosed delivery system (e.g., gene delivery).
Figure 29:
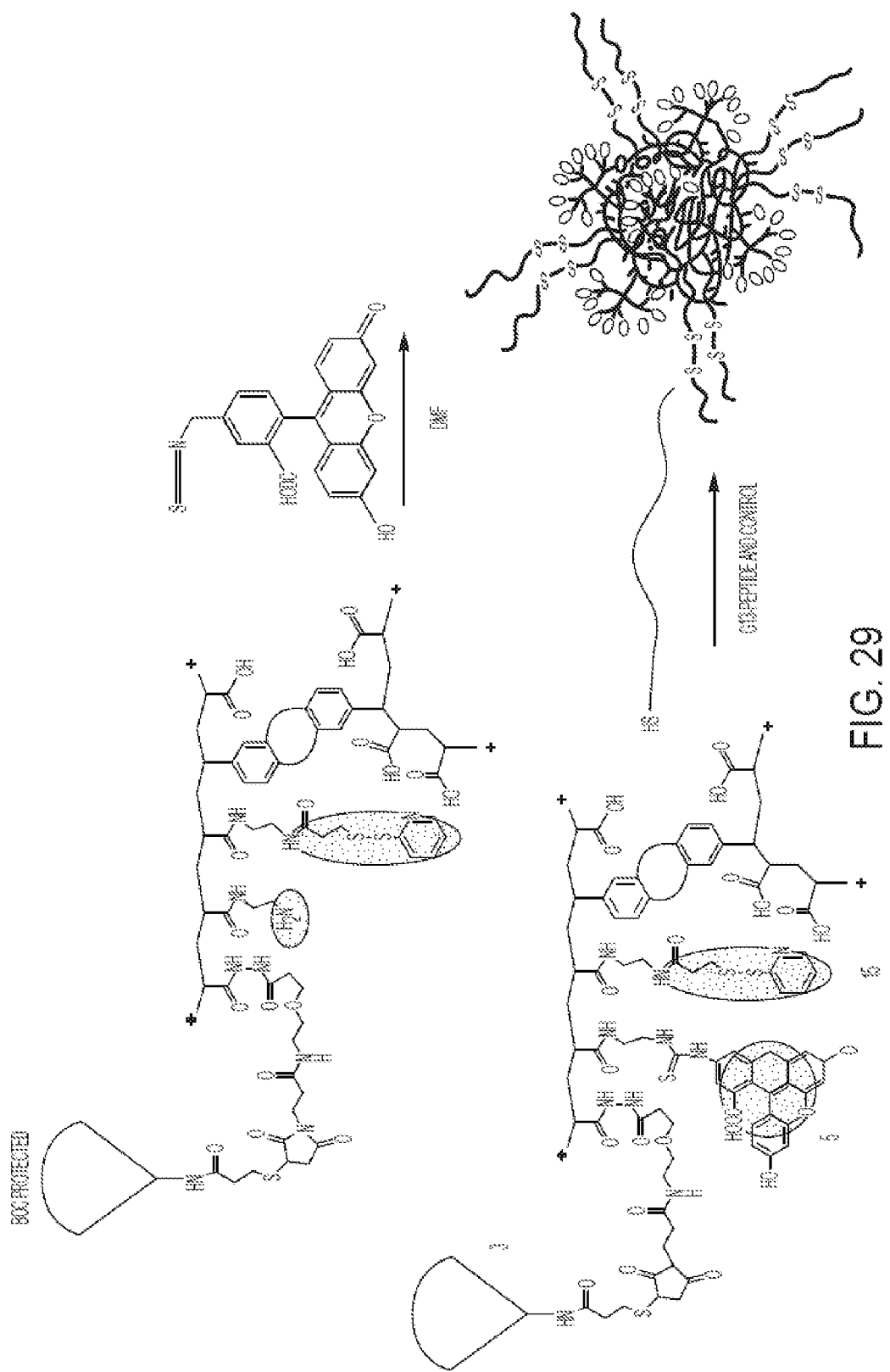
FIG. 29 illustrates preparation of a disclosed delivery system (e.g., gene delivery).
Figure 30:
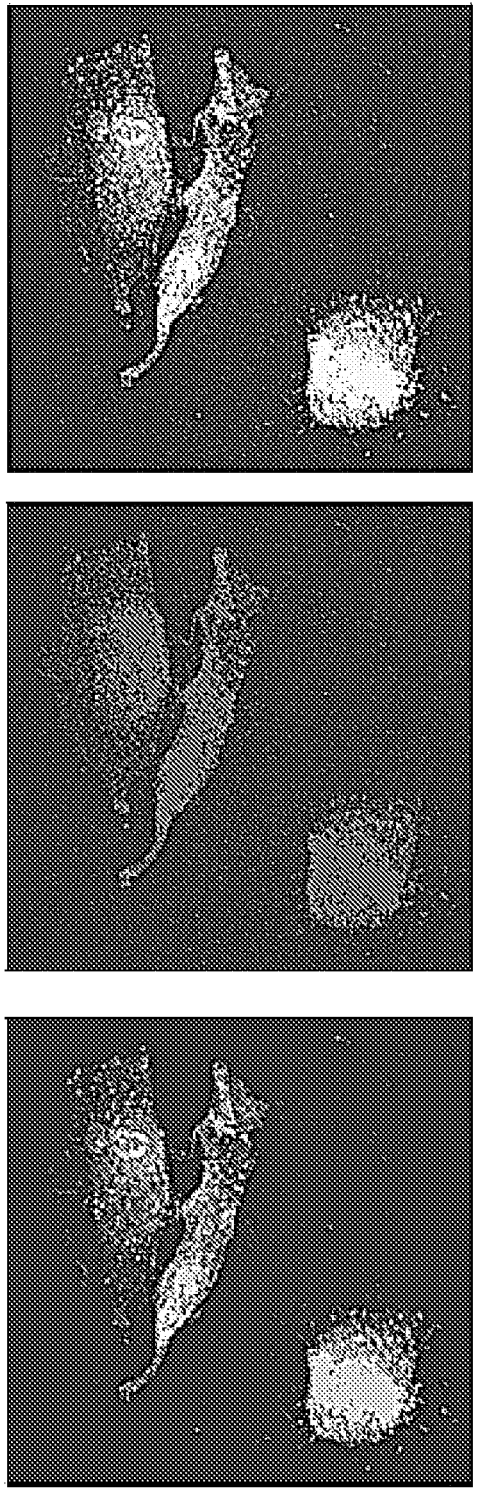
FIG. 30 shows micrographs demonstrating mitrochondrial localization of the disclosed delivery systems (e.g., gene delivery).
Figure 30:
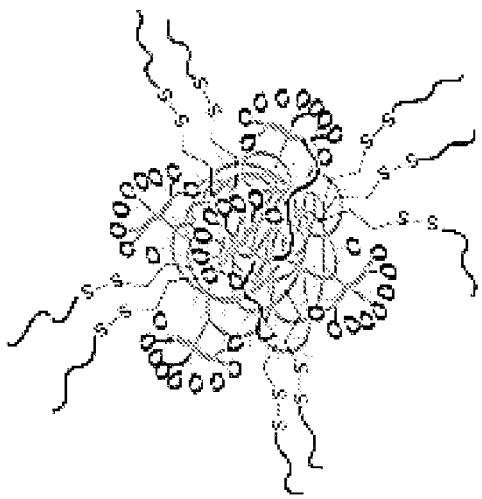
Figure 31:
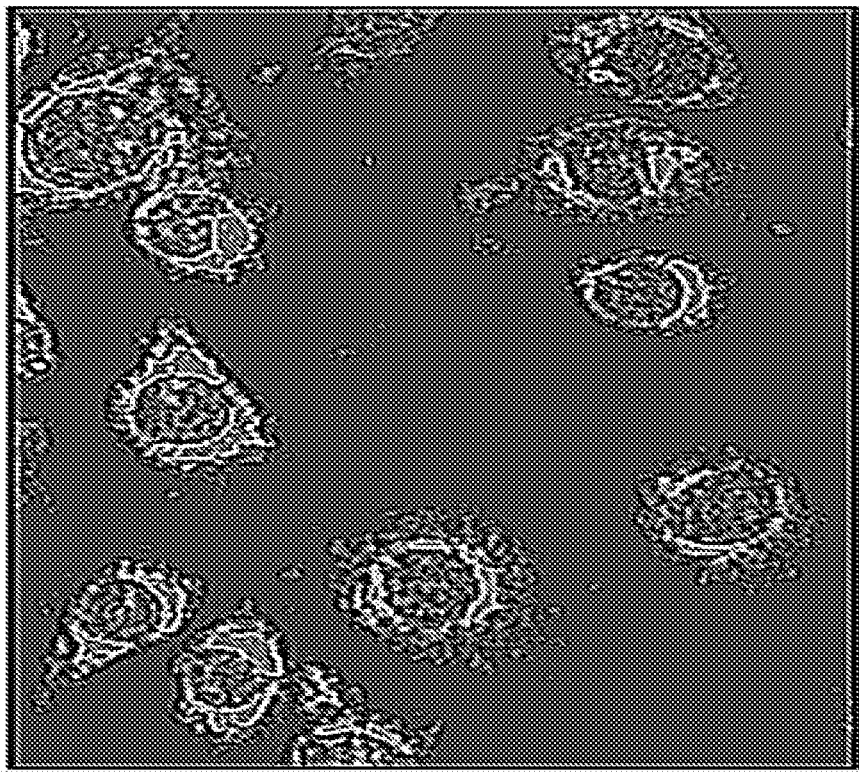
FIG. 31 shows micrographs demonstrating uptake of a disclosed delivery system (e.g., gene delivery) in ciEndothelial cells.
Figure 31:
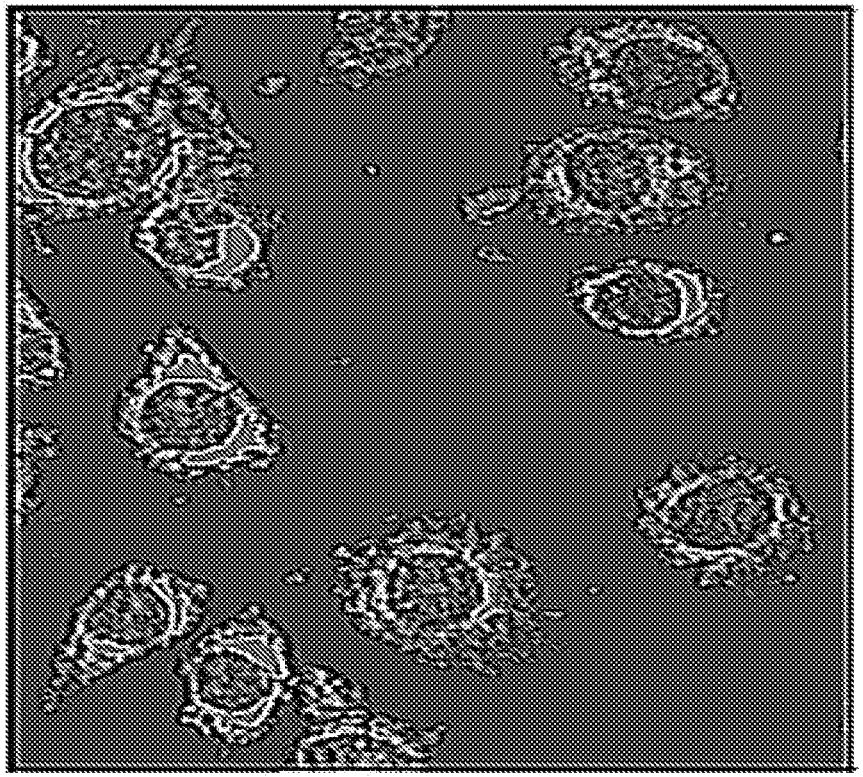
Figure 31:
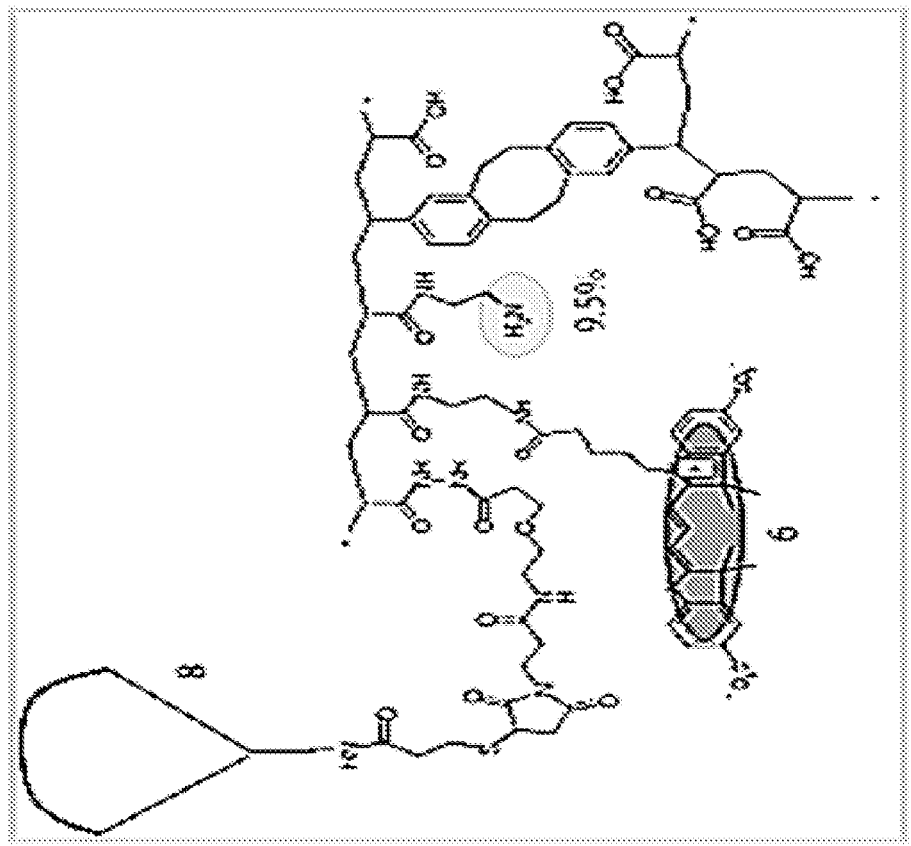
Figure 31:
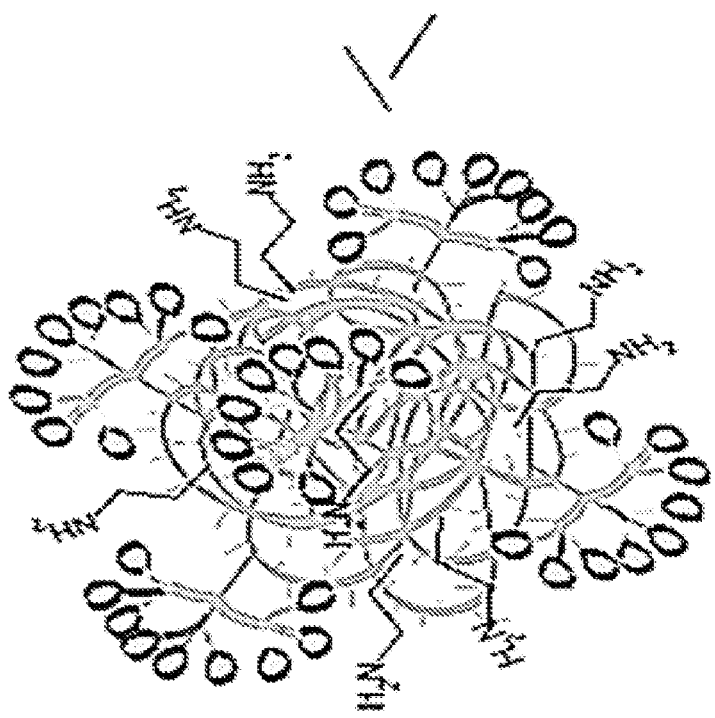

In control experiments, cells treated with free FITC and Boc-protected guanidinylated FITC-dendrimer showed no or extremely weak fluorescence, respectively. Therefore, the guanidino groups play an important role in the cell permeability of these molecules, while the length of the spacing chain determines both the differential rate of uptake and subcellular localization patterns. Although the mechanism of Tat translocation remains to be understood, it has been demonstrated that the rate of uptake is not temperature dependent. [Futaki, S.; Nakase, I.; Suzuki, T.; Youjun, Y.; Sugiura, Y. Biochemistry 2002, 41, 7925; Vivès, E.; Brodin, P.; Lebleu, B. J. Biol. Chem. 1997, 272, 16010.] This indicates that endocytosis does not play a crucial role in the translocation process. Evaluation of the effect of temperature on the internalization of FD-1 and FD-2 indicated that the two conjugates are able to get into cells not only at 37° C., but also at 4° C., even at a lower dendrimer concentration (1 µM) (see FIGS. 3 and 4 in contrast to control experiments, as shown in FIG. 24). No significant decrease in fluorescence intensity of cells treated with FD-1 or FD-2 was observed, indicating that the uptake process does not occur via endocytosis.

27. Synthesis of Dendrimer B11

A three-neck round bottom flask was flame-dried under argon, to which nitrotriacid B3 (3.192 g, 0.0115 mmol), 1-hydrobenzotriazole (HOBt) (5.609 g, 0.0415 mol), DCC (8.560 g, 0.0415 mol) and 100 mL THF were added sequentially. After 2 hours activation, aminotriester B2 (17.216 g, 0.0415 mol) was added. The solution was stirred at room temperature for 40 h, and the crude product was purified by flash column chromatography, eluting first with hexane/ethyl acetate (10:1) and then hexane/ethyl acetate (3:2) to yield dendrimer B11 (15.91 g, 94.1%). $^1$H NMR (400 MHz, CDCl$_3$): δ=☐1.44 (m, CH$_3$, 81H), 1.95 (m, CH$_2$, 18H), 2.21 (m, CH$_2$, 30H), 6.20 (s, NH, 3H); $^{13}$C NMR (400 MHz, CDCl$_3$): δ=28.04, 29.74, 29.85, 31.28, 57.56, 80.69, 92.47, 170.46, 172.76.

28. Synthesis of Dendrimer B12

A solution of B11 (10.0 g, 0.0 mol) in 150 mL of absolute ethanol in the presence of 8 grams of Raney-Nickel was hydrogenated at 60 psi of hydrogen at room temperature for 24 h. The suspension was carefully filtered through Celite and removal of the solvent under reduced pressure yielded B12 (9.86 g, 98.5%). $^1$H NMR (400 MHz, CD$_3$OD): δ=☐1.44 (m, CH$_3$, 81H), 1.61 (m, CH$_2$, 6H), 1.95 (m, CH$_2$, 12H), 2.21 (m, CH$_2$, 30H); $^{13}$C NMR (400 MHz, CD$_3$OD): δ=28.42, 30.24, 30.47, 32.02, 36.24, 53.53, 58.37, 81.18, 173.96, 175.39.

29. Synthesis of B25

To a room temperature stirred solution of 6-bromo-hexanoic acid (2.0 g, 0.0102 mol) in 7 mL of DMF was added NaN₃ (1.30 g, 0.020 mol). The reaction mixture was heated and stirred at 85° C. for 5 h. After DMF was removed, DCM was added to dissolve the residue. The mixture was washed with 0.1 N HCl and dried over anhydrous NaSO₄. Removal of the solvent gave a crude oil that was purified by flash column chromatography, eluting first with DCM and then ethyl acetate/DCM (3:7) to yield B25 (1.67 g, 69.07%). $^1$H NMR (400 MHz, MeOD): δ=☐1.38-1.49 (m, CH₂, 2H), 1.54-1.70 (m, CH₂, 4H), 2.32 (t, CH₂, 2H), 3.30 (t, CH₂, 2H); $^{13}$C NMR (400 MHz, MeOD): δ=☐25.57, 27.32, 29.62, 34.72, 52.27, 177.38.

30. Synthesis of Dendrimer B13

To a stirred solution of B25 (1.29 g, 8.22 mmol) in anhydrous THF (50 mL) were added DCC (1.70 g, 8.22 mmol) and HOBt (1.112 g, 8.22 mmol) at room temperature. The mixture was stirred for 2 h, then dendrimer B12 (9.86 g, 6.85 mmol) was added and the resulting solution was stirred for 40 h. After filtration and removal of THF, the product was purified by flash column chromatography, eluting with hexane/ethyl acetate (1:1) to yield B13 (8.50 g, 78.53%). $^1$H NMR (400 MHz, CD₃OD): δ=☐1.44 (m, CH₃, CH₂, 83H), 1.95 (m, CH₂, 18H), 2.21 (m, CH₂, 32H), 3.30 (m, CH₂, 2H); $^{13}$C NMR (400 MHz, CD₃OD): δ=26.47, 27.47, 28.43, 29.62, 30.35, 30.61, 32.07, 32.23, 37.56, 52.28, 58.63, 58.77, 81.54, 174.21, 175.35, 175.66.

31. Synthesis of Dendrimer B14

To a 0° C. stirred solution of nona-amine B5 (4.06 g, 2.43 mmol) in a methanol/acetonitrile (25 mL/15 mL) were added triethylamine (6.87 g, 68.0 mmol) and ethyl trifluoroacetate (9.32 g, 65.6 mmol) and the reaction mixture was stirred at 0° C. for 1 h and then at room temperature overnight. The solvent was removed in vacuo and the residue was taken up in ethyl acetate, and the resulting organic solution was washed with 1N HCl and brine and dried over anhydrous NaSO₄. Removal of the solvent in vacuo gave a crude solid that was purified by flash chromatography (EtOAc/Methanol gradient) to yield a solid (3.02 g, 56.3%). $^1$H NMR (400 MHz, CD₃OD): δ=01.85-2.10 (m, CH₂, 18H), 2.11-2.35 (m, CH₂, 30H), 3.24-3.48 (m, CH₂, 36H); $^{13}$C NMR (400 MHz, CD₃OD): δ=☐31.08, 31.26, 31.75, 32.01, 39.42, 40.42, 58.93, 94.33, 111.74, 115.54, 119.33, 123.13, 158.57, 159.06, 159.55, 160.04, 173.57, 176.14. The resulting white solid (1.0 g, 0.453 mmol) was dissolved in ethanol (45 mL) and transferred into a hydrogenation vessel containing Raney-Nickel catalyst (5 g) and the suspension was stirred at 80 psi of hydrogen at 50° C. for 48 h. After filtration through Celite, the solvent was removed under reduced pressure to give a B14 as a white solid (0.964 g, 97.7%). $^1$H NMR (400 MHz, CD₃OD): δ=1.67☐ (m, ☐CH₂, 6H), ☐☐986 (m, ☐QCH₂, 12H), 2.188 (m, CH₂, 30H), 3.30-3.55 (m, CH₂, 36H); $^{13}$C NMR (400 MHz, CD₃OD)

δ=31.20, 32.11, 36.17, 39.38, 40.52, 54.06, 58.80, 111.79, 115.53, 119.36, 123.10, 158.58, 1 59.04, 159.50, 160.11, 175.55, 176.24.

32. Synthesis of Dendrimer B15

To a stirred solution of 6-heptynoic acid (0.3022 g, 2.40 mmol) in anhydrous THF (50 mL) were added DCC (0.4952 g, 2.40 mmol) and HOBt (0.3245 g, 2.40 mmol) at room temperature. The mixture was stirred for 2 h, then dendrimer B14 (1.0432 g, 0.48 mmol) was added and the resulting solution was stirred for 40 h. After filtration and removal of THF, the product was purified by flash column chromatography, eluting with ethyl acetate/methanol gradient to yield B15 (0.620 g, 56.57%). $^1$H NMR (400 MHz, CD₃OD): δ=1.53 (m, CH₂, 2H), 1.71 (m, CH₂, 3H), 1.890-2.5 (m, CH₂, 50H), 3.30 (m, CH₂, 36H); $^{13}$C NMR (400 MHz, CD₃OD): δ☐=☐18.81, 26.14, 29.43, 31.27, 31.80, 37.37, 39.35, 40.43, 58.83, 59.05, 69.95, 83.4, 111.74, 115.57, 119.37, 123.13, 158.55, 159.07, 159.53, 159.99, 175.60, 176.25.

33. Synthesis of Dendrimer B16

Azide dendron B13 (100 mg, 0.044 mmol) and alkyne dendron B15 (70 mg, 0.044 mmol) were dissolved in THF/H₂O (4:1) and DIPEA (0.017 g, 0.132 mmol, 3 equiv) followed by Cu(PPh₃)₃Br (0.0042 g, 0.0044 mmol) were added. The reaction mixture was placed in the microwave reactor (Biotage) and irradiated at 120° C. for 20 min. After completion of the reaction, THF was removed and the residue was taken up in DCM. The organic layer was washed with water once and dried over anhydrous Na₂SO₄. $^1$H NMR of B16 (400 MHz, CD₃OD): δ=☐1.43 (m, CH₃, 81H), 1.71 (m, CH₂, 8H), 1.890-2.5 (m, CH₂, 96H), 2.71 (m, CH₂, 2H), 3.30 (m, CH₂, 36H), 4.38 (m, CH₂, 2H), 7.75 (s, 1H).

34. Synthesis of B17 and B18

The "Bow-Tie" B16 was stirred in formic acid overnight at room temperature. After the solvent was evaporated under reduced pressure, toluene was added and concentrated in vacuo to remove any residue of formic acid to give a white nonacid (100%). To a solution of the above resulting solid in DMF, HOBt and DCC were added and the solution was cooled to 0° C. N-Boc-ethylenediamine or N-Boc-hexyldiamine was added dropwise and the mixture was stirred for 48 h at room temperature, filtered and concentrated under reduced pressure. The residue was dissolved in dichloromethane and the resulting organic solution was washed sequentially with 1N HCl, water and dried over anhydrous Na₂SO₄. The solvent was evaporated under reduced pressure and the crude residue was purified by flash column chromatography to yield B17 or B18.

35. Synthesis of B19 and B20

Potassium carbonate was added to B17 or B18 in methanol/water, the mixture was stirred at room temperature for 6 h. The crude product was purified by dialysis against methanol with Spectra®Por Biotech regenerated cellulose membranes (MWCO=3500) for 24 h to give B19 or B20.

36. Synthesis of B21 and B22

The above B19 or B20 was then dissolved in 1, 4-dioxane and the solution cooled 0° C., 4 M HCl in dioxane was added and stirred for 1 hr at room temperature. Removal of the solvent under reduced pressure gave a white solid. The resulting HCl salt was dissolved in methanol and the solution was cooled to 0° C. Et₃N was added, followed by N,N'-diBoc-N"-triflylguanidine and the mixture was stirred for 24 h at room temperature. After the solvent was evaporated under reduced pressure, the residue was dissolved in dichloromethane and the solution was washed with 1N HCl water, and dried over anhydrous Na₂SO₄. After removal of the solvent under reduced pressure, the crude product was purified by dialysis against methanol with Spectra®Por Biotech regenerated cellulose membranes (MWCO=3500) for 24 h to give B21 or B22.

37. Synthesis of B23 and B24

The resulting solid B21 or B22 was dissolved in 1,4-dioxane and the solution cooled to 0° C., 4 M HCl in dioxane was added and the solution stirred overnight at room temperature. The precipitate was filtered off and dried to give a crude product. The solid was re-dissolved in water and insoluble precipitate was filtered off and the filtrate was dialyzed against water with Spectra®Por Biotech cellulose ester membranes (MWCO=1000) for 48 hrs and lyophilized to yield a water-soluble B23 or B24.

Synthesis of Copolymer poly(vl-avl-opd) (AbD)

To a 25 mL 3-necked round bottom flask, equipped with stir bar, gas inlet and 2 rubber septa, 2-oxepane-1,5-dione (0.7000 g, 5.46 mmol) was added. The round bottom flask was purged with argon. After purging for 30 min, dry toluene (4 mL) was added. The mixture stirred in an oil bath at 80° C. to dissolve the monomer. Upon dissolving, $Sn(Oct)_2$ (0.011 g, $2.73 \times 10^2$ mmol) in 0.5 mL dry toluene, absolute ethanol (0.020 g, $4.4 \times 10^{-1}$ mmol), α-allyl-δ-valerolactone (1.15 g, 8.2 mmol) and δ-valerolactone (1.37 g, 13.7 mmol) were then added to the reactor and the mixture was heated for 48 h at 105° C. Residual monomer and catalyst were removed by dialyzing with Spectra/Por® dialysis membrane (MWCO=1000) against $CH_2Cl_2$ to give a golden brown polymer. Yield: 1.7 g. $M_w$=3287 Da, PDI=1.17: $^1$H NMR (300 MHz, $CDCl_3$/TMS, ppm) δ: 5.72 (m, $H_2C$=CH—), 5.06 (m, $H_2C$=CH—), 4.34 (m, —$CH_2CH_2C(O)$ $CH_2CH_2O$—), 4.08 (m, —$CH_2O$—), 3.67 (m, —$OCH_2CH_3$), 2.78 (m, opd, —OC(O)$CH_2CH_2C(O)$ $CH_2$—), 2.58 (m, opd, —OC(O)$CH_2CH_2C(O)CH_2$—), 2.34 (m, vl, —$CH_2CH_2C(O)O$—, avl, $H_2C$=CH$CH_2CH$—, $H_2C$=CH$CH_2CH$—), 1.66 (m, avl & vl, —CH$CH_2CH_2$—), 1.25 (t, —$CH_2CH_3$); $^{13}$C NMR (400 MHz, $CDCl_3$, ppm) δ: 204.9, 175.2, 173.7, 173.2, 135.0, 117.0, 63.9, 44.8, 36.4, 33.6, 28.0, 26.3, 21.3. (10.39% avl, 7.97% evl, 6.42% opd and 75.21% vl).

38. Synthesis of poly(vl-evl-avl-opd) (ABbD)

In a 200 mL round bottom flask, equipped with stir bar, poly(vl-avl-opd) (1.7 g, 1.56 mmol) was dissolved in 30 mL $CH_2Cl_2$. To this solution, 3-chloroperoxybenzoic acid (0.2210 g, 1.28 mmol) was added slowly. The mixture was stirred for 72 h at room temperature and then concentrated via rotary evaporator. The crude product was dissolved in a minimal amount of THF (5 mL) and poured into a round-bottomed flask containing 1 L diethyl ether. The solution was kept overnight at 0° C. and a white solid was obtained. The solution was decanted off and the solid was dried in vacuo to obtain poly(avl-evl-vl-opd). Yield: 1.2 g (71%). $^1$H NMR (300 MHz, $CDCl_3$/TMS, ppm) δ: 5.72 (m, $H_2C$=CH—), 5.06 (m, $H_2C$=CH—), 4.34 (m, —$CH_2CH_2C(O)CH_2CH_2O$—), 4.08 (m, —$CH_2O$—), 3.67 (m, —$OCH_2CH_3$), 2.96 (n, epoxide proton), 2.78 (m, evl epoxide proton, opd, —OC(O)$CH_2CH_2C(O)CH_2$—), 2.58 (m, opd, —OC(O)$CH_2CH_2C(O)CH_2$—), 2.47 (epoxide proton), 2.34 (m, vl, —$CH_2CH_2C(O)O$—, avl, $H_2C$=CH$CH_2CH$—, $H_2C$=CH$CH_2CH$—), 1.66 (m, avl & vl, —CH$CH_2CH_2$—), 1.25 (t, —$CH_2CH_3$).

39. Nanoparticle Formation from poly(vl-evl-avl-opd)

In a 250 mL three-necked round bottom flask equipped with stir bar, condenser and septa, a solution of 2,2'-(ethylenedioxy)diethylamine (26.4 μL, 0.18 mmol) in 55.6 mL $CH_2Cl_2$ was heated at 44° C. A solution of poly(avl-evl-vl-opd) (0.2500 g, $M_w$=3287 Da, PDI=1.17) dissolved in $CH_2Cl_2$ (0.36 mL) was added dropwise via a peristaltic pump at 13 mL/min with vigorous stirring. The reaction mixture was heated for 12 h. Residual diamine was removed by dialyzing with SnakeSkin® Pleated Dialysis Tubing (MWCO=10,000) against dichloromethane. $^1$H NMR (300 MHz, $CDCl_3$/TMS, ppm) δ: The significant change is the disappearance of the epoxide protons at 2.96, 2.75 and 2.47 ppm and the appearance of signals at 3.5 and 2.89 ppm corresponding to the protons neighboring the secondary amine of the PEG linker after cross-linking. All other aspects of the spectrum are similar. To demonstrate the reactivity of the ally groups to thiols, in a model reaction we added benyl mercaptan to the allyl groups. We found a high reactivity using no other reactant. We also added the molecular transporter in the same fashion.

40. Attachment of Benzyl Mercaptan to poly(vl-evl-avl-opd) Nanoparticles (General Procedure to Attach Thiol Functionalized Compounds Including "Molecular Transporter" and Peptides)

In a vial equipped with a stir bar, poly(avl-evl-vl-opd) nanoparticles (0.030 g, 0.0268 mmol) and benzyl mercaptan (9.48 mg, 0.0764 mmol) were dissolved in 0.6 mL toluene. The reaction mixture was heated for 72 h at 30° C. The remaining toluene was removed in vacuo and residual benzyl mercaptan was removed by dialyzing with SnakeSkin® Pleated Dialysis Tubing (MWCO=10,000) against dichloromethane. $^1$H NMR (300 MHz, $CDCl_3$/TMS, ppm) δ: The significant change is the disappearance of the allyl protons at 5.72 and 5.06 ppm and the appearance of signals at 3.52 ppm and 7.30 ppm corresponding to the methylene and benzene protons respectively of the attached benzyl mercaptan. All other aspects of the spectrum are similar.

41. Attachment of N-boc-ethylenediamine to Succinimidyl 2-Vinylsulfonylethyl Carbonate (SVEC)

To a solution of SVEC (1.03 g, 3.72 mmol) in acetonitrile (50 mL), N-boc-ethylenediamine (0.77 mL, 4.86 mmol) and water (50 mL) were added. Sodium bicarbonate (0.4066 g, 4.84 mmol) was added and the reaction stirred for 4 h at room temperature. The acetonitrile was removed in vacuo and the remaining aqueous phase was diluted with brine (45 mL). The aqueous phase was extracted three times with dichloromethane (90 mL). The organic phases were combined, washed with brine, dried with $MgSO_4$, and concentrated in vacuo. The crude product was purified by flash chromatography (eluent: ethyl acetate) to give a white solid in 90% yield. $^1$H NMR (300 MHz, $CDCl_3$/TMS, ppm) δ: 6.6 (m, $H_2C$=CH—), 6.4 & 6.17 (m, $H_2C$=CH—), 4.43 (t, —$CH_2CH_2OC(O)$—), 3.3 (t, —$CH_2CH_2$ OC(O)—), 3.24 (m, —NH$CH_2CH_2$NHC(O)—), 1.41 (s, —NHC(O)OC$(CH_3)_3$).

42. Attachment of Sulfonyl Linker to Nanoparticles from poly(vl-evl-opd)

In a 100 mL round bottom flask, equipped with stir bar, poly(vl-evl-opd) (ABD) nanoparticles (84.6 mg, $2.45 \times 10^{-7}$ mol) were dissolved in 12.5 mL $CH_2Cl_2$. To this solution, sulfonyl linker (69 μL of 0.85 M linker in methanol, 5.89×$10^5$ mol), $NaCNBH_3$ (0.0111 g in 0.1 mL methanol, 1.77×$10^{-4}$ mol) and methanol (12.4 mL) were added. The pH was adjusted to 6.5 using 0.1 M hydrochloric acid aqueous solution and 0.1 M sodium hydroxide aqueous solution. The reaction mixture stirred for 25 h at room temperature and was purified by dialyzing with SnakeSkin® Pleated Dialysis Tubing (MWCO=10,000) against 1:1 dichloromethane/methanol. $^1$H NMR (300 MHz, $CDCl_3$/TMS, ppm) δ: The significant change is the appearance of the following peaks: 6.8 (m, $CH_2$=CH—), 6.5 & 6.3 (m, $CH_2$=CH—), 4.5 (m, $CH_2$=$CHSO_2CH_2CH_2$—), 3.3 (m, —$NHCH_2CH_2NH$—), 3.1 (m, $CH_2$=$CHSO_2CH_2CH_2$—). All other aspects of the spectrum are similar.

43. General Procedure for Attachment of Peptide-Alexa Fluor® 750 to Linker Conjugated Nanoparticles In a small vial, equipped with stir bar, peptide (33 μL of 0.013 mg/mL peptide in phosphate buffer-pH 7.2) and Alexa Fluor® 750 (26.5 μL of 20 mg/mL Alexa Fluor® in dimethylformamide were added. The reaction stirred for 24 h in an aluminum foiled. In a small vial, poly(vl-evl-opd) (ABD) nanoparticles (29.9 mg) were dissolved in 800 μL phosphate buffer (pH=7.2) and 700 μL dimethylformamide. To the peptide-Alexa Fluor® solution, 251 μL of dissolved nanoparticles was added. After stirring for 45 min at room temperature, additional peptide (2 mg, 1.84×$10^{-6}$ mol) was added. The reaction mixture was purified using concentrator tubes with a molecular weight cut-off of 10,000 Da.

44. Attachment of Alexa Fluor® 750 to poly(vl-evl-opd) Nanoparticles

In a 25 mL round bottom flask, poly(vl-evl-opd) nanoparticles (63.55 mg, 1.92×$10^{-7}$ mol) was dissolved in 6.4 mL tetrahydrofuran. The round bottom flask was sealed with a rubber septum and purged with argon. To the purged solution, Alexa Fluor® 750 (5 mg in 0.5 mL anhydrous dimethylformamide was added. The reaction mixture stirred for 24 h at room temperature. After 24 h, N-acetoxy succinimide (50 mg, 0.3 mmol) was added to quench the remaining unreacted amines. $^1$H NMR (300 MHz, $CDCl_3$/TMS, ppm) δ: The significant change is the appearance of the following peaks: 7.12, 5.6, 5.5, 5.1, 3.81, 1.90 ppm. The structure of Alexa Fluor® 750 is not publicly known. All other aspects of the spectrum are similar.

45. General Reductive Amination for the Attachment of Peptides to Alexa Fluor® Conjugated Nanoparticles In a small vial, equipped with stir bar, peptide (2.6 mg, 2.4×$10^{-6}$ mol) was dissolved in 2 mL tetrahydrofuran. To this solution, dye conjugated nanoparticles (0.0923 g, 2.8×$10^{-8}$ mol, in 0.5 mL tetrahydrofuran) and $NaCNBH_3$ (2.23 μL of 1.0 M $NaCNBH_3$ in tetrahydrofuran) were added. The reaction mixture stirred for 12 h at room temperature. The reaction mixture was purified by dialyzing with SnakeSkin® Pleated Dialysis Tubing (MWCO=10,000) against tetrahydrofuran. $^1$H NMR (300 MHz, $CDCl_3$/TMS, ppm) δ: The significant change is the appearance of the following peaks: 5.2, 5, 4.8, 2.6, 2.45, 2.0, 1.22 and 0.89 ppm.

46. Attachment of N-(boc)-2,2(ethylenedioxy)diethylamine

A 50 mL 3-neck round bottom flask was flame-dried under argon. The deprotected nanoparticles (27.6 mg, 0.79 μmol) were dissolved in DriSolv DMF and transferred to the sealed flask, which was then cooled to 0° C. via an ice bath. N-methylmorpholine (6.37 mg, 0.063 mmol) followed by isobutyl chloroformate (9.46 mg, 0.0693 mmol) was added to the cooled solution and allowed to activate for 1.5 h. Next, N-(boc)-2,2(ethylenedioxy)diethylamine (15.6 mg, 0.063 mmol) was added, the ice bath was removed and the reaction was allowed to stir overnight. The reaction was concentrated in vacuo, the residue was dissolved in MeOH, transferred to SnakeSkin® Pleated Dialysis Tubing (MWCO=10 000), and was dialysed against MeOH.

47. Deprotection of Nanoparticles Containing N-(Boc)-2,2(ethlenedioxy)diethylamine The nanoparticles were dissolved in 2 M HCl/Dioxane (15 mL). The reaction was allowed to stir overnight. The reaction was dissolved in MeOH/$H_2O$ and transferred to SnakeSkin® Pleated Dialysis Tubing (MWCO=10 000), and was dialysed against MeOH/$H_2O$.

48. Attachment of Alexa Fluor 750®

PBS Buffer (pH 7.3) was purged with argon for 1 h. The Alexa Fluor® 750 (3 mg, 2.3 μmol) in 0.3 mL DMF was added to a solution of deprotected nanoparticles (15.8 mg) in PBS Buffer (1.2 mL) and was allowed to stir for 24 h. The reaction was diluted with $H_2O$, was transferred to SnakeSkin® Pleated Dialysis Tubing (MWCO=10 000), and was dialyzed against $H_2O$.

49. Attachment of SVEC

The nanoparticles were dissolved in 4 mL of $H_2O$ followed by the addition of sodium bicarbonate (2.7 mg, 0.0318 mmol). Next, the SVEC was added in 1 mL of ACN followed by an additional 3 mL of ACN. The reaction was allowed to proceed for 2 h at which time acetoxysuccinimide (127 mg, 0.79 mmol) was added in order to quench any remaining amines. This reaction was allowed to proceed for 2 h. The reaction was diluted with $H_2O$ and was transferred to SnakeSkin® Pleated Dialysis Tubing (MWCO=10 000), and was dialyzed against $H_2O$ (pH 4.5).

50. Targeting Peptide Attachment

The modified nanoparticles (2 mg) were dissolved in 0.2 mL of PBS Buffer (pH 7.3) and to that a solution of GCGGGNHVGGSSV (11.4 mg, 0.0105 mmol) in 0.4 mL of PBS Buffer (pH 7.3) was added. This reaction was allowed to proceed for 24 h. The reaction was diluted with $H_2O$ and was transferred to SnakeSkin® Pleated Dialysis Tubing (MWCO=10 000), and was dialyzed against $H_2O$.

51. Control Peptide Attachment

The modified nanoparticles (2 mg) were dissolved in 0.2 mL of PBS Buffer (pH 7.3) and to that a solution of GCGGGSGVSGHNG (11.0 mg, 0.0105 mmol) in 0.4 mL of PBS Buffer (pH 7.3) was added. This reaction was allowed to proceed for 24 h. The reaction was diluted with $H_2O$ and was transferred to SnakeSkin®) Pleated Dialysis Tubing (MWCO=10 000), and was dialyzed against $H_2O$.

52. Attachment of N-(Boc)-2,2(ethylenedioxy)diethylamine

A 50 mL 3-neck round bottom flask was flame-dried under argon. The deprotected nanoparticles (27.6 mg, 0.79 µmol) were dissolved in DriSolv DMF and transferred to the sealed flask, which was then cooled to 0° C. via an ice bath. N-methylmorpholine (6.37 mg, 0.063 mmol) followed by isobutyl chloroformate (9.46 mg, 0.0693 mmol) was added to the cooled solution and allowed to activate for 1.5 h. Next, N-(boc)-2,2(ethylenedioxy)diethylamine (15.6 mg, 0.063 mmol) was added, the ice bath was removed and the reaction was allowed to stir overnight. The reaction was concentrated in vacuo, the residue was dissolved in MeOH, transferred to SnakeSkin® Pleated Dialysis Tubing (MWCO=10 000), and was dialysed against MeOH.

53. Deprotection of Nanoparticles Containing N-(Boc)-2,2(ethlenedioxy)diethylamine The nanoparticles were dissolved in 2 M HC/Dioxane (15 mL). The reaction was allowed to stir overnight. The reaction was dissolved in MeOH/$H_2O$, was transferred to SnakeSkin® Pleated Dialysis Tubing (MWCO=10 000), and was dialysed against MeOH/$H_2O$.

54. Attachment of 1,4,7,10-Tetraazacyclododecane-1,4,7-tris(t-butyl acetate)-10-succinimidyl Acetate (DOTA)

The nanoparticles were dissolved in DMF followed by the addition of triethylamine (TEA). To this solution, DOTA was added and the reaction was allowed to stir overnight. The reaction was concentrated in vacuo, the residue was dissolved in MeOH/$H_2O$, transferred to SnakeSkin® Pleated Dialysis Tubing (MWCO=10 000), and dialyzed against MeOH/$H_2O$.

55. Deprotection of Nanoparticles Containing t-butyl Protected DOTA

The nanoparticles were dissolved in 2 M HCl/Dioxane (15 mL). The reaction was allowed to stir overnight. The reaction was dissolved in MeOH/$H_2O$, transferred to SnakeSkin® Pleated Dialysis Tubing (MWCO=10 000), and dialyzed against MeOH/$H_2O$.

56. Attachment of SVEC

The nanoparticles were dissolved in $H_2O$ followed by the addition of sodium bicarbonate. Next, the SVEC was added in ACN followed by an additional ACN. The reaction was allowed to proceed for 2 h at which time acetoxysuccinimide was added in order to quench any remaining amines. This reaction was allowed to proceed for 2 h. The reaction was diluted with $H_2O$, was transferred to SnakeSkin® Pleated Dialysis Tubing (MWCO=10 000), and was dialyzed against $H_2O$ (pH 4.5).

57. Modification of Alexa Fluor 750®

Alexa Fluor 750® (1.43 mg. 1.1 µmol) was dissolved in 143 µL DMSO and added to cysteamine (0.077 mg, 1.0 µmol) in 30.9 µL of PBS Buffer (pH 7.5). The reaction was allowed to proceed overnight.

58. Simultaneous Attachment of Modified Alexa Fluor 750® and Peptide

The modified nanoparticles were dissolved in PBS Buffer (pH 7.3), which had been purged with argon for 20 min. Next, the modified Alexa Fluor 750® and one equivalent of GCGGGNHVGGSSV was added and allowed to react for 2 h. An additional 4 equivalents of peptide was then added and the reaction stirred overnight. The solution was diluted in $H_2O$, transferred to SnakeSkin® Pleated Dialysis Tubing (MWCO=10 000), and dialyzed against $H_2O$.

59. Synthesis of Linear RGD

A typical Fmoc solid phase peptide synthesis was performed to synthesize the linear peptide. A cysteine preloaded 2-chlorotrityl resin was employed. HOBt:HBTU:DIPEA (1:1:2) in DMF was used as the coupling reagent and amino acids were double coupled. A 20% piperdine (v/v) in DMF employed to deprotect the Fmoc. An amino-hexyl spacer was coupled to the cystine on the resin, followed by glutamic acid, aspartic acid, glycine, arginine, phenylalanine, and finally lysine.

60. Cyclization of RGD

The peptide was cyclized by utilizing an ODmab group, which allows for the selective deprotection carboxylic acid side chain of the glutamic acid, which can then be coupled to the N-terminus. The ODmab was deprotected using 2% v/v hydrazine-$H_2O$/DMF added to the resin and allowed to react for 7 min. Next it was washed with 20 mL of DMF followed by 10 mL of a 5% v/v DIPEA/DMF solution which was allowed to shake for 10 min. Carboxy activation was achieved through the use of DCC (44.6 mg, mmol) and HOBt (29.2 mg, mmol) was added to 10 mL of DMF and then added to the resin and allowed to shake for 18 h.

Reagent R was used to deprotect all side groups and cleave the cyclic peptide from the resin. Reagent R was prepared by combining 5.4 mL TFA, 0.3 mL thioanisole, 0.18 mL anisole, and 0.12 mL ethanedithiol. This was allowed to react for 3 hours at which time the resin was filtered off. The supernatant was cooled to 0° C. and the peptide was precipitated using cold diethyl ether. It was collected through centrifugation and then washed three times using diethyl ether. The pellet was dissolved in 0.6 mL $H_2O$ and 0.4 mL ACN with 0.3% TFA and purified using HPLC.

61. Synthesis of N-Boc-N-Tfa-Ethylenediamine

To a solution of N-boc-ethylenediamine (5.0 g, 31.2 mmol) in 20 mL THF, ethyl trifluoroacetate (3.72 mL, 31.2 mmol) was added dropwise and the reaction stirred overnight. The reaction solution was concentrated to yield a white crystalline product (8.0 g, 100%). $^1$H NMR (400 MHz, CDCl$_3$) δ 1.44 (s, 9H, CH$_3$), 3.37 (dd, 2H, J=5.4 Hz, J=10.2 Hz, CH$_2$), 3.46 (dd, 2H, J=5.1 Hz, J=10.4 Hz, CH$_2$), 5.01 (s, 1H, NH), 7.85 (s, 1H, NH); $^{13}$C NMR (400 MHz, CDCl$_3$) δ 28.2, 39.1, 42.2, 80.6, 140.6, 151.2, 157.7.

62. Boc Deprotection of N-Boc-N-Tfa-Ethylenediamine

N-Boc-N-Tfa-ethylenediamine (8.0 g, 31.5 mmol) was dissolved in 50 mL formic acid and stirred for 14 h at room temperature. After the solvent was evaporated under reduced pressure, toluene was added and concentrated to remove any residual formic acid, yielding an orange oil (4.90 g, 99.7%). $^1$H NMR (400 MHz, MeOD) δ 2.31 (s, 2H, NH$_2$), 3.15 (t, 2H, J=6.1 Hz, CH$_2$), 3.61 (t, 2H, J=6.1 Hz, CH$_2$), 8.35 (s, 1H, NH); $^{13}$C NMR (400 MHz, MeOD) δ 38.5, 39.7, 113.1, 115.9, 118.8, 121.6, 159.7, 160.1.

63. Attachment of N-Tfa-Ethylenediamine

The deprotected nanoparticles (162.3 mg, 4.58 µmol) in DriSolv DMF (10.0 mL) were stirred under argon at 0° C. with N-methylmorpholine (47.8 mg, 472.6 µmol) followed by dropwise addition of isobutyl chloroformate (71.0 mg, 519.8 µmol) in DriSolv DMF (0.75 mL). After 1.5 h, a solution of N-Tfa-ethylenediamine (73.8 mg, 472.6 µmol) in DriSolv DMF (2.5 mL) was added dropwise. The reaction was allowed to warm to room temperature and stirred overnight. After removal of DMF in vacuo, the product was dissolved in methanol and dialyzed against methanol with SnakeSkin® Pleated Dialysis Tubing (MWCO=10,000). $^1$H NMR (400 MHz, MeOD) δ 7.61-6.45 (br m, aromatic from crosslinker), 3.15-3.00 (br m, N-Tfa-ethylenediamine), 3.00-2.69 (br m, backbone and N-Tfa-ethylenediamine), 2.69-1.34 (br m, backbone).

64. Deprotection of MAL-dPeg™$_4$-t-boc-hydrazide

In a 100 mL round bottomed flask, MAL-dPeg™$_4$-t-boc-hydrazide (127.1 mg, 239.5 µmol) was dissolved in 80.0 mL of formic acid and stirred over night at room temperature. After the solvent was evaporated under reduced pressure, toluene was added and concentrated to remove any residual formic acid to give MAL-dPeg™$_4$-hydrazide (103.1 mg, 100%).

65. Attachment of MAL-dPeg™$_4$-Hydrazide

The deprotected nanoparticles (141.1 mg, 3.13 µmol) in DriSolv DMF (10.0 mL) were stirred under argon at 0° C. with N-methylmorpholine (17.1 mg, 169.1 µmol) followed by dropwise addition of isobutyl chloroformate (25.4 mg, 86.0 µmol) in DriSolv DMF (0.7 mL). After 1.5 h, a solution of MAL-dPeg™$_4$-hydrazide (103.1 mg, 239.5 µmol) was added dropwise. The reaction was allowed to warm to room temperature and stirred overnight. After removal of DMF in vacuo, the product was dissolved in methanol and dialyzed against methanol with SnakeSkin® Pleated Dialysis Tubing (MWCO=10,000). $^1$H NMR (400 MHz, MeOD) δ 7.67-6.47 (br m, aromatic from crosslinker and maleimide linker), 3.89-3.48 (br t, maleimide linker), 3.21-3.02 (br m, N-Tfa-ethylenediamine), 3.02-2.69 (br m, backbone and N-Tfa-ethylenediamine), 2.69-1.01 (br m, backbone).

66. Hydrogenation of G1

A solution of G1 (8.36 g, 5.69 mmol) in ethanol (214 mL) in a Parr hydrogenation bottle with Raney-Nickel (3.49 g) was shaken at 65 psi for 3 days at room temperature. Another 1 g of Raney-Nickel was added to the reaction and it was again shaken at 65 psi for 3 days at room temperature. The reaction was filtered through Celite, and the removal of the solvent under reduced pressure gave the crude product. The residue was dissolved in ethyl acetate and subsequently washed with saturated sodium bicarbonate solution (2×, 100 mL) and brine (2×, 100 mL) then the organic layer was dried over anhydrous sodium sulfate. The solution was filtered and concentrated under reduced pressure to yield amine G1 (8.19 g, 93.7%).

67. PDPOH Attachment to G1

PDPOH (91.46 mg, 4.25 mmol) in dry THF (100 mL) was stirred under argon at room temperature with 1-hydrobenzotriazole (HOBt) (68.90 mg, 5.10 mmol) and DCC (1.05 g, 5.10 mmol). After 1 h, amine G1 (7.34 g, 5.10 mmol) was added to the solution and the reaction proceeded for 48 h, after which, it was filtered and concentrated under reduced pressure. The crude material was purified via flash column chromatography eluting with 10:1 hexanes:ethyl acetate increasing to 100% ethyl acetate to give white SS-G1 (4.67 g, 67.1%).

68. SSG1 Deprotection Via Formic Acid

SSG1 (4.67 g, 2.85 mmol) was dissolved with stirring in formic acid (100 mL) and the reaction proceeded at room temperature overnight. Upon completion, the formic acid was removed azeotropically with toluene under reduced pressure to yield the product (3.29 g, 100.0%).

69. N-Boc-1,6-Diaminohexane Attachment to SSG1

SSG1OH (3.29 g, 2.91 mmol) in anhydrous THF (100 mL) was stirred under argon at room temperature with HOBt (4.23 g, 31.25 mmol) and DCC (6.45 g, 31.25 mmol). After one hour, N-boc-1,6-diaminohexane (6.76 g, 31.25 mmol) was added to the solution and the reaction proceeded for 48 h at room temperature. Upon completion, the reaction solution was filtered to remove the DCC salt and the filtrate concentrated and purified via flash column chromatography eluting with 1% methanol in dichloromethane and gradually increasing to 10% methanol in dichloromethane to yield a white solid (4.42 g, 52.0%).

The resulting solid was dissolved in 1,4-dioxane (20 mL), the solution was cooled to 0° C., and 4 M HCl in 1,4-dioxane (20 mL) was added and the reaction stirred for 24 h at room temperature. Removal of the solvent under pressure gave a white solid (3.55 g, 100.0%).

70. Attachment of Goodman's Reagent to SSG1LL

The resulting SSG1LL HCl salt (3.55 g, 1.51 mol) was dissolved in methanol (50 mL), and the solution was cooled to 0° C. Triethylamine (TEA) (3.41 mL, 24.56 mmol) was added followed by N,N'-diboc-N"-triflylguanidine (6.94 g, 17.74 mmol) and the reaction was stirred 24 h at room temperature. After removal of the solvent under reduced pressure, the crude product was purified via flash column chromatography eluting with 1% methanol in dichloromethane and gradually increasing to 10% methanol in dichloromethane to yield a white solid (838.2 mg, 13.13%). $^1$H NMR (300 MHz, MeOD) δ 1.33-1.47 (m, 246 H, $CH_2$, $CH_3$), 2.03 (d, 48H, J=65.3 Hz, $CH_2$), 3.15 (td, 30 H, J=6.3 Hz, J=12.7 Hz, $CH_2$), 3.29 (m, 45H, $CH_2$), 7.42 (m, 1H, ArH), 7.67 (d, 1H, J=8.2 Hz, ArH), 7.79 (d, 1H, J=8.1 Hz, ArH), 8.02 (s, 1H, ArH).

71. Cleavage of Disulfide Bridge on Molecular Transporter

The disulfide linker hexyl molecular transporter (257.8 mg, 61.41 µmol) in DriSolv DMF (5 mL) was stirred under argon and a solution of DL-dithiothreitol (740.0 mg, 4.80 mmol) in DMF (5 mL) was added dropwise and the reaction proceeded for 2 h at room temperature. After removal of DMF in vacuo, the reaction was purified using a Sephadex LH-20 column, eluting with DMF and concentrating the fractions in vacuo again yielding the product (251.0 mg, 100%).

72. Attachment of Molecular Transporter to Nanoparticles

The nanoparticles (147.4 mg, 3.07 µmol) in DriSolv DMF (10.0 mL) were stirred under argon and the free thiol hexyl molecular transporter (251.0 mg, 61.41 µmol) in DriSolv DMF (10.0 mL) was added dropwise followed by the addition of a catalytic amount of N-methylmorpholine. After removal of DMF in vacuo, the product was dissolved in methanol and dialyzed against a 1:1 methanol:water solution, eventually dialyzing against pure methanol with SnakeSkin® Pleated Dialysis Tubing (MWCO=10,000). $^1$H NMR (400 MHz, MeOD) δ 7.55-6.21 (br m, aromatic from crosslinker), 3.85-3.49 (br t, maleimide linker), 3.22-3.00 (br m, N-Tfa-ethylenediamine and molecular transporter), 3.00-2.70 (br m, backbone, N-Tfa-ethylenediamine, and molecular transporter), 2.70-1.00 (br m, backbone and molecular transporter).

73. Deprotection of Trifluoroacetyl Protected Amines on Modified Particles

The nanoparticles (142.0 mg, 1.54 µmol) were dissolved in methanol (5.0 mL) and a 10% K2CO3 solution of 5:3 methanol:water (13.0 mL) was added to the solution and the reaction proceeded overnight at room temperature. The reaction was purified by dialysis with SnakeSkin® Pleated Dialysis Tubing (MWCO=10 000) against a 5:3 methanol:water solution, eventually dialyzing against pure methanol then dialyzing against a 1:1 methanol THF solution, eventually dialyzing against pure THF. 1H NMR (400 MHz, THF d8) δ 8.26-6.53 (br m, aromatic from crosslinker), 3.94-3.52 (br m, maleimide linker), 3.28-3.12 (br t, ethylenediamine and molecular transporter), 3.12-2.68 (br m, backbone, ethylenediamine, and molecular transporter), 2.68-1.05 (br m, backbone and molecular transporter).

74. Attachment of 3-(pyridine-2-yl disulfanyl)propanoic Acid Nanoparticles

A solution of 3-(pyridine-2-yl disulfanyl)propanoic acid (16.8 mg, 77.9 µmol) in anhydrous THE (2.5 mL) was stirred under argon at 0° C. with N-methylmorpholine (7.88 mg, 77.9 µmol) followed by dropwise addition of isobutyl chloroformate (11.7 mg, 85.7 mol). After 1.5 h, a solution of the deprotected nanoparticles (111.0 mg, 1.30 µmol) in anhydrous THF (35.0 mL) was added dropwise. The reaction was allowed to warm to room temperature and stirred for 24 h. The reaction was diluted and purified by dialysis with SnakeSkin® Pleated Dialysis Tubing (MWCO=10, 000) against methanol, eventually dialyzing against a 3:1 THF:MeOH solution. $^1$H NMR (400 MHz, THF $d_8$) δ 7.58-6.22 (br m, aromatic from crosslinking and disulfide linker), 3.87-3.67 (br m, maleimide linker), 3.24-3.16 (br m, disulfide linker), 3.15-3.04 (br m, diamine and molecular transporter), 2.93-2.83 (br m, diamine and molecular transporter), 2.78-2.62 (br m, disulfide linker), 2.62-1.06 (br m, backbone).

75. Attachment of Alexa Fluor® 568

To a solution of multifunctional nanoparticles (10.0 mg, 106.0 nmol) in DriSolv DMF (3.0 mL), a solution of Alexa Fluor® 568 (3.78 mg, 4.77 µmol) in anhydrous DMSO (377.7 µL) and triethylamine (50.0 µL, 358.7 µmol) was added to the solution and the reaction proceeded in the dark for 24 h at room temperature. The reaction was diluted with THF and purified by dialysis with SnakeSkin® Pleated Dialysis Tubing (MWCO=10,000) against 1% $H_2O$ in THF eventually dialyzing against pure THF.

76. Capping of the Remaining Amines

Upon completion of the Alexa Fluor 568 addition to the nanoparticles, a solution of N-acetoxysuccinimide (47.1 mg, 299.5 µmol) in DriSolv DMF (1.0 mL) was added to the reaction solution. The reaction was allowed to proceed for 3 h at RT. After removal of DMF in vacuo, the product was dissolved in methanol and dialyzed against methanol with SnakeSkin-Pleated Dialysis Tubing (MWCO=10,000). $^1$H NMR (400 MHz, MeOD) δ 1.29-2.43 (br m, backbone and molecular transporter), 2.59-2.83 (br m, disulfide linker), 2.84-2.95 (br m, disulfide linker), 2.98-3.02 (br m, disulfide linker), 3.04-3.09 (br m, disulfide linker), 3.16 (br t, diamine and molecular transporter), 3.67 (br t, maleimide linker), 6.53-7.98 (br m, aromatic from crosslinking, disulfide linker, and FITC).

77. Boc Deprotection of Modified Nanoparticles

Modified nanoparticles (30.0 mg, 434.0 nmol) were dissolved in anhydrous 1,4-dioxane (10 mL) and chilled to 0°

C. A solution of 4 M HCl in 1,4-dioxane (10 mL) was added dropwise to the stirring nanoparticles and the reaction was allowed to proceed overnight at room temperature The nanoparticle solution was diluted to three times the original volume with water and dialyzed against water with Snake-Skin® Pleated Dialysis Tubing (MWCO=10,000). Upon completion of dialysis, the aqueous solution was lyophilized to yield a yellow solid. 1H NMR (400 MHz, $D_2O$) δ 1.18-2.37 (br m, backbone and molecular transporter), 2.71-2.79 (br m, disulfide linker), 2.81-2.86 (br m, disulfide linker), 2.89-2.93 (br m, disulfide linker), 2.94-2.99 (br m, disulfide linker), 3.12 (br t, diamine and molecular transporter), 3.69 (br t, maleimide linker), 6.53-8.41 (br m, aromatic from crosslinking, disulfide linker, and FITC).

78. Synthesis of Copolymer poly(vl-avl) (Ab)

A 50 mL 3-necked round bottom flask, equipped with stir bar, was sealed with two septa and a gas inlet. The flask was evacuated and refilled with nitrogen three times. Stock solutions of 1.7 M ethanol (EtOH) in THF and $3.7 \times 10^{-2}$ M tin(II) 2-ethylhexanoate ($Sn(Oct)_2$) in THF were made in sealed $N_2$ purged flasks. Solutions of EtOH (0.32 mL, $5.41 \times 10^{-1}$ mmol) and $Sn(Oct)_2$ (0.30 mL, $1.12 \times 10^{-2}$ mmol) were combined in the nitrogen purged 50 mL flask. After stirring the mixture for 30 min, α-allyl-δ-valerolactone (1.16 g, 8.32 mmol) and δ-valerolactone (vi, 2.50 g, 24.97 mmol) were added. The reaction vessel stirred at 105° C. for 48 h. Residual monomer and catalyst were removed by dialyzing with Spectra/Por® dialysis membrane (MWCO=1000) against $CH_2Cl_2$ to give a golden brown polymer. Yield: 3.24 g (88%). $M_w$=3042 Da, PDI=1.18; $^1$H NMR (300 MHz, $CDCl_3$/TMS, ppm) δ: 5.7 (m, $H_2C=CH-$), 5.09 (m, $H_2C=CH-$), 4.09 (m, $-CH_2-O-$), 3.65 (m, $CH_3CH_2O-$), 2.35 (m, vl, $-CH_2CH_2C(O)O-$, avl, $H_2C=CHCH_2CH-$, $H_2C=CHCH_2CH-$), 1.68 (m, avl & vl, $-CHCH_2CH_2-$), 1.25 (t, $CH_3CH_2O-$); $^{13}$C NMR (400 MHz, $CDCl_3$, ppm) δ: 174.6 (avl, $-C(O)-$), 172.7 (vl, $-C(O)-$), 134.6 ($H_2C=CH-$), 116.4 ($H_2C=CH-$), 63.3, 44.3, 35.9, 33.1, 27.5, 25.9, 23.6, 20.9.

79. Nanoparticle Formation from Ab

A solution of Ab (0.0804 g, $M_w$=3042 Da, PDI=1.18) dissolved in $CH_2Cl_2$ (0.18 mL) was added to a solution of 3,6-dioxa-1,8-octanedithiol (30.0 μL, 0.18 mmol) in $CH_2Cl_2$ (28.4 mL) at 44° C. The reaction mixture was heated for 12 h. Residual dithiol was removed by dialyzing with Snake-Skin® Pleated Dialysis Tubing (MWCO=10,000) against dichloromethane. Yield: 0.078 g. $^1$H NMR (300 MHz, $CDCl_3$/TMS) δ: The significant change is the reduction of the allyl protons at 5.06 and 5.77 ppm and the appearance of signals at 3.65 and 2.71 ppm corresponding to the protons neighboring the thiols of the PEG linker after cross-linking. All other aspects of the spectrum are similar to that of Ab. The reaction can also be conducted with photoinitiators at RT in organic solvents. The particle sizes of the resulting particles correspond to those produced in analogous epoxide/amine procedures.

When reaction times are increased to from about 24 h to about 48 h, the particle sizes increase due to the total consumption of allyl moieties. Reaction at room temperature was found to be sufficient. Addition of radical starters or other photoinitiators does not significantly increase the quality of the particles.

80. One Pot Synthesis of Nanoparticles from poly(vl-evl-avl-opd) (ABbD)

Figure 41:
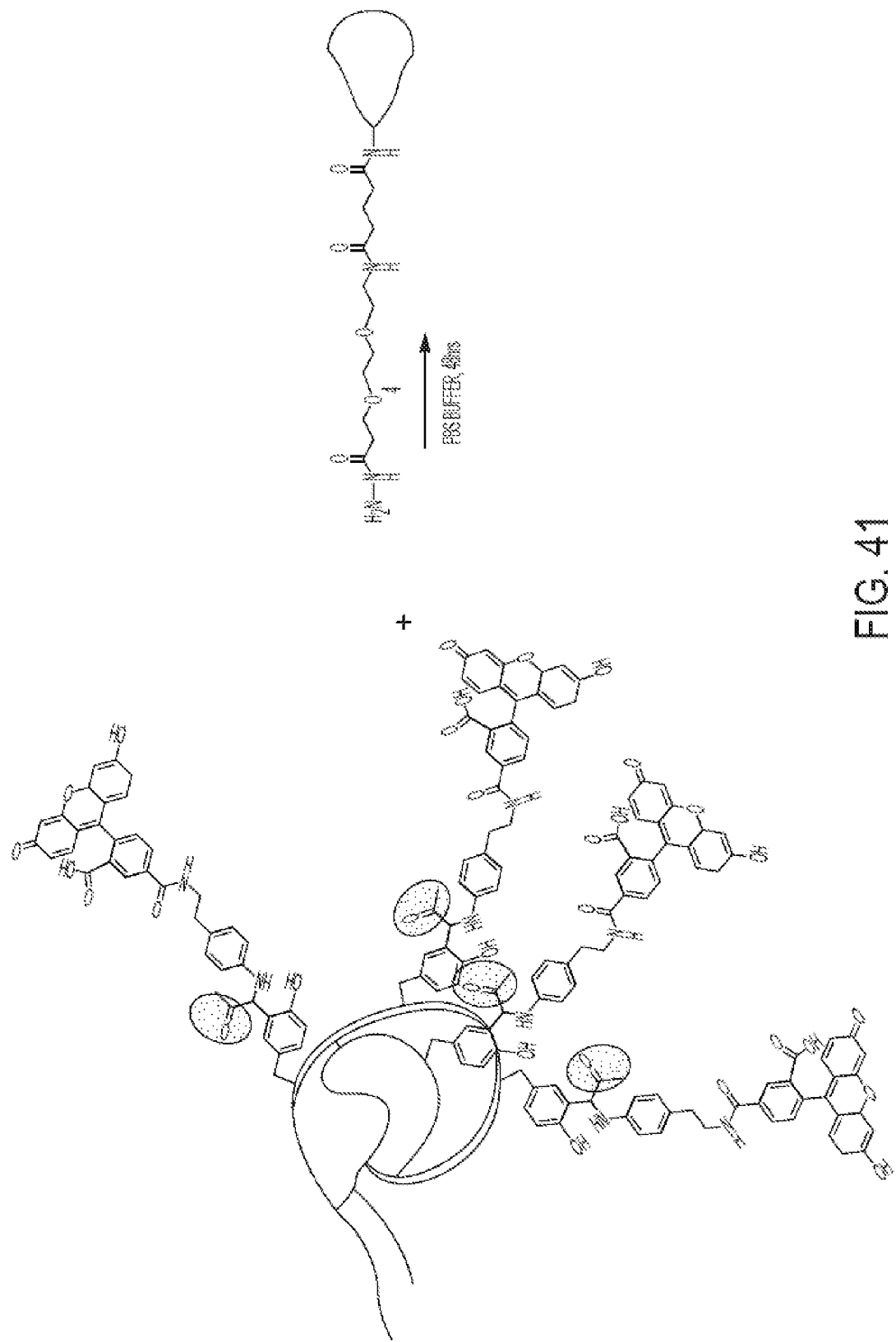
FIG. 41 illustrates incorporation of transporter moieties through conjugation to carbonyl-functionalized proteins.
Figure 41:
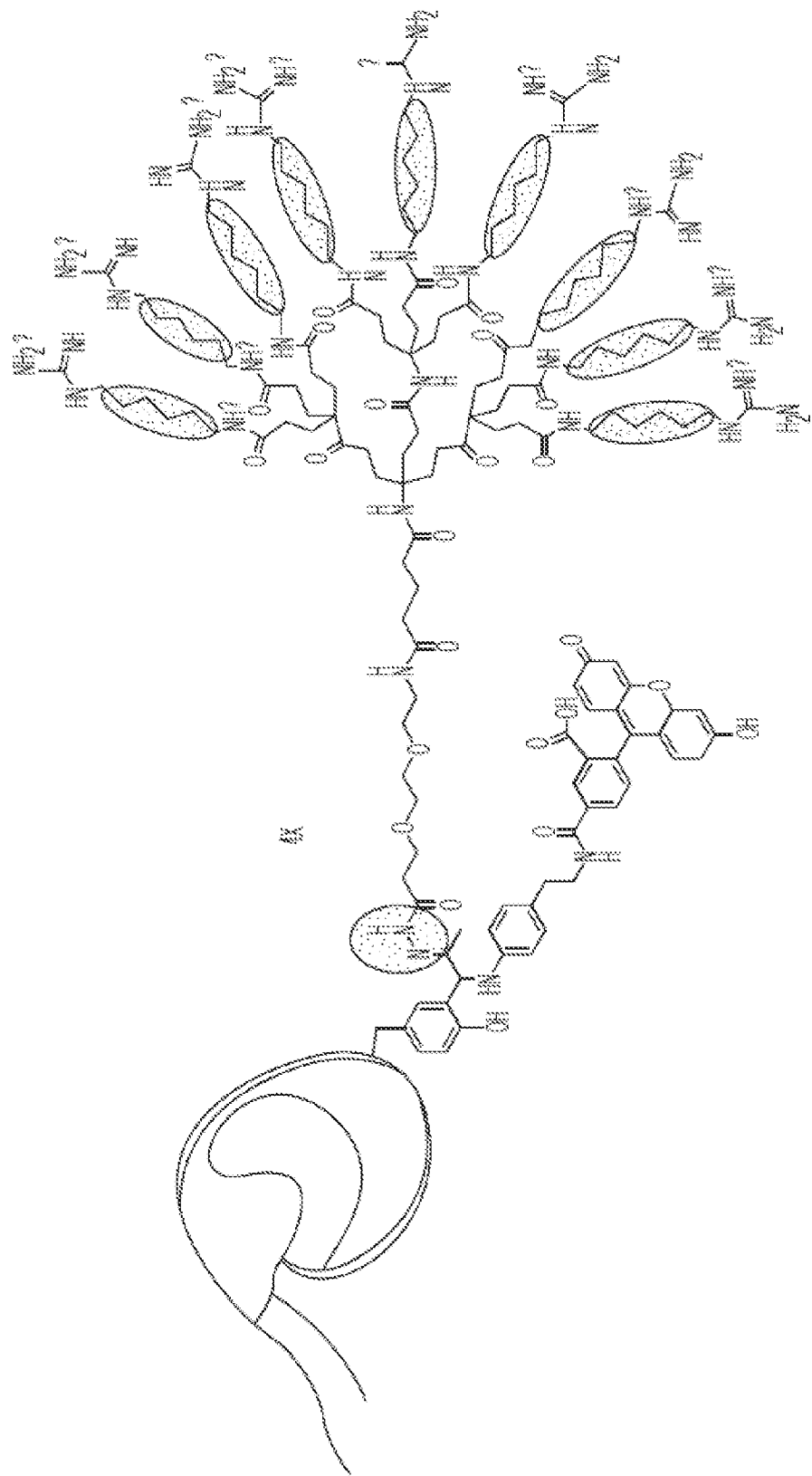
Figure 42:
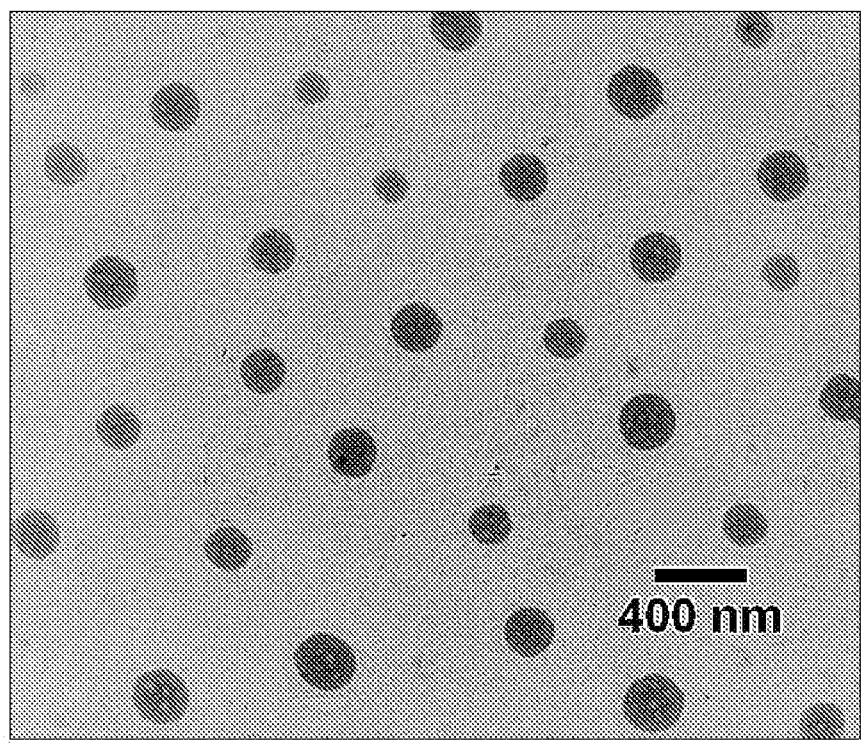
FIG. 42 shows TEM analysis of the nanoparticles (225.6 nm) produced from crosslinking of poly(vl-evl-avl-opd) (ABbD).
Figure 43:
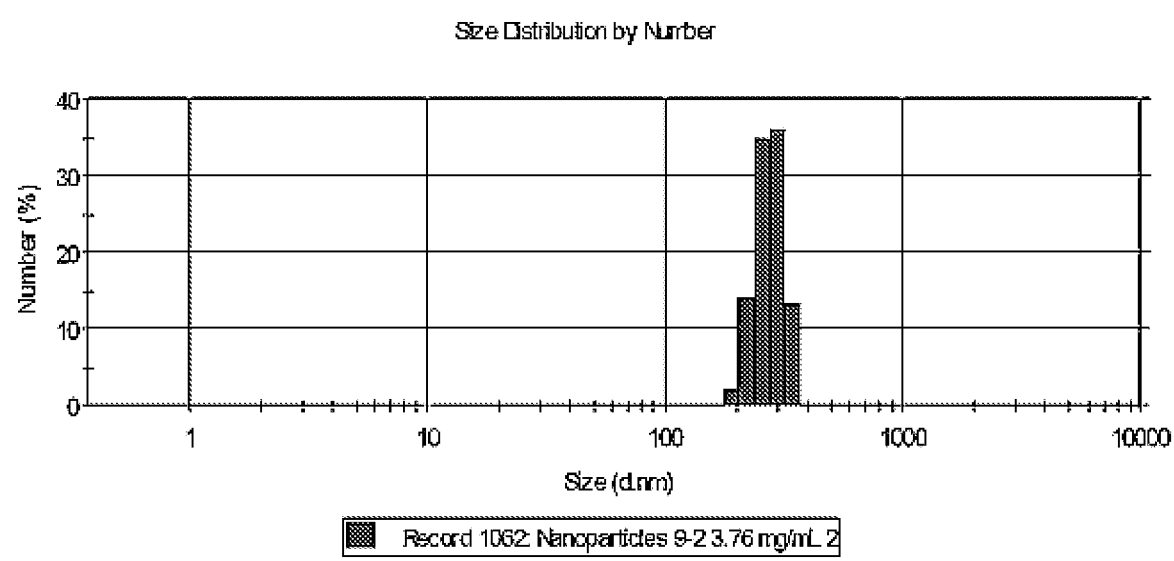
FIG. 43 shows the particle size distribution measured by dynamic light scatter analysis of "one-pot" nanoparticles (272.3+23.3 nm) produced from crosslinking of poly(vl-evl-avl-opd) (ABbD).

In a 25 mL three-necked round bottom flask equipped with stir bar, condenser and septa, 2,2'-(ethylenedioxy) diethylamine (18.3 μL, $1.25 \times 10^{-4}$ mol), 17.1 mL $CH_2Cl_2$ and a solution of poly(vl-evl-were added. A solution of poly(vl-evl-avl-opd), ABbD, (0,0781 g, $M_w$=3500 Da, PDI=1.29). The mixture was heated at 44° C. for 12 h. Residual diamine was removed by dialyzing with Snake-Skin® Pleated Dialysis Tubing (MWCO=10,000) against dichloromethane. $^1$H NMR (300 MHz, $CDCl_3$/TMS, ppm) δ: The significant change is the disappearance of the epoxide protons at 2.94, 2.75 and 2.47 ppm and the appearance of signals at 3.64 and 2.97 ppm corresponding to the protons neighboring the secondary amine of the PEG linker after cross-linking. All other aspects of the spectrum are similar. TEM analysis of the resulting nanoparticles is shown in FIG. 41. The particle size distribution, with unusually narrow polydispersity, of the resulting nanoparticles is shown in FIG. 43. To increase particle sizes, reaction times can be increased to from about 24h to about 48h.

81. Uptake Experiment Protocol

Fluorescent multifunctional nanoparticle, negative control particle, FD-1, and FD-2 uptake by mammalian cells was assessed using HeLa cells, cancer cells, grown in uncoated, 14 mm diameter Microwell, No. 1.5 MatTek Dishes and a Zeiss LSM 510 META confocal microscope. HeLa cells were grown in Dulbecco's Modified Eagle's Medium-Low Glucose (DMEM) (Sigma Aldrich) supplemented with 10% (v/v) fetal bovine serum (Gibco) and 1% (v/v) antibiotic-antimycotic (Gibco). The cells were treated with the multifunctional nanoparticles, negative control particles, FD-1, or FD-2 for one hour, washed three times with $Ca^{2+}/Mg^{2+}$ free Phosphate Buffered Saline with EDTA (PBS), fixed with 3.3% paraformaldehyde at room temperature for 10 minutes, and analyzed using confocal microscopy.

82. Bioconjugate Molecular Transporter

Figure 44:
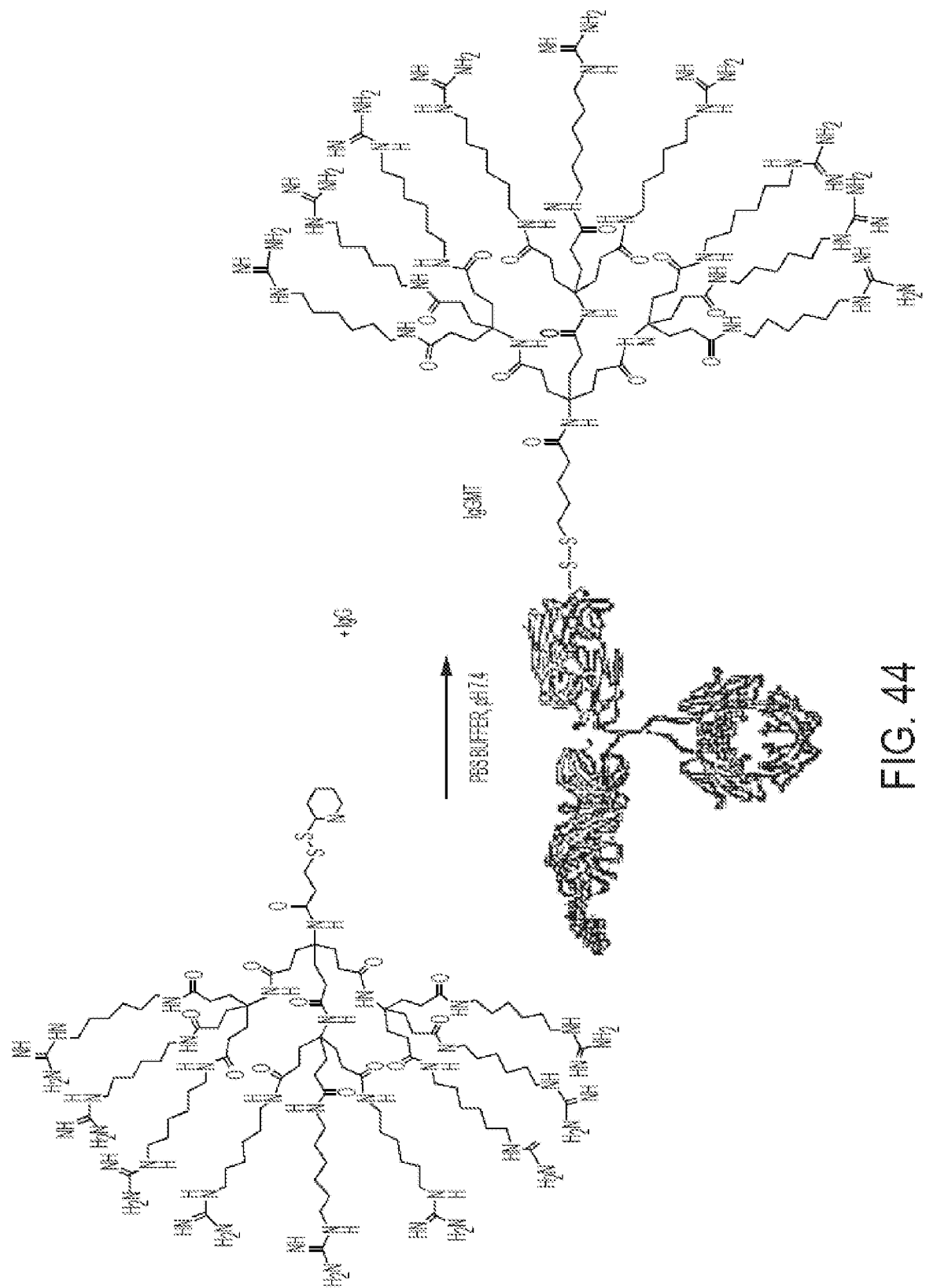
FIG. 44 shows a scheme for a thiol exchange reaction with an IgG antibody to form an IgGMT bioconjugate.

To prepare an exemplary antibody conjugated molecular transporter, a G1-Newkome dendrimer that contains nine t-butyl end functionalities and a primary amine group at the focal point was prepared using disclosed methods (FIG. 44). The amine functionality was reacted with 3-(2-pyridinyldithio)propanoic acid via amide coupling reactions with DCC/HOBt to form a protected dendrimer with a reactive core. The t-butyl ester groups on the periphery of the dendritic scaffold were deprotected with formic acid to give free carboxylic acid groups that were coupled with N-Boc-1,6-diaminohexane. After deprotection of the Boc protecting groups with 2M HCl in dioxane the free amines were transformed into guanidine groups with N,N-diBoc-N-triflylguanidine and the subsequent deprotection of the Boc groups using 2 M HCl in dioxane gave the desired compound (Scheme 21).

Scheme 21. Synthesis of dendrimer bioconjugate precursor.
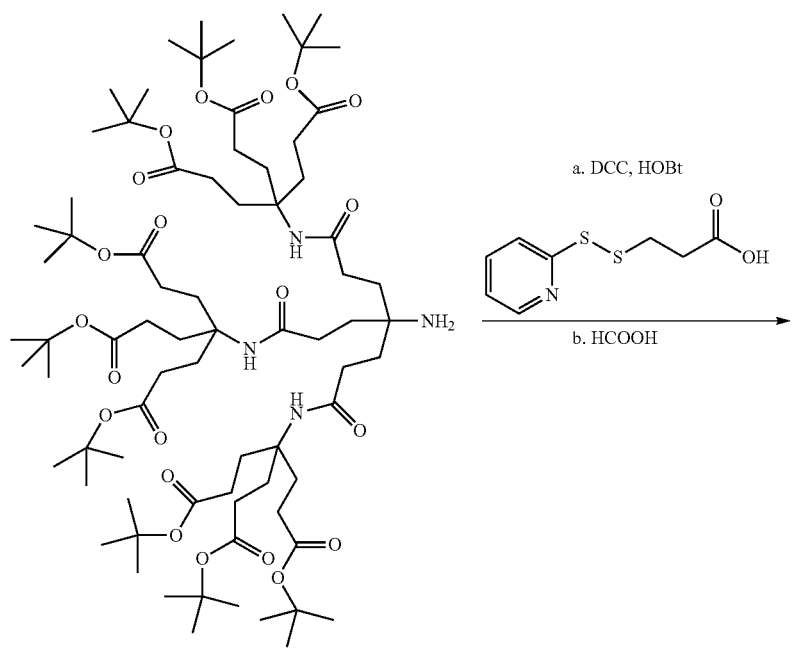
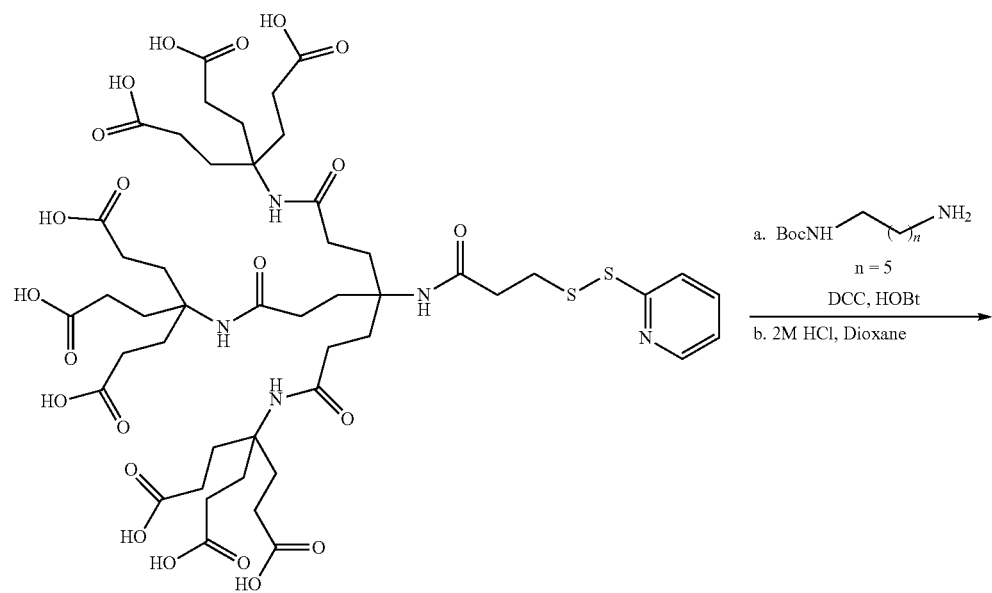

-continued
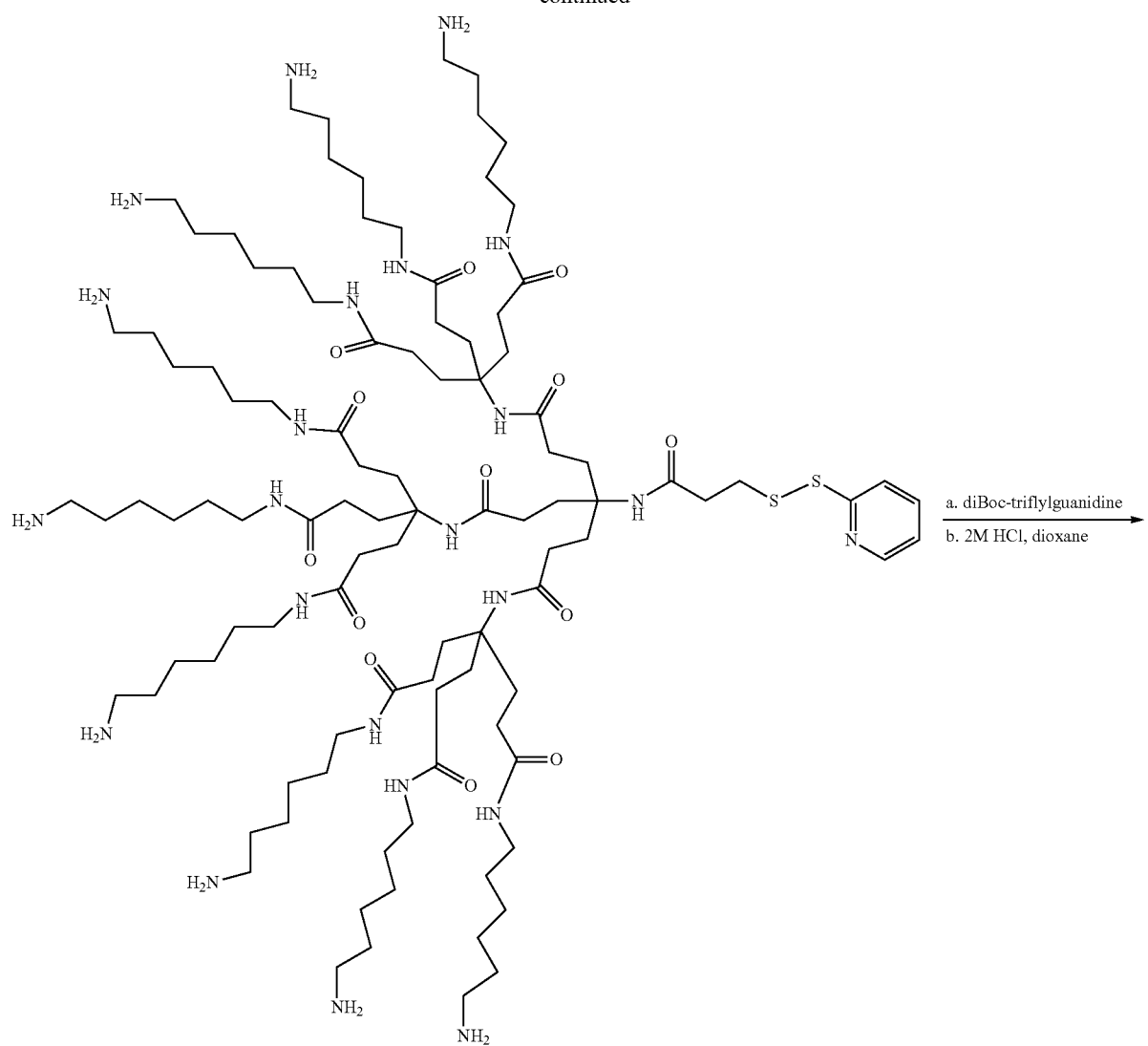

-continued

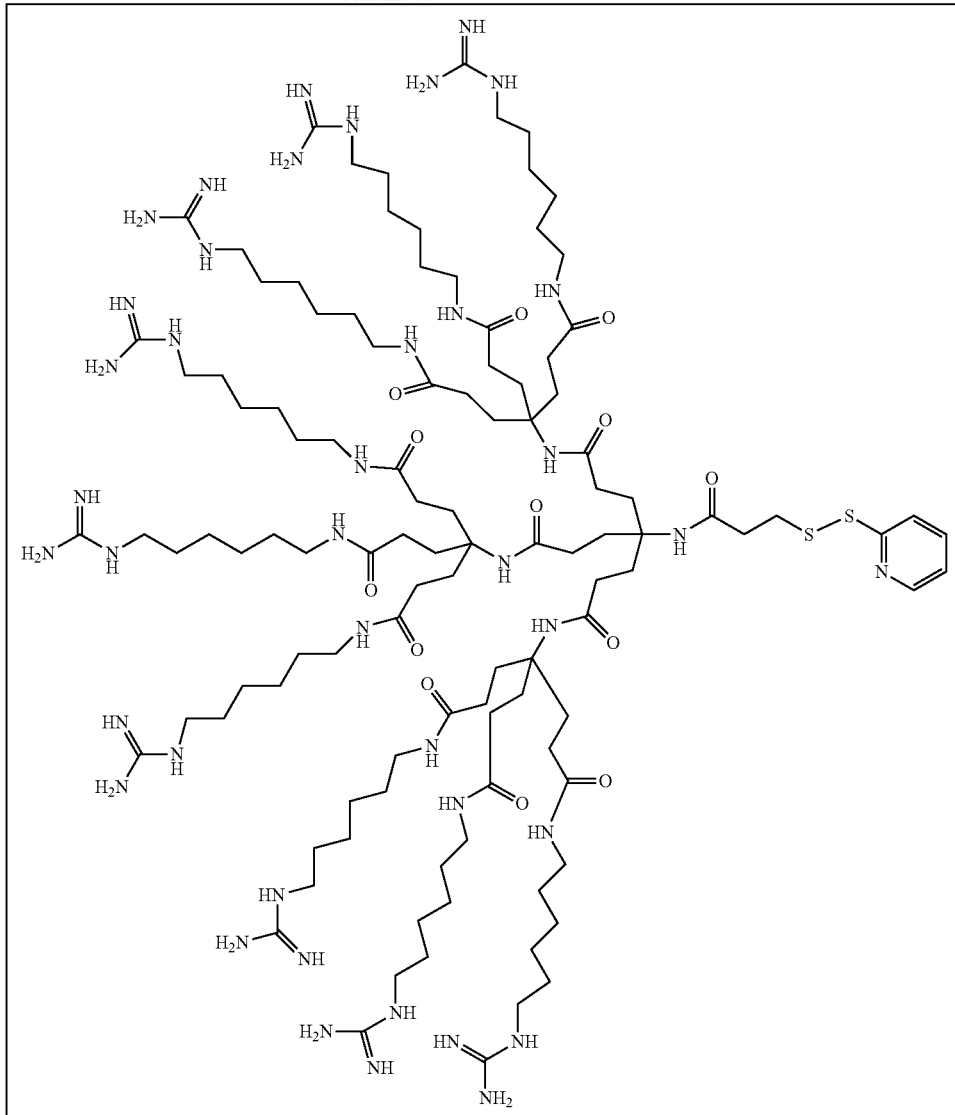

The final compound is designed to localize in the cytoplasm of the cells, as an integrated a hexyl alkyl spacer is present at the periphery of the dendrimer scaffold that was previously found to be a feature for the specificity of its subcellular location. Furthermore, the pyidinyldithio linker at the focal point allows for the exchange with sulfhydryl groups to form bioconjugates that are connected over a disulfide bond to afford a reductive cleavable linker that can maintain activity of the biomolecule in cells. The IgG molecular transporter conjugate (IgGMT) was formed by the mild reaction of Alexa Fluor® 568 labeled IgG antibody in PBS buffer at RT with the dendrimer (FIG. 44). Five transporter dendrimers were attached to the IgG structure which has a molecular weight of 148 kDa. The conjugate was dialyzed against PBS buffer to remove any unreacted dendrons and the concentration in the dialysis tubing was chosen to be 1 mg ml$^{-1}$ IgGMT, that allowed for the use of the solution directly for the uptake and neutralization experiments.

Figure 45:
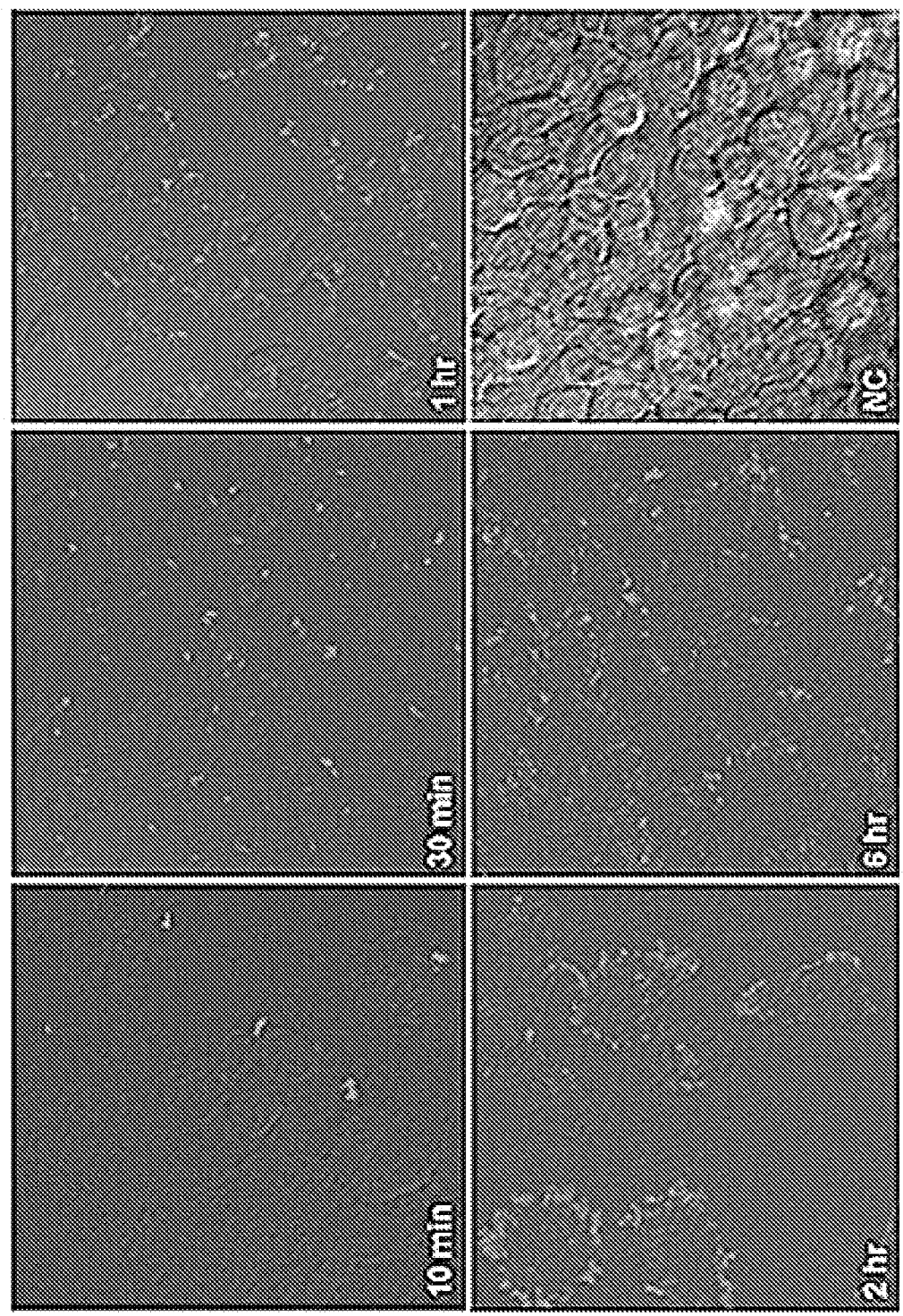
FIG. 45 shows microscopy images of uptake of IgGMT into HEp-2 cells for 10 min, 30 min, 1 h, 2 h, 6 h and negative control experiment (NC) with Alexa Fluor® 568 labeled IgG.
Figure 46:
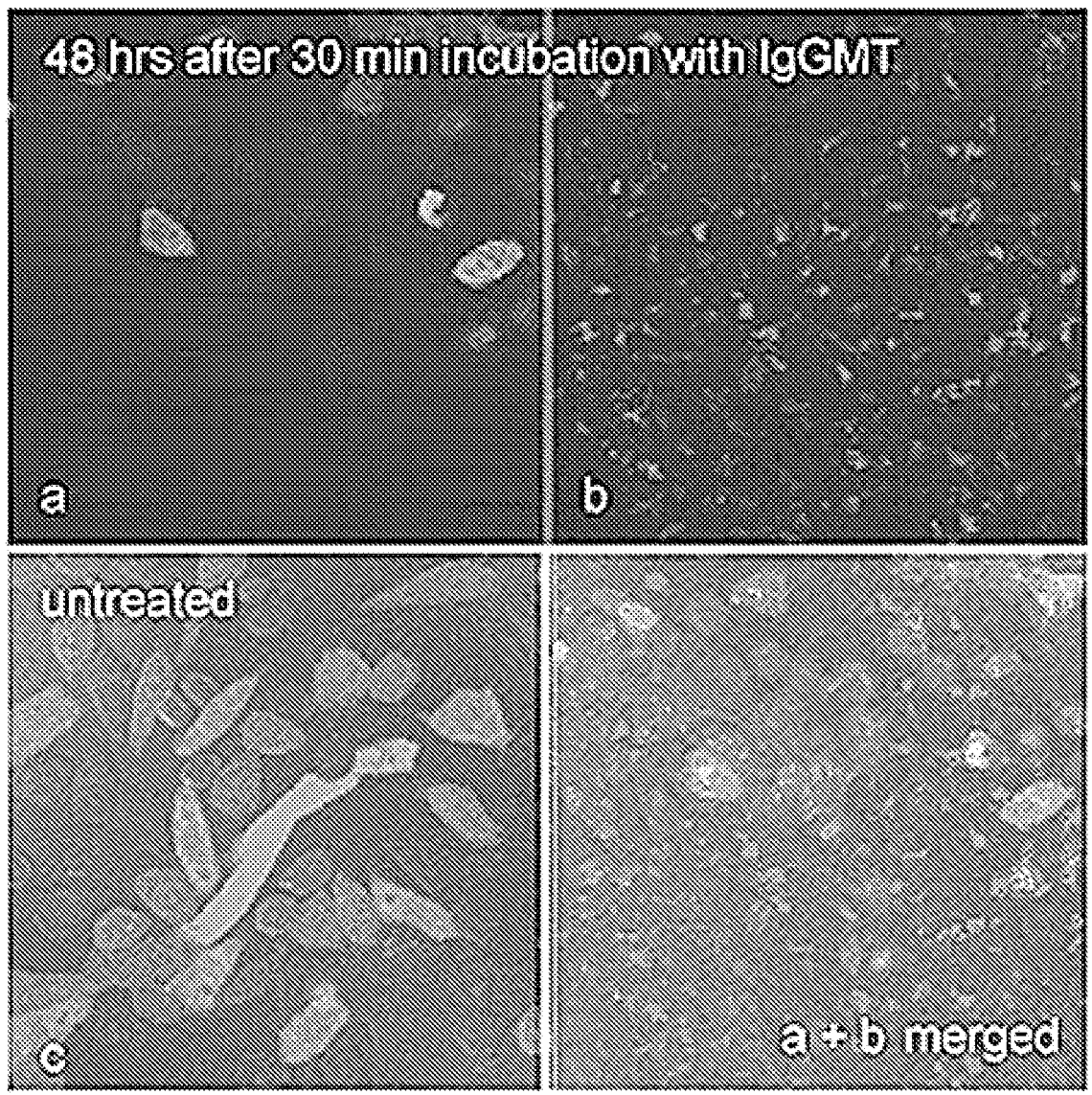
FIG. 46 shows microscopy images of HEp-2 cells infected with RSV for 24 h, washed and imaged 48 h after infection for the fluorescence of GFP (c). HEp-2 cells infected with RSV for 24 h, incubated for 30 min with IgGMT and imaged after 48 h for the fluorescence of GFP (a) and Alexa Fluor® 568 of the IgGMT (b), merged images (a) and (b) (merged a+b).
Figure 47:
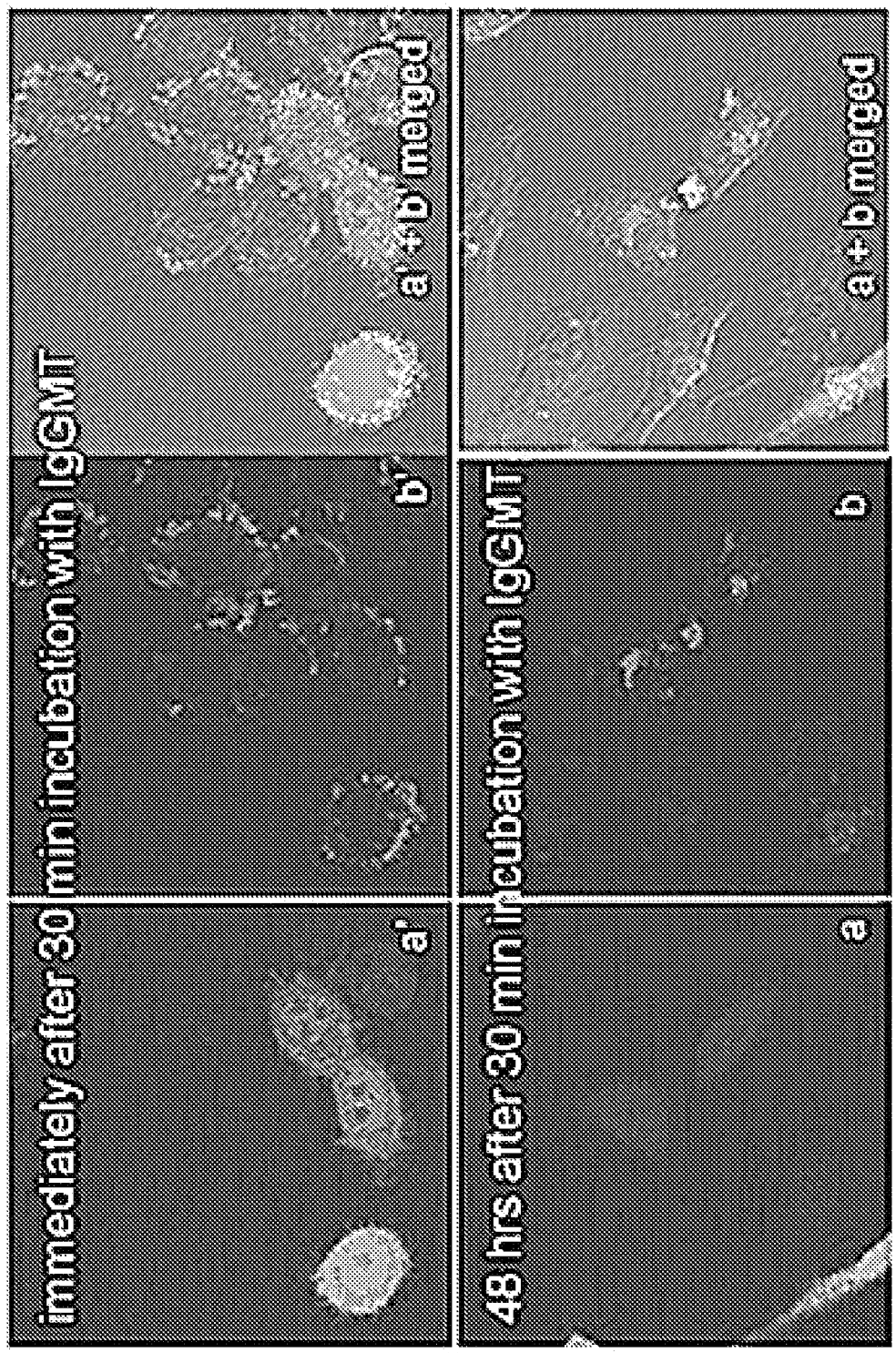
FIG. 47 shows microscopy images of HEp-2 cells infected with RSV for 24 h, incubated for 30 min with IgGMT and imaged immediately for the green fluorescence of the GFP (a) and the red fluorescence of the IgGMT conjugate (b), merged images of (a) and (b) (a+b merged). HEp-2 cells infected with RSV for 24 h, incubated for 30 min with IgGMT and imaged after 48 h for the fluorescence of GFP (a) and Alexa Fluor® 568 of the IgGMT conjugate (b), merged images (a) and (b) (merged a+b).
Figure 48:
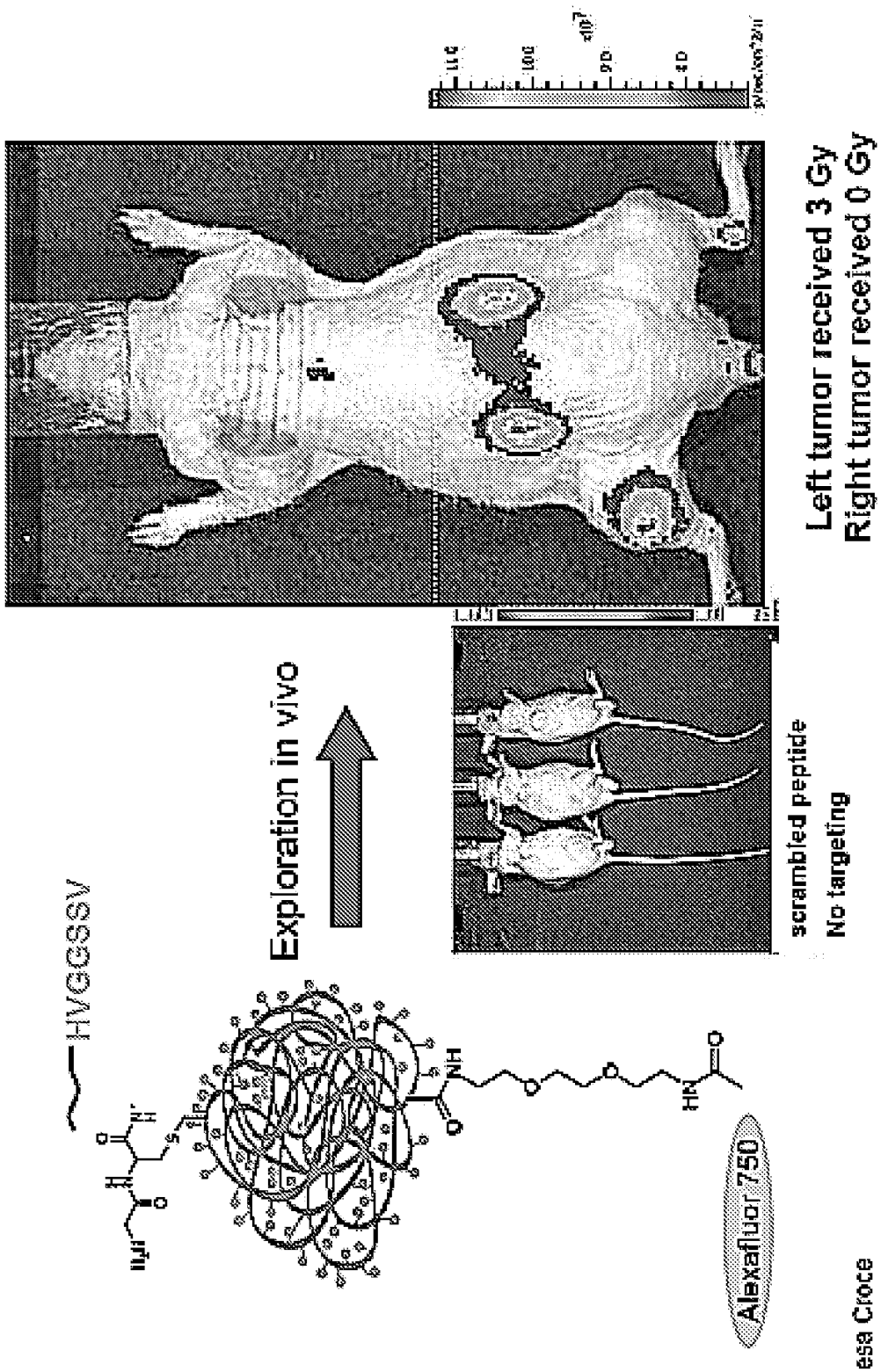
FIG. 48 shows results for a radiation guided Nanoparticle-peptide targeting in a Lewis-Lung Carcinoma Tumor Model. The peptide shown is Seq. I.D. 1.
Figure 49:
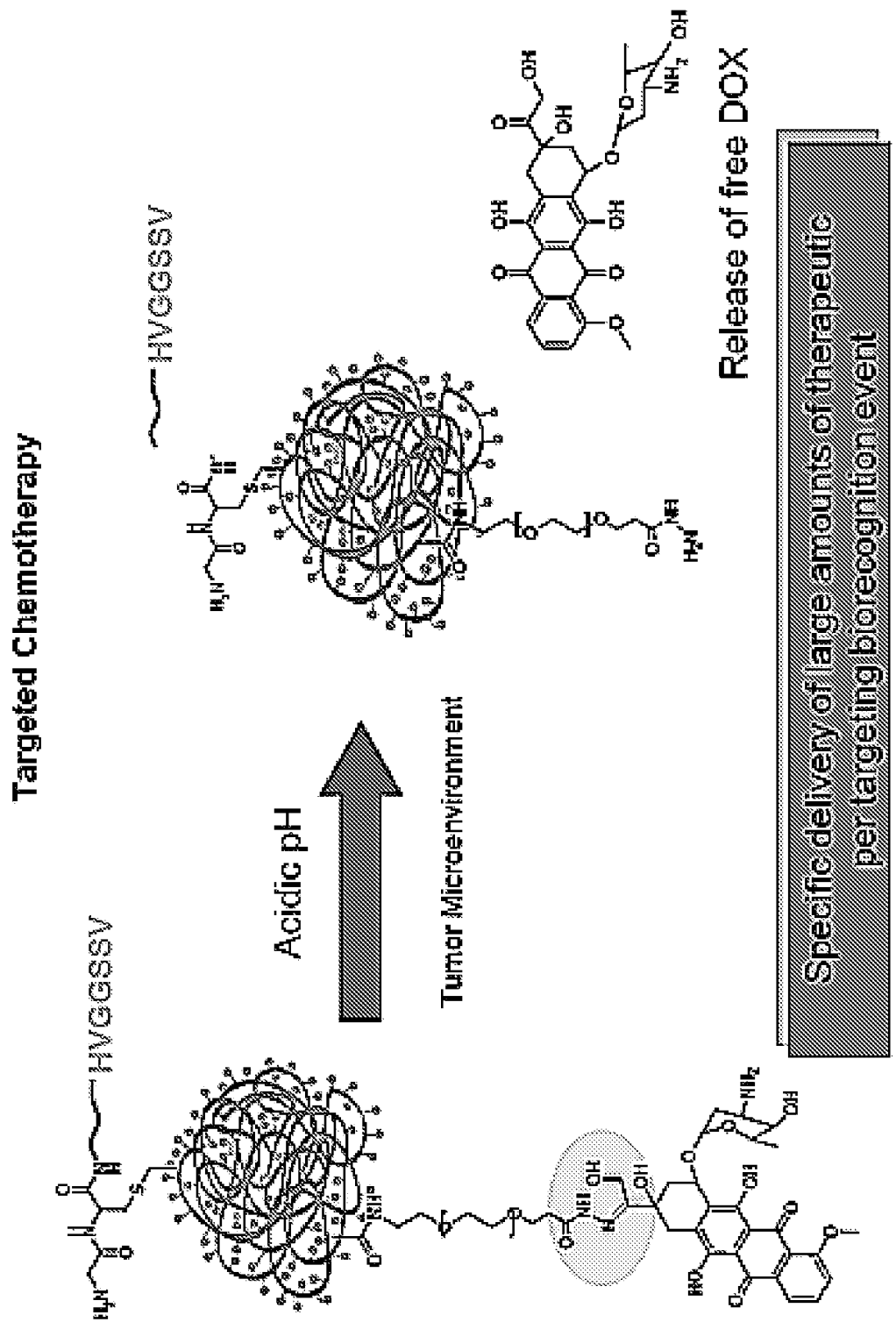
FIG. 49 shows a scheme for delivery of a biological active substance. The peptide shown in Seq. I.D. 1.
Figure 50B:
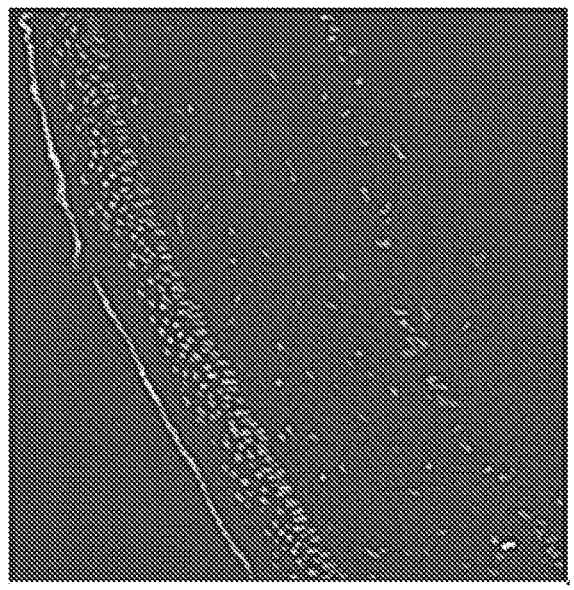
FIGS. 50A-D shows fluorescence microscopy images of portions of the eye of a rat after administration of a nanoparticle bioconjugate comprising an imaging agent.
Figure 50A:
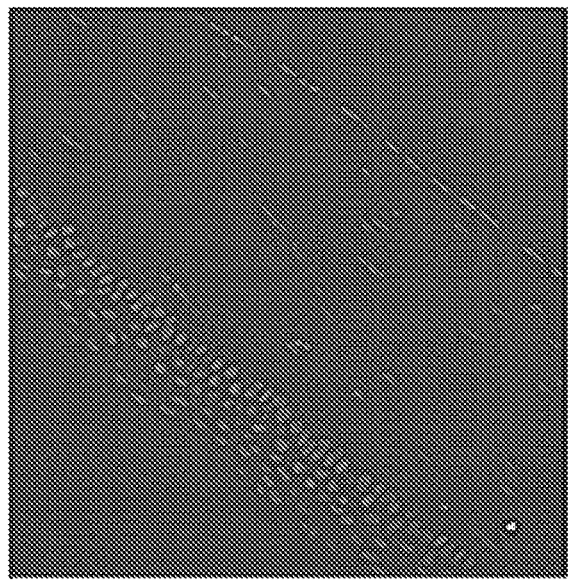
Figure 50D:
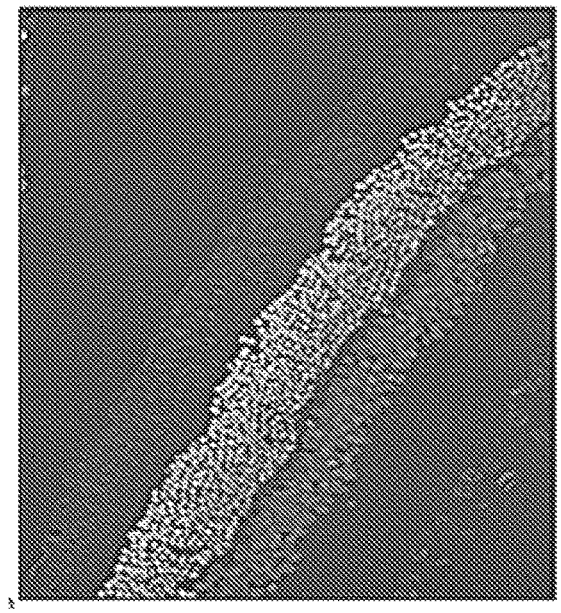
Figure 50C:
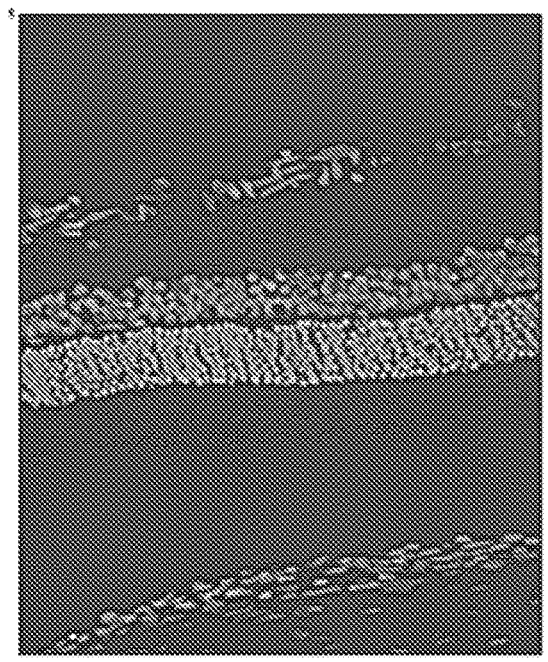

First, the uptake efficiency of the IgGMT conjugate into human epithelial cells (HEp-2) was tested. The 60% confluently grown cells were incubated with IgGMT initially for 10 min then for 30 min, 1, 2 and 6 h. The uptake efficiency was studied with confocal microscopy and the uptake of the bioconjugate could be observed as early as 10 min. Later time points showed an increase of red fluorescence of the IgGMT conjugate, progressing from the cell surface membrane to localize intracellularly in the perinuclear area at time points of 2 and 6 h. Contrary to the affinity and uptake of the IgGMT bioconjugate, the Alexa Fluor® 568 labeled, unmodified IgG did not enter the cell at all times points investigated (FIG. 45). After the uptake into HEp-2 cells was confirmed with no evidence of cellular damage, the activity of the conjugate in RSV infected cells that expressed green fluorescent protein GFP as a result of RSV infection was examined. First, HEp-2 cells were infected for 24 h with recombinant RSV-GFP, washed and allowed to incubate for an additional 48 h. The cells were then imaged with confocal microscopy at a total of 72 h after initial infection (FIG. 46). The typical syncytia formation was observed, a combination and fusion of the infected cells, together with the expression of the green fluorescent protein (GFP). To study the neutralization effect of the IgGMT, HEp-2 cells infected for 24 h with RSV-GFP were incubated for 30 min with a solution of IgGMT in PBS buffer, washed and imaged 48 h later (FIGS. 46a and b). By confocal microscopy it was observed that a significant reduction of the green fluorescence of GFP (a) and a strong red fluorescence of the Alexa Fluor® 568 labeled IgGMT conjugate (b). The merged images of (a) and (b) combined with differential interference contrast (DIC) also gave evidence of healthier cells with significantly less syncytia formation than the untreated infected cells at the same time period (FIG. 46c). This result illustrated the significant reduction of GFP in treated cells in contrast to the untreated cells observed at a total incubation time of 72 h after infection with RSV for 24 h. Besides the presence of neutralized cells that showed only the red fluorescence of the conjugate, cells that showed the coexsistance of RSV-GFP and the red fluorescence of the IgGMT, appearing in the center of the cells (FIG. 46 and FIG. 47, a+b merged) were also observed. Imaging directly after the 30 min incubation of the RSV infected cells with the IgGMT, showed the green fluorescence localized intracellularly, whereas the red fluorescence was observed on the cell-surface membranes (FIG. 47, a+b merged). These images documented the high affinity of the conjugate with the cells surface directly after the incubation period followed by the uptake into the Hep-2 cells after an additional incubation time of 48 h. Parallel investigations of the RSV titres of the supernatant showed a significant reduction by 80-90% in viral replication when compared to cells not exposed to the IgGMT conjugate. Without wishing to be bound by theory, the intracellular delivery of IgG antibody directed to the surface protein inhibits the syncytial formation mediated by the F protein and has an effect on total virus production when added 24 h after the initiation of RSV infection.

83. Tailored Polyester Nanoparticles

In this example, polyester nanoparticles in controlled nanoscopic dimensions have been prepared through a one-pot procedure that contains amine, keto, and allyl groups and is tailored towards the conjugation of bioactive building blocks, such as a dendritic molecular transporter to facilitate cellular uptake, or peptides and dyes to accomplish targeting and imaging. In several examples of bioconjugate synthesis, demonstrated is the versatility and the orthogonal attachment strategies involving high yielding thiol-ene reactions under mild conditions and reductive amination reactions, circumventing the integration of linker and multi-step post-modification pathways. Several linear nanoparticle precursors were prepared according to Scheme 22.

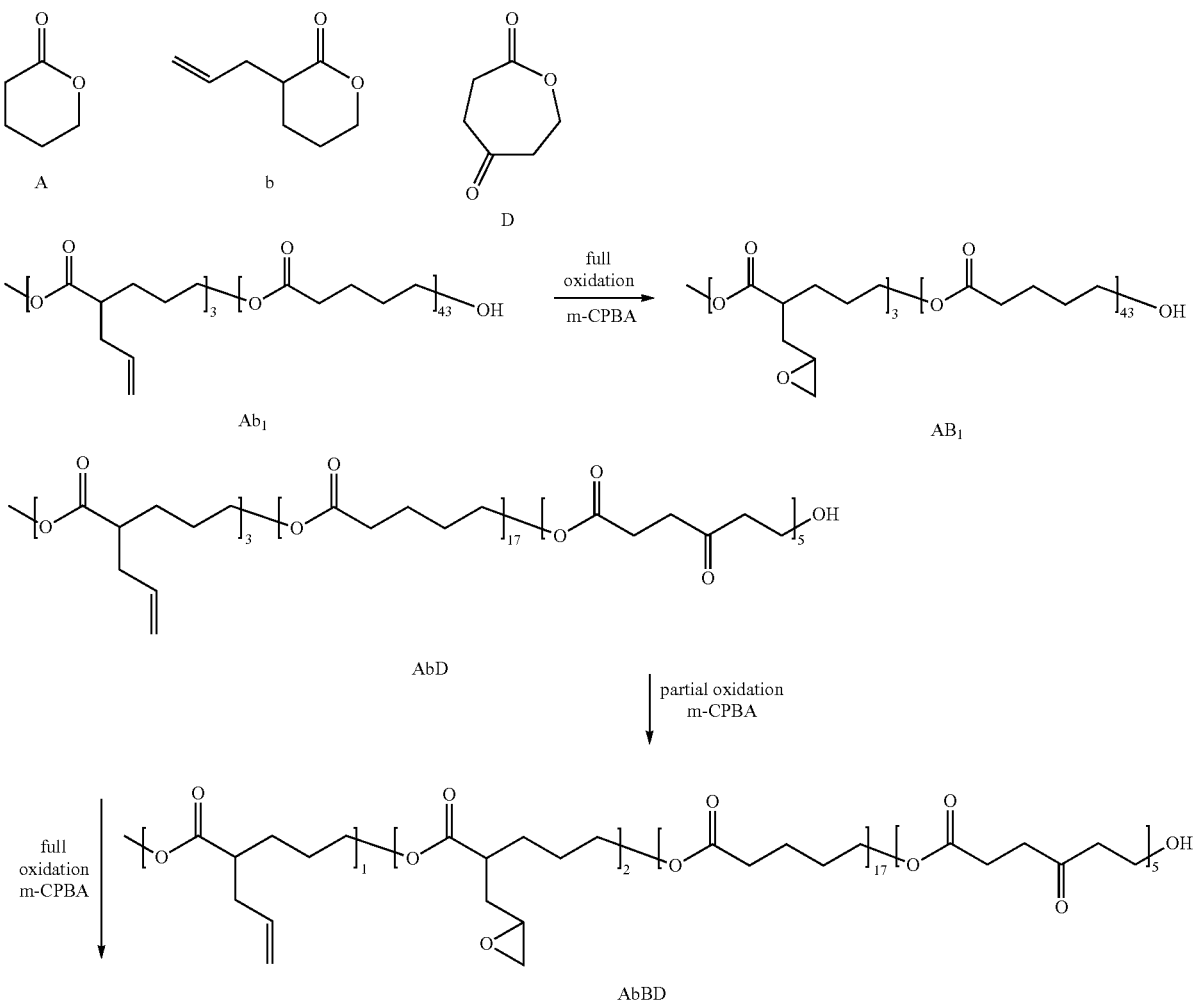

Scheme 22. Linear precursor.

-continued

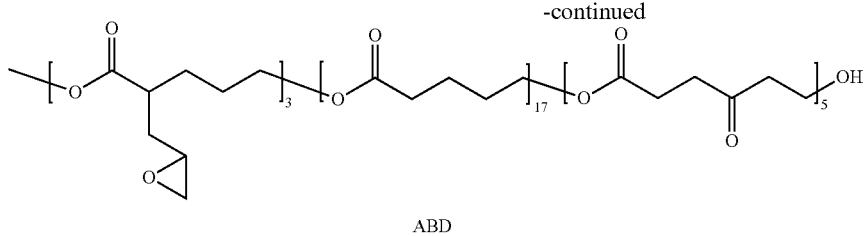

ABD

After the collapse of the above linear precursors using disclosed methods, the nanoparticle can be functionalized with a desired moiety. In contrast to reported strategies that form amide bonds with polyester scaffolds using EDC activation that are typically not very high yielding and require a high excess of expensive peptides, in this example the N-terminus of the targeting unit (e.g., a peptide) was reacted with the keto group, integrated in the polymer backbone of the developed polyester particle. In a model reaction, the successful reductive amination of N-Boc-ethylenediamine with keto groups of the particle has been shown and applied these reaction conditions to test the addition of peptidic units. Here, the targeting peptide sequence GCGGGNHVGGSSV was tested and chosen for the reaction with the ABD nanoparticle, with the nanoscopic dimension of 118 nm prepared from the ABD linear precursor polymer with 1.5 equivalents of 2,2'-(ethylenedioxy)bis(ethylamine) cross-linking units with the conditions as described above (Scheme 22). The amine groups of the nanoparticle were first capped with N-acetoxysuccinimide and the modified nanoparticle and the peptide were solubilized in tetrahydrofuran with NaCNBH3 as the reducing reagent.

After purification through dialysis the modified particles, 3, were characterized with $^1$H NMR and DLS. The increase in hydrodynamic diameter from 118±10 nm to 120±10 nm indicated the addition of peptides to the polyester backbone and further investigations with 1H NMR showed the conjugation of peptides with the characteristic resonance peaks at 4.39 and 7.42 ppm. With additional analysis through static light scattering (SLS) we could determine the amount of peptide attached to the nanoparticle that was estimated to be between 36 of the intended attachment of 40 peptides per particle.

This result confirmed the efficiency of the reductive amination reactions with the N-terminus of the selected peptidic units. Targeting units, however, that contain more than one amine group give mixed conjugation products and an alternative strategy has to be developed. For this reason, we wanted to pursue thiol-ene type reactions that will be performed between cysteine units, integrated into the sequence close to the N-terminus, and double bonds that we find in maleiimides, vinylsulfones or allyl groups. To integrate the reaction partner for the thiol/cysteine containing units, such as peptides, or oligonucleotides, into the nanoparticles, either a suitable linker that would be attached to the prepared nanoparticle was synthesized or a method that would circumvent the conjugation of a linker molecule to facilitate the attachment of thiol containing entities was found. Therefore, the integration of allyl groups in the polyester backbone as pendant functional units that would be already present in the linear polyester precursor before nanoparticle formation was studied. The available allyl groups that stem from the α-allyl-δ-valerolactone of the linear polyester precursors were oxidized and converted entirely into epoxide groups to provide units that would cross-link with the diamine. However, with partial oxidation of the allyl group, linear polyester precursors containing epoxide units and remaining allyl groups, could be accomplished. In the next step, a linear polyester AbD that was partially oxidized to comprise 16% of allyl units and 11% of epoxide units was cross-linked with 1.5 equivalents of diamine, using the novel one-pot reaction procedure to examine the compatibility of the allyl groups to the conditions of nanoparticle formation. The investigation of the resulting particles with DLS showed that hydrodynamic diameters corresponded to the size and solubility of the particles that did not contain any allyl groups. The allyl resonance peaks were still present in the $^1$H NMR spectra of the particles and were found to be analogous to the resonances of the allyl functionalities in the linear precursor.

Figure 77:
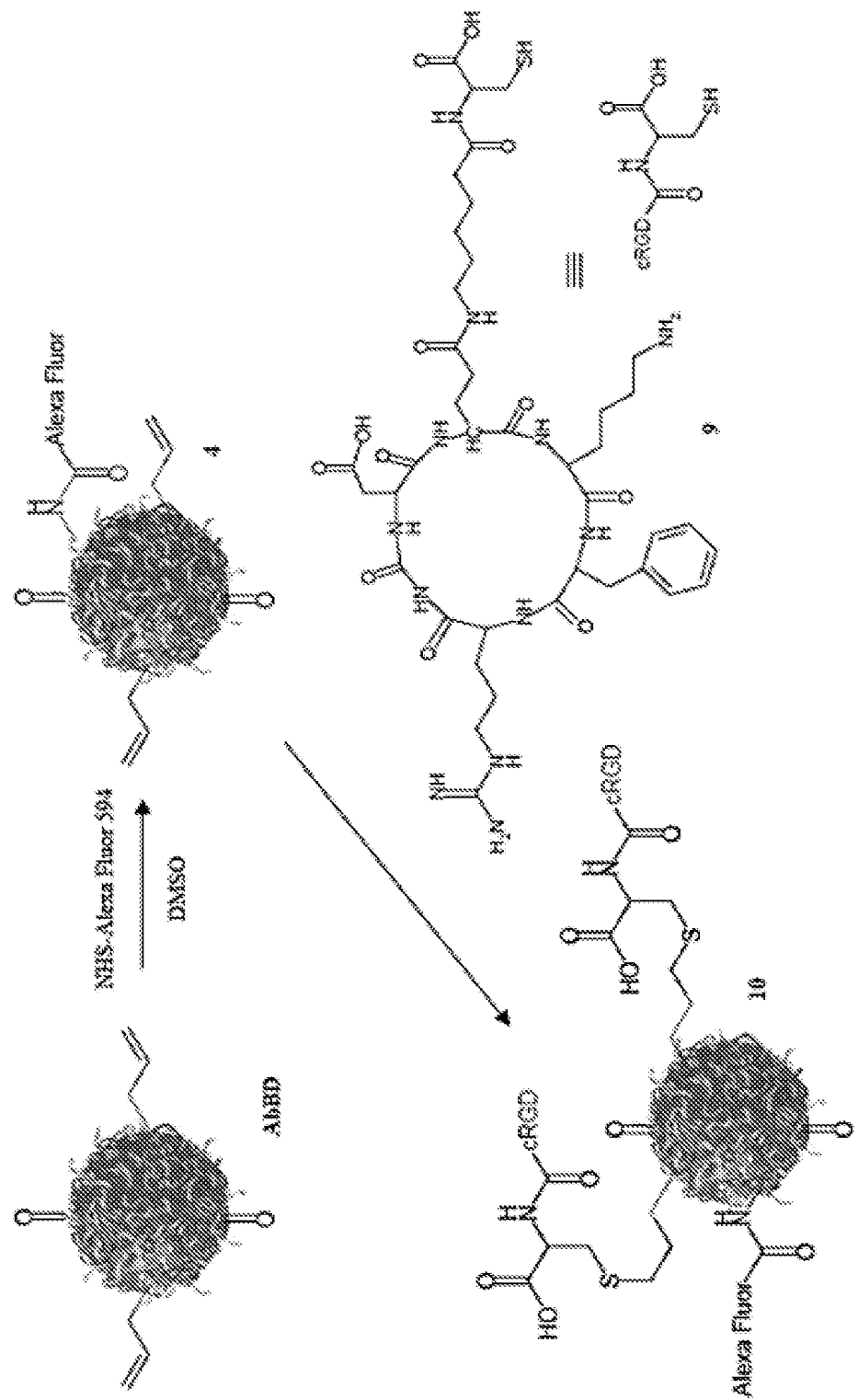
FIG. 77 shows the attachment of c-RGD.

After attaching a fluorescent probe, a disclosed cyclic peptide was attached, as shown in Scheme 23 in FIG. 77.

Figure 78:
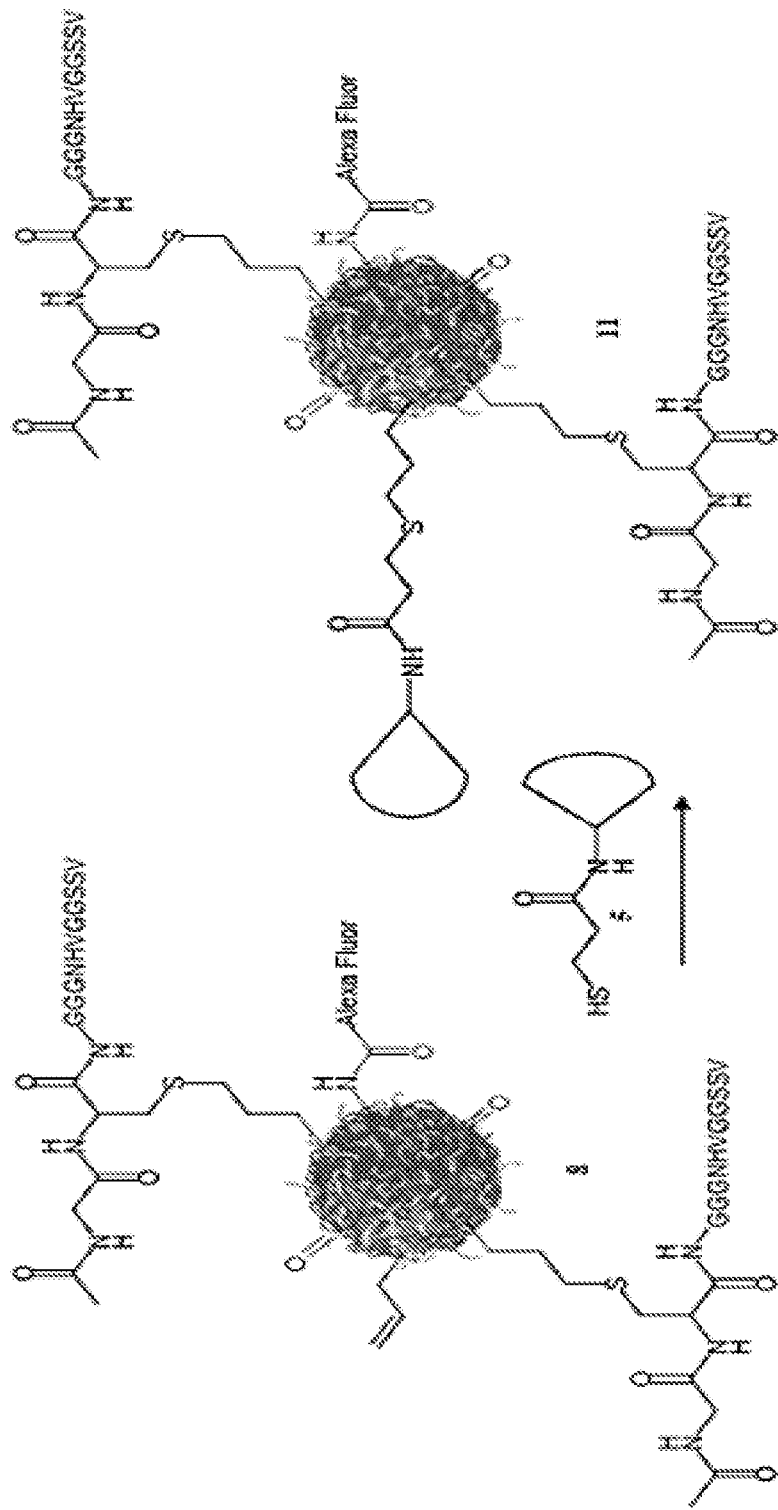
FIG. 78 shows the combination of dendritic and peptidic scaffold.

In the next step, a combined dendritic, peptidic, nanoparticle scaffold was synthesized according to Scheme 24 in FIG. 78.

For the first approach, linear peptides GCGGG-NHVGGSSV with the recognition unit HVGGSSV with protected amines after capping with N-acetoxysuccinimide, were conjugated to the allyl functionality of a ABbD nanoparticle of 126.6 nm through the thiol of the cysteine unit as discussed above. In a following reaction, the imaging reagent Alexa Fluor®594 was introduced to label around 20 of the incorporated amine units of the nanoparticle. In a sequential thiolene reaction, the conjugation of 30 dendritic transporter molecules was achieved (Scheme 7), as was confirmed via $^1$H NMR spectroscopy. The sequential conjugation of the bioactive compounds can be followed with an overlay of the $^1$H NMR spectra that show the addition of first the peptide and the remaining allyl groups of the nanoparticle and the characteristic peaks of the molecular transporter molecule at 2.0 and 3.2 ppm.

Figure 79:
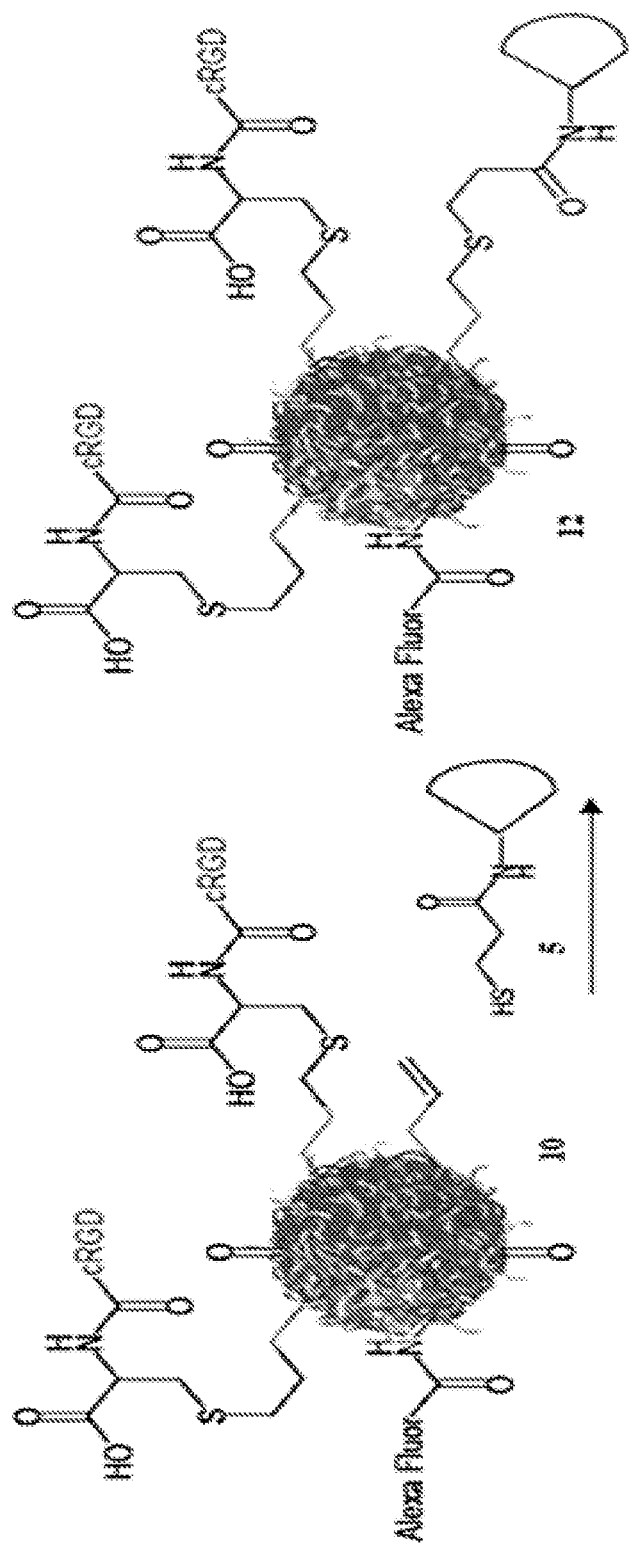
FIG. 79 shows the synthesis of NP-P-MT-dye, ABbD-NP-596-cRGD-MT (12), utilizing thiol-ene chemistry.

The reaction sequence was changed to obtain a similar bioconjugate product that was only differentiated by the peptidic targeting unit. The amine groups of the c-RGD unit were not capped to avoid inactivation of the Arginine® recognition unit. Therefore the conjugation strategy included that the amine groups of the nanoparticle were first labeled with the NHS Alex Fluor dye followed by the thiol-ene reaction with the targeting unit as shown in Scheme 6. In the last step, same as in the previous reaction, the dendritic transporter unit was added in a sequential thiol-ene reaction (Scheme 25 in FIG. 79).

Figure 80:
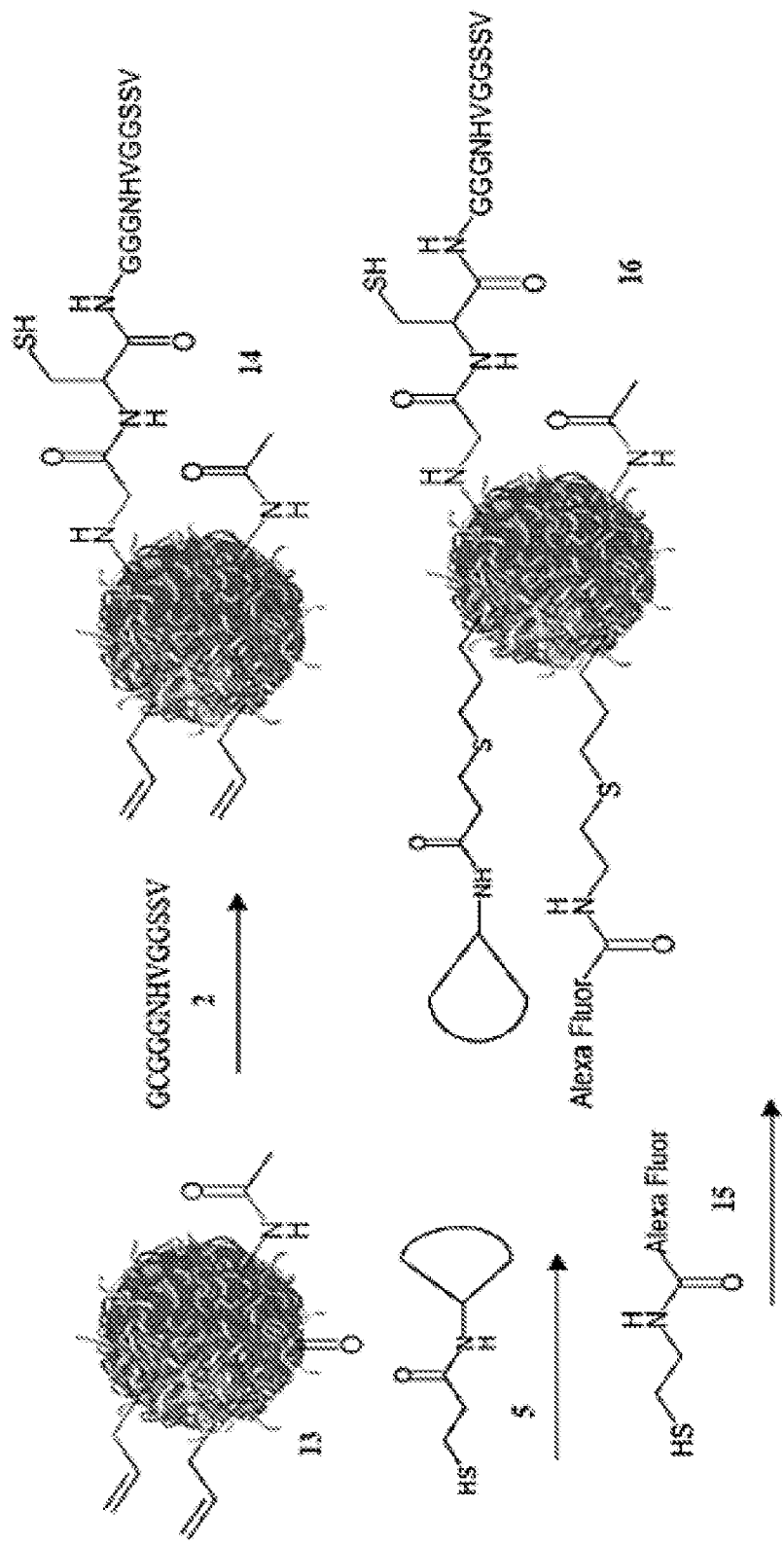
FIG. 80 shows the synthesis of NP-P-MT-dye conjugate, ABbD-NP-594-MT utilizing reductive amination and thiol-ene chemistry.

In a third and last reaction sequence, we could demonstrate the versatility of the provided functional units of the nanoparticle and proceeded with an orthogonal conjugation approach. The free amine groups of the nanoparticle are capped with N-acetoxysuccinimide to not interfere with the following reductive amination reaction between the keto group of the polyester backbone and the N-terminus of the unmodified targeting peptide HVGGSSV. After the reductive amination reaction was completed in the same fashion as described for compound 3, a thiolene reaction between the allyl groups of the nanoparticle and the thiol group of the molecular transporter could achieve the attachment of 30 units according to 1H NMR spectroscopy analysis. The additional final characterization of the modified particles with static light scattering (SLS) the number of conjugated peptides peptides could determine the addition of 36 peptides to the particle. In a last step, the NHS ester Alexa Fluor dye was modified with thiolethylamine (Scheme 26 in FIG. 80) to label exclusively the particle through a thiol-ene reaction to image the system in vitro. The Alexa Fluor 594 dye proved to be stable under the conditions and another example of the chemical versatility of the system was given.

then concentrated via rotary evaporator. The crude product was dissolved in a minimal amount of tetrahydrofuran (THF) (5 mL) and dropped into a round bottom flask containing 1 L diethyl ether. The solution was kept overnight at 0° C. and a white solid was obtained. The solution was decanted off and the solid was dried in vacuo to obtain ABD. Yield: 1.95 g (72%). Mw=3392 Da, PDI=1.19. 1H NMR (300 MHz, CDCl3/TMS) δ: The significant change is the disappearance of the allylic protons at 5.74 and 5.09 ppm and the appearance of small broad resonance peaks at 2.94, 2.75 and 2.47 ppm due to the formation of the epoxide ring. All other aspects of the spectrum are similar.

Nanoparticle Formation from poly(vl-evl-opd) (ABD).

A solution of ABD (0.11 g, Mw=3392 Da, PDI=1.19) dissolved in CH2Cl2 (0.26 mL) was added dropwise via a

TABLE 6

Summary of nanoparticle conjugates with definition of particle type depending on linear polymer precursora and connected targeting peptideb: 'c' for capped N-terminus of peptide with HVGGSSV recognition unit via N-acetoxysuccinimide and 'c' for cyclic RGD. c Dendritic molecular transporter is abbreviated as MT, and the compound name is given in the order of the attachment d.

| Particle Type[a] | Targeting Peptides[b] | Alexa Fluor® Dye | Dendritic Molecular Transporter[c] | Compound Named | Compound Class |
|---|---|---|---|---|---|
| ABD | HVGGSSV | — | — | ABD-NP-HVGGSSV (3) | NP-P |
| ABbD | HVGGSSV | — | — | ABbD-NP-HVGGSSV (14) | NP-P |
| ABbD | cHVGGSSV | 594 | — | ABbD-NP-cHVGGSSV-594 (8) | NP-P-dye |
| ABbD | cRGD | 594 | — | ABbD-NP-594-cRGD (10) | NP-P-dye |
| ABbD | — | 594 | MT | ABbD-NP-594-MT (6) | NP-MT-dye |
| ABbD | cHVGGSSV | 594 | MT | ABbD-NP-cHVGGSSV-594-MT(11) | NP-P-MT-dye |
| ABbD | cRGD | 594 | MT | ABbD-NP-594-cRGD-MT (12) | NP-P-MT-dye |
| ABbD | HVGGSSV | 594 | MT | ABbD-NP-594-MT (16) | NP-P-MT-dye |

Below are the experimental procedures relevant to Example 123.

Synthesis of Copolymer poly(vl-avl-opd) (AbD)

To a 25 mL 3-necked round bottom flask, equipped with stir bar, gas inlet and 2 rubber septa, 2-oxepane-1,5-dione (0.70 g, 5.46 mmol) was added. The round bottom flask was purged with argon. After purging for 30 min, dry toluene (4 mL) was added. The mixture stirred in an oil bath at 80° C. to dissolve the monomer. Upon dissolving, Sn(Oct)2 (11.1 mg, 27.3 µmol) in 0.5 mL dry toluene, absolute ethanol (20.5 mg, 440 µmol), α-allyl-δ-valerolactone (1.15 g, 8.19 mmol) and δ-valerolactone (1.37 g, 13.7 mmol) were then added to the reactor and the mixture was heated for 48 h at 105° C. Residual monomer and catalyst were removed by dialyzing with Spectra/Por® dialysis membrane (MWCO=1000) against CH2Cl2 to give a golden brown polymer. Yield: 2.70 g (85%). Mw=3287 Da, PDI=1.17; $^1$H NMR (300 MHz, CDCl3/TMS, ppm) δ: 5.72 (m, H2C=CH—), 5.06 (m, H2C=CH—), 4.34 (m, —CH2CH2C(O)CH2CH2O—), 4.08 (m, —CH2O—), 3.67 (m, —OCH2CH3), 2.78 (m, opd, —OC(O)CH2CH2C(O)CH$_2$—), 2.58 (m, opd, —OC(O)CH2CH2C(O)CH2-), 2.34 (m, vl, —CH2CH2C(O)O—, avl, H2C=CHCH2CH—, H2C=CHCH2CH—), 1.66 (m, avl & vl, —CHCH2CH$_2$—), 1.25 (t, —CH2CH3); 13C NMR (400 MHz, CDCl3, ppm) δ: 204.9, 175.2, 173.7, 173.2, 135.0, 117.0, 63.9, 44.8, 36.4, 33.6, 28.0, 26.3, 21.3.

Synthesis of poly(vl-evl-opd) (ABD)

To a solution of AbD (2.70 g, 4.67 mmol) in CH2Cl2 (37 mL), 3-chloroperoxybenzoic acid (1.46 g, 8.48 mmol) was added. The mixture stirred for 72 h at room temperature and peristaltic pump at 13 mL/min with vigorous stirring to a solution of 2,2'-(ethylenedioxy)diethylamine (76.4 µL, 0.52 µmol) in CH2Cl2 (40.3 mL) at 44° C. The mixture was heated for 12 h. Residual diamine was removed by dialyzing with SnakeSkin® Pleated Dialysis Tubing (MWCO=10,000) against dichloromethane. Yield: 0.17 g (91%). DLS: DH=118.3±9.6 nm. SLS: Mw=323,000. 1H NMR (300 MHz, CDCl3/TMS) δ: The significant change is the disappearance of the epoxide protons at 2.94, 2.75 and 2.47 ppm and the appearance of signals at 3.54 and 2.97 ppm corresponding to the protons neighboring the secondary amine of the PEG linker after cross-linking. All other aspects of the spectrum are similar.

N-Boc-ethylenediamine (NBED) Conjugated ABD Nanoparticles.

To a solution of ABD nanoparticles (20 mg, 0.06 µmol) in THF (2 mL), N-acetoxysuccinimide (0.02 g, 0.13 mmol) was added. The reaction mixture stirred for 3 h. Residual N-acetoxysuccinimide was removed by dialyzing with SnakeSkin® Pleated Dialysis Tubing (MWCO=10,000) against THF. Once the product was concentrated and dried, the nanoparticles (18 mg, 0.05 µmol) were dissolved in a mixture of CH2Cl2 and CH3OH (1:1, v/v, 2 mL). To this solution, N-Boc-ethylenediamine (4.6 µL of 1.59 M NBED in CH3OH) and NaCNBH3 (21.8 µL of 1.0 M NaCNBH3 in THF) were added. The reaction mixture stirred for 12 h at room temperature and then was purified by dialyzing with SnakeSkin® Pleated Dialysis Tubing (MWCO=10,000) against 1:1 CH2Cl2/CH3OH. Yield: 18 mg (88%). DLS: DH=119.5±10.3 nm; original particle DH=118.3±9.6 nm. 1H NMR (300 MHz, CDCl3/TMS) δ: The significant change is the appearance of the peak at 1.43 ppm due to the Boc protecting group. All other aspects of the spectrum are similar to that of the ABD nanoparticles.

General Procedures for the Synthesis of HVGGSSV Peptide (1).

The HVGGSSV peptide was synthesized by solid-phase peptide synthesis using standard Fmoc chemistry on a Model 90 Peptide Synthesizer (Advanced ChemTech). General procedure: Attachment of N-Fmoc amino acids to resin. After swelling with dichloromethane (20 mL) for 20 min, H-val-2-Cl-Trt resin (0.20 g, 1.03 mmol/g, 0.21 mmol surface amino acids) was treated with a solution of Fmoc-protected amino acids (4.4 equiv, 0.9 mmol) in dimethylformamide (DMF) (9 mL). The amino acids were attached to the resin using double coupling with a solution (9 mL) consisting of N-hydroxybenzotriazole monohydrate (HOBt) (0.9 mmol, 0.14 g) o-(benzotriazole-N,N,N',N'-tetramethyluronium hexafluorophosphate (0.9 mmol, 0.34 g), N,N'-diisopropylethylamine (DIPEA) (1.8 mmol, 0.31 mL) in 9 mL DMF. The reaction mixture was shaken for 60 min and washed with DMF (4×10 mL), methanol (4×10 mL) and DMF (4×10 mL). The end of the coupling was controlled by the Ninhydrin test. A 20% (v/v) piperidine in DMF solution was used to deprotect the Fmoc groups. The amino acids were attached to the resin in the following sequence: Ser, Ser, Gly, Gly, Val, His, Asn, Gly, Gly, Gly, Cys, and Gly.

General Procedure: Cleavage from Resin.

The resin was treated with Reagent R, a solution of TFA, thioanisole, anisole, and ethanedithiol (90:5:3:2, 6 mL), for 4 h. After removal of the resin by filtration, the filtrate was concentrated to precipitate the peptide with cold diethyl ether. Crude peptides were purified by RP-HPLC and lyophilized. Peptide identity was confirmed by MALDI-MS (m/z: 1087.1).

HVGGSSV Conjugated ABD Nanoparticles (3).

To a solution of ABD nanoparticles (20.0 mg, 0.06 µmol) in THF (2 mL), N-acetoxysuccinimide (3 mg, 18.1 µmol) was added. The reaction mixture stirred for 3 h. Residual N-acetoxysuccinimide was removed by dialyzing with SnakeSkin® Pleated Dialysis Tubing (MWCO=10,000) against 1:1 THF/CH3OH to give amine capped ABD nanoparticles, 2. To a solution of 2 (0.0174 g, 0.05 µmol, in 3 mL THF), 1 (3.5 mg. 3.18 Nmol) dissolved in DMSO (2 mL) and NaCNBH3 (6.36 µL 1.0 M NaCNBH3 in THF) were added. The reaction mixture stirred for 12 h at room temperature. The reaction mixture was purified by dialyzing with SnakeSkin® Pleated Dialysis Tubing (MWCO=10,000) against 1:1 THF/CH3CN. Yield: 19 mg (88%) DLS: DH=120.5±10.2 nm; original particle DH=118.3±9.6 nm. SLS: Mw=362,000; original particle Mw=323,000. 1H NMR (600 MHz, (CD3)2SO) δ: The significant change is the appearance of the following peaks: 8.26-7.87, 7.42, 6.90, 4.39, and 4.25 ppm due to the attachment of the peptide. All other aspects of the spectrum are similar to that of the ABD nanoparticles.

Synthesis of poly(vl-evl-avl-opd) (ABbD).

To a solution of AbD (1.70 g, 1.56 mmol) in CH2Cl2 (30 mL), 3-chloroperoxybenzoic acid (0.22 g, 1.28 mmol) was added. The mixture stirred for 72 h at room temperature and then was concentrated via rotary evaporator. The crude product was dissolved in a minimal amount of THF (5 mL) and poured into a round bottom flask containing 1 L diethyl ether. The solution was kept overnight at 0° C. and a white solid was obtained. The solution was decanted off and the solid was dried in vacuo to obtain ABbD. Yield: 1.2 g (71%). Mw=3356 Da, PDI=1.18. 1H NMR (300 MHz, CDCl3/TMS, ppm) δ: 5.72 (m, H2C=CH—), 5.06 (m, H2C=CH—), 4.34 (m, —CH2CH2C(O)CH2CH2O—), 4.08 (m, —CH2O—), 3.67 (m, —OCH2CH3), 2.96 (m, epoxide proton), 2.78 (m, evl epoxide proton, opd, —OC(O)CH2CH2C(O)CH2-), 2.58 (m, opd, —OC(O)CH2CH2C(O)CH2-), 2.47 (epoxide proton), 2.34 (m, vl, —CH2CH2C(O)O—, avl, H2C=CHCH2CH—, H2C=CHCH2CH—), 1.66 (m, avl & vl, —CHCH2CH2-), 1.25 (t, —CH2CH3).

Nanoparticle Formation from ABbD.

A solution of ABbD (0.21 g, Mw=3356 Da, PDI=1.18) dissolved in CH2Cl2 (0.39 mL) was added dropwise via a peristaltic pump at 13 mL/min with vigorous stirring to a solution of 2,2'-(ethylenedioxy)diethylamine (42.6 µL, 0.29 mmol) in CH2Cl2 (60 mL) at 44° C. The reaction mixture was heated for 12 h. Residual diamine was removed by dialyzing with SnakeSkin® Pleated Dialysis Tubing (MWCO=10,000) against dichloromethane. Yield: 0.24 g (96%). DLS: DH=123.4±9.22 nm. SLS: Mw=345,000. 1H NMR (300 MHz, CDCl3/TMS) δ: The significant change is the disappearance of the epoxide protons at 2.96, 2.75 and 2.47 ppm and the appearance of signals at 3.56 and 2.98 ppm corresponding to the protons neighboring the secondary amine of the PEG linker after crosslinking. All other aspects of the spectrum are similar to that of ABbD.

One Pot Synthesis of Nanoparticles from ABbD.

To a solution of 2,2' (ethylenedioxy)diethylamine (26.2 µL, 0.18 mmol) in CH2Cl2 (34.6 mL), a solution of ABbD (0.13 g, Mw=3356 Da, PDI=1.18) in CH2Cl2 (0.24 mL) was added. The mixture was heated at 44° C. for 12 h. Residual diamine was removed by dialyzing with SnakeSkin® Pleated Dialysis Tubing (MWCO=10,000) against CH2Cl2. Yield: 0.15 g (94%). DLS: DH=126.6±9.3 nm. SLS: Mw=350,000. 1H NMR (300 MHz, CDCl3/TMS) δ: The significant change is the disappearance of the epoxide protons at 2.94, 2.75 and 2.47 ppm and the appearance of signals at 3.54 and 2.97 ppm corresponding to the protons neighboring the secondary amine of the PEG linker after cross-linking. All other aspects of the spectrum are similar to that of ABbD.

General Procedure for the Attachment of Benzyl Mercaptan to ABbD Nanoparticles.

To a solution of ABbD nanoparticles (15 mg. 0.04 µmol) in toluene (0.5 mL), benzyl mercaptan (3.5 µL, 29 µmol) was added. The reaction mixture was heated for 72 h at 35° C. The remaining toluene was removed in vacuo and residual benzyl mercaptan was removed by dialyzing with Snake-Skin® Pleated Dialysis Tubing (MWCO=10,000) against CH2Cl2. 1H NMR (300 MHz, CDCl3/TMS) δ: The significant change is the reduction of the allyl protons at 5.72 and 5.06 ppm and the appearance of signals at 3.73 and 7.30 ppm corresponding to the methylene and benzene protons respectively of the attached benzyl mercaptan. All other aspects of the spectrum are similar to that of ABbD nanoparticles.

Deprotection of molecular transporter (MT) (5) (contribution of Sharon Hamilton). To a solution of LL-MT (15 mg, 4.56 µmol) in CH3OH (0.4 mL), a solution of D,L-dithiothreitol in CH3OH (0.2 mL) was added. The reaction mixture stirred for 3 h at room temperature. Residual dithiothreitol was removed by purification with Sephadex LH-20. The product was immediately attached to ABbD nanoparticles.

Model reaction of attachment of MT to ABbD nanoparticles. To a solution of ABbD nanoparticles (15 mg, 0.04 µmol) in CH3OH (0.2 mL), 5 (11 mg, 3.35 µmol) in CH3OH (0.4 mL) was added. The reaction mixture was heated for 72 h at 37° C. Residual 5 was removed by dialyzing with SnakeSkin® Pleated Dialysis Tubing (MWCO=10,000) against methanol. Yield: 31.3 mg (89%). DLS: DH=128.9±10.2 nm; original particle DH=126.6±9.3 nm.

$^1$H NMR (300 MHz, CD3OD) δ: The significant change is the reduction of the allyl protons at 5.72 and 5.06 ppm and the appearance of signals at 2.20-1.98 (CH2), 1.57 (CH2) and 1.39 (CH2) ppm due to the dendritic backbone of the MT. All other aspects of the spectrum are similar to that of ABbD nanoparticles.

Alexa Fluor® 594 conjugated ABbD nanoparticles (4). To a solution of ABbD nanoparticles (0.021 g, 0.06 μmol) in dry THF (1.5 mL), Alexa Fluor®, 594 (0.14 mL of 10 mg/mL Alexa Fluor®& 594 in DMF, 1.7 μmol) was added. The reaction mixture stirred for 24 h at room temperature. Residual Alexa Fluor® 594 was removed by dialyzing with SnakeSkin® Pleated Dialysis Tubing (MWCO=10,000) against CH3OH. Yield: 15.2 mg (88%). 1H NMR (300 MHz, CD3OD) δ: The significant change is the appearance of the following peaks due to Alexa Fluor® 594: 7.14-7.20, 6.78, 5.48, 4.48, 3.62, 3.43, and 1.24 ppm. 1H NMR (600 MHz, (CD3)2SO) δ: The significant change is the appearance of the following peaks due to Alexa Fluor® 594: 7.52, 7.47, 7.08, 5.32, 4.44, 4.35, 3.58, 3.16, 2.03, and 1.25 ppm. All other aspects of the spectrum are similar to that of ABbD nanoparticles.

Attachment of MT to Alexa Fluor® 594 Conjugated ABbD Nanoparticles, NP-594-MT (6).

To a solution of 4 (8 mg, 0.89 μmol) in CH3OH (0.2 mL), 5 (7.5 mg, 2.27 μmol) in CH3OH (0.4 mL) was added. The reaction mixture was heated for 72 h at 37° C. Residual 5 was removed by dialyzing with SnakeSkin® Pleated Dialysis Tubing (MWCO=10,000) against CH3OH. Yield: 10.0 mg (91%). DLS: DH=129.4±9.8 nm; original particle DH=126.6±9.3 nm. 1H NMR (300 MHz, CD3OD) δ: The significant change is the reduction of the allyl protons at 5.72 and 5.06 ppm and the appearance of signals at 2.20-1.98 (CH2), 1.57 (CH2) and 1.39 (CH2) ppm due to the dendritic backbone of the MT. All other aspects of the spectrum are similar to that of 4.

N-acetoxysuccinimide Conjugated HVGGSSV Peptide, cHVGGSSV (7).

To a solution of 1 (29.4 mg, 2.7×10−5 mol) dissolved in CH$_3$CN (3 mL), N-acetoxysuccinimide (0.42 g, 2.7×10−3 mol) was added. The reaction mixture stirred for 3 h at room temperature. After removal of the solvent under reduced pressure, the crude product was purified by RP-HPLC. MALDI-MS: m/z=(M+H+) 1174.2.

Capped HVGGSSV Conjugated Alexa Fluor® 594-ABbD Nanoparticles, NP-cHVGGSSV-594.

To a solution of ABbD nanoparticles (0.021 g, 0.06 μmol) in dimethylsulfoxide (0.7 mL), 7 (6.4 mg, 5.46 μmol) was added. The reaction mixture was heated for 72 h at 33° C. To this solution, Alexa Fluor® 594 (0.14 mL of 10 mg/mL Alexa Fluor® 594 in DMF, 1.7 μmol) was added. Residual Alexa FluorX 594 and peptide were removed by dialyzing with SnakeSkin® Pleated Dialysis Tubing (MWCO=10,000) against 1:1 CH3OH/CH3CN. Yield: 20.1 mg (80%). DLS: DH=128.9±10.9 nm; original particle DH=126.6±9.3 nm. 1H NMR (600 MHz, (CD3)2SO) δ: The significant change is the reduction of the allyl protons at 5.72 and 4.97 ppm and the appearance of the following sets of significant signals: 8.21, 7.83, 4.55, 3.73 and 0.80 ppm due to the peptide, and 7.25, 7.16, 6.53, 5.32, 4.44, 4.37, and 1.25 ppm due to the Alexa Fluor® 594. All other aspects of the spectrum are similar to that of ABbD nanoparticles.

Attachment of MT to cHVGGSSV Conjugated Alexa Fluor® 594-ABbD Nanoparticles, NP-cHVGGSSV-594-MT.

To a solution of 8 (6 mg. 0.02 μmol) in DMSO (0.1 mL), 5 (2 mg, 0.88 μmol) in CH3OH (0.3 mL) was added. The reaction mixture was heated for 48 h at 33° C. Residual 5 was removed by dialyzing with SnakeSkin® Pleated Dialysis Tubing (MWCO=10,000) against 1:1 CH3OH/CH3CN. Yield: 7.4 mg (93%). DLS: DH=130.7±9.4 nm; original particle DH=126.6±9.3 nm. 1H NMR (600 MHz, (CD3)2SO) δ: The significant change is the reduction of the allyl protons at 5.72 and 4.97 ppm and the appearance of signals at 3.06 (CH2), 2.96 (CH2), 1.97 (CH2), 1.77 (CH2), 1.41 (CH2) and 1.35 (CH2) ppm due to the dendritic backbone of the MT. All other aspects of the spectrum are similar to that of 8.

Synthesis of Cyclic RGD, cRGD (9)

The RGD peptide was synthesized by solid-phase peptide synthesis using standard Fmoc chemistry on a Model 90 Peptide Synthesizer (Advanced ChemTech).

Synthesis of Linear RGD.

After swelling with dichloromethane (20 mL), Fmoc-Cys-2-Cl-Trt resin (0.20 g, 0.9 mmol/g, 0.18 mmol surface amino acids) was deprotected with a 20% (v/v) piperidine in DMF solution and treated with a solution of Fmoc-protected amino acid (4.4 equiv, 0.9 mmol) in dimethylformamide (DMF) (9 mL). The amino acids were attached to the resin using double coupling with a solution (9 mL) consisting of N-hydroxybenzotriazole monohydrate (0.9 mmol, 0.14 g) o-(benzotriazole-N,N,N',N'-tetramethyluronium hexafluorophosphate (0.9 mmol, 0.34 g), N,N'-diisopropylethylamine (1.8 mmol, 0.31 mL) in 9 mL DMF. The reaction mixture was shaken for 60 min and washed with DMF (4×10 mL), methanol (4×10 mL) and DMF (4×10 mL). A 20% (v/v) piperidine in DMF solution was used to deprotect the Fmoc groups. An amino-hexyl spacer was coupled to the cystine on the resin, followed by glutamic acid, aspartic acid, glycine, arginine, phenylalanine, and finally lysine.

Cyclization of RGD.

The peptide was cyclized by utilizing an ODmab group, which allows for the selective deprotection carboxylic acid side chain of the glutamic acid, which can then be coupled to the N-terminus. The ODmab was deprotected using 2% v/v hydrazine monohydrate/DMF added to the resin and shaken for 7 min. Next it was washed with 20 mL of DMF followed by 10 mL of a 5% v/v DIPEA/DMF solution which was allowed to shake for 10 min. Carboxy activation was achieved through the use of N,N'-dicyclohexylcarboimide (DCC) (44.6 mg, 0.22 mmol) and hydroxybenzotriazole (HOBt) (29.2 mg, 0.22 mmol) which was added to 10 mL of DMF and then added to the resin and allowed to shake for 18 h.

General Procedure: Cleavage from Resin.

The resin was treated with Reagent R, a solution of TFA, thioanisole, anisole, and ethanedithiol (90:5:3:2, 6 mL), for 3 h. After removal of the resin by filtration, the filtrate was concentrated to precipitate the peptide with cold diethyl ether. The crude peptide was collected by centrifugation, purified by RP-HPLC and lyophilized. Peptide identity was confirmed by MALDI-MS (m/z: 945).

Attachment of cRGD to Alexa Fluor® 594 Conjugated ABbD Nanoparticles, NP-594-cRGD (10).

To a solution of ABbD nanoparticles (23.0 mg, 0.07 μmol) in THF (2.3 mL), Alexa Fluor® 594 (0.15 mL of 10 mg/mL Alexa Fluor® 594 in DMF, 1.83 μmol) was added. After stirring the reaction mixture for 24 h at room temperature, the solvent was removed via rotary evaporator. To the Alexa FluorX 594 conjugated nanoparticles, methanol (0.35 mL) and 9 (5.7 mg, 6.0 μmol), dissolved in DMSO (0.35 mL), were added. The reaction mixture was heated for 72 h at 33° C. Residual Alexa Fluor® 594 and peptide were removed by dialyzing with SnakeSkin® Pleated Dialysis Tubing (MWCO=10,000) against 1:1 CH3OH/CH3CN. Yield: 22.0 mg (81%). DLS: DH=129.8±9.6 nm; original particle DH=126.6±9.3 nm. 1H NMR (600 MHz, (CD3)2SO) δ: The significant change is the reduction of the allyl protons at 5.72 and 4.97 ppm and the appearance of the following sets of significant signals: 7.37, 4.79, 2.23 and 1.66 ppm due to cRGD, and 7.25, 6.55, 5.31, 4.44, and 1.23 ppm due to the Alexa Fluor® 594. All other aspects of the spectrum are similar to that of ABbD nanoparticles.

Attachment of MT to cRGD Conjugated Alexa Fluor® 594-ABbD Nanoparticles, NP-594-cRGD-MT (12).

To a solution of 10 (7.8 mg, 0.02 μmol) in DMSO (0.1 mL), 5 (1.4 mg, 0.67 μmol) in CH3OH (0.3 mL) was added. The reaction mixture was heated for 48 h at 33° C. Residual 5 was removed by dialyzing with SnakeSkin® Pleated Dialysis Tubing (MWCO=10,000) against 1:1 CH3OH/CH3CN. Yield: 7.6 mg (83%). DLS: DH=131.9±10.6 nm; original particle DH=126.6±9.3 nm. 1H NMR (600 MHz, (CD3)2SO) δ: The significant change is the reduction of the allyl protons at 5.72 and 4.97 ppm and the appearance of signals at 3.04 (CH2), 2.98 (CH2), 1.98 (CH2), 1.75 (CH2), 1.41 (CH2), and 1.35 (CH2) ppm due to the dendritic backbone of the MT. All other aspects of the spectrum are similar to that of 11.

HVGGSSV Conjugated ABbD Nanoparticles, NP-HVGGSSV (14).

To a solution of ABbD nanoparticles (50.0 mg, 0.14 μmol) in THF (2 mL), N-acetoxysuccinimide (7 mg, 44.5 μmol) was added. The reaction mixture stirred for 3 h. Residual N-acetoxysuccinimide was removed by dialyzing with SnakeSkin® Pleated Dialysis Tubing (MWCO=10,000) against 1:1 THF/CH3OH to give amine capped ABbD nanoparticles, 13. To a solution of 13 (50.0 mg, 0.14 μmol, in 3 mL THF), 1 (9.3 mg, 8.57 μmol) dissolved in DMSO (2 mL) and NaCNBH3 (17.1 μL 1.0 M NaCNBH3 in THF) were added. The reaction mixture stirred for 12 h at room temperature. The reaction mixture was purified by dialyzing with SnakeSkin® Pleated Dialysis Tubing (MWCO=10,000) against 1:1 THF/CH3CN. Yield: 43.2 mg (83%). DLS: DH=129.7±9.5 nm; original particle DH=126.6±9.3 nm. SLS: Mw=391,000; original particle Mw=350,000. 1H NMR (600 MHz, (CD3)2SO, ppm) δ: The significant change is the appearance of the following peaks: 8.21, 7.85, 4.55, 3.73 and 0.80 ppm due to the peptide. All other aspects of the spectrum are similar to that of ABbD nanoparticles.

Thiolated Alexa Fluor® 594 (15).

To a solution of Alexa Fluor® 594 (0.2 mL of 10 mg/mL Alexa Fluor® 594 in DMF, 2.4 μmol), cysteamine (68.4 μL of 2.5 mg/mL cysteamine in DMSO, 2.2 μmol) was added. The reaction mixture stirred for 3 h at room temperature. The product was immediately attached to 14.

Attachment of MT to HVGGSSV conjugated Alexa Fluor® 594-ABbD nanoparticles, NPHVGGSSV-594-MT (16). To a solution of 14 (16 mg, 0.04 μmol) in DMSO (0.2 mL), 15 (2 mg, 1.95 μmol) in DMSO (0.2 mL) and 5 (2.7 mg, 1.2 μmol) in CH3OH (0.4 mL) were added. The reaction mixture was heated for 48 h at 33° C. Residual 5 and 15 were removed by dialyzing with SnakeSkin® Pleated Dialysis Tubing (MWCO=10,000) against CH3OH. Yield: 18.5 mg (86%). DLS: DH=132.1±9.3 nm; original particle DH=126.6±9.3 nm. 1H NMR (600 MHz, (CD3)2SO) δ: The significant change is the reduction of the allyl protons at 5.72 and 4.97 ppm and the appearance of the following sets of significant signals: 3.08, 2.99, 1.97, 1.79, 1.43 and 1.34 ppm due to the dendritic backbone of the MT, and 7.27, 7.07, 6.53, 5.32, 4.46, 4.37, and 1.24 ppm due to the Alexa Fluor® 594. All other aspects of the spectrum are similar to that of 14.

84. Paclitaxel Encapsulation in poly(vl-evl-avl-opd) (ABbD) Nanoparticles

To a 150 mL beaker containing D-α-tocopherol polyethylene glycol 1000 succinate (0.39 g) dissolved in Lonza cell culture water (78 mL), poly(vl-evl-avl-opd), ABbD, nanoparticles (0.17 g) and paclitaxel (34.0 mg) dissolved in dimethyl sulfoxide (0.75 mL) was added slowly with vigorous stirring. The solution was split into two 50 mL centrifuge tubes. The paclitaxel loaded nanoparticles were purified by applying two cycles of centrifugation (8000 rpm for 1 h) and reconstitution with cell culture water. The nanoparticle suspension was then lyophilized. The loading ratio of paclitaxel for the encapsulation was determined by NanoDrop UV/Vis and was found to be 11.34%.

85. In Vivo Administration of Nanoparticle-Bioconjugate

Five adult Sprague-Dawley rats were sacrificed by lethal inhalation of C02. At the moment of euthanasia, eight eyes of four rats were treated with a solution of $2 \times 10^{-2}$ M nanoparticle conjugate in a molar ratio of 5:1 (dye:transporter) up to 15 minutes, one rat served as the no treatment control. The solution was dropped with a micropipette on to the cornea and multiple drops were instilled in series to maintain a tear meniscus over the cornea. The rats were kept in the dark in a cold room for two hours after the treatment and underwent enucleation of the globe with optic nerve stump attached. The eye globes with attached optic nerves were placed in 4% paraformaldehyde until paraffin embedding. The paraffin blocks were cut into 4-μm sections and were stained with traditional DAPI dye. Slides were viewed at 40×'s magnification using a digital fluorescent microscope Olympus Provis AX70 digitally interfaced with a semi-cooled CCD camera to visualize Alexa Fluor 594-labeled transporter. Background autofluorescence was subtracted and the settings were held constant for both the control and the treatment eyes. To proof and image the intended eye region, images of the same location were measured under the DAPI and Alexafluor wavelength with the microscope-mounted camera (see FIG. 50, A-D).

86. Synthesis of Copolymer poly(vl-opd)

To a 25 mL 3-necked round bottom flask, equipped with stir bar, 2-oxepane-1,5-dione (0.7 g, 5.46 mmol) was added and the flask was sealed with two septa and a gas inlet. The flask was evacuated and refilled with argon three times. Dry toluene (4 mL) was added and the mixture stirred in an oil bath at 70° C. to dissolve the monomer. Upon dissolving, Sn(Oct)$_2$ (20 mg, $5.48 \times 10^{-2}$ mmol in 0.5 mL dry toluene), absolute ethanol (51.1 μL, $8.86 \times 10^{-1}$ mmol), and δ-valerolactone (2.87 mL, 30.7 mmol) were added. The temperature of the oil bath was increased to 105° C. and the mixture stirred for 48 h. The crude product was dissolved in a minimal amount of THF (5 mL) and poured into a round bottom flask containing 1 L diethyl ether. The solution was kept overnight at 0° C. and a white solid was obtained. The solution was decanted off and the solid was dried in vacuo to obtain poly(vl-opd). Yield: 2.31 g. $M_w$=3525 Da, PDI=1.27; $^1$H NMR (300 MHz, CDCl$_3$/TMS, ppm) δ: 4.34 (m, opd, —CH$_2$CH$_2$C(O)CH$_2$CH$_2$O—), 4.08 (m, vl, —CH$_2$O—), 3.65 (m, —OCH$_2$CH$_3$), 2.74 (m, opd, —OC(O)CH$_2$CH$_2$C(O)—), 2.60 (m, opd, —CH$_2$CH$_2$C(O)CH$_2$CH$_2$—), 2.34 (m, vl, —CH$_2$CH$_2$C(O)O—), 1.68 (m, vl, —CHCH$_2$CH$_2$—), 1.25 (m, —CH$_2$CH$_3$).

87. Nanoparticle Formation from poly(vl-opd) Via Reductive Amination

In a 100 mL round bottom flask equipped with stir bar, poly(vl-opd) (0.16 g) was dissolved in CH$_2$Cl$_2$(11.5 mL). After dissolving the polymer, tetrahydrofuran (11.5 mL), 2,2'-(ethylenedioxy)bisethylamine (16.9 µL, 0.12 mmol), and NaBH$_3$CN (1.2 mL, 1.2 mmol) were added. The pH was adjusted to 6-7 using 1M NaOH and the reaction stirred for 12 h at room temperature. Residual polymer, diamine and NaBH$_3$CN were removed by dialyzing with SnakeSkin® Pleated Dialysis Tubing (MWCO=10,000) against 50/50 CH$_2$Cl$_2$/CH3OH. $^1$H NMR (300 MHz, CDCl$_3$/TMS, ppm) δ: The significant change is the appearance of signals at 3.66 ppm corresponding to the protons neighboring the secondary amine of the PEG linker after cross-linking. All other aspects of the spectrum are similar. The particle size of the nanoparticles formed for various stoichiometries was investigated by dynamic light scattering, as tablated in Table 5, below.

TABLE 5

| | Size Analysis from Dynamic Light Scattering | |
|---|---|---|
| Anime/1 Keto | Diameter (nm) Ab$_1$ nanoparticles 7% keto | Diameter (nm) Ab$_2$ nanoparticles 12% keto |
| 2 | 11.3 ± 1.2 | 18.6 ± 1.9 |
| 3 | 20.7 ± 1.8 | 26.4 ± 2.4 |
| 4 | 38.1 ± 4.0 | 47.1 ± 4.9 |
| 6 | 77.4 ± 6.7 | 107.6 ± 8.9 |

Figure 51:
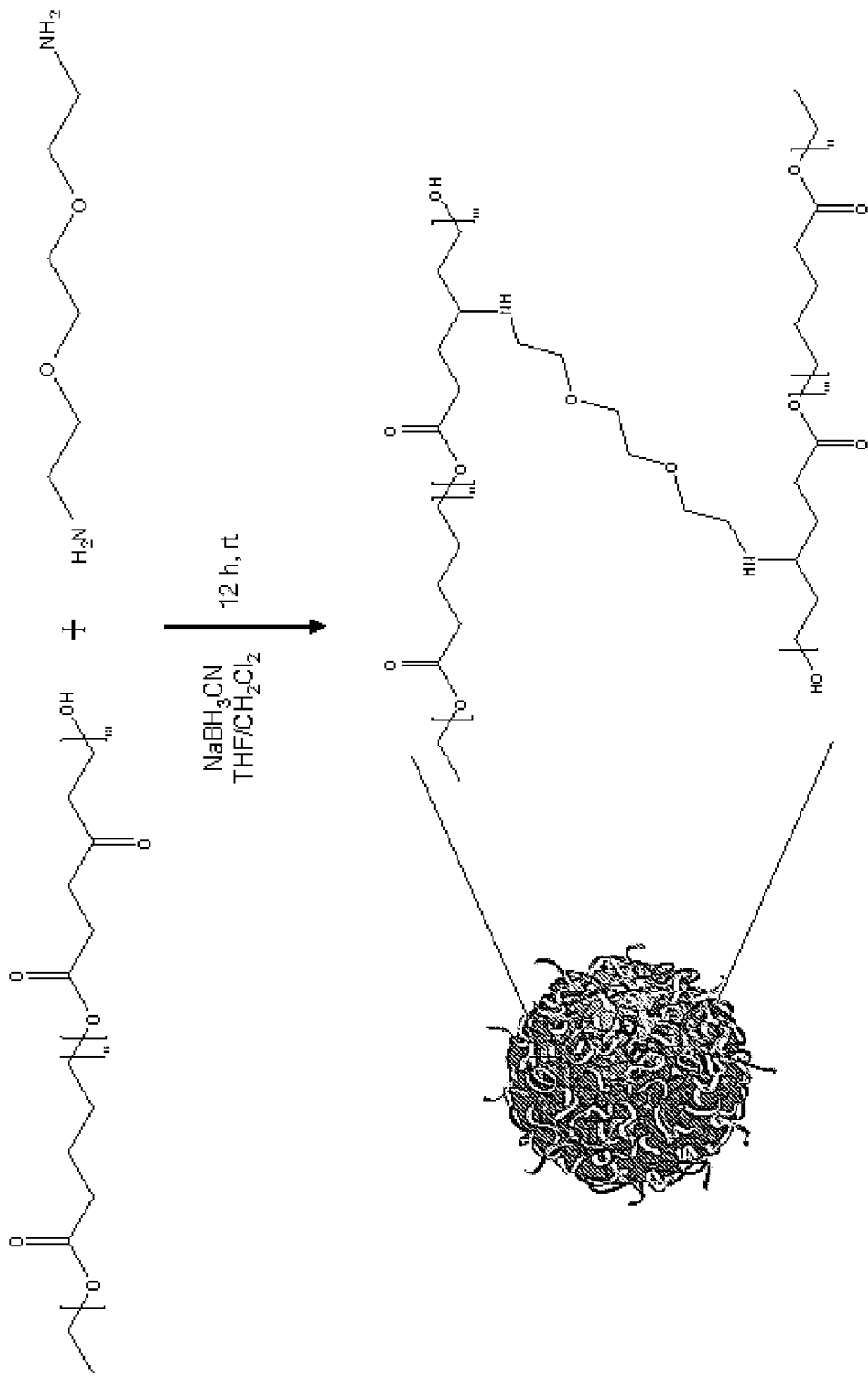
FIG. 51 shows a schematic of nanoparticle formation from poly(vl-opd) via reductive amination.
Figure 52:
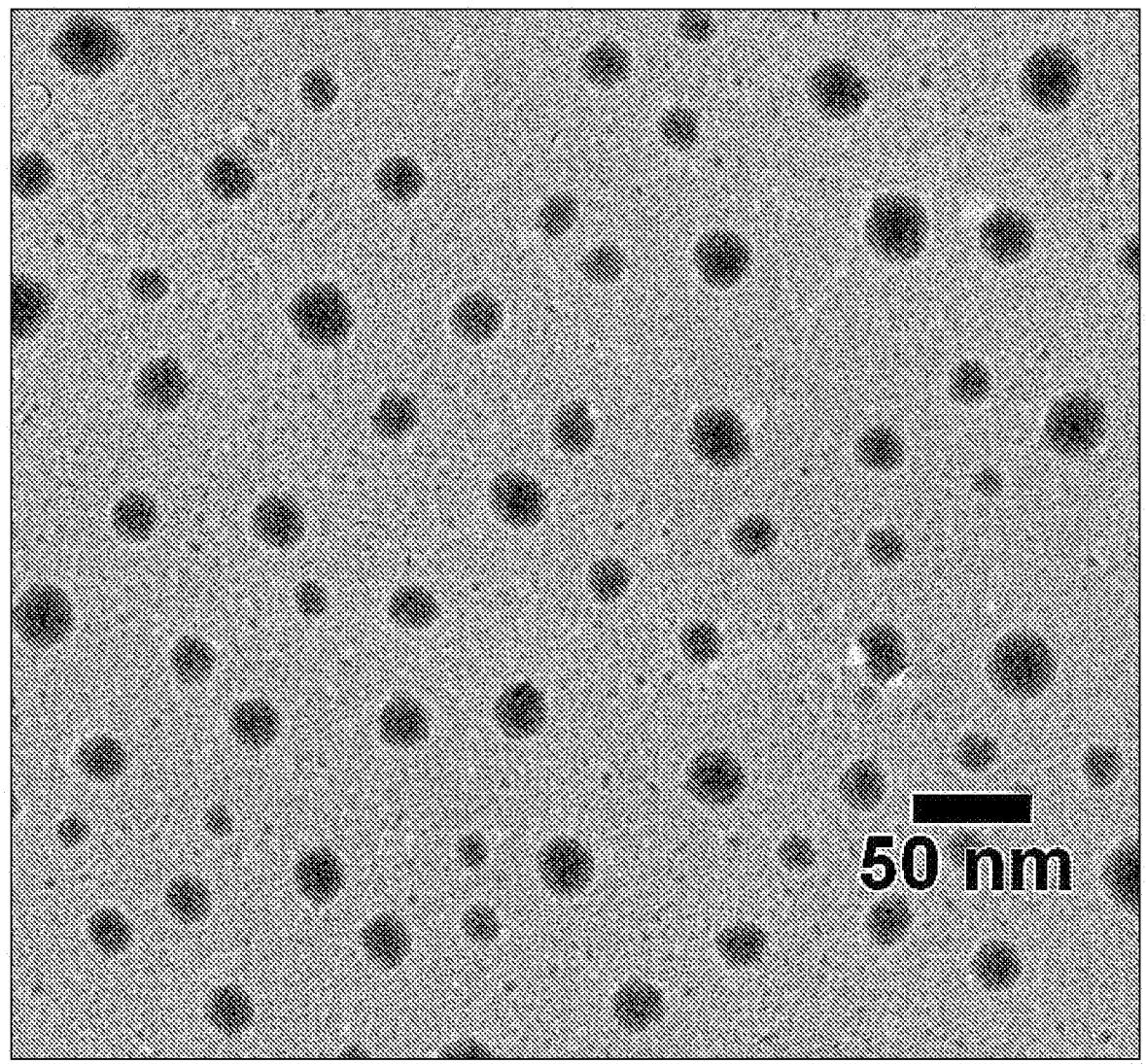
FIG. 52 shows a transmission electron microscopy (TEM) image of nanoparticles formed from poly(vl-opd) via reductive amination.
Figure 53A:
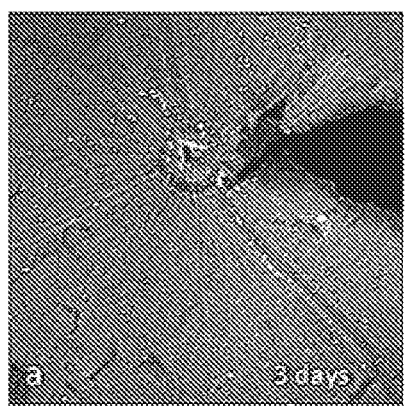
FIGS. 53A-F shows deposition of DiO dye on the retinal surface over time after a single injection of DiO nanoparticle complex.
Figure 53B:
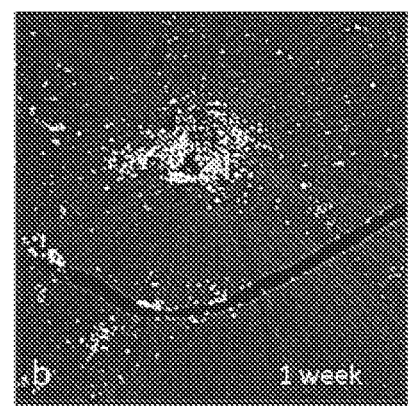
Figure 53C:
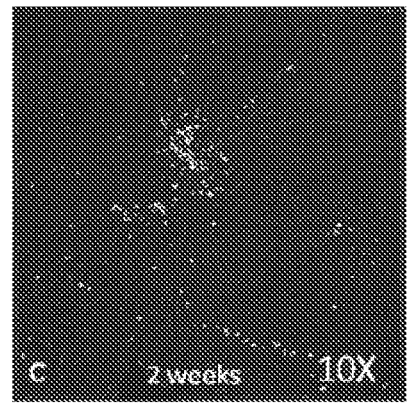
Figure 53D:
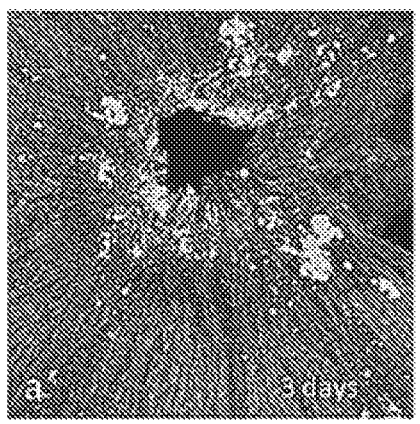
Figure 53E:
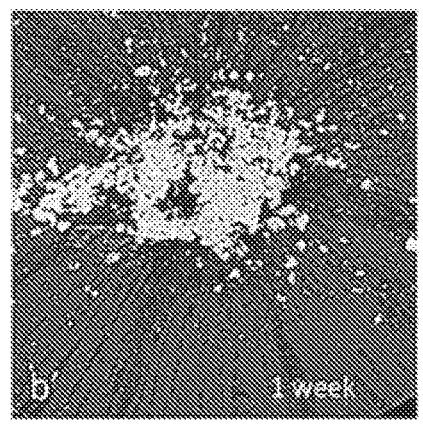
Figure 53F:
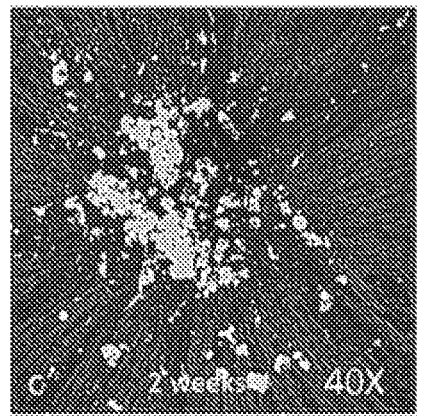

A example preparation of degradable polyester nanoparticle from copolymer poly(vl-opd) is illustrated in FIG. 51. A transmission electron microscopy (TEM) image of particles formed is provided in FIG. 52.

88. General Nanoparticle Formation Utilizing 3,6-dioxa-1,8-octanedithiol

A solution of poly(avl-vl) (0.14 g, M$_w$=3042 Da, PDI=1.18) dissolved in CH$_2$Cl$_2$ (0.16 mL) was added to a solution of 3,6-dioxa-1,8-octanedithiol (19.6 µL, 0.12 mmol) in CH$_2$Cl$_2$ (24.6 mL). The reaction mixture was heated for 12 h at 45° C. Residual dithiol was removed by dialyzing with SnakeSkin® Pleated Dialysis Tubing (MWCO=10,000) against CH$_2$Cl$_2$. Yield: 0.13 g. DLS: DH=72.6±2.8 nm. $^1$H NMR (300 MHz, CDCl$_3$/TMS) δ: The significant change is the reduction of the allyl protons at 5.06 and 5.77 ppm and the appearance of signals at 3.65 and 2.71 ppm corresponding to the protons neighboring the thiols of the PEG linker after cross-linking. All other aspects of the spectrum are similar to that of poly(avl-vl).

89. General Nanoparticle Formation Utilizing PEG Dithiol

A solution of poly(avl-vl) (0.13 g, M$_w$=3042 Da, PDI=1.18) dissolved in CH$_2$Cl$_2$ (0.16 mL) was added to a solution of PEG dithiol (0.13 g, 38.1 µmol) in CH$_2$Cl$_2$ (23.5 mL). The reaction mixture was heated for 12 h at 45° C. Residual dithiol was removed by dialyzing with Snake-Skin® Pleated Dialysis Tubing (MWCO=25,000) against CH$_2$Cl$_2$. Yield: 0.11 g. DLS: DH=33.7±3.8 nm. $^1$H NMR (300 MHz, CDCl$_3$/TMS) δ: The significant change is the reduction of the allyl protons at 5.06 and 5.77 ppm and the appearance of signals at 3.65 and 2.71 ppm corresponding to the protons neighboring the thiols of the PEG linker after cross-linking. All other aspects of the spectrum are similar to that of poly(avl-vl).

90. Synthesis of Copolymer poly(propargylvalerolactone-valerolactone)(poly(pvl-vl))

A 25 mL 3-necked round bottom flask, equipped with stir bar, was sealed with two septa and a gas inlet. The flask was evacuated and refilled with argon three times. Stock solutions of 1.7 M ethanol (EtOH) in THF and 3.7×10-2 M tin(II) 2-ethylhexanoate (Sn(Oct)$_2$) in THF were made in sealed Ar$_{(g)}$ purged flasks. Solutions of EtOH (0.13 mL, 0.22 mmol) and Sn(Oct)$_2$ (0.12 mL, 4.3×10$^{-3}$ mmol) were combined in the Ar$_{(g)}$ purged 3-necked round bottom flask. After stirring the mixture for 20 min, α-propargyl-δ-valerolactone (pvl, 0.35 g, 2.5 mmol) and δ-valerolactone (vl, 1.1 g, 10.0 mmol) were added. The reaction vessel stirred at 105° C. for 48 h. Residual monomer and catalyst were removed by precipitating the polymer into cold diethyl ether to give a golden brown polymer. Yield: 1.18 g (81.4%). M$_w$=3000 Da, PDI=1.18. $^1$H NMR (300 MHz, CDCl$_3$/TMS): δ 4.10 (m, —CH$_2$—O—), 3.64 (m, CH$_3$CH$_2$O—), 2.59 (m, pvl, HC≡CCH2CH—), 2.35 (m, vl, —CH$_2$CH$_2$C(O)O—, pvl, HC≡CCH$_2$CH—, HC≡CCH2CH—), 2.03 (m, HC≡C—), 1.68 (m, pvl & vl, —CHCH$_2$CH$_2$—), 1.25 ppm (t, CH$_3$CH$_2$O—). $^{13}$C NMR (400 MHz, CDCl$_3$): δ 173.6 (pvl, —C(O)—), 172.5 (vl, —C(O)—), 78.2 (HC≡C—), 71.3, 68.4, 63.8, 36.7, 33.6, 29.7, 28.3, 24.6, 21.5, 19.0, 16.7 ppm.

91. Click Reaction Conditions for Nanoparticle Formation Utilizing Polyoxyethylene bis(azide)

Poly(pvl-vl) (10 mg, M$_w$=3000 Da, PDI=1.18) was added to a vial, which was then sealed and purged with argon. Polyoxyethylene bis(azide) (58.7 mg, 1.2×10$^{-2}$ mmol) dissolved in anhydrous dimethylformamide (0.5 mL) and copper (1) bromide (23.4 µL, 3.5×10$^{-2}$ M solution in DMF) were added. The reaction mixture stirred for 24 h at room temperature. Residual azide and copper bromide were removed by dialyzing with SnakeSkin® Pleated Dialysis Tubing (MWCO=25,000) against 50/50 dichloromethane/methanol. Yield: 43.4 mg. DLS: DH=21.9±1.9 nm. $^1$H NMR (300 MHz, CDCl$_3$/TMS): δ The significant change is the reduction of the alkyne proton at 2.03 ppm and the appearance of signals at 3.65 and 3.40 ppm corresponding to the protons of the PEG linker and the signal at 7.49 ppm due to the protons from triazole formation as a result of cross-linking. All other aspects of the spectrum are similar to that of poly(vl-pvl).

92. Click Reaction Conditions for Nanoparticle Formation Utilizing 1,8-Diazide-3,5-Dioxaoctane Poly(pvl-vl) (40.8 mg. M$_w$=3000 Da, PDI=1.18) was added to a vial, which was then sealed and purged with argon. To the vial, 1,8-diazide-3,5-dioxaoctane (19.5 mg, 9.7×10$^2$ mmol) dissolved in anhydrous dimethylformamide (0.8 mL) and copper (I) bromide (115.3 µL, 5.9×10$^{-2}$ mM solution in DMF) were added. The reaction mixture stirred for 24 h at 40° C. Residual azide and copper bromide were removed by dialyzing with SnakeSkin® Pleated Dialysis Tubing (MWCO=10,000) against 50/50 CH$_2$Cl$_2$/CH3OH. Yield: 37.8 mg. DLS: D$_H$=21.9±1.9 nm. $^1$H NMR (300 MHz, CDCl$_3$/TMS): δ The significant change is the reduction of the alkyne proton at 2.03 ppm and the appearance of signals at 3.65 and 3.40 ppm corresponding to the protons of the PEG linker and the signal at 7.49 ppm due to the protons from triazole formation as a result of cross-linking. All other aspects of the spectrum are similar to that of poly(pvl-vl).

93. General Procedure for Formulating Nanoparticles with TPGS-Vitamin E

To a 150 mL beaker containing D-α-tocopheryl polyethylene glycol 1000 succinate (vitamin E TPGS) (0.28 g) dissolved in Lonza cell culture water (55 mL), nanoparticles (0.0977 g) dissolved in dimethyl sulfoxide (DMSO) (0.50 mL) were added slowly with vigorous stirring. The solution was split equally into two 50 mL centrifuge tubes. The nanoparticles were rinsed by applying three cycles of centrifugation (8000 rpm for 30 min) and reconstituted with cell culture water. The nanoparticle suspension was then lyophilized.

94. General Procedure for In Vitro Cytotoxicity of Formulated Nanoparticles (MTT Assay)

The cytotoxicity of the formulated nanoparticles was evaluated using an MTT assay. HeLa cells were cultured in Eagle's Minimum Essential Medium supplemented with 10% heat inactivated fetal bovine serum, L-glutamine, penicillin streptomycin sulfate antibiotic-antimycotic mixture and gentamicin. Cells were maintained at 37° C. with 5% CO$_2$ in a 95% humidity incubator. The cells were seeded in a 96-well plate in 100 µL media per well at a density of 10,000 cells/well and incubated for 24 h. The media was then replaced with 100 µL of phenol red free medium-containing nanoparticles at different concentrations in triplicate and incubated for 24 h. After incubation, the nanoparticle containing media was removed, the cells were rinsed three times with DPBS, to avoid interference in the assays, and 100 µL of fresh phenol red free media was added, followed by 10 µL MTT solution (5 mg/mL). The cells were incubated for 4 h, after which time the medium was carefully removed. To the resulting purple crystals, 100 µL DMSO was added to lyse the cells and was incubated for 10 min at 37° C. The MTT absorbance was measured at 540 nm using a Synergy HT Multi-mode microplate reader (Bio Tek Instruments, Winooski, Vt.). Optical densities measured for wells containing cells that received no nanoparticle were considered to represent 100% viability. Results are expressed as the mean±S.D. of viable cells.

95. ENCAPSULATION of Brimonidine in Nanoparticles

To a 150 mL beaker containing D-α-tocopherol polyethylene glycol 1000 succinate (0.15 g) dissolved in Lonza cell culture water (30 mL), nanoparticles (60.5 mg) and brimonidine (6.1 mg) dissolved in dimethyl sulfoxide (0.50 mL) were added slowly with vigorous stirring. The solution was split equally into two 50 mL centrifuge tubes. The brimonidine loaded nanoparticles were purified by applying three cycles of centrifugation (8000 rpm for 30 min) and reconstituted with cell culture water. The nanoparticle suspension was then lyophilized. The concentration of encapsulated brimonidine was determined by NanoDrop™ UV-Vis at a wavelength of 389 nm. Brimonidine standards (0.32-1.92 mg/mL) were measured by UV-Vis and a calibration curve was rendered. With the calibration curve, the concentration of encapsulated brimonidine was determined by the absorbency of the brimonidine in the nanoparticle at 389 nm and the loading ratio was found to be 6.5%.

96. General Procedure for the Formation of Nanoparticles from poly(vl-evl)

In a 100 mL three-necked round bottom flask equipped with stir bar, condenser and septa, 2,2'-(ethylenedioxy)bisethylamine (34.1 µL, 2.32×10$^{-4}$ mol), 28.7 mL CH$_2$Cl$_2$ and a solution of poly(vl-evl) (0.14 g, M$_w$=3400 Da, PDI=1.16) in 0.19 mL CH$_2$Cl$_2$ were added. The mixture was heated at 44° C. for 12 h. Residual diamine was removed by dialyzing with SnakeSkin® Pleated Dialysis Tubing (MWCO=10,000) against dichloromethane. DLS: D$_H$=272.3±23.3 nm. $^1$H NMR (300 MHz, CDCl$_3$/TMS) δ: The significant change is the disappearance of the epoxide protons at 2.94, 2.75 and 2.47 ppm and the appearance of signals at 3.64 and 2.97 ppm corresponding to the protons neighboring the secondary amine of the PEG linker after cross-linking. All other aspects of the spectrum are similar to that of poly(vl-evl), as referenced in the literature.[8]

97. General Procedure for In Vitro Nanoparticle Degradation Studies

Poly(vl-evl) nanoparticles (10 mg) were suspended in 2 mL of Dulbecco's Phosphate Buffered Saline (pH 7.2) in 2 dram vials equipped with stir bars. The vials were sealed to avoid evaporation and the samples were maintained at 37° C. under continuous stirring. At 48 h intervals, samples were removed and dichloromethane was added (3×4 mL) to extract remaining nanoparticles and degradation products. The extraction solutions were concentrated via rotary evaporator and dried in vacuo. The degradation of the nanoparticles was monitored by the change in molecular weight, as determined by static light scattering, with incubation time.

98. General Procedure for Nanoparticle Formation from poly(vl-evl-avl-opd)

To a solution of 2,2'-(ethylenedioxy)diethylamine (23.4 µL, 0.16 mmol) in CH$_2$Cl$_2$ (98.7 mL), a solution of poly(vl-evl-avl-opd) (0.1840 g, M$_w$=3440 Da) in CH$_2$Cl$_2$ (0.64 mL) was added. The mixture was heated at 44° C. for 12 h. Residual diamine was removed by dialyzing with SnakeSkin® Pleated Dialysis Tubing (MWCO=10,000) against CH$_2$Cl$_2$. Yield: 0.15 g (94%). DLS: D$_H$=52.9±3.3 nm. SLS: M$_w$=147,000 Da. $^1$H NMR (300 MHz, CDCl$_3$/TMS) δ: The significant change is the disappearance of the epoxide protons at 2.94, 2.75 and 2.47 ppm and the appearance of signals at 3.54 and 2.97 ppm corresponding to the protons neighboring the secondary amine of the PEG linker after cross-linking. All other aspects of the spectrum are similar to that of poly(vl-evl-avl-opd), as referenced in the literature.[9]

99. Formulation of poly(vl-evl-avl-opd) Nanoparticles with TPGS-Vitamin E

To a 150 mL beaker containing D-α-tocopheryl polyethylene glycol 1000 succinate (vitamin E TPGS) (0.28 g) dissolved in Lonza cell culture water (55 mL), nanoparticles (0.0977 g) dissolved in dimethyl sulfoxide (DMSO) (0.50 mL) were added slowly with vigorous stirring. The solution was split equally into two 50 mL centrifuge tubes. The nanoparticles were rinsed by applying three cycles of centrifugation (8000 rpm for 30 min) and reconstituted with cell culture water. The nanoparticle suspension was then lyophilized.

100. In Vitro poly(vl-evl-avl-opd) Nanoparticle Degradation Studies

TPGS formulated poly(vl-evl-avl-vl) nanoparticles (10 mg) were suspended in 2 mL of Dulbecco's Phosphate Buffered Saline (pH 7.4) in 2 dram vials equipped with stir bars. The vials were sealed to avoid evaporation and the samples were maintained at 37° C. under continuous stirring. At 48 h intervals, samples were removed and dichloromethane was added (3×4 mL) to extract remaining nanoparticles and degradation products. The extraction solutions were concentrated via rotary evaporator and dried in vacuo. The degradation of the nanoparticles was monitored by the change in molecular weight, as determined by static light scattering, with incubation time.

101. In Vitro Cytotoxicity of Formulated poly(vl-evl-avl-opd) Nanoparticles (MTT Assay)

The cytotoxicity of TPGS formulated nanoparticles was evaluated using an MTT assay. HeLa cells were cultured in Eagle's Minimum Essential Medium supplemented with 10% heat inactivated fetal bovine serum, L-glutamine, penicillin streptomycin sulfate antibiotic-antimycotic mixture and gentamicin. Cells were maintained at 37° C. with 5% $CO_2$ in a 95% humidity incubator. The cells were seeded in a 96-well plate in 100 µL media per well at a density of 10,000 cells/well and incubated for 24 h. The media was then replaced with 100 µL of phenol red free medium-containing nanoparticles at different concentrations in triplicate and incubated for 24 h. After incubation, the nanoparticle containing media were removed, the cells were rinsed three times with DPBS, to avoid interference in the assays, and 100 µL of fresh phenol red free media was added, followed by 10 µL MTT solution (5 mg/mL). The cells were incubated for 4 h, after which time the medium was carefully removed. To the resulting purple crystals, 100 µL DMSO was added to lyse the cells and was incubated for 10 min at 37° C. The MTT absorbance was measured at 540 nm using a Synergy HT Multi-mode microplate reader (Bio Tek Instruments, Winooski, Vt.). Optical densities measured for wells containing cells that received no nanoparticle were considered to represent 100% viability. Results are expressed as the mean±S.D. of viable cells.

102. In Vitro Release of Paclitaxel from poly(vl-evl-avl-opd) Nanoparticles

To a 150 mL beaker containing D-α-tocopherol polyethylene glycol 1000 succinate (0.34 g) dissolved in Lonza cell culture water (68 mL), poly(vl-evl-avl-opd) nanoparticles (56.5 mg) and paclitaxel (8.5 mg) dissolved in dimethyl sulfoxide (0.50 mL) were added slowly with vigorous stirring. The solution was split equally into two 50 mL centrifuge tubes. The paclitaxel loaded nanoparticles were purified by applying three cycles of centrifugation (8000 rpm for 30 min) and reconstituted with cell culture water. The nanoparticle suspension was then lyophilized. The concentration of encapsulated paclitaxel was determined by Nano-Drop™ UV-Vis at a wavelength of 254 nm. Paclitaxel standards (0.398-2.39 mg/mL) were measured by UV-Vis and a calibration curve was rendered. With the calibration curve, the concentration of encapsulated paclitaxel was determined by the absorbency of the paclitaxel in the nanoparticle at 254 nm and the loading ratio was found to be 11.3%. The release of paclitaxel from the nanoparticles was measured in PBS (pH 7.4) at 37° C. The paclitaxel-loaded nanoparticles (20 mg) were suspended in PBS (20 mL). At particular time intervals, the nanoparticle dispersion was centrifuged, the supernatant was removed and the released paclitaxel was extracted from the supernatant with $CH_2Cl_2$. The concentration of released paclitaxel was determined by NanoDrop™ UV-Vis at a wavelength of 254 nm as mentioned above.

103. General Procedures for the Synthesis of HVGGSSV Peptide

The peptide was synthesized by solid-phase peptide synthesis using standard Fmoc chemistry on a Model 90 Peptide Synthesizer (Advanced ChemTech).

General Procedure: Attachment of N-Fmoc Amino Acids to Resin.

After swelling with dichloromethane (20 mL) for 20 min, H-Val-2-Cl-Trt resin (0.20 g, 1.03 mmol/g, 0.21 mmol surface amino acids) was treated with a solution of Fmoc-protected amino acids (4 equiv, 0.9 mmol) in dimethylformamide (DMF) (6 mL). The amino acids were attached to the resin using double coupling with a solution (9 mL) consisting of N-hydroxybenzotriazole monohydrate (HOBt) (0.9 mmol, 137.8 mg) o-(benzotriazole-N,N,N',N'-tetramethyluronium hexafluorophosphate (0.9 mmol, 0.34 g), N,N'-diisopropylethylamine (DIPEA) (1.8 mmol, 0.31 mL) in 9 mL DMF. The reaction mixture was shaken for 60 min and washed with DMF (4×10 mL), methanol (4×10 mL) and DMF (4×10 mL). A 20% (v/v) piperidine in DMF solution was used to deprotect the Fmoc groups. The amino acids were attached to the resin in the following sequence: Ser, Ser, Gly, Gly, Val, His, Asn, Gly, Gly, Gly, Cys, and Gly.

General Procedure: Cleavage from Resin.

The resin was treated with Reagent R, a solution of TFA, thioanisole, anisole, and ethanedithiol (90:5:3:2, 6 mL), for 4 h. After removal of the resin by filtration, the filtrate was concentrated to precipitate the peptide with cold diethyl ether. Crude peptides were purified by RP-HPLC and lyophilized. Peptide identity was confirmed by MALDI-MS (m/z: 1086.45).

104. Attachment of HVGGSSV Peptide to Nanoparticles

To a solution of nanoparticles (105.6 mg, 0.78 µmol) in DMSO (1 mL), HVGGSSV peptide (56 mg, 53.6 µmol) in DMSO (2 mL) was added. The reaction mixture was heated for 72 h at 34° C. Residual peptide was removed by dialyzing with SnakeSkin® Pleated Dialysis Tubing (MWCO=10,000) against 50/50 THF/$CH_3CN$. Yield: 77 mg. DLS: $D_H$=55.3±3.6 nm: original particle $D_H$=52.9±3.3 nm. SLS: $M_w$=185,000 Da; original particle $M_w$=147,000 Da. $^1$H NMR (600 MHz, DMSO-$d_6$) δ: The significant change is the reduction of the allyl protons at 5.69 and 5.00 ppm and the appearance of signals at 0.80, 1.39, 1.65, 2.74, 3.07, 3.75, 4.40 and 7.11-8.32 ppm due to the peptide. All other aspects of the spectrum are similar to that of the poly(vl-evl-avl-opd) nanoparticles.

105. Encapsulation of Paclitaxel in HVGGSSV Conjugated poly(vl-evl-avl-opd) Nanoparticles To a 150 mL beaker containing D-α-tocopherol polyethylene glycol 1000 succinate (0.30 g) dissolved in Lonza cell culture water (60 mL), HVGGSSV-nanoparticles (0.0681 g) and paclitaxel (10.2 mg) dissolved in dimethyl sulfoxide (0.50 mL) were added slowly with vigorous stirring. The solution was split into two 50 mL centrifuge tubes. The paclitaxel loaded nanoparticles were purified by applying two cycles of centrifugation (8000 rpm for 30 min) and reconstituted with cell culture water. The nanoparticle suspension was then lyophilized. The loading ratio of paclitaxel for the encapsulation was determined by NanoDrop™ UV-Vis at 254 nm as mentioned above and was found to be 11%.

106. Lowering Intraocular Pressure (IOP) with Brimonidine Nanoparticle Injection Two groups of mice (N=3 each) were compared to determine the effect of a single intravitreal injection of brimonidine-laced nanoparticle relative to a single topical drop (eyedrop) of clinical-grade brimonidine. For each mouse, intraocular pressure (IOP) was acutely elevated by an injection (1 µl) of polystyrene microbeads into the anterior chamber of the eye. This induces a 35-40% elevation in IOP that persists for 3-4 weeks. One group had a single topical application (1 µl) of brimonidine; the other a single intravitreal injection (1 dl) of the nanoparticle-brimonidine complex. IOP was tracked using TonoPen XL measurements until any lowering effect was dissipated.

For the topical application group, microbead injection induced a 35% elevation in IOP from a normal reading of 14 mmHG to 19-20 mmHG, one day after injection (FIG. 1). This elevation persisted until day 4, when topical brimonidine was applied; the application lowered IOP to normal levels one day later. Six days following topical administration of brimonidine, IOP returned to elevated levels.

For the nanoparticle group, microbead injection again induced a 40% elevation in IOP one day after injection, from a normal baseline of 15 mmHG to 21 mmHG (FIG. 2). This elevation persisted until day 4, when a single intravitreal injection (1 µl) of the nanoparticle-brimonidine complex was applied. The nanoparticle complex actually lowered IOP below normal levels to 11.5 mmHG one day later; this depression was significant ($p<0.01$). IOP remained below or at baseline for 6 days. For this period, IOP was indistinguishable from pre-microbead/baseline levels ($p=0.43$). This is dramatically different than topical application, which returned to elevated LOP during the same period. For the nanoparticle group, IOP returned to elevated levels by day 18. Control groups for both experiments demonstrated continuously elevated LOP due to microbead injection for the duration.

107. Measuring Retinal Diffusion after Nanoparticle Injection

For glaucoma, there is no FDA approved neuroprotective therapy for preventing or treating retinal and optic nerve degeneration. All available drugs have as their action LOP lowering. Thus, a secondary use of the nanoparticle delivery system would be to expose the retina and optic nerve to a slow-release of directly neuroprotective compounds, such as memantine or brimonidine, which is known to have secondary neuronal actions independent of IOP lowering. For macular degeneration, the best available practice is a monthly or biweekly intravitreal injection of antiangiogenic compounds, such as LUCENTIS® (ramibizumab) or AVASTIN® (bevaizumab). Again the nanoparticle delivery system could ameliorate the need for such frequent injections.

To determine how much of the retina could be stained over time with a common neuronal dye (DiO) interlaced into the nanoparticle after a single intravitreal injection, the area of the retina covered by DiO released from the nanoparticle complex was measured as a function of time after the injection (N=2-3 mice for each time). Deposition of DiO was defined very conservatively, as that portion of the retina contained DiO signal intensity of 100% contrast compared to background. The area of the retina represented by DiO label was compared to the total surface area of the retina. Retinas were examined at 3 days, 1 week, 2 weeks, and 4 weeks post-nanoparticle injection.

Figure 54B:
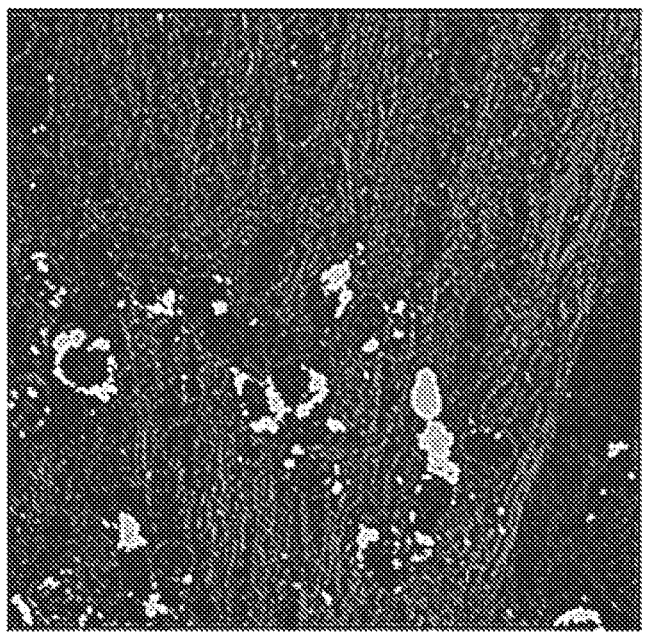
FIGS. 54A-C shows deposition of DiO dye in ganglion cells over time after a single injection of DiO nanoparticle complex.
Figure 54A:
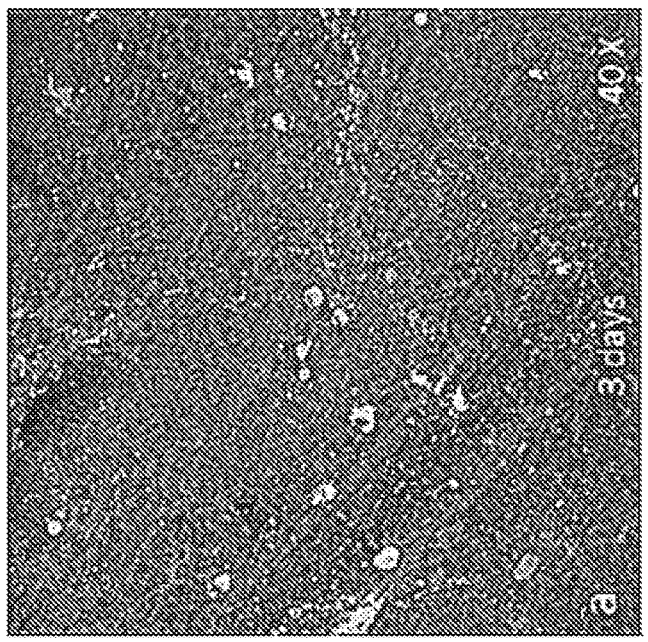
Figure 54C:
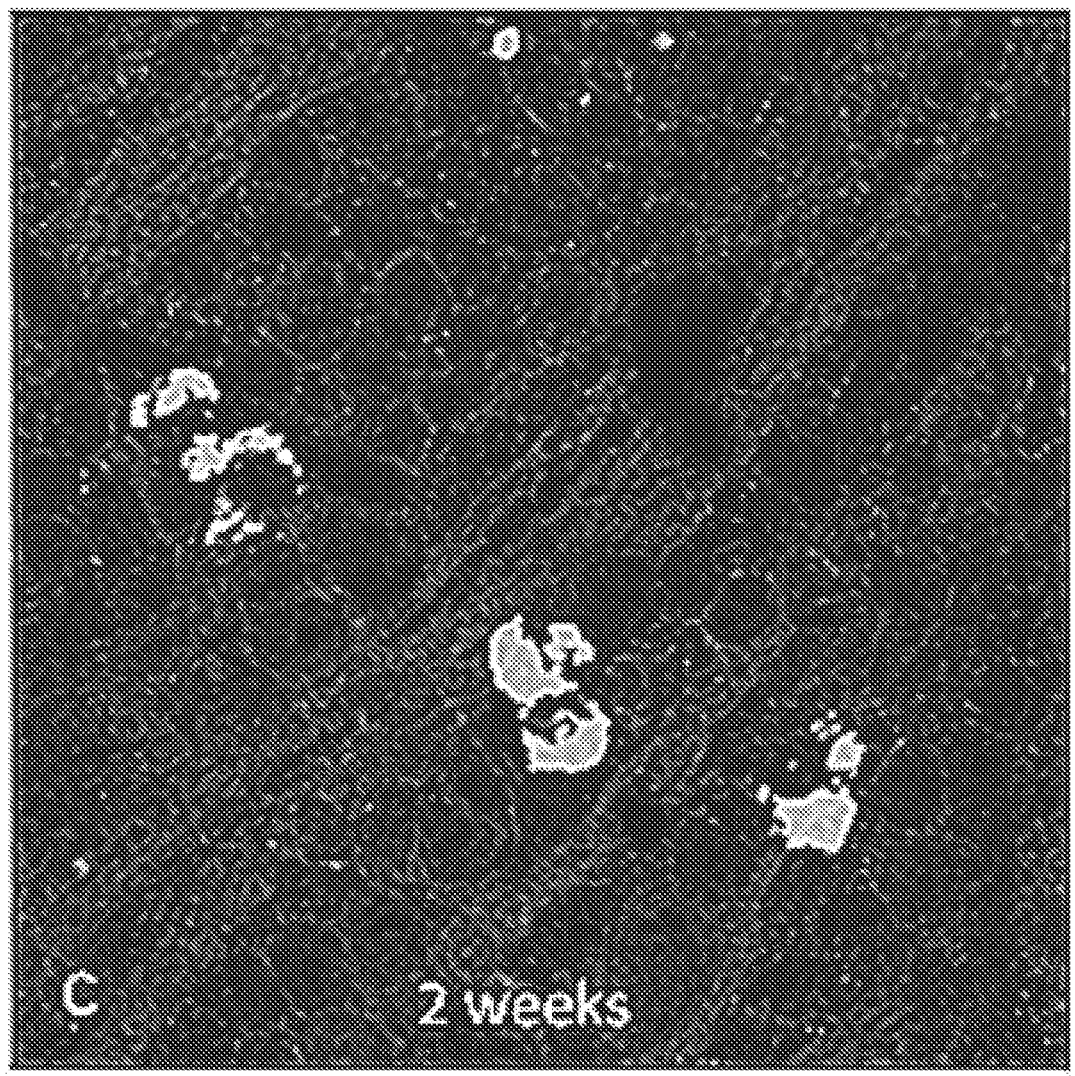
Figure 55A:
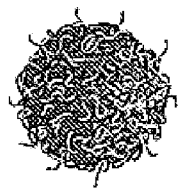
FIG. 55A-C shows "nanosponges," which are three-dimensional nano-networks formed from degradable materials, in particular, formed by crosslinking degradable linear polyesters.
Figure 55B:
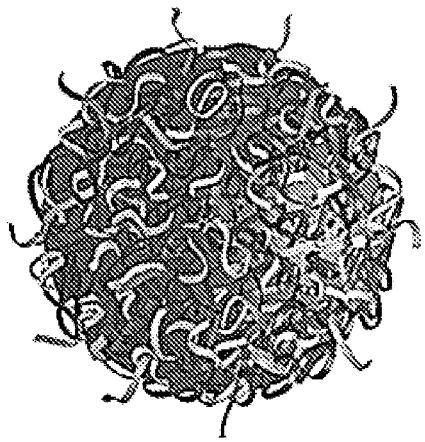
Figure 55C:
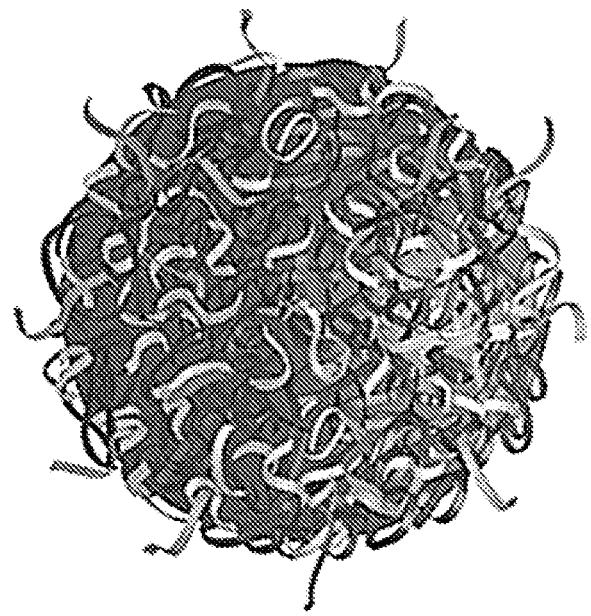
Figure 56:
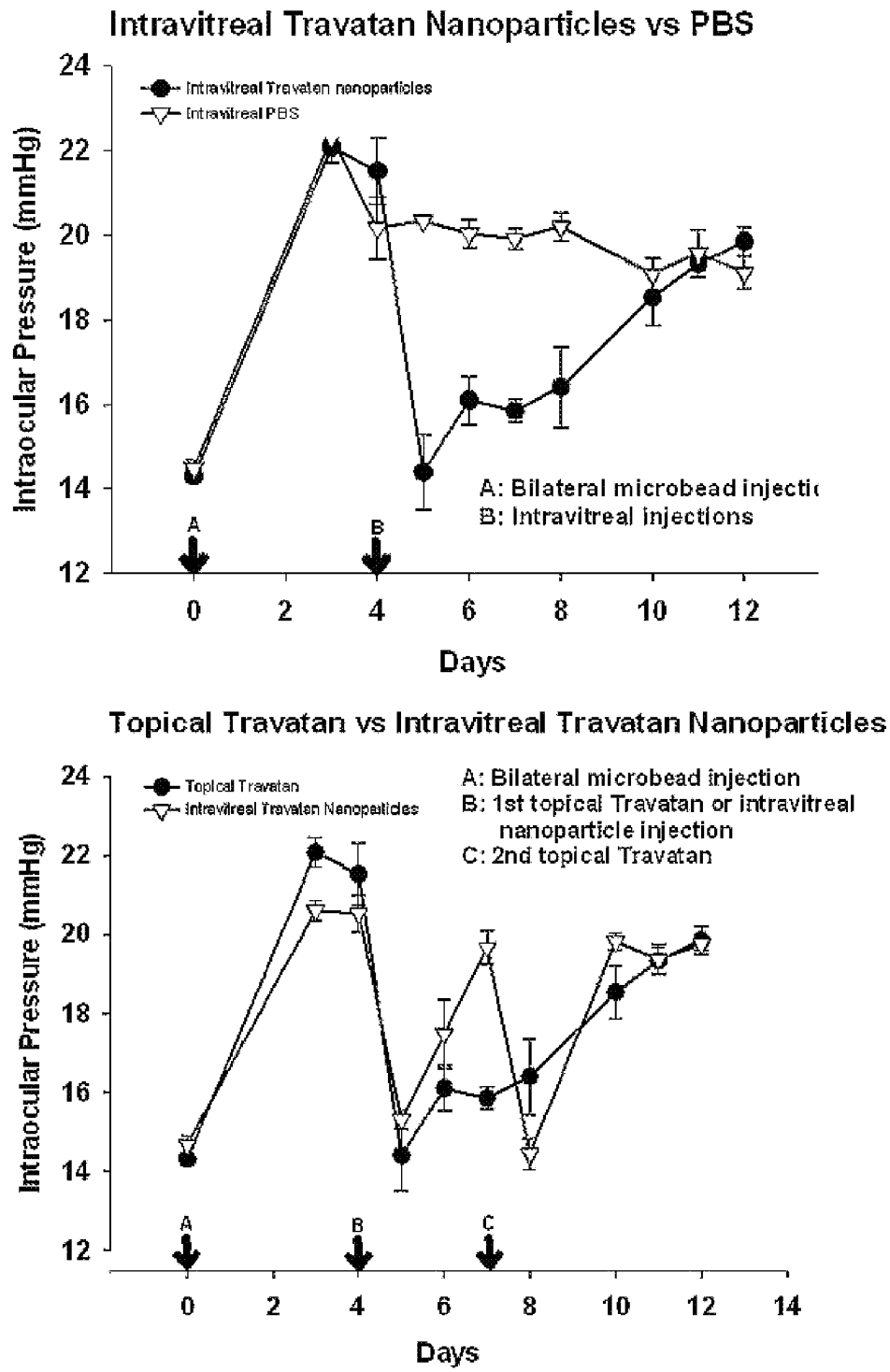
FIG. 56 summarizes hypotensive drug trials with a 50 nm "nanosponge" (7% cross-linking density, 1.3% travatan, 0.38 mg/mL). The upper panel is a graph of intraocular pressure as a function of time after intravitreal administration of the nanosponge (intravitreal travatan nanoparticles) (-●-) versus time after intravitreal administration of PBS (-∇-). The lower panel is a graph of intraocular pressure as a function of time after intravitreal administration of topical travatan (-●-) versus time after intravitreal administration of the nanosponge (intravitreal travatan nanoparticles) (-∇-).
Figure 57:
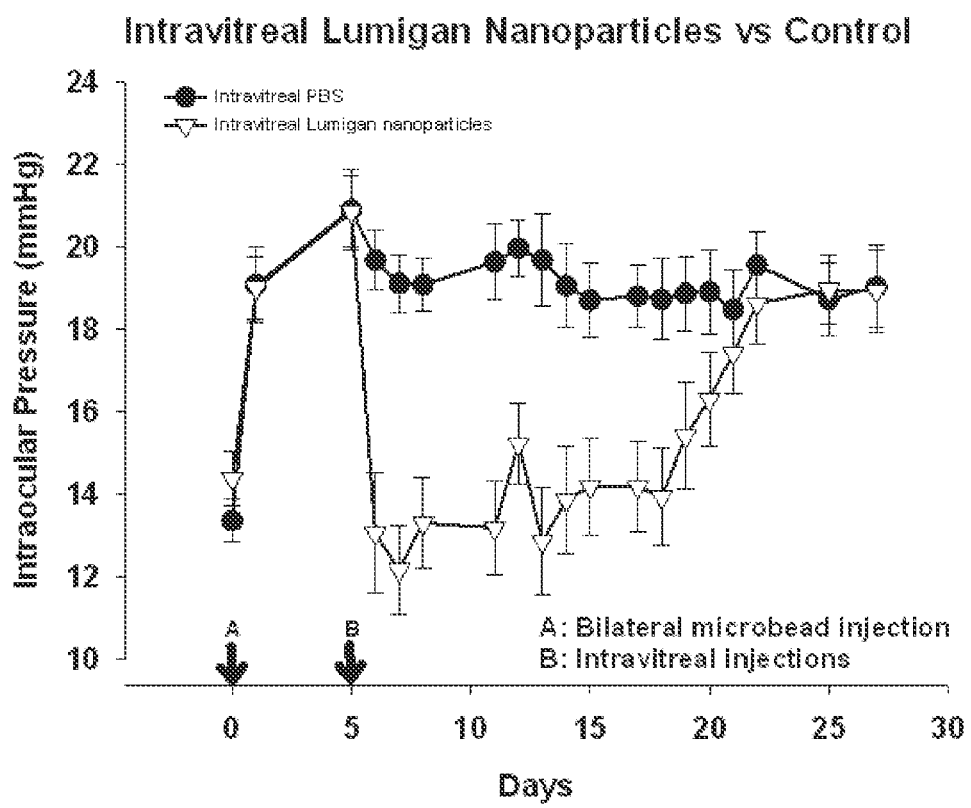
FIG. 57 summarizes hypotensive drug trials with a Lumigan (Bimatoprost Ophthalmic)-loaded 400 nm "nanosponge" (14% cross-linking density, 22.4% bimatoprost, 3.58 mg/mL), with a 700 nm "nanosponge" (14% cross-linking density, 29.35% bimatoprost, 4.7 mg/mL), and with a 700 nm "nanosponge" (14% cross-linking density, 25.41% bimatoprost, 4.07 mg/mL). The upper panel is a graph of intraocular pressure as a function of time after intravitreal administration of control (PBS) (-●-) versus time after intravitreal administration of the 400 nm nanosponge (intravitreal bimatoprost nanoparticles) (-∇-). The lower panel is a graph of intraocular pressure as a function of time after intravitreal administration of control (PBS) (-●-) versus time after intravitreal administration of the 700 nm nanosponge (intravitreal bimatoprost nanoparticles) (-∇-).
Figure 57:
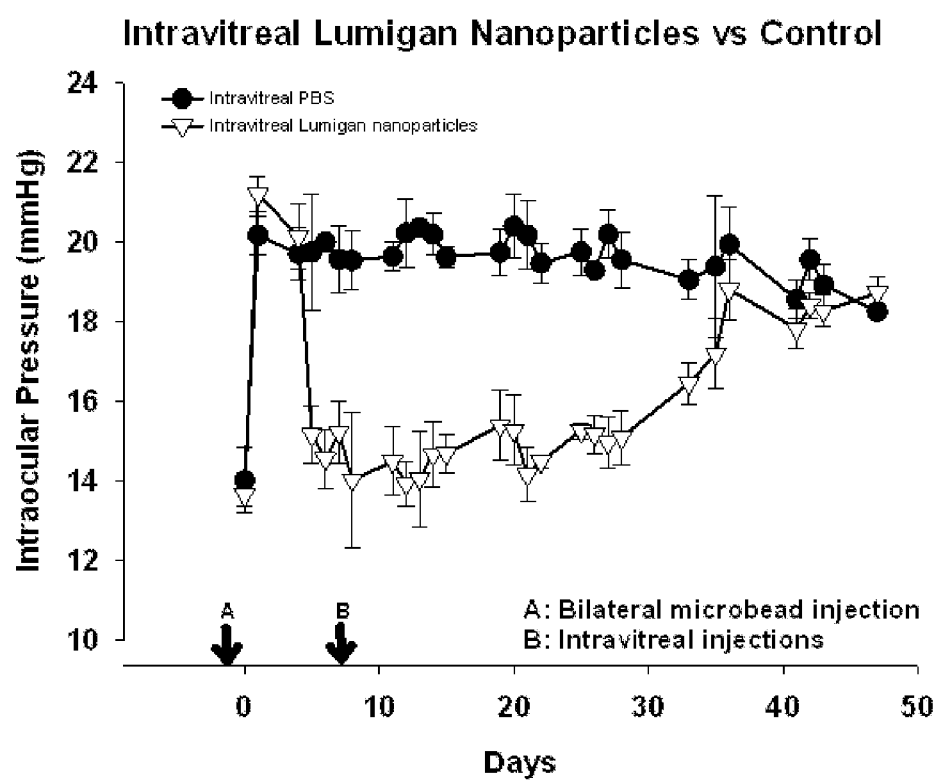

Over a 4 week period, DiO deposition appeared to increase on the retinal surface by about 15% compared to the initial measurement at 3 days; this was not significant ($p=0.50$) (FIG. 53). In between, deposition was statistically constant compared to the initial measurement as well. This indicates that retinal uptake of the DiO is fairly consistent and matched to its slow release from the nanoparticle complex. Thus, retinal exposure to a released drug would be constant in between nanoparticle injections. Additionally, the ability of nanoparticles to pas through the inner limiting membrane and deliver DiO to ganglion cells was measured at 3 days, 1 week, and 2 weeks following injection. Micrographs show that deposition was observed in ganglion cells and maintained over the observatory period (FIG. 54).

108. Preparation of Nanoparticles from Linear Polymer Precursor a. Formation of 50 nm Nanoparticles To a 100-mL round bottom flask equipped with a stir bar, poly(vl-evl) (0.1001 g, $M_w$=2350 Da, 7% cross-linking) and 20.2 mL $CH_2Cl_2$ were added, followed by 2,2'-(ethylenedioxy)diethylamine (9.6 µL, $6.55 \times 10^5$ mol). The mixture was heated at reflux at 44° C. for 12 h and promptly transferred to SnakeSkin® Pleated Dialysis Tubing (MWCO=10,000) and dialyzed against dichloromethane to remove residual diamine. $^1$H NMR (400 MHz), $CDCl_3$/TMS, ppm) δ: The significant change, proving conversion from the linear polymer to the nanoparticle, is the disappearance of epoxide protons at 2.96, 2.75, and 2.47 ppm and the appearance of signals at 3.5 ppm and 2.9 ppm due to the protons near the secondary amine of the PEG linker.

b. Formation of 400 nm Nanoparticles

To a 200-mL round bottom flask equipped with a stir bar, poly(vl-evl) (0.1210 g, $M_w$=2325 Da, 13% cross-linking) and 45.1 mL $CH_2Cl_2$ were added, followed by 2,2'-(ethylenedioxy)diethylamine (75.1 µL, $5.13 \times 10^{-4}$ mol). The mixture was heated at reflux at 44° C. for 12 h and promptly transferred to SnakeSkin® Pleated Dialysis Tubing (MWCO=10,000) and dialyzed against dichloromethane to remove residual diamine. $^1$H NMR (400 MHz), $CDCl_3$/TMS, ppm) δ: The significant change is the disappearance of epoxide protons at 2.93, 2.76, and 2.47 ppm and the appearance of signals at 3.5 and 2.9 ppm, correlating to the protons of the PEG linker.

c. Formation of 700 nm Nanoparticles

To a 200-mL round bottom flask equipped with a stir bar, poly(vl-evl-avl) (0.1057 g, $M_w$=7200 Da, 15% cross-linking) and 46.4 mL $CH_2Cl_2$ were added, followed by 2,2'-(ethylenedioxy)diethylamine (82.5 µL, $5.64 \times 10^{-4}$ mol). The mixture was heated at reflux at 44° C. for 12 h and promptly transferred to SnakeSkin® Pleated Dialysis Tubing (MWCO=10,000) and dialyzed against dichloromethane to remove residual diamine. $^1$H NMR (400 MHz), $CDCl_3$/TMS, ppm) δ: The significant change is the disappearance of epoxide protons at 2.94, 2.75, and 2.48 ppm and the appearance of signals at 3.5 and 2.9 ppm, correlating to the protons of the PEG linker.

d. Formation of 700 nm Nanoparticles

To a 200-mL round bottom flask equipped with a stir bar, poly(vl-evl-avl) (0.1001 g, $M_w$=7200 Da, 15% cross-linking) and 43.9 mL $CH_2Cl_2$ were added, followed by 2,2'-(ethylenedioxy)diethylamine (39.1 μL, $2.67×10^{-4}$ mol) and 1,8-diaminooctane (38.5 mg, $2.67×10^{-4}$ mol). The mixture was heated at reflux at 44° C. for 12 h and transferred to SnakeSkin® Pleated Dialysis Tubing (MWCO=10,000) and dialyzed against dichloromethane to remove residual diamines. $^1$H NMR (400 MHz), $CDCl_3$/TMS, ppm) δ: The significant change, confirming incorporation of 1,8-diaminooctane, is the appearance of a signal at 1.32 ppm corresponding to the protons between the secondary amines of the cross-linker. The spectrum shows otherwise similar shifts as the particles of 50 and 400 nm.

109. General Procedure for Encapsulation of NP

The 700 nm nanoparticle with 15% cross-linking (100% PEG linker) (16.7 mg) and bimatoprost (7-[3,5-dihydroxy-2-(3-hydroxy-5-phenyl-pent-1-enyl)-cyclopentyl]-N-ethyl-hept-5-enamide; a prostaglandin analog/prodrug used topically to control the progression of glaucoma and in the management of ocular hypertension; 5.0 mg) were accurately weighed together into a vial. The two solids were dissolved in a minimal amount of DMSO (150 μL) and added dropwise to a vigorously stirring solution of water (8.3 mL) and vitamin E (0.125 g). The solution turned cloudy and was immediately centrifuged at 8500 rpm for 20 min. The supernatant was carefully removed, fresh water was added and the pellet disturbed to ensure thorough washing of the drug-loaded particles. The centrifugation wash was repeated for a total of three washes. Finally, the particles were frozen and lyophilized to yield the drug-loaded particles as a light and fluffy white solid with 29.4% bimatoprost encapsulated.

The 700 nm nanoparticle with the 50:50 mixture of amorphous and crystalline cross-linkers encapsulated 25.4% bimatoprost. The 400 nm nanoparticle encapsulated 22.4% bimatoprost, and the 50 nm nanoparticle encapsulated 1.3% travatan (i.e., Travoprost, propan-2-yl 7-[3,5-dihydroxy-2-[3-hydroxy-4-[3-(trifluoromethyl)phenoxy]-but-1-enyl]-cyclopentyl]hept-5-enoate; topical medication used for controlling the progression of glaucoma or ocular hypertension, by reducing intraocular pressure), and the other 50 nm nanoparticle encapsulated 3.3% brimonidine (5-Bromo-N-(4,5-dihydro-1H-imidazol-2-yl)quinoxalin-6-amine; used to treat open-angle glaucoma or ocular hypertension).

110. Nanodrop to Determine % Drug Loading

About 0.4 mg of drug-loaded nanoparticles were weighed and dissolved in 50 uL DMSO. 2 uL of sample solution was pipetted onto the pedestal of a UV-VIS spectrometer (Nano-Drop) and the absorbance measured at 262 nm. A calibration curve between concentration of drug and absorbance was made using a spread of samples with known concentrations of drug. Using the calibration curve, the amount of drug within the nanoparticle could be quantified and reported as a weight percent.

111. General Procedure for Mouse Study Preparation

The nanoparticle (1.20 mg, 700 nm amorphous) was accurately weighed into an eppendorff tube and dispersed in PBS (75 μL) for an over-all concentration of 16 mg/mL, or 3.6 mg/mL bimatoprost.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

---

What is claimed is:

1. A composition comprising a crosslinked degradable polyester particle including polymer backbones comprising δ-valerolactone monomers residues, the crosslinked degradable polyester particle produced by crosslinking a polymer comprising:

(a) at least one epoxide-functionalized monomer residue having an optionally substituted structure represented by a formula:

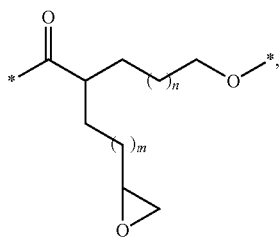

wherein m is an integer from 0 to 6, and
wherein n is an integer from 0 to 2; or (b) at least one propargyl-functionalized monomer residue having an optionally substituted structure represented by a formula:

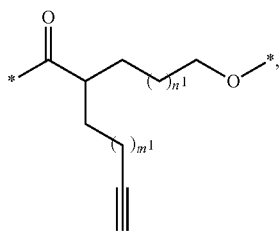

wherein $m^1$ is an integer from 0 to 6, and
wherein $n^1$ is an integer from 0 to 2; or (c) at least one monomer residue having an optionally substituted structure represented by a formula:

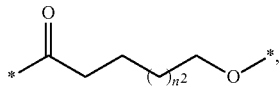

wherein $n^2$ is an integer from 0 to 2; or (d) at least one keto-functionalized repeating unit having an optionally substituted structure represented by a formula:

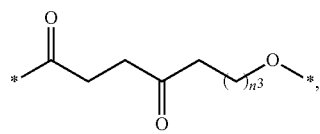

wherein $n^3$ is an integer from 0 to 2, wherein the composition is produced by a nucleophilic substitution reaction between a nucleophile including at least one of a biologically active agent, a pharmaceutically active agent, or an imaging agent and the polymer backbones.

2. The composition of claim 1, wherein at least one of the biologically active agent, the pharmaceutically active agent, or the imaging agent are attached to an optionally substituted organic radical comprising 1 to 24 carbon atoms.

3. The composition of claim 2, wherein the biologically active agent, the pharmaceutically active agent, or the imaging agent is covalently bonded to the optionally substituted organic radical comprising 1 to 24 carbon atoms.

4. The composition of claim 2, wherein the optionally substituted organic radical comprising 1 to 24 carbon atoms includes substituted or unsubstituted monovalent organic radicals selected from the group consisting of ethyl, propyl, butyl, pentyl, hexyl, heptyl, octyl, decyl, dodecyl, hexadecyl, higher cyclic or acyclic alkyl, and alkoxylene.

5. The composition of claim 1, wherein the at least one of a biologically active agent, a pharmaceutically active agent, or an imaging agent are encapsulated within the crosslinked degradable polyester particle.

6. The composition of claim 1, wherein the crosslinked degradable polyester particle is a copolymer and/or a nanoparticle.

7. A composition comprising a crosslinked degradable polyester particle including polyvalerolactone backbones polymerized from δ-valerolactone monomers, wherein the composition is produced by a nucleophilic substitution reaction between a nucleophile including at least one of a biologically active agent, a pharmaceutically active agent, or an imaging agent and the polymer backbones.

8. The composition of claim 7, wherein at least one of the biologically active agent, the pharmaceutically active agent, or the imaging agent are attached to an optionally substituted organic radical comprising 1 to 24 carbon atoms.

9. The composition of claim 7, wherein the biologically active agent, the pharmaceutically active agent, or the imaging agent is covalently bonded to the optionally substituted organic radical comprising 1 to 24 carbon atoms.

10. The composition of claim 7, wherein the optionally substituted organic radical comprising 1 to 24 carbon atoms includes substituted or unsubstituted monovalent organic radicals selected from the group consisting of ethyl, propyl, butyl, pentyl, hexyl, heptyl, octyl, decyl, dodecyl, hexadecyl, higher cyclic or acyclic alkyl, and alkoxylene.

11. The composition of claim 7, wherein the at least one of a biologically active agent, a pharmaceutically active agent, or an imaging agent are encapsulated within a crosslinked degradable polyester particle.

12. The composition of claim 7, wherein the crosslinked degradable polyester particle is a copolymer and/or a nanoparticle.

\* \* \* \* \*

SEQUENCE LISTING

```
<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1

His Val Gly Gly Ser Ser Val
1               5

<210> SEQ ID NO 2
<211> LENGTH: 13
<212> TYPE: PRT
<213> ORGANISM: Artificial Sequence
<220> FEATURE:
<223> OTHER INFORMATION: Synthetic Construct

<400> SEQUENCE: 2

Gly Cys Gly Gly Gly Asn His Val Gly Gly Ser Ser Val
1               5                   10
```

```
<210> SEQ ID NO 3
<211> LENGTH: 13
<212> TYPE: PRT
<213> ORGANISM: Artificial Sequence
<220> FEATURE:
<223> OTHER INFORMATION: Synthetic Construct

<400> SEQUENCE: 3

Gly Cys Gly Gly Gly Ser Gly Val Ser Gly His Asn Gly
1               5                   10
```